(12) United States Patent
Hung et al.

(10) Patent No.: US 11,542,274 B1
(45) Date of Patent: *Jan. 3, 2023

(54) THERAPEUTIC COMPOUNDS AND METHODS OF USE THEREOF

(71) Applicant: **AGENCY FOR SCIENCE, TECHNOLOGY AND RESEARCH (A*STAR)**, Singapore (SG)

(72) Inventors: Wei Hung, Singapore (SG); Thomas Hugo Keller, Singapore (SG); Wei Ling Wang, Singapore (SG); Gang Wang, Singapore (SG); Congbao Kang, Singapore (SG)

(73) Assignee: **Agency for Science, Technology and Research (A*STAR)**, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,731

(22) Filed: Sep. 23, 2021

Related U.S. Application Data

(63) Continuation of application No. 17/028,574, filed on Sep. 22, 2020.

(30) Foreign Application Priority Data

Sep. 26, 2019 (SG) .............................. 10201908967P

(51) Int. Cl.
*C07D 495/14* (2006.01)
*C07D 519/00* (2006.01)

(52) U.S. Cl.
CPC ......... *C07D 495/14* (2013.01); *C07D 519/00* (2013.01)

(58) Field of Classification Search
CPC ........................... C07D 495/14; C07D 519/00
See application file for complete search history.

(56) References Cited

U.S. PATENT DOCUMENTS

2021/0147441 A1* 5/2021 Hung .................. C07D 519/00

* cited by examiner

*Primary Examiner* — Rebecca L Anderson

(57) ABSTRACT

There are provided new heterobifunctional agents designed to mediated formation of protein-protein dimers and promote ubiquitination of a protein of the dimer. Also provided are methods of synthesizing the agents, pharmaceutical formulations including the agents, and methods of using the agents to treat, ameliorate or cure diseases characterized by protein over-expression or malfunction.

6 Claims, 4 Drawing Sheets

(4 of 4 Drawing Sheet(s) Filed in Color)

THERAPEUTIC COMPOUNDS AND METHODS OF USE THEREOF

CROSS-REFERENCE TO RELATED APPLICATIONS

This application is a continuation of U.S. application Ser. No. 17/028,574 filed on Sep. 22, 2020, the disclosure of which is incorporated herein in its entirety for all purposes

TECHNICAL FIELD

The present disclosure relates, in general terms, to therapeutic compounds for use as modulators of ubiquitination. The present disclosure also relates to methods of use thereof.

BACKGROUND

Drug development is a lengthy, complex, and costly process, entrenched with a high degree of uncertainty that a drug will actually succeed. This is further acerbated by the unknown pathophysiology for many disorders which makes target identification and drug development challenging. Further, animal models often cannot recapitulate an entire disorder or disease, and hence critical decisions about a pipeline drug are often made at too late a stage at too high a cost. Challenges are also present when relating to the heterogeneity of the patient population. All in all, the inability to target and modulate certain classes of bio macromolecules limits our ability to develop effective anti-cancer drugs.

The Ubiquitin—Proteasome Pathway (UPP) is a critical pathway regulating proteins and degrading misfolded or abnormal proteins. UPP is central to multiple cellular processes and, if defective or imbalanced, leads to pathogenesis in a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity. For example, cereblon (CRBN) interacts with damaged DNA binding protein 1 and forms an E3 ubiquitin ligase complex with Cullin 4 in which the proteins recognized by CRBN are ubiquitinated and degraded by proteasomes. Various immunomodulatory drugs (IMiDs), e.g., thalidomide and lenalidomide, bind to CRBN and modulate CRBN's role in the ubiquitination and degradation of protein factors involved in maintaining regular cellular function.

Harnessing the ubiquitin-proteasome pathway for therapeutic intervention has received significant interest from the scientific community. The publication by Gosink et al. (*Proc. Natl. Acad. Sci. USA* 1995, 92, 9117-9121) demonstrated proof of concept in vitro engineering peptides selectively directing ubiquitination to intracellular proteins. Nawaz et al. (Proc. Natl. Acad. Sci. U.S.A. 1999, 96, 1858-1862) described ER degradation as a target for the ubiquitin-proteasome pathway, and Zhou et al. (*Mol. Cell* 2000, 6, 751-756) demonstrated an engineered receptor capable of directing ubiquitination in mammalian and yeast cells.

Protein dimers formed between a target protein and an E3 ubiquitin ligase have been shown to induce proteasome-mediated degradation of selected proteins. See, e.g., U.S. Pat. Nos. 6,306,663; 7,041,298; 7,041,298; U.S. 2016/0058872; U.S. 2016/0045607; U.S. 2020/0102298; U.S. 2014/0356322; U.S. 2016/0176916; U.S. 2016/0235730; U.S. 2016/0235731; U.S. 2016/0243247; WO 2016/105518; WO 2016/077380; WO2016/105518; WO 2016/077375; WO2017/007612; WO2017/02431; WO 2013/170147; WO 2013/170147; WO 2015/160845; Sakamoto et al. (*Proc. Natl. Acad. Sci. USA* 2001, 98, 8554-8559); Sakamoto et al. (*Mol. Cell. Proteomics* 2003, 2, 1350-1358); Schneekloth et al. (*J. Am. Chem. Soc.* 2004, 126, 3748-3754); Schneekloth et al. (*ChemBioChem* 2005, 6, 40-46); Schneekloth et al. (*Bioorg. Med. Chem. Lett.* 2008, 18, 5904-5908); Buckley et al. (*Angew. Chem. Int. Ed. Engl.* 2014, 53, 2312-2330); Lu et al. (*Chem. Biol.* 2015, 22, 755-763); Bondeson et al. (*Nat. Chem. Biol.* 2015, 11, 611-617); Gustafson et al. (*Angewandte Chemie, Int. Ed. Engl.* 2015, 54, 9659 9662); Buckley et al. (*J. Am. Chem. Soc.* 2012, 134, 4465-4468); Lai et al. (*Angewandte Chemie, Int. Ed. Engl.* 201,55, 807-810); and Toure et al. (*Angew. Chemie. Int. Ed. Engl.* 2016, 5, 1966-1973).

Heterobifunctional compounds composed of a target protein-binding moiety and an E3 ubiquitin ligase-binding moiety, which promote formation of a dimer between a target protein and E3 ubiquitin ligase have been shown to chemically induce targeted protein degradation using heterobifunctional compounds (small molecule ligands often referred to as degraders or PROTACs for PROteolysis-TArgeting Chimeras). Targeted protein degradation refers to small molecule induced ubiquitination and degradation of disease targets, in which a small molecule simultaneously recruits both an ubiquitin E3 ligase and the target protein to be ubiquitinylated; therefore representing a functional application of chemically induced protein dimerization. Clinical proof of concept for targeted protein degradation is provided by the recent discovery that the potent anti-cancer drugs thalidomide, lenalidomide and pomalidomide (collectively known as IMiDs) exert their therapeutic effects through induced degradation of key efficacy targets, such as IKZF1, IKZF3, or caseine kinase 1 alpha (Ck1α).

Heterobifunctional PROTACs typically comprise an E3 ligase binding scaffold (hereafter E3-moiety), often an analogue of thalidomide, or a ligand to the von Hippel-Lindau tumor suppressor (VHL) protein, attached through a linker to another small molecule (hereafter target-moiety) that binds a target protein of interest. Recruitment of this target protein to the E3 ubiquitin ligase facilitates ubiquitination and subsequent degradation of the target protein. This principle has been successfully applied to several targets including the Bromodomain and Extra Terminal (BET) family (BRD2, BRD3, BRD4), RIPK2, BCR-ABL, FKBP12, BRD9, and ERRa and is a promising new pharmacologic modality now widely explored in chemical biology and drug discovery.

Bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/GI, including growth-associated genes, and remains bound to chromatin throughout the cell cycle (Dey, et al. (2009) Mol. Biol. Cell 20:4899-4909). BRD4 also physically associates with Mediator and P-TEFb (CDK9/cyclin TI) to facilitate transcriptional elongation (Yang, et al. (2005) Oncogene 24:1653-1662; Yang, et al. (2005) Mol. Cell 19:535-545). CDK9 is a validated target in chronic lymphocytic leukemia (CLL), and is linked to c-MYC-dependent transcription (Phelps, et al. Blood 113: 2637-2645; Rahl, et al. (2010) Cell 141:432-445).

In general, PROTACs have been found to exhibit different efficacy and selectivity profiles depending on the nature of the E3-moiety used, often exhibiting improved selectivity over the parental target-moiety (Zengerle et al., *Chem. Biol.* 2015, 10, 8, 1770-1777). While positive cooperativity can explain certain cases such as MZ1, it is unlikely to exist for a broad number of ligase-substrate pairs and whether desired selectivity profiles can be achieved for highly homologous proteins such as BRD2/3/4 is unknown. Based upon these current limitations, there remains a need for heterobifunctional compounds (PROTACs) that can selectively target a target protein, especially, over highly homologous related proteins.

Induced protein degradation represents a new mode of therapeutic intervention that have the potential to disrupt the way conventional small molecule drug discovery is performed. Specifically, the ability to directly decrease protein abundance in a post-translational manner presents huge advantages in the discovery of new therapeutics. Ligand binding to E3-ubiquitin ligases form the cornerstone towards the generation of new bifunctional compounds for protein degradation. However, to date most of the protein degradation compounds revolves around thalidomide-based analogs and HIF1α peptidomimetic compounds as E3-binding ligands to trigger protein degradation. Clearly, there exist a dearth of new ligands binding to novel E3 ligases which hold the key to development of high quality small molecule protein degraders.

Based upon these limitations, prior to the invention described herein, there was a need for improved methods for generating small molecule degraders and dimerizers (e.g., heterobifunctional).

It would be desirable to overcome or ameliorate at least one of the above-described problems, or at least to provide a useful alternative.

SUMMARY

Proteolysis targeting chimeras (PROTACs) are bivalent ligands in which a compound that binds to the protein target of interest is connected to a second molecule that binds an E3 ligase via a linker. The E3 protein is usually either Cereblon or Von Hippel-Lindau. Small molecule induced protein degradation by PROTACs or other small molecules, requires ligand mediated binding of two proteins that typically do not interact. While this is evidently possible, the design of such molecules remains an empirical process in which molecules for new targets frequently fail, likely due to insufficient understanding of the fundamental principles that govern these neo-interactions.

The present invention is based, at least in part, upon the discovery and development of new and improved methods for designing and generating heterobifunctional binders. The heterobifunctional binders can be "small molecule," or "low molecular weight" compounds that bind, and promote interaction between, two proteins. The methods can be used to create libraries of heterobifunctional binder and/or screen heterobifunctional binder (e.g., for drug discovery, development). The methods can be used to assess/predict the suitability of a target to ligand for inducing protein dimerization and/or protein degradation. The methods can be used to screen and/or interrogate protein interactions and function. A heterobifunctional binder developed using methods of the invention can be used for medical treatment, for example a cancer treatment.

In various embodiments, the methods are used for generating small molecule heterobifunctional degraders (e.g., PROTACs).

Exemplary aspects of the present disclosure are predicated on the discovery that specific oxindole compounds can act as modulators of targeted ubiquitination and, subsequently, degradation. When formed as a hetero-bifunctional molecule via a linker to, for example, a protein binding moiety (small molecule) for targeting a protein, the protein binding moiety is ear-marked for ubiquitination and degradation. In this regard, accumulation of the protein is avoided, the accumulation of which can, in some instances, trigger cellular stress responses and/or induce specific death pathways.

In various embodiments, the present disclosure relates to a compound of Formula (I) or a pharmaceutically acceptable salt, solvate, stereoisomer or prodrug thereof:

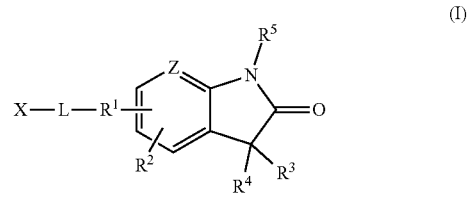

(I)

wherein $R^1$ is selected from optionally substituted heterocyclylene, optionally substituted arylene, optionally substituted heteroarylene, optionally substituted aminylacylene, optionally substituted acylaminylene and optionally substituted acylene;

$R^2$ is selected from H, halogen optionally substituted heteroaryl, and optionally substituted alkyl (e.g., methyl);

$R^3$ and $R^4$ are independently selected from H, optionally substituted cycloalkyl (e.g., cyclopropyl) and optionally substituted alkyl (e.g., methyl);

$R^5$ is selected from H and optionally substituted alkyl (e.g., methyl);

L is an optionally substituted linker having 2 to 18 atoms in the chain length;

X is a protein binding moiety; and

Z is N or CH.

In an exemplary embodiment, X is selective for a protein overexpressed or malfunctioning in a disease state. In an exemplary embodiment, X is specific for a protein overexpressed or malfunctioning in a disease state.

In exemplary embodiments, $R^1$ is located at either a 5' or 6' position of the oxindole ring.

In some embodiments, $R^1$ is optionally substituted heteroarylene and $R^2$ is selected from H, halogen or methyl.

In some embodiments, L is selected from optionally substituted alkylene, optionally substituted heteroalkylene, optionally substituted cycloalkylene and optionally substituted heterocyclylene, each having 1 to 18 atoms in the chain length, and optionally substituted ethoxy, e.g., polyethoxy, having 3 to 18 atoms in the chain length. In various embodiments, L is optionally substituted polyethoxy having 2, 3, 4, 5, 6, 7 or 8 repeating ethoxy units.

In some embodiments, X is selected from bromodomain-containing protein 4 (BRD4) binding moiety, transcriptional enhanced associate domain (TEAD) binding moiety, Polycomb Repressive Complex 2 (PRC2) binding moiety, focal adhesion kinase (FAK) binding moiety, BCR-ABL binding moiety, Hippo pathway protein binding moiety and transcription factor binding moiety.

In some embodiments, the compound of Formula (I) is represented by Formula (I'):

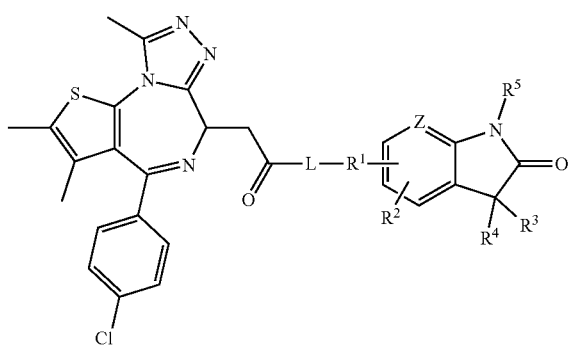

(I')

wherein $R^1$, $R^2$, $R^3$, $R^4$, $R^5$ and L are as defined herein; and wherein $R^1$ is located at either a 5' or 6' position of the oxindole ring.

The compound of Formula (I), as represented by Formula (I''):

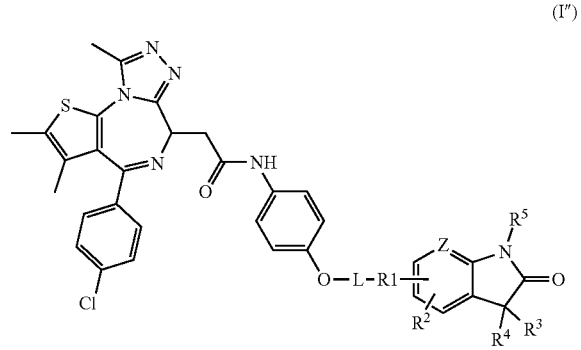

(I'')

wherein $R^1$, $R^2$, $R^3$, $R^4$, $R^5$ and L are as defined herein; and wherein $R_1$ is located at either a 5' or 6' position of the oxindole ring.

In another aspect, the present disclosure relates to a compound of Formula (II) or a pharmaceutically acceptable salt, solvate, stereoisomer or prodrug thereof:

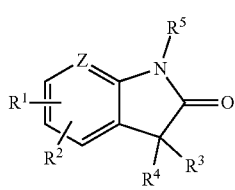

(II)

wherein $R_{1'}$ is selected from optionally substituted heterocyclyl, optionally substituted aryl, optionally substituted heteroaryl, optionally substituted aminoacyl, optionally substituted acylamino, and optionally substituted acyl;

$R^2$ is selected from H, halogen and methyl;

$R^3$ and $R^4$ are independently selected from H and methyl; and $R_5$ is selected from H and methyl;

wherein $R^{1'}$ is located at either a 5' or 6' position of the oxindole ring.

In another aspect, the present disclosure relates to a compound of Formula (III) or a pharmaceutically acceptable salt, solvate, stereoisomer or prodrug thereof.

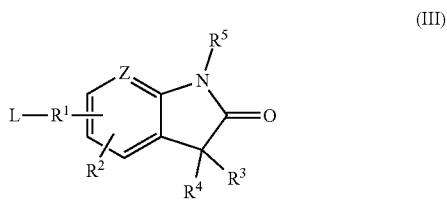

(III)

wherein $R^1$, $R^2$, $R^3$, $R^4$ and $R^5$ are as defined herein;

wherein $R_1$ is located at either a 5' or 6' position of the oxindole ring; and L is an optionally substituted linker having 1 to 18 atoms in the chain length.

In another aspect, the present disclosure relates to a pharmaceutical composition comprising an effective amount of compound of a Formula set forth herein or a pharmaceutically acceptable salt, solvate, stereoisomer or prodrug thereof, optionally in combination with a pharmaceutically acceptable carrier, excipient or diluent.

In another aspect, the present disclosure relates to a method of inducing degradation of an overexpressed protein in a cell, including a step of contacting a compound of a Formula set forth herein with the cell to induce degradation of the overexpressed protein in the cell.

In another aspect, the present disclosure relates to a method of treating a disease or condition associated with an overexpressed protein, comprising administering a compound of Formula set forth herein or a pharmaceutically acceptable salt, solvate, stereoisomer or prodrug thereof in a patient in need thereof.

In another aspect, the present disclosure relates to a compound of Formula set forth herein or a pharmaceutically acceptable salt, solvate, stereoisomer or prodrug thereof for use as a medicament.

In another aspect, the present disclosure relates to a compound of Formula set forth herein or a pharmaceutically acceptable salt, solvate, stereoisomer or prodrug thereof for use in the treatment of a disease or condition associated with an overexpressed protein.

In another aspect, the present disclosure relates to a use of a compound of Formula set forth herein or a pharmaceutically acceptable salt, solvate, stereoisomer or prodrug thereof in the manufacture of a medicament for the treatment of a disease or condition associated with an overexpressed protein.

In some embodiments, the overexpressed protein is selected from BRD4, transcriptional enhanced associate domain (TEAD), Polycomb Repressive Complex 2 (PRC2), focal adhesion kinase (FAK), BCR-ABL, Hippo pathway protein and transcription factor.

In other embodiments, the disease or condition is selected from hyperplasia and cancer (such as multiple myeloma, glioblastoma, uveal melanoma, liposarcoma, hepatocellular carcinoma, midline carcinoma, acute myeloid leukemia, Burkitt lymphoma and prostate cancer). The diseases can also be a protein accumulation disease, for example Alzheimer's disease and amyotrophic lateral sclerosis.

DESCRIPTION OF THE DRAWINGS

FIG. 2 098 induced ternary complex formation. The $^1$H-$^{15}$N-HSQC spectra of a mixture of 0.5 mM CRBN and 0.5 mM BRD4 BD2 in the absence and presence of different concentrations of 098 were collected, and processed. The signal broadening of the cross peaks in the spectra confirms the formation of ternary complex.

DETAILED DESCRIPTION

I. Introduction

Figure 1A:
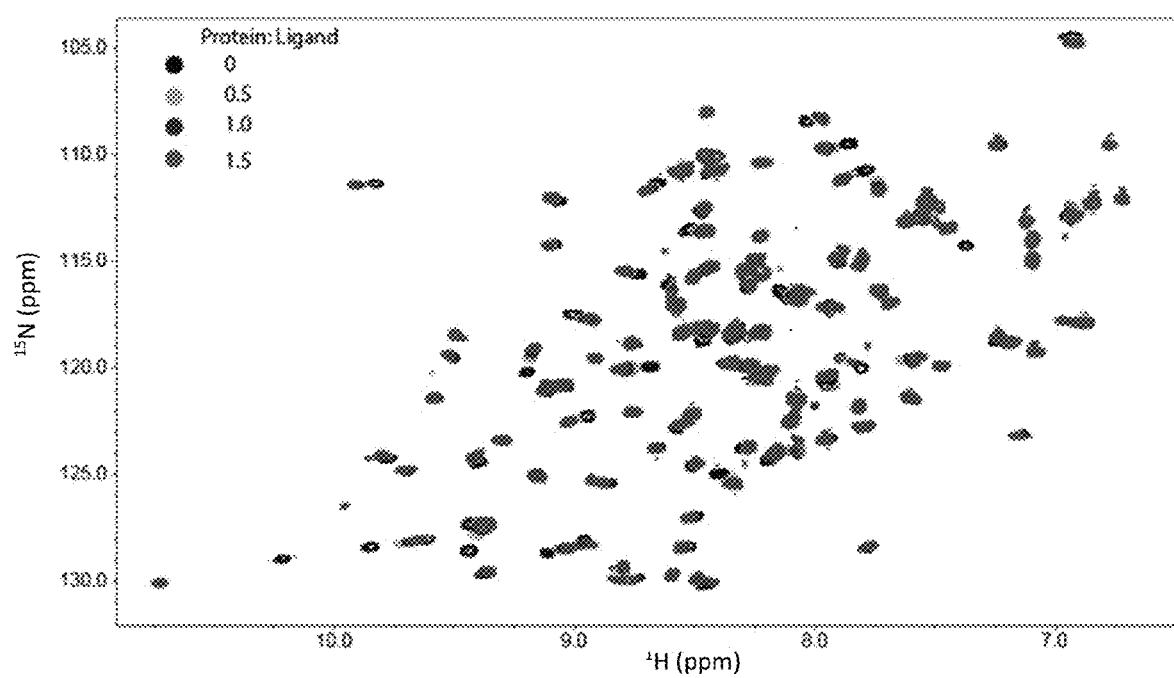
FIG. 1A-FIG. 1F is a display of $^1$H-$^{15}$N-HSQC spectra of selected ligands bound to protein CRBN. The $^1$H-$^{15}$N-HSQC spectra of a mixture of 0.5 mM CRBN in the absence (black) and presence of different concentration of ligands were collected, processed and shown. The concentration-dependent chemical shift perturbations for a few residues suggest that ligands bind to protein CRBN. The ligand to CRBN ratios are shown. The binding was saturated when ligand to protein ratio was 1 to 1. (a) 011; (b) 012; (c) 013; (d) 040; (e) 042; (f) 045.
Figure 1B:
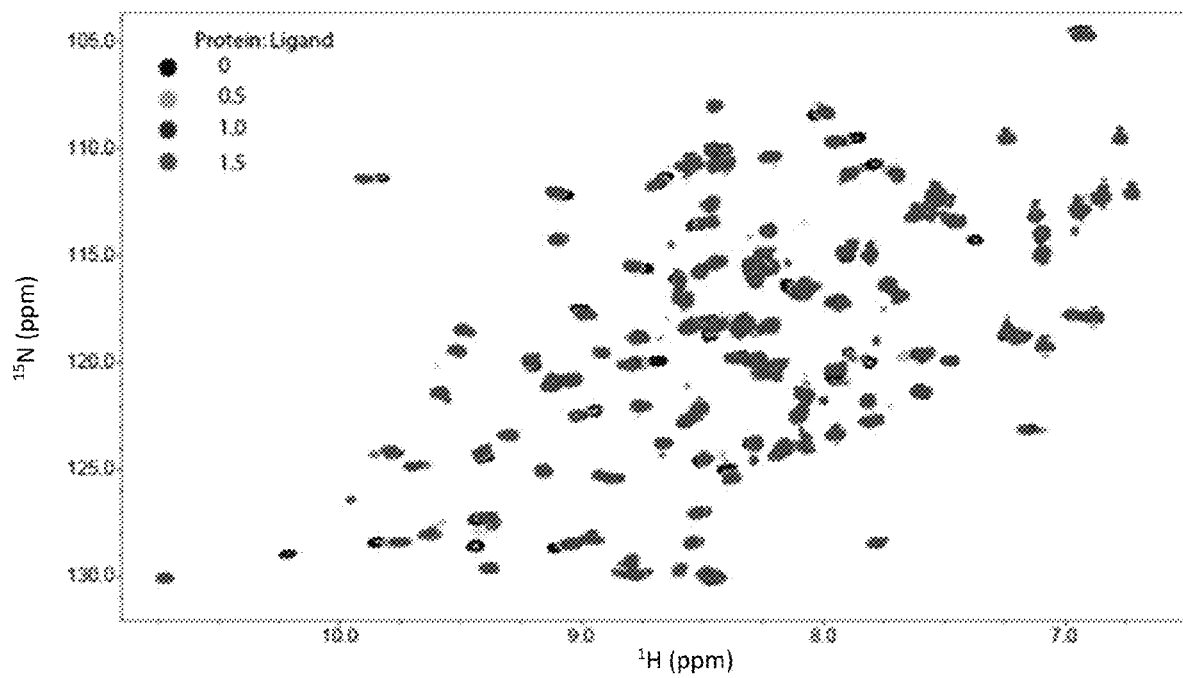
Figure 1C:
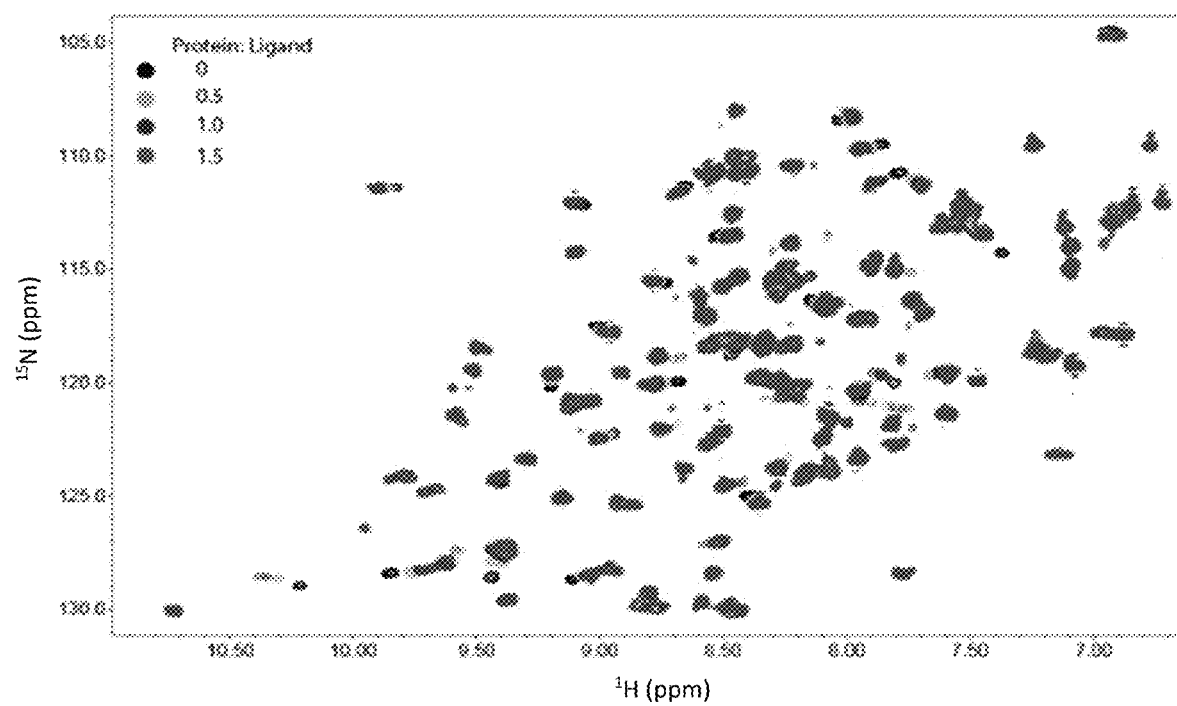
Figure 1D:
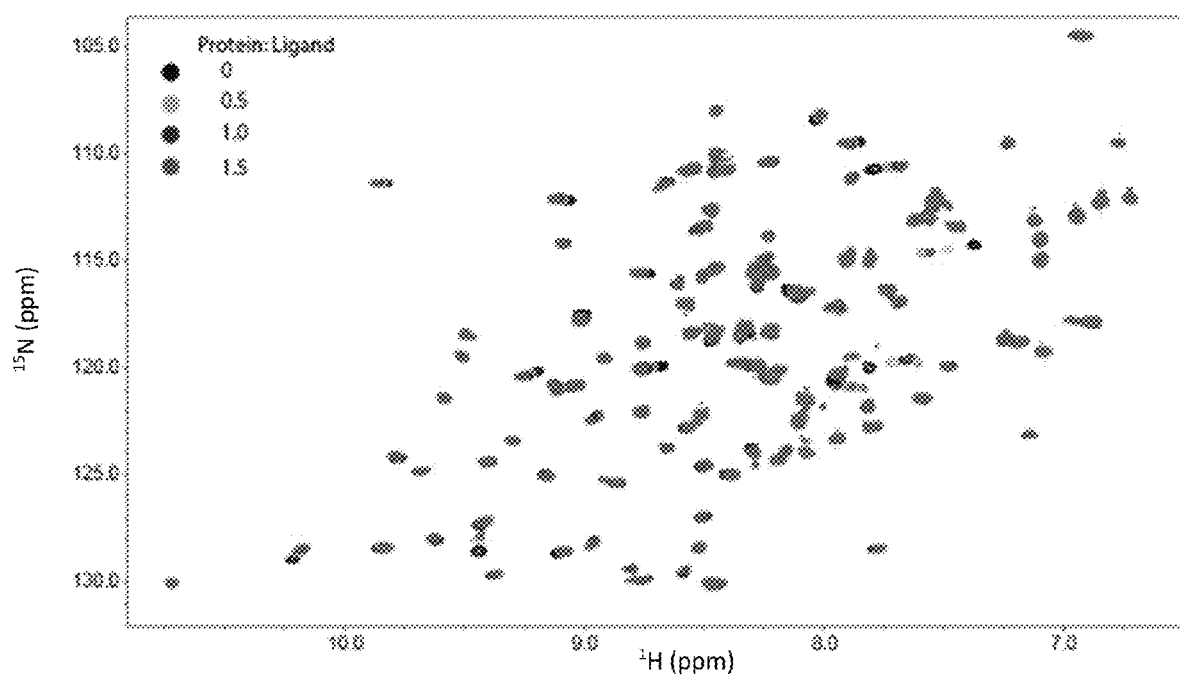
Figure 1E:
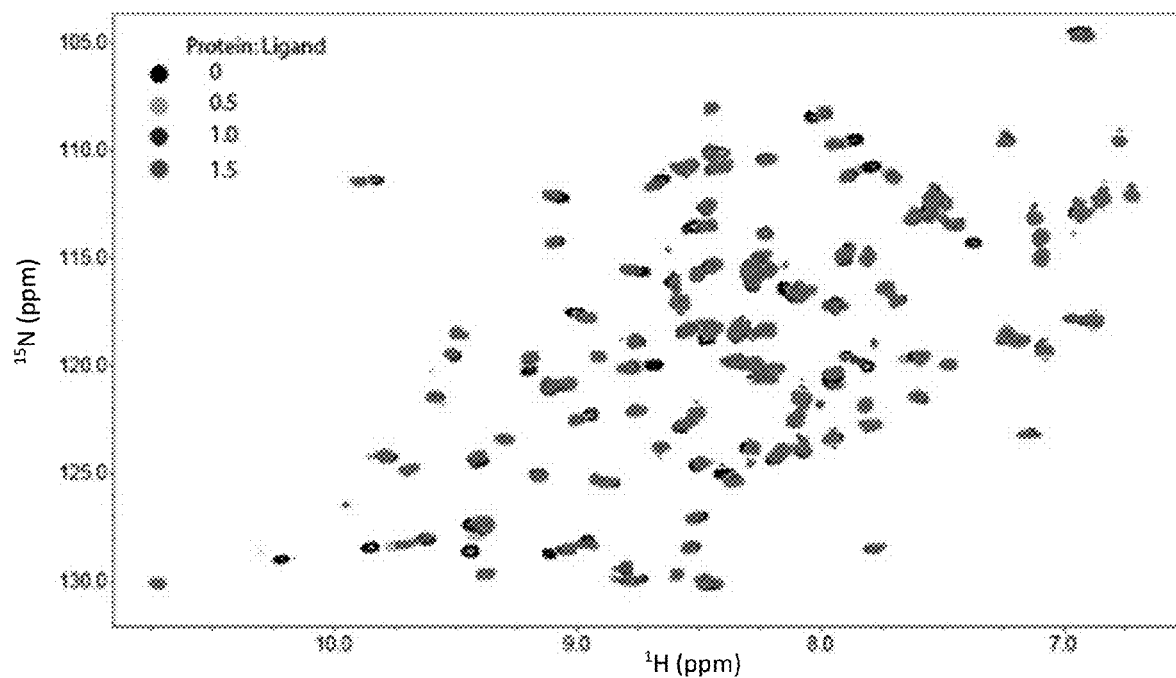
Figure 1F:
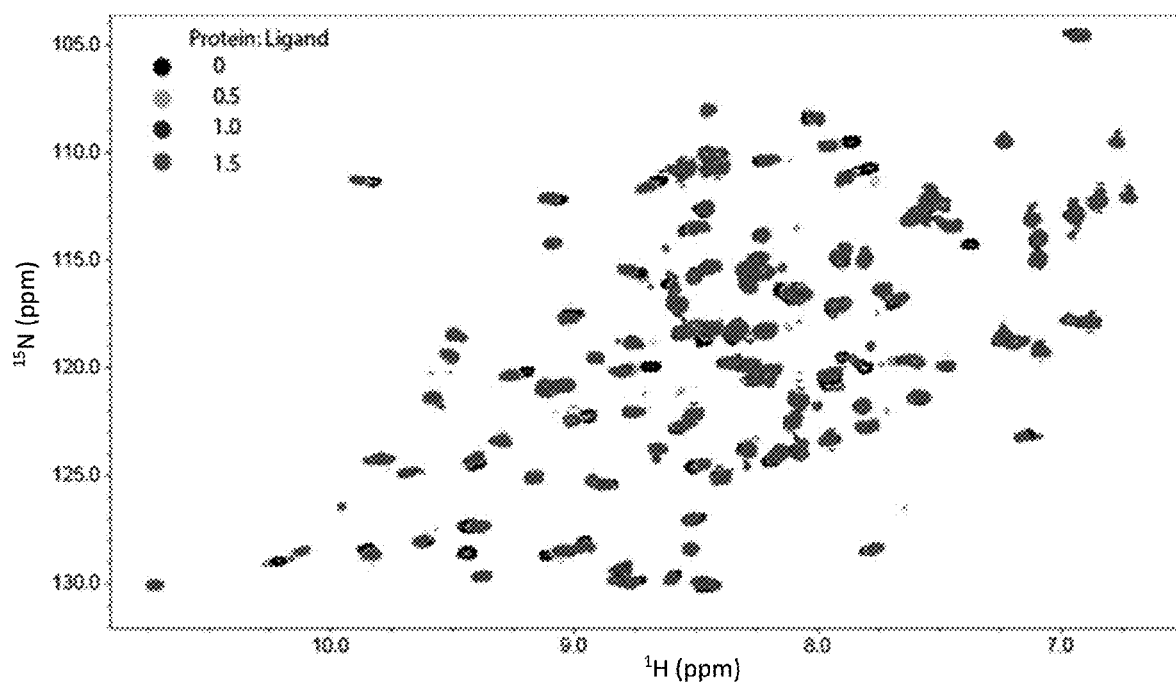

The present invention provides a novel class of heterobifunctional molecules operating to promote degradation of a protein of interest (POI) by initiating ubiquitination of the POI. The compounds of the invention operate in a manner differentiated by the standard occupancy-driven paradigm of drug development in which potency is dependent on binding affinity. For example, protein inhibition likely cannot influence non-catalytic target protein function(s). Additionally, sustained target engagement is difficult in cases of target overexpression, the presence of competing native ligand(s), or target protein mutations that result in loss of target engagement and subsequent resistance. Since the compounds of the invention inhibit protein function via degradation, this event-driven technology can be used to circumvent these common disadvantages of traditional occupancy-driven inhibitors described above.

II. Definitions

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the content clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the terms "compounds herein described", "compounds of the present application" and equivalent expressions refer to compounds described in the present application, e.g., those encompassed by the structural Formulae, optionally with reference to any of the applicable embodiments, and also includes exemplary compounds, as well as their pharmaceutically acceptable salts, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of the present description. Such compounds are useful, for example, as analytical tools, as probes in biological assays, or as therapeutic agents in accordance with the present description.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., Enantiomers, Racemates and Resolutions (Wiley Interscience, New York, 1981); Wilen, et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions, p. 268 (E. L. Eliel, Ed., Univ. of Notre Dame Press, Notre Dame, Ind. 1972). In certain embodiments, the invention provides compounds according to a Formula set forth herein which are "optically enriched".

Definitions of specific functional groups and chemical terms are described in more detail below. For purposes of the present description, the chemical elements are identified in accordance with the Periodic Table of the Elements, CAS version, Handbook of Chemistry and Physics, 75$^{th}$, Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5.sup.th, Edition, John Wiley & Sons, Inc., New York, 2001; Larock, Comprehensive Organic Transformations, VCH Publishers, Inc., New York, 1989; Carruthers, Some Modern Methods of Organic Synthesis, 3.sup.rd Edition, Cambridge University Press, Cambridge, 1987.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For greater certainty, examples of abbreviations used in the present application are listed in a table in the Examples section.

The number of carbon atoms in a hydrocarbyl or other substituent can be indicated by the prefix "$C_x$-C.sub.$y$," where x is the minimum and y is the maximum number of carbon atoms in the substituent. When reference is made to "x to y membered" heterocyclic ring (e.g., heterocycloalkyl or heteroaryl), then x and y define respectively, the minimum and maximum number of atoms in the cycle, including carbons as well as heteroatom(s).

The prefix "halo" indicates that the substituent to which the prefix is attached is substituted with one or more independently selected halogen atoms. More specifically, the terms "halo" and "halogen" as used herein refer to an atom selected from fluorine (fluoro, —F), chlorine (chloro, —Cl), bromine (bromo, —Br), and iodine (iodo, —I). For example, "haloalkyl" means an alkyl substituent wherein at least one hydrogen atom is replaced with a halogen atom and "haloalkoxy" means an alkoxy substituent wherein at least one hydrogen atom is replaced with a halogen atom.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl).

As used herein a "direct bond" or "covalent bond" refers to a single, double or triple bond. In certain embodiments, a "direct bond" or "covalent bond" refers to a single bond. This term is also synonymous with a "zero-order linker".

Where substituent groups are specified by their conventional chemical formulae, written from left to right, they optionally equally encompass the chemically identical substituents, which would result from writing the structure from right to left, e.g., —CH$_2$O— is intended to also recite —OCH$_2$—.

The term "alkyl", by itself or as part of another substituent, means a straight or branched chain hydrocarbon, which may be fully saturated, mono- or polyunsaturated and includes mono-, di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" can refer to "alkylene", which by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 30 carbon atoms. A "lower alkyl" or "lower alkylene" is a shorter chain alkyl or alkylene group, generally having eight or fewer carbon atoms. In some embodiments, alkyl refers to an alkyl or combination of alkyls selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl. In exemplary embodiments, "Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—CH$_2$-), ethylene (—CH$_2$CH$_2$-), and the propylene isomers (e.g., —CH$_2$CH$_2$CH$_2$— and —CH(CH$_3$)CH$_2$-), and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2-enyl (—CH$_2$CH═CHCH$_3$), and the like.

"Alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyloxy" refers to the group alkenyl-O— wherein the alkenyl group is as described above.

"Alkynyloxy" refers to the group alkynyl-O— wherein the alkynyl groups is as described above.

The terms "cycloalkyl" and "heterocycloalkyl", by themselves or in combination with other terms, refer to cyclic versions of "alkyl" and "heteroalkyl", respectively.

Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

"Haloalkyl" refers to an alkyl group wherein the alkyl group is substituted by one or more halo group as described above. The terms "haloalkenyl", "haloalkynyl" and "haloalkoxy" are likewise defined.

The term "heteroalkyl," by itself or in combination with another term, means an alkyl in which one or more carbons are replaced with one or more heteroatoms selected from the group consisting of O, N, Si and S, (preferably O, N and S), wherein the nitrogen and sulfur atoms may optionally be oxidized and the nitrogen heteroatom may optionally be quaternized. The heteroatoms 0, N, Si and S may be placed at any interior position of the heteroalkyl group or at the position at which the alkyl group is attached to the remainder of the molecule. In some embodiments, depending on whether a heteroatom terminates a chain or is in an interior position, the heteroatom may be bonded to one or more H or substituents such as ($C_1$, $C_2$, $C_3$, $C_4$, $C_5$ or $C_6$) alkyl according to the valence of the heteroatom. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. No more than two heteroatoms may be consecutive, as in, for example, —$CH_2$—NH—O$CH_3$ and —$CH_2$—O—Si($CH_3$)$_3$, and in some instances, this may place a limit on the number of heteroatom substitutions. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. The designated number of carbons in heteroforms of alkyl, alkenyl and alkynyl includes the heteroatom count. For example, a ($C_1$, $C_2$, $C_3$, $C_4$, $C_5$ or $C_6$) heteroalkyl will contain, respectively, 1, 2, 3, 4, 5 or 6 atoms selected from C, N, O, Si and S such that the heteroalkyl contains at least one C atom and at least one heteroatom, for example 1-5 C and 1 N or 1-4 C and 2 N. Further, a heteroalkyl may also contain one or more carbonyl groups. In some embodiments, a heteroalkyl is any $C_2$-$C_{30}$ alkyl, $C_2$-$C_{25}$ alkyl, $C_2$-$C_{20}$ alkyl, $C_2$-$C_{15}$ alkyl, $C_2$-$C_{10}$ alkyl or $C_2$-$C_6$ alkyl in any of which one or more carbons are replaced by one or more heteroatoms selected from O, N, Si and S (or from O, N and S). In some embodiments, each of 1, 2, 3, 4 or 5 carbons is replaced with a heteroatom. The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

"Aryl" refers to an unsaturated aromatic carbocyclic group having a single ring (eg. phenyl) or multiple condensed rings (e.g., naphthyl or anthryl), preferably having from 6 to 14 carbon atoms. Examples of aryl groups include phenyl, naphthyl and the like.

"Heteroaryl" refers to a monovalent aromatic heterocyclic group which fulfils the Hückel criteria for aromaticity (ie. contains 4n+2 π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl).

Examples of heteroaryl groups include, but are not limited to, azaoxindole, oxazole, pyrrole, imidazole, pyrazole, pyridine, pyrazine, pyrimidine, pyridazine, indolizine, isoindole, indole, indazole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, thiazole, thiadiazoles, oxadiazole, oxatriazole, tetrazole, thiophene, benzo[b]thiophene, triazole, imidazopyridine and the like.

"Arylene" refers to a divalent aryl group wherein the aryl group is as described above.

"Aryloxy" refers to the group aryl-O— wherein the aryl group is as described above.

"Arylalkyl" refers to—alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

The term "acyl" refers to a species that include the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl. Exemplary acyl groups include H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein. In some embodiments, R is selected from H and ($C_1$-$C_6$)alkyl.

'Oxy' or 'oxo' refers to —O—.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Acylene" refers to the group —C(O)—.

"Amino" refers to the group —NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminylacylene" refers to a divalent group group —C(O)NR"— where each R" is independently hydrogen, alkyl, cycloalkyl, aryl, heteroaryl, and heterocyclyl and where each of alkyl, cycloalkyl, aryl, heteroaryl and heterocyclyl is as described herein. As used herein, the divalent group is attached as L-C(O)NR"-oxindolyl moiety.

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acylaminylene" refers to the divalent group —NR"C(O)— where each R" is independently hydrogen, alkyl, cycloalkyl, aryl, heteroaryl and heterocyclyl and where each of alkyl, cycloalkyl, aryl, heteroaryl, and heterocyclyl are as described herein. As used herein, the divalent group is attached as L-NR"C(O)-oxindolyl moiety.

"Acyloxy" refers to the groups —OC(O)-alkyl, —OC(O)-aryl, —C(O)O— heteroaryl, and —C(O)O-heterocyclyl where alkyl, aryl, heteroaryl and heterocyclyl are as described herein.

"Aminoacyloxy" refers to the groups —OC(O)NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O— heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like. As used herein, 'cycloalkyl' comprises bridged cycloalkyl, spiro cycloalkyl and fused cycloalkyl. The skilled person would understand that bridged cycloalkyl comprises two or more rings bonded to each other at bridgehead atoms (ring junctions). In fused bicyclic compounds, two rings share two adjacent atoms; i.e. the rings share one covalent bond or the so-called bridgehead atoms are directly connected. In spiro cycloalkyl, two or more rings are linked together by one common atom.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, $R_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond. Spiro heterocyclyl are also included within this definition.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR"—P(O)(R''')(OR"") where R" represents H, alkyl, cycloalkyl, alkenyl, or aryl, R''' represents OR"" or is hydroxy or amino and R"" is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkylO—S(O)—NR"—, cycloalkylO—S(O)—NR"—, arylO—S(O)—NR"—, heteroarylO—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkylO—S(O)$_2$—NR"—, cycloalkylO—S(O)$_2$—NR"—, arylO—S(O)$_2$—NR"—, heteroarylO—S(O)$_2$—NR"—, and heterocyclylO—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In some embodiments, any of alkyl, heteroalkyl, cycloalkyl, heterocycloalkyl, aryl and heteroaryl is optionally substituted. That is, in some embodiments, any of these groups is substituted or unsubstituted or fused (so as to form a condensed polycyclic group) with one or more groups.

In some embodiments, substituents for selected radicals are selected from those provided below.

Substituents for the alkyl, heteroalkyl, cycloalkyl and heterocycloalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from -halogen, —OR', =O, =NR', =N—OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. In one embodiment, R', R", R"' and R"" are each independently selected from hydrogen, alkyl (e.g., $C_1$, $C_2$, $C_3$, $C_4$, $C_5$ and $C_6$ alkyl). In one embodiment, R', R", R"' and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R"' and R"" are each independently selected from hydrogen, alkyl, heteroalkyl, cycloalkyl, heterocycloalkyl, aryl, heteroaryl, alkoxy, thioalkoxy groups, and arylalkyl. When R' and R" are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Similar to the substituents described for the alkyl radical, substituents for the aryl and heteroaryl groups are generically referred to as "aryl group substituents". In some embodiments, an aryl group substituent is selected from -halogen, —OR', =O, =NR', =N—OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. In some embodiments, R', R", R"' and R"" are independently selected from hydrogen and alkyl (e.g., $C_1$, $C_2$, $C_3$, $C_4$, $C_5$ and $C_6$ alkyl). In some embodiments, R', R", R"' and R"" are independently selected from hydrogen, substituted or unsubstituted alkyl, substituted or unsubstituted heteroalkyl, substituted or unsubstituted aryl and substituted or unsubstituted heteroaryl. In some embodiments, R', R", R"' and R"" are independently selected from hydrogen, alkyl, heteroalkyl, aryl and heteroaryl. In some embodiments, an aryl group substituent is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

In various embodiments, one or more substituents are selected from hydroxyl, acyl, acyliminoxy, acylimino, alkyl, alkoxy, alkenyl, aryl, aryloxy, alkynyl, alkenyloxy, alkynyloxy, halo, haloalkyl, aryl, arylene, aryloxy, arylalkyl, arylalkoxy, cycloalkyl, cycloalkenyl, oxy, oxyacyl, acylene, amino, aminylacylene, acylamino, acylaminylene, acyloxy, aminoacyloxy, carboxyl, acylamino, cyano, halogen, nitro, oxyacylamino, oxyacyloxy, oxyacylimino, phosphono, sulfo, phosphorylamino, phosphinyl, heteroaryl, heteroarylalkyl, heteroaryloxy, heterocyclyl, heterocyclylalkyl, heterocyclyloxy, heteroarylene, heterocyclylene, thio, thioacyl, oxythioacyl, oxythioacyloxy, thioacyloxy, sulfinyl, sulfonyl, sulfinylamino, sulfonylamino, oxysulfinylamino, oxysulfonylamino, aminothioacyl, thioacylamino, aminosulfinyl, aminosulfonyl, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

A "linker", "linking member", or "linking moiety" as used herein is a moiety that joins or potentially joins, covalently or noncovalently, a first moiety to a second moiety. In particular, a linker attaches or could potentially attach a ligand described herein to another molecule, such as a targeting moiety. A wide variety of linkers L comprised of stable bonds are known in the art, and include by way of example and not limitation, alkyldiyls, substituted alkyldiyls, alkylenos, substituted alkylenos, heteroalkyldiyls, substituted heteroalkyldiyls, heteroalkylenos, substituted heteroalkylenos, acyclic heteroatomic bridges, aryldiyls, substituted aryldiyls, arylaryldiyls, substituted arylaryldiyls, arylalkyldiyls, substituted arylalkyldiyls, heteroaryldiyls, substituted heteroaryldiyls, heteroaryl-heteroaryldiyls, substituted heteroaryl-heteroaryldiyls, heteroarylalkyldiyls, substituted heteroarylalkyldiyls, heteroaryl-heteroalkyldiyls, substituted heteroaryl-heteroalkyldiyls, and the like. Thus, linker L may include single, double, triple or aromatic carbon-carbon bonds, nitrogen-nitrogen bonds, carbon-nitrogen, carbon-oxygen bonds and/or carbon-sulfur bonds, and may therefore include functionalities such as carbonyls, ethers, thioethers, carboxamides, sulfonamides, ureas, urethanes, hydrazines, etc. In one embodiment, linker L has from 1-20 non-hydrogen atoms selected from the group consisting of C, N, O, and S and is composed of any combination of ether, thioether, amine, ester, carboxamide, sulfonamides, hydrazide, aromatic and heteroaromatic bonds.

Choosing a linker having properties suitable for a particular application is within the capabilities of those having skill in the art. For example, where a rigid linker is desired, L may be a rigid polypeptide such as polyproline, a rigid polyunsaturated alkyldiyl or an aryldiyl, biaryldiyl, arylaryldiyl, arylalkyldiyl, heteroaryldiyl, biheteroaryldiyl, heteroarylalkyldiyl, heteroaryl-heteroaryldiyl, etc. Where a flexible linker is desired, L may be a flexible polypeptide such as polyglycine or a flexible saturated alkanyldiyl or heteroalkanyldiyl. Hydrophilic linkers may be, for example, polyalcohols or polyethers such as polyalkyleneglycols. Hydrophobic linkers may be, for example, alkyldiyls or aryldiyls.

The symbol , displayed perpendicular to a bond, indicates the point at which the displayed moiety is attached to the remainder of the molecule.

In some embodiments, the definition of terms used herein is according to IUPAC.

The expression "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts). Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative base addition alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

The term "solvate" refers to a physical association of one of the present compounds with one or more solvent molecules. This physical association includes hydrogen bonding. In certain instances, the solvate will be capable of isolation, for example when one or more solvent molecules are incorporated in the crystal lattice of a crystalline solid. "Solvate" encompasses both solution-phase and insoluble solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Class 3 solvents described in the International Conference on Harmonization (ICH), Guide for Industry, Q3C Impurities: Residual Solvents (1997). The compounds as herein described also include each of their solvates and mixtures thereof.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instant description. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38 (1992); Bundgaard, J. Of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology", John Wiley and Sons, Ltd. (2002).

Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in treatment, healing, prevention, or amelioration of a disease, disorder, or side effect, or a decrease in the rate of advancement of a disease or disorder. The term also includes within its scope amounts effective to enhance normal physiological function.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "bromodomain inhibitor" denotes a compound which inhibits the binding of a bromodomain with its cognate acetylated proteins. In one embodiment the bromodomain inhibitor is a compound which inhibits the binding of a bromodomain to acetylated lysine residues. In a further embodiment the bromodomain inhibitor is a compound which inhibits the binding of a bromodomain to acetylated lysine residues on histones, particularly histones H3 and H4.

In a particular embodiment the bromodomain inhibitor is a compound that inhibits the binding of BET family bromodomains to acetylated lysine residues (hereafter referred to as a "BET family bromodomain inhibitor"). The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In various embodiments, the binding is selective for the bromodomain-containing protein, or it is specific for this protein.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "patient or subject" as used herein refers to a mammal. A subject therefore refers to, for example, humans, dogs, cats, horses, cows, pigs, guinea pigs, and the like. Generally the subject is a human. When the subject is a human, the subject may be either a patient or a healthy human.

The term "proliferative disorder" refers to cells having the capacity for autonomous growth, i.e., an abnormal state of condition characterized by rapidly proliferating cell growth which generally forms a distinct mass that show partial or total lack of structural organization and functional coordination with normal tissue. In various embodiments, the compounds of the invention are used to treat, ameliorate or cure a proliferative disorder.

In some embodiments, the therapeutically effective amount of a compound as defined herein can be administered to a patient alone or admixed with a pharmaceutically acceptable carrier, adjuvant, or vehicle.

The expression "pharmaceutically acceptable carrier, adjuvant, or vehicle" and equivalent expressions, refer to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester, prodrug, salt of a prodrug, or other derivative of a compound of the present description that, upon administration to a recipient, is capable of providing, either directly or indirectly, a compound of the present description or an inhibitory active metabolite or residue thereof.

III. The Embodiments

The present disclosure relates to compounds which are heterobifunctional molecules consisting of: (1) a protein binding moiety that binds a protein of interest (POI); (2) a ubiquitination moiety for recruiting an E3 ubiquitin ligase to promote ubiquitination of the protein of interest; and (3) a linker covalently connecting these moieties. In this regard, the compounds mediate the degradation of select proteins of interest by hijacking the activity of E3 ubiquitin ligases for POI ubiquitination and subsequent degradation by the 26S proteasome. Advantageously, since the compounds of the present invention are not degraded in this process, they can "recycle" and promote ubiquitination and degradation of multiple proteins, thus operating substoichiometrically. This catalytic, event-driven modality contrasts with the traditional inhibitor paradigm in which sustained target binding is indispensable for eliciting a desired biological response.

The compounds of the present application may be prepared by conventional chemical synthesis, such as exemplified in the Examples appended hereto. As will be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present description. Synthetic chemistry transformations and/or protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The synthesized compounds can be separated from a reaction mixture and further purified by standard methods such as column chromatography, high pressure liquid chromatography, or recrystallization.

The compounds of the present description may be modified by appending various functionalities via any synthetic means delineated herein or otherwise know in the art to enhance selective chemical (e.g. stability) and biological (e.g., affinity for the POI) properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof. As such, the following embodiments are present alone or in combination if applicable.

Accordingly, the present disclosure relates to a compound of Formula (I) or a pharmaceutically acceptable salt, solvate, stereoisomer or prodrug thereof is:

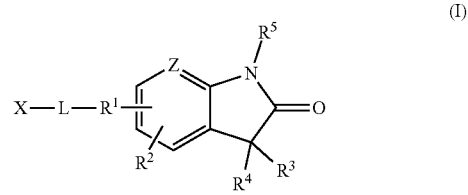

wherein $R^1$ is selected from optionally substituted heterocyclylene, optionally substituted arylene, optionally substituted heteroarylene, optionally substituted aminylacylene, optionally substituted acylaminylene and optionally substituted acylene;

$R^2$ is selected from H, halogen and optionally substituted $C_1$-$C_6$ alkyl, e.g., methyl;

$R^3$ and $R^4$ are independently selected from H and optionally substituted $C_1$-$C_6$ alkyl, e.g., methyl;

$R^5$ is selected from H and optionally substituted $C_1$-$C_6$ alkyl, e.g., methyl;

L is an optionally substituted linker having 2 to 18 atoms in the chain length;

X is a protein binding moiety; and

Z is N or CH.

In some embodiments, $R^1$ is located at either a 5' or 6' position of the oxindole (or azaoxindole) ring.

The inventors have found that this particular 2-oxindole (2-indolone) structure is advantageous for binding to the E3 ligase. This was determined based on a fragment based screening using thermal shift and structure-activity relationship (SAR) between the chemical structure of the oxindole molecule and its biological activity to E3 ligase. The binding was further validated using ligand-based NMR methods.

For the compounds to act in the catalytic, event-driven modality, there is no need for the compound to continue to bind to the POI once it is ubiquitinated; i.e. it would be more advantageous for it to dissociate and find a fresh target to be ubiquitinated. Very tight binding of the compound to the POI (i.e. slow off-rate) may even reduce the overall efficiency of the compound: too short residence time (low affinity) and the E3 will not have enough time to catalyse the transfer of ubiquitin from the E2 to the POI. A residence time, on the other hand, that is too long may slow down the traveling of the compound between different POI copies. In this regard, once the POI is being degraded, the (non-covalent) compound can be released so it will always be able to achieve a base level of catalysis. Accordingly, there is no need for very strong affinity of the compound for the POI and/or E3 ligase.

In this regard, advantageously, and as shown in the examples, compounds of Formula (I), and in particular the ubiquitination moiety, have an $IC_{50}$ (thalidomide binding domain CRBN) value of from about 30 µM to >300 µM, e.g., about 100 µM. This allows compounds of the present invention to have an acceptable residence time with E3 ligase, such that the catalytic, event-driven modality can be achieved.

In this regard, advantageously, and as shown in the examples, compounds of Formula (I), and in particular the ubiquitination moiety, have a $GI_{50}$ value of from about 0.005 µM to >10 µM. This allows compounds of the present invention to have an acceptable residence time with E3 ligase, such that the catalytic, event-driven modality can be achieved. The range would be from 0.005 µM to >10 µM.

In various embodiments, the oxindole moiety is not a drug, e.g., an immunomodulatory drug, known in the art as of the International Filing Date of this application. In various embodiments, the oxindole moiety is not such a known drug derivatized to allow its attachment to the linker and incorporation into a compound of the invention. Such known drug moieties and derivatives thereof are, in these embodiments, expressly removed by proviso.

As used herein, the positioning on the oxindole ring is as follows:

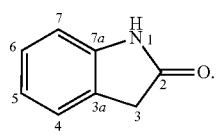

In some embodiments, $R^1$ is selected from optionally substituted heterocyclylene, optionally substituted arylene, optionally substituted heteroarylene, optionally substituted aminylacylene, optionally substituted acylaminylene and optionally substituted acylene. In other embodiments, $R^1$ is selected from optionally substituted heterocyclylene, optionally substituted arylene, optionally substituted heteroarylene, optionally substituted aminylacylene and optionally substituted acylaminylene. In other embodiments, $R^1$ is selected from optionally substituted arylene, optionally substituted heteroarylene, optionally substituted aminylacylene and optionally substituted acylaminylene.

In some embodiments, $R^1$ is selected from optionally substituted phenylene, optionally substituted pyridinylene, optionally substituted pyrazolylene, optionally substituted indolylene, optionally substituted azaindolylene, optionally substituted aminylacylene, optionally substituted acylaminylene, optionally substituted heterocyclylacylene, optionally substituted heterocyclyloxyene, optionally substituted heteroaryloxyene, optionally substituted alkoxyene and optionally substituted piperidinylene. In other embodiments, $R^1$ is selected from optionally substituted phenylene, optionally substituted pyridinylene, optionally substituted pyrazolylene, optionally substituted aminylacylene and optionally substituted acylaminylene.

In some embodiments, the optional substituent at $R^1$ is selected from halogen, optionally substituted alkyl, optionally substituted cycloalkyl, optionally substituted heterocyclyl, optionally substituted alkoxy, optionally substituted amino, optionally substituted oxyacyl, optionally substituted acyl, optionally substituted aminoacyl, optionally substituted acylamino, optionally substituted aryl, optionally substituted heteroaryl and optionally substituted heterocyclylacyl. In other embodiments, the optional substituent at $R^1$ is selected from optionally substituted heterocyclyl, optionally substituted amino, optionally substituted aminoacyl, optionally substituted acylamino, optionally substituted aryl, optionally substituted heteroaryl. In other embodiments, the optional substituent at $R^1$ is selected from fluoro, chloro, bromo, methyl, ethyl, methoxy, amino and acyloxy.

In an exemplary embodiment, $R^1$ is pyridyl substituted with an amine moiety, which is a terminal moiety of linker $L^3$.

In some embodiments, $R^2$ is selected from H, halogen and optionally substituted methyl. In other embodiments, $R^2$ is selected from H, halogen and methyl. In an exemplary embodiment, $R^2$ is fluoro.

In some embodiments, $R^1$ is optionally substituted heteroarylene and $R^2$ is selected from H, halogen or optionally substituted methyl. In other embodiments, $R^2$ is optionally substituted phenylene, optionally substituted pyridinylene, optionally substituted pyrazolylene, optionally substituted indolylene, optionally substituted azaindolylene and optionally substituted piperidinylene, and $R^2$ is selected from H, halogen or methyl.

In some embodiments, $R^3$, $R^4$ and $R^5$ are independently selected from H, optionally substituted methyl. In other embodiments, $R^3$, $R^4$ and $R^5$ are independently selected from H and methyl.

As will be apparent to those of skill in the art, each combination of the substituents set forth above, in any number, variation and combination is within the purview of the instant disclosure.

In some embodiments, the compounds of the invention have a structure according to Formula (II):

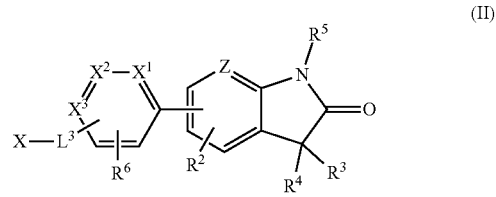

wherein X, Z, $R^2$, $R^3$, $R^4$, and $R^5$ are as described herein. $R^6$ is H or $C_1$-$C_6$ alkyl, e.g., methyl. $X^1$, $X^2$ and $X^3$ are independently selected from N and CH, and C-$L^3$, such that when $X^1$ and $X^3$ are N, $X^2$ is C-$L^3$. $L^3$ is a linker as that term is defined herein. In an exemplary embodiment, $X^2$ is N, $X^1$ and $X^3$ are CH. In an exemplary embodiment, $X^2$ is N, $X^1$ and $X^3$ are C-$L^3$ or CH, and the pyridyl moiety is attached at the 5-position of the oxindole ring. In an exemplary embodiment, $X^2$ is N and $X^1$ is C-$L^3$.

In various embodiments, the compounds of the invention have a structure according to Formula (III):

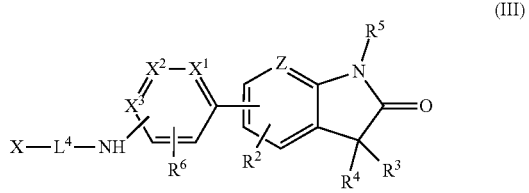

(III)

in which X, $X^1$, $X^2$ and $X^3$, Z, $R^2$, $R^3$, $R^4$, $R^5$ and $R^6$ are as described herein. $L^4$ is a linker as described herein. $X^1$, $X^2$ and $X^3$ are independently selected from N and CH, and C-$L^4$, such that when $X^1$ and $X^3$ are N, $X^2$ is C-$L^4$. In an exemplary embodiment, $X^2$ is N, $X^1$ and $X^3$ are CH. In an exemplary embodiment, $X^2$ is N, $X^1$ and $X^3$ are C-$L^4$ or CH, and the pyridyl moiety is attached at the 5-position of the oxindole ring. In an exemplary embodiment, $X^2$ is N and $X^1$ is C-$L^4$.

In some embodiments, the compounds of the invention have a structure according to Formula (IV):

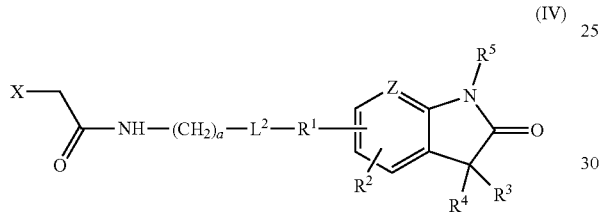

(IV)

in which X, Z, $R^1$, $R^2$, $R^3$, $R^4$, and $R^5$ are as described herein. $L^2$ is a linker as that term is defined herein. The index a represents an integer selected from 2, 3, 4, 5, 6, 7, 8, 9, and 10.

In exemplary embodiments, the compounds of the invention have a structure according to Formula (V):

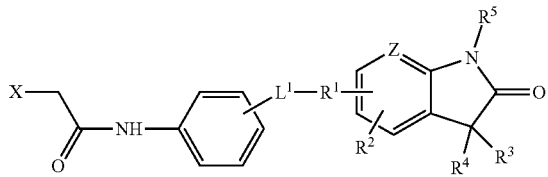

(V)

in which X, Z, $R^1$, $R^2$, $R^3$, $R^4$, and $R^5$ are as described herein. $L^1$ is a linker as that term is defined herein.

The protein binding moiety X can be any moiety that is able to target a desired protein of interest. In this regard, X can be a bromodomain-containing protein 4 (BRD4) binding moiety. For example, X can be a BRD4 inhibitor. BRD4 belongs to the bromodomain and extraterminal domain (BET) family of proteins, which is characterized by two bromodomains (BD) at the N-terminus and an extraterminal domain (ET domain) at the C-terminus. The two BDs recognize and interact with acetylated lysine residues at the N-terminal tails of histones; the ET domain is largely considered to serve a scaffolding function in recruiting diverse transcriptional regulators. Thus, BRD4 plays a key role in regulating gene expression by recruiting relevant transcription modulators to specific genomic loci. Owing to its pivotal role in modulating the expression of essential oncogenes, BRD4 has emerged as a promising therapeutic target in multiple cancer types, including midline carcinoma, acute myeloid leukemia, multiple myeloma, Burkitt lymphoma and prostate cancer. Additionally, by using BRD4 to target c-MYC, many of human cancers that has remained undruggable can be targeted.

In some embodiments, X is a derivative of JQ1:

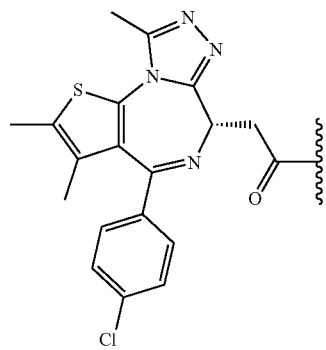

In other embodiments, X is a derivative of OTX015 (e.g., S enantiomer):

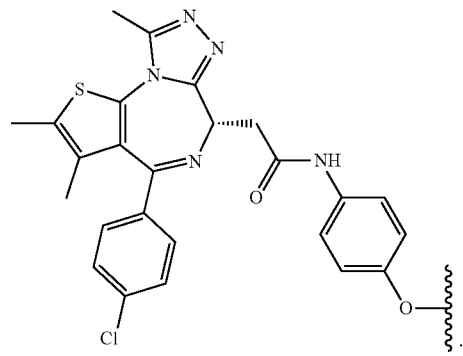 [SMILES: *Oc1ccc(NC(=O)C[C@@H]2N=C(c3ccc(Cl)cc3)c3c(sc(C)c3C)-n3c(C)nnc32)cc1]

Alternatively, X can be selected from bromodomain-containing protein 4 (BRD4) binding moiety, transcriptional enhanced associate domain (TEAD) binding moiety, Polycomb Repressive Complex 2 (PRC2) binding moiety, focal adhesion kinase (FAK) binding moiety, BCR-ABL binding moiety, Hippo pathway protein binding moiety and transcription factor binding moiety.

As an alternative, the protein binding moiety can be a drug compound with a low or moderate binding affinity with the protein of interest. This is in accordance with what is discussed above; i.e. there is no need for very strong affinity of the compound for the POI and/or E3 ligase to achieve the catalytic, event-driven modality. In this regard, X can be a small molecule, for example a drug compound.

As will be appreciated by those of skill in the art, these precursor molecules are modifiable by placement of one or more reactive functional group, such as those set forth herein, thereby allowing the resulting reactive derivative to be covalently joined to a component of a linker and forming a compound of the invention.

In exemplary embodiments, the invention provides compounds according to Formula (VI):

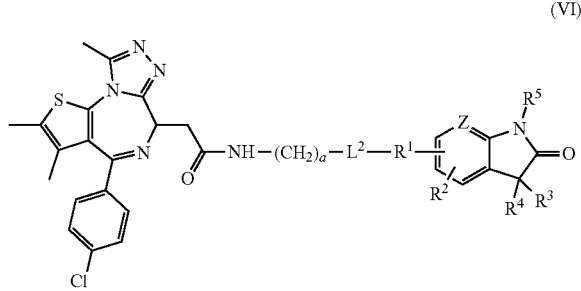

(VI)

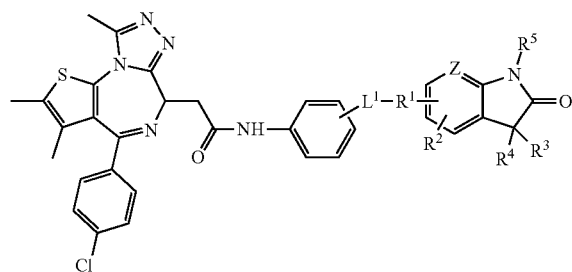

(VII)

in which Z, R$^1$, R$^2$, R$^3$, R$^4$, and R$^5$ are as described herein. L$^2$ is a linker as that term is defined herein. The index a represents an integer selected from 1-18, e.g., 1, 2, 3, 4, 5, 6, 7, 8, 9, and 10.

In some embodiments, the invention provides compounds according to Formula (VII):

in which Z, R$^1$, R$^2$, R$^3$, R$^4$, and R$^5$ are as described herein. L$^1$ is a linker as that term is defined herein.

In certain embodiments, the invention provides compound according to Formula (VIII):

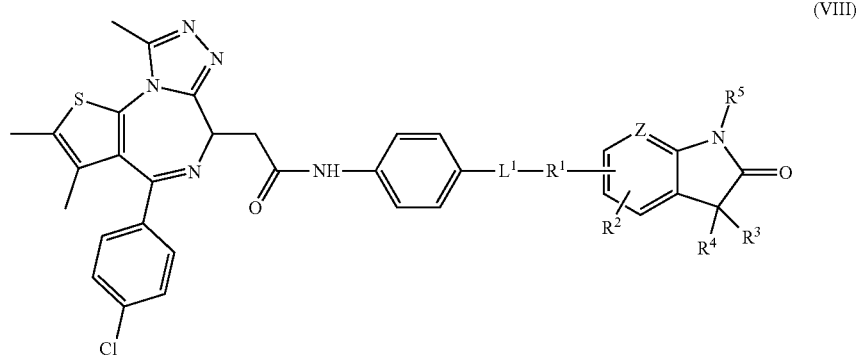

(VIII)

in which Z, R$^1$, R$^2$, R$^3$, R$^4$, and R$^5$ are as described herein. L$^1$ is a linker as that term is defined herein.

In exemplary embodiments, there are provided compounds according to Formula (IX):

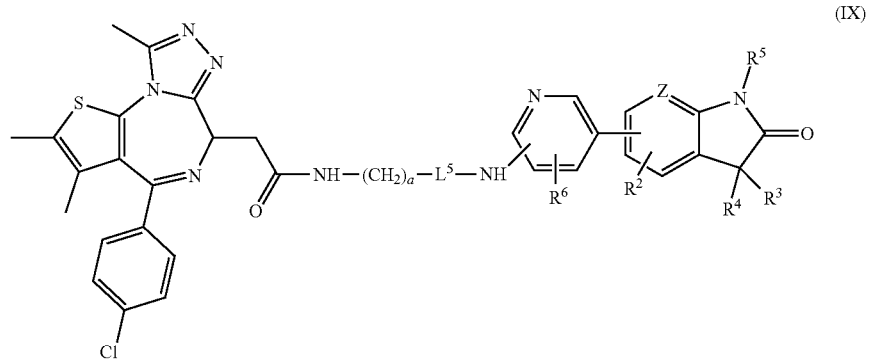

(IX)

in which Z, R$^1$, R$^2$, R$^3$, R$^4$, R$^5$, R$^6$, and a are as described herein. L$^5$ is a linker as that term is defined herein.

In an exemplary embodiment, the compounds of the invention have the formula:

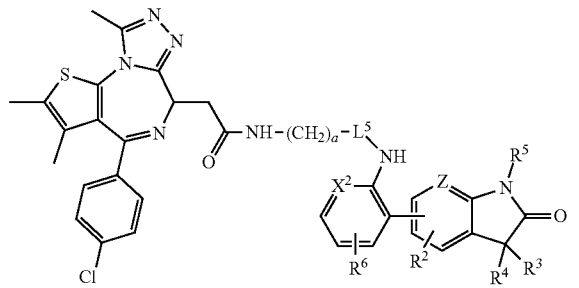
(X)

in which the index a, $X^2$, Z, $R^2$, $R^3$, $R^4$, $R^5$ and $R^6$ are as described herein. $L^5$ is a linker as that term is defined herein.

In some embodiments, when $R^1$ is selected from optionally substituted heterocyclylene, optionally substituted arylene, optionally substituted heteroarylene, optionally substituted heteroarylaminoacylene, optionally substituted heteroarylacylaminoene, optionally substituted heteroarylacylene, optionally substituted arylaminoacylene, optionally substituted arylacylaminoene and optionally substituted arylacylene.

In various embodiments, $R^1$ is selected from the formulae below:

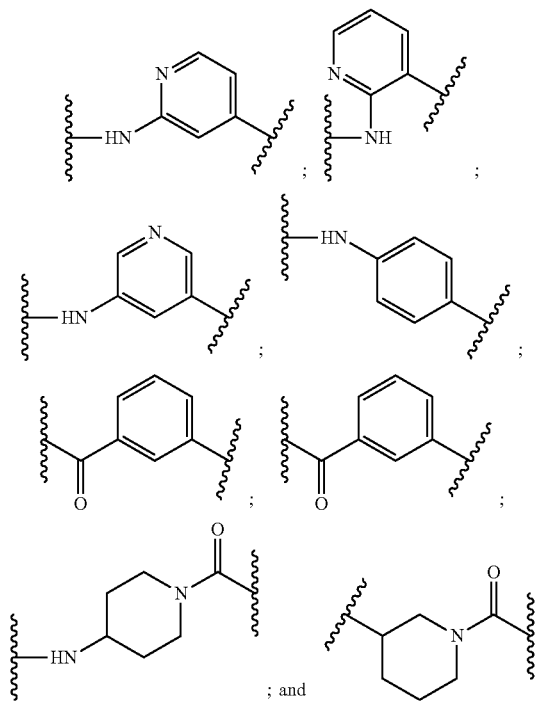

In various embodiments, the linker moiety ("L") is attached at a para or ortho position of the 6 membered ring. Some examples are as follows, where/represents the connection to the oxindolyl moiety:

Para vector:

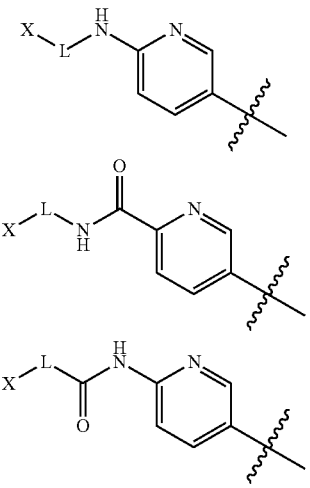

Ortho vector:

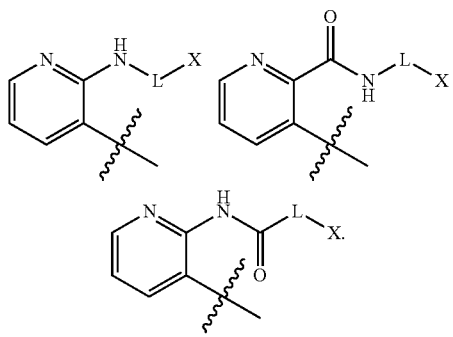

The ubiquitination moiety (oxindole ring, azaoxindole ring) is connected to the protein binding moiety X by means of a linker L. In some embodiments, the connection is by means of covalent bond via the linker L.

A linker can be any useful structure for that joins a ligand to a reactive functional group or a targeting moiety, such as an antibody. Examples of a linker include 0-order linkers (i.e., a bond), substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Further exemplary linkers include substituted or unsubstituted ($C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$) alkyl, substituted or unsubstituted heteroalkyl, —C(O)NR'—, —C(O)O—, —C(O)S—, and —C(O)CR'R", wherein R' and R" are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. In some embodiments, a linker includes at least one heteroatom. Exemplary linkers also include —C(O)NH—, —C(O), —NH—, —S—, —O—, and the like. In an exemplary embodiment, a linker is a heteroalkyl substituted with a reactive functional group.

In some embodiments, L is an optionally substituted linker having 2 to 18 atoms in the chain length. In other embodiments, L is an optionally substituted linker having 2 to 15 atoms in the chain length. In other embodiments, L is an optionally substituted linker having 2 to 12 atoms in the chain length. In some embodiments, L is a linker selected from optionally substituted alkyl, optionally substituted heteroalkyl, optionally substituted cycloalkyl (such as spirocycloalkyl) and optionally substituted heterocyclyl, each having 2 to 15 atoms in the chain length. In other embodiments, L is a linker selected from optionally substituted $C_2$-$C_{15}$ alkyl and optionally substituted polyethoxy having 2 to 15 atoms in the chain length. In other embodiments, L is a linker selected from optionally substituted $C_2$-$C_{10}$ alkyl and optionally substituted polyethoxy having 2 to 10 atoms in the chain length.

In an exemplary embodiment, the linker is ethylene glycol or polyethylene glycol includes 1, 2, 3, 4, 5, 6, 7, 8, 9 or 10, e.g., 1-6, ethylene glycol ($OCH_2CH_2O$), or ($CH_2CH_2OCH_2CH_2$) subunits. In some embodiments, the linker is polyethylene glycol with one repeating unit (PEG-1) or polyethylene glycol with three repeating units (PEG-3). In other embodiments, the linker is selected from piperidinylene, piperazinylene, pyrrolidinylene, azetidinylene, spirocycloalkylene (such as spiro[3.3]heptanylene, spiro[4.4]nonanylene) and amides. The linker L can be selected from, but is not limited to (wherein ∿ represents the connection to the ubiquitination moiety or oxindolyl moiety and the protein targeting moiety):

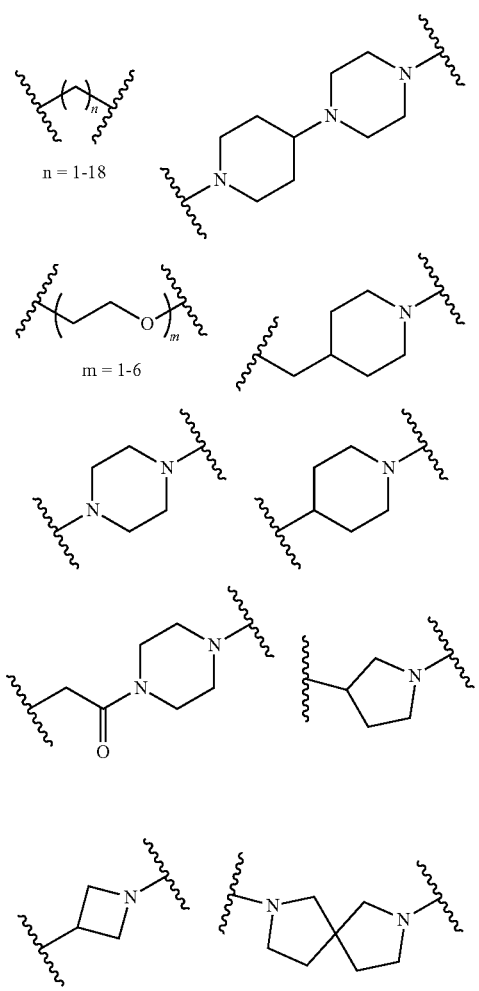

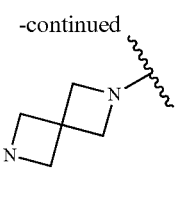

During synthesis of the compound of the invention, a linker precursor is used, which has one or more reactive functional group as a component thereof. The functional group(s) is reacted with a reactive group on other components of the molecule to form the final molecule. In the finished compound, the linker precursor becomes the linker. Reactive functional groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in March, Advanced Organic Chemistry (3rd Ed., John Wiley & Sons, New York, 1985); Hermanson, Bioconjugate Techniques (Academic Press, San Diego, 1996); and Feeney et al., Modification of Proteins, Advances in Chemistry Series, Vol. 198 (American Chemical Society, Washington, D.C., 1982).

In some embodiments, a reactive functional group refers to a group selected from olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds., Organic Functional Group Preparations, (Academic Press, San Diego, 1989)).

A reactive functional group can be chosen according to a selected reaction partner. As an example, an activated ester, such as an NHS ester will be useful to label a a moiety via amine residues. Sulfhydryl reactive groups, such as maleimides can be used to label moieties carrying an SH-group (e.g., cysteine). Compounds with hydroxyl groups may be reacted by first oxidizing their carbohydrate moieties (e.g., with periodate) and reacting resulting aldehyde groups with a hydrazine containing ligand.

The reactive functional groups can be chosen such that they do not participate in, or interfere with reactions with which they are not involved, which are necessary to assemble the compound. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In one embodiment, a reactive functional group is selected from an amine, (such as a primary or secondary amine), hydrazine, hydrazide and sulfonylhydrazide. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides, thiazolides and carboxyl groups.

NHS esters and sulfo-NHS esters react preferentially with primary (including aromatic) amino groups of a reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with amine groups of a molecule such as a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus cross-linking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., F-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry*, 1981, 20: 4836-4842, e.g., teach how to modify a protein with carbodiimides.

In another embodiment, a reactive functional group is selected from a sulfhydryl group (which can be converted to disulfides) and sulfhydryl-reactive group. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

Other exemplary reactive functional groups include:
(i) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(ii) hydroxyl groups, which can be converted to esters, ethers, aldehydes, etc.;
(iii) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(iv) dienophile groups, which are capable of participating in Diels-Alder reactions such as, for example, maleimido groups;
(v) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(vi) alkenes, which can undergo, for example, cycloadditions, acylation, Michael addition, etc;
(vii) epoxides, which can react with, for example, amines and hydroxyl groups;
(ix) phosphoramidites and other standard functional groups useful in nucleic acid synthesis and
(x) any other functional group useful to form a covalent bond between the functionalized ligand and a molecular entity or a surface.

As will be apparent to those of skill in the art, any of these reactive functional groups in any useful combination can be placed on any component of the precursors of the compounds of the invention in the course of the synthesis of the compounds of the invention.

The compounds of the present disclosure initiate a degradation cascade by forming a ternary complex with a POI and an E3, bringing the ubiquitination machinery in close proximity for subsequent POI ubiquitination. The polyubiquitinated POI is then recognized and degraded by the 26S proteasome. Accordingly, the 'close proximity' is part of the key for proper functioning of this mechanism.

The inventors have found that, in some embodiments, a specific linker length is particularly advantageous for the purpose of this invention. In particular, if the linker length is too short, it was found that the oxindole moiety hinders the protein binding moiety in binding to the target protein. On the other hand, if the linker length is too long, ubiquitination does not occur or occurs at a very slow rate as the proper signals are not transmitted to the target protein. In this regard, it was found that the chain length as disclosed herein is optimal such that the oxindole moiety does not hinder the protein binding moiety and the rate of ubiquitination is acceptable.

In an exemplary embodiment, the linker is of the para-vector motif with a poly(ethylene glycol) moiety, and the poly(ethylene glycol) and m is 3 or 4. Preferred compounds according to this motif form a ternary complex as discussed herein.

In an exemplary embodiment, the linker is of the ortho-vector motif with a poly(ethylene glycol) moiety, and the poly(ethylene glycol) and m is 1, 2, 3 or 4. Preferred compounds according to this motif form a ternary complex as discussed herein.

The skilled person would understand that the linker is, at one end of the linker, connected to the ubiquitination moiety, and that the linker is, at the other end, connected to the protein binding moiety. Such connection can be the same at both ends or different at both ends. For example, the connection can be by means of an amide bond.

The type of connection can play a role in influencing the activity of the compounds as it increases the linker length and also add to the electron density of the compound. The nature of the linkage site, linker length and linker composition also play an important role. Additionally, some moieties are more labile than others and may not be suitable for use in a linker. In this regard, the pharmacophore of the compound may change as the 3D spatial arrangement of the protein binding moiety and/or ubiquitination moiety may be impacted.

The attachment of the linker to the protein binding moiety and/or ubiquitination moiety also play a role. It is believed that the attachment of the linker alters the spatial availability of the protein binding moiety and/or ubiquitination moiety to their respective targets, and according influences the affinity. In this regard, a one atom difference can potentially result in a large difference in activity.

In this regard, the inventors have found that $R^1$ is, in some embodiments, advantageously located at either a 5' or 6' position of the oxindole ring. The compound of Formula (I) may alternatively be represented by Formula (Ia) or (Ib):

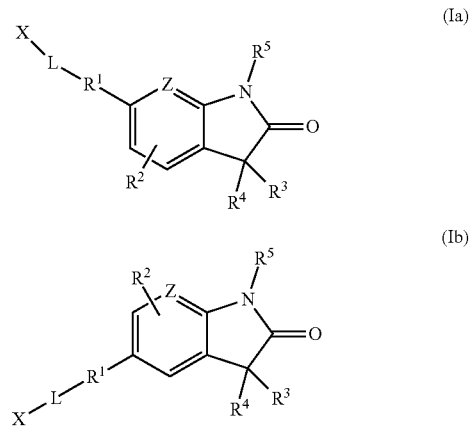

wherein $R^1$, $R^2$, $R^3$, $R^4$ and $R^5$ are as defined herein.

In some embodiments, compounds of the present invention are represented by Formulae (Ia') or (Ib'):

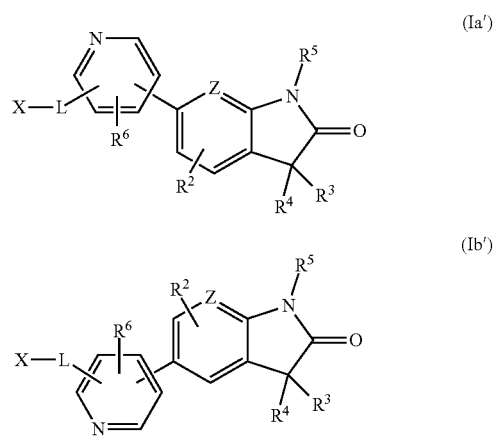

wherein $R^2$, $R^3$, $R^4$, $R^5$ and $R^6$ are as defined herein.

In an exemplary embodiment, the compound of the invention has a formula selected from:

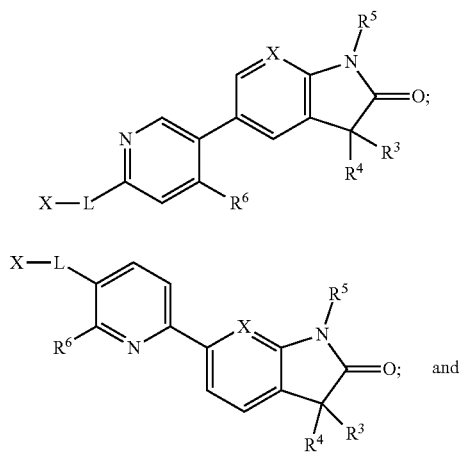

-continued

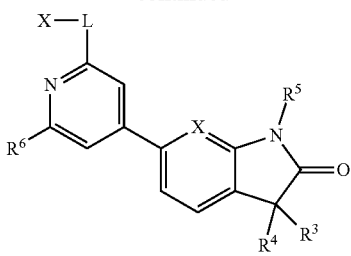

In various embodiments, the compound of the invention has a formula selected from:

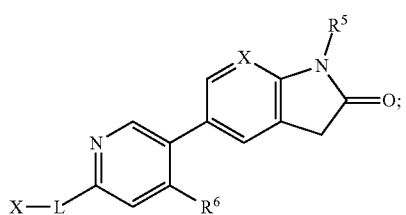

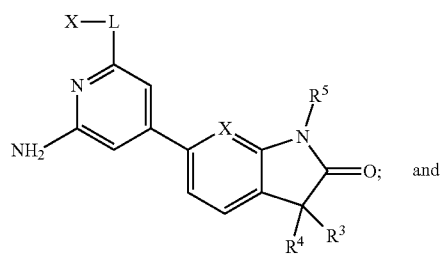

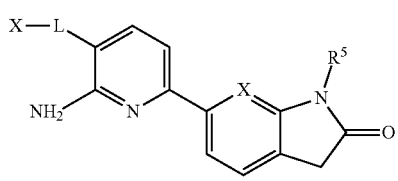

In various embodiments, the compound of the invention has a formula selected from:

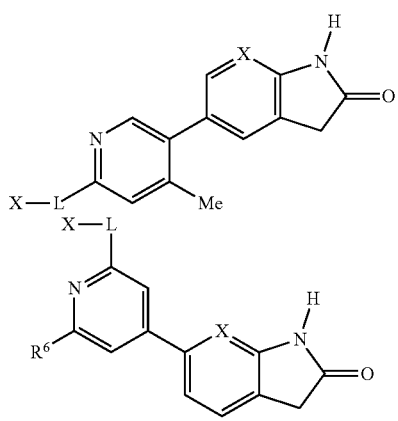

-continued

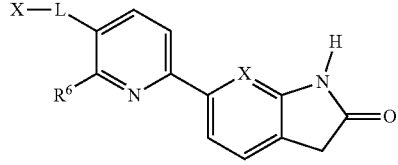

In the formulae set forth above, the substituents $R^3$, $R^4$, $R^5$ and $R^6$, and X are as described herein. In various embodiments, the six-member ring of the oxindole (or oxazaindole) is substituted with halogen, e.g., fluoro.

In various embodiments, an exemplary compound of the invention is selected from 148, 151, 152, 154, 156, 157, 158, 159 and 160.

In exemplary compound according to the formulae set forth above, L is poly(ethylene glycol) and L is covalently attached to the oxindole (or oxazaindole) moiety via O, or NH. An exemplary poly(ethylene glycol) includes 2, 3, or 4 ethylene glycol subunits.

In some embodiments, $R^6$ is selected from halogen, optionally substituted alkyl, optionally substituted cycloalkyl, optionally substituted heterocyclyl, optionally substituted alkoxy, optionally substituted amino, optionally substituted oxyacyl, optionally substituted acyl, optionally substituted aminoacyl and optionally substituted acylamino.

In some embodiments, $R^6$ is selected from halogen, optionally substituted alkyl, optionally substituted alkoxy and optionally substituted amino. In other embodiments, $R^6$ is selected from Cl, F, Br, methyl, ethyl, propyl, methoxy, —$NH_2$, —$NHCH_3$, —$C(O)NH_2$, —$C(O)NHCH_3$, —NHC(O)$CH_3$, and —$C(O)OCH_2CH_3$.

The compound of the invention may be represented as Formula (I'):

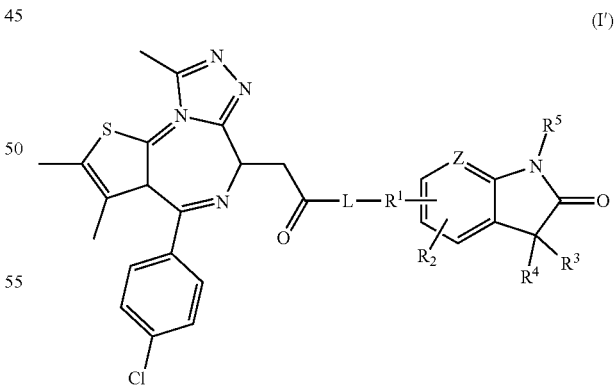

(I')

wherein $R^1$, $R^2$, $R^3$, $R^4$, $R^5$ and L are as defined herein; and wherein $R^1$ is optionally located at either a 5' or 6' position of the oxindole ring.

The compound of the invention may be represented by Formula (I"):

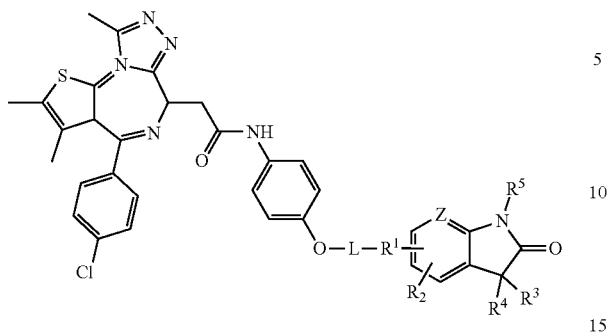

(I″)

wherein $R^1$, $R^2$, $R^3$, $R^4$, $R^5$ and L are as defined herein; and wherein $R^1$ is optionally located at either a 5' or 6' position of the oxindole ring.

Advantageously, the exemplary compounds of the invention are able to permeate cells to exert their effect, and accordingly have good cellular activity.

In some embodiments, the compound the invention can be selected from the following compounds in Table 1:

TABLE 1

| Compound ID | Structure |
|---|---|
| 096 | 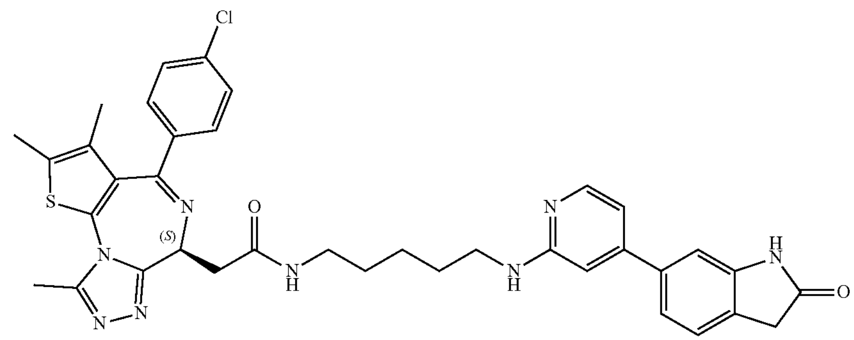 |
| 097 | 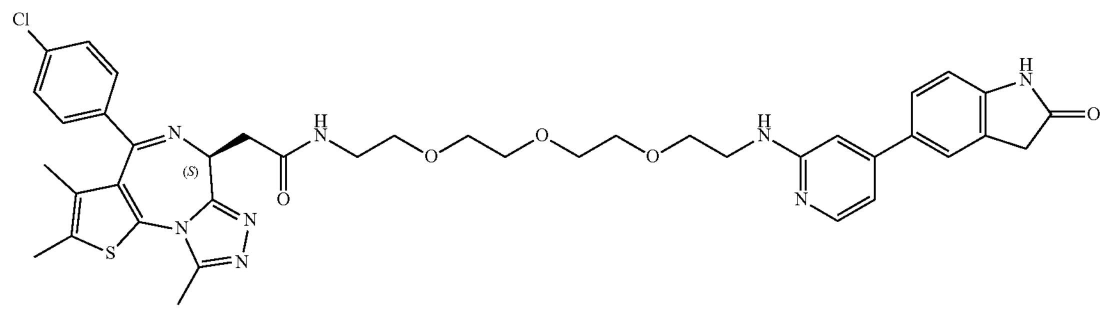 |
| 098 | 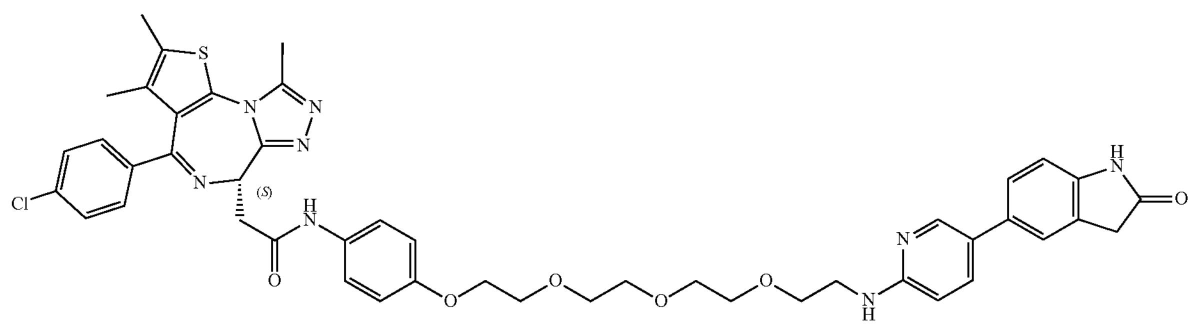 |

TABLE 1-continued
| Compound ID | Structure |
|---|---|
| 099 | 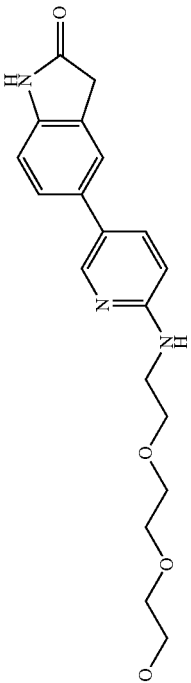 |
| 100 | 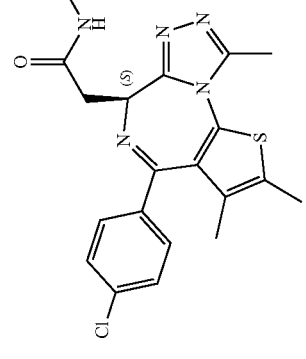 |

TABLE 1-continued
| Compound ID | Structure |
|---|---|
| 101 | 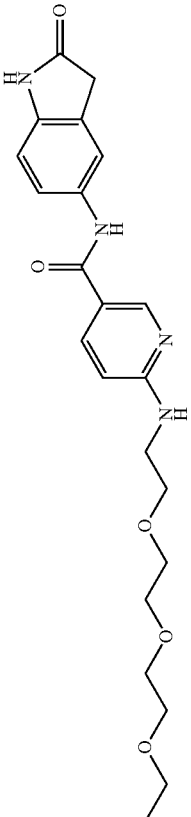 |
| 102 | 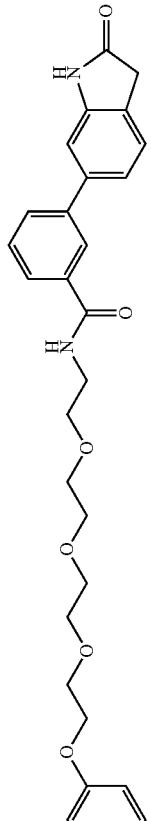 |
| 103 | 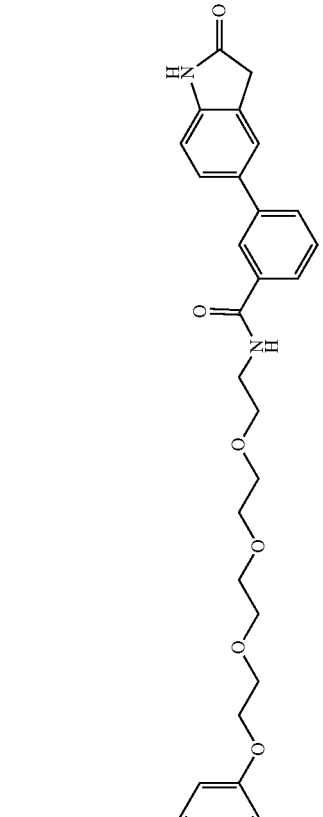 |

TABLE 1-continued

| Compound ID | Structure |
|---|---|
| 104 | 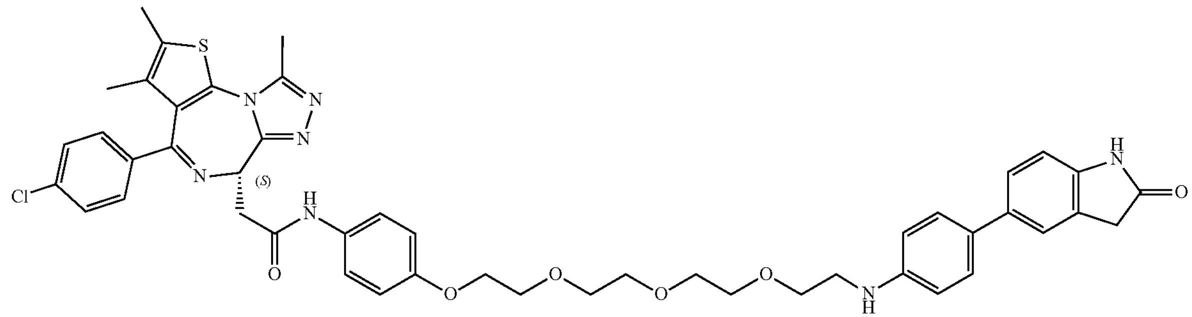 |
| 105 | 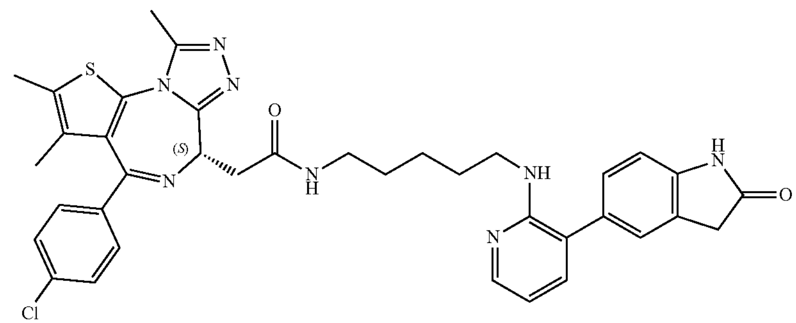 |
| 106 | 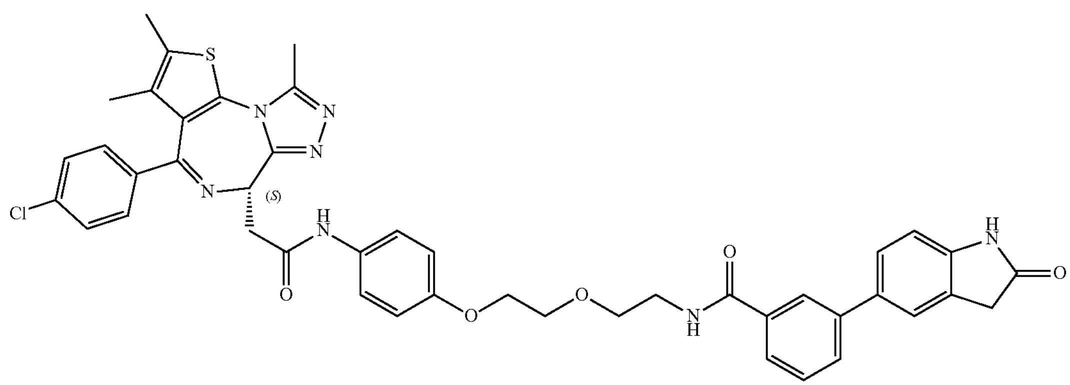 |

TABLE 1-continued
| Compound ID | Structure |
|---|---|
| 107 | 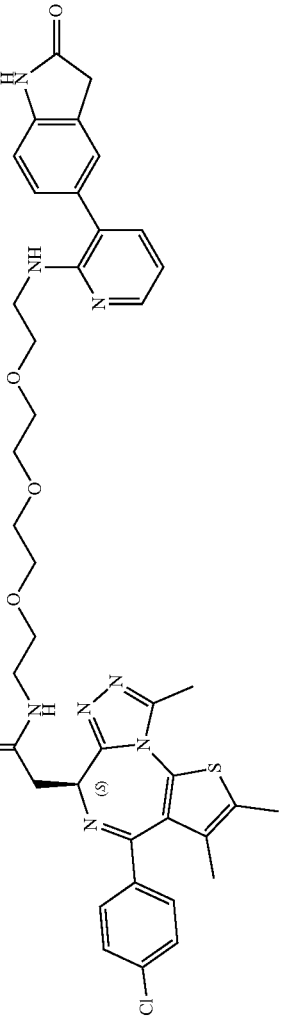 |
| 108 | 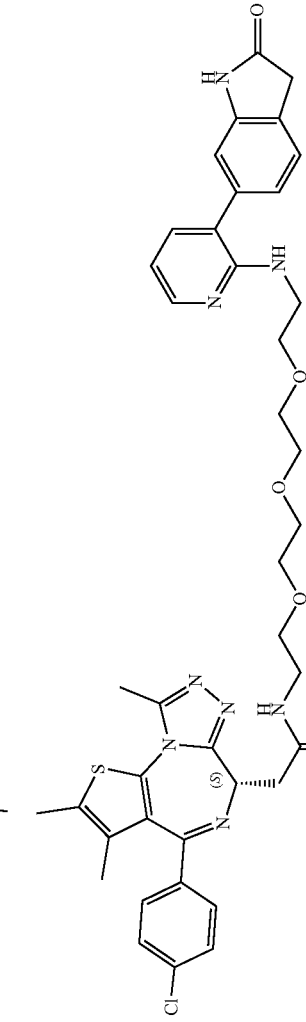 |
| 109 | 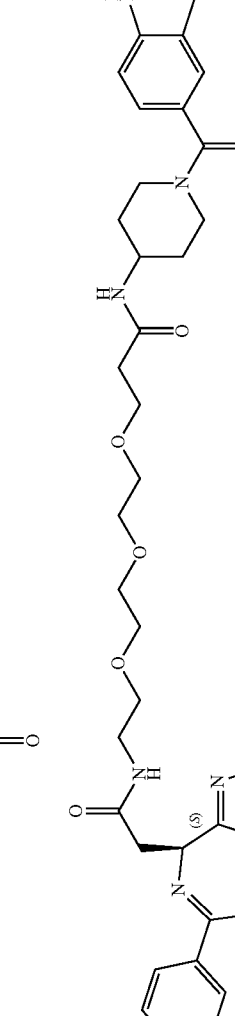 |

TABLE 1-continued

| Compound ID | Structure |
|---|---|
| 110 | 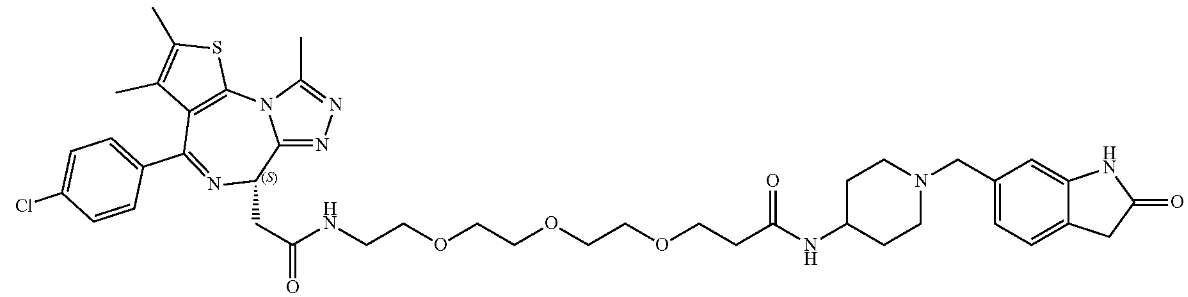 |
| 111 | 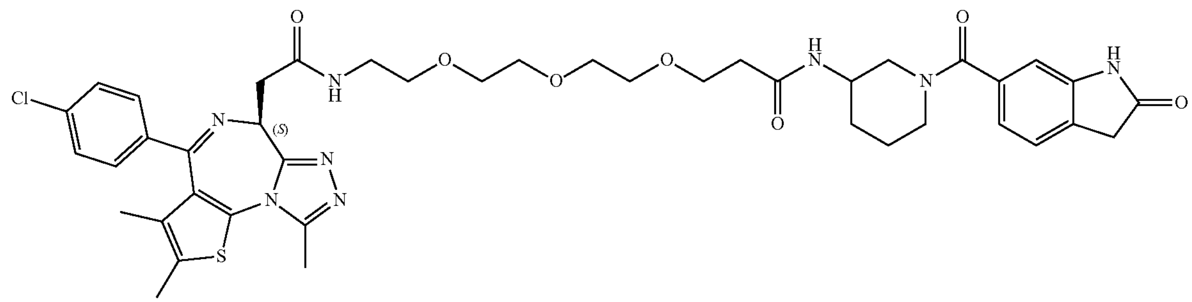 |
| 112 | 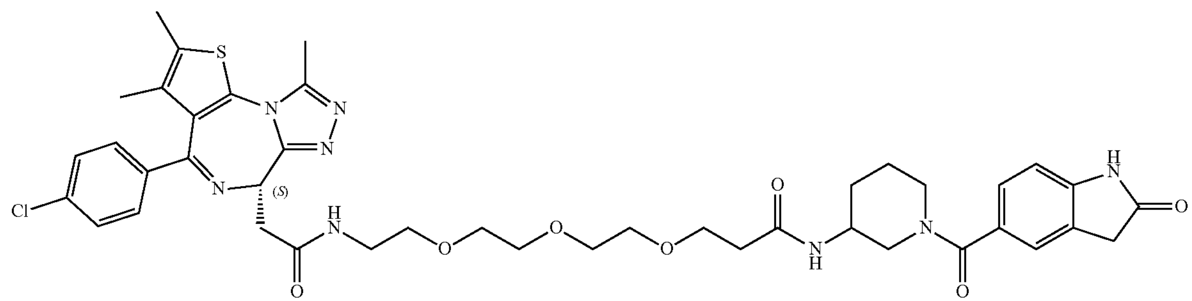 |

TABLE 1-continued

| Compound ID | Structure |
|---|---|
| 113 | 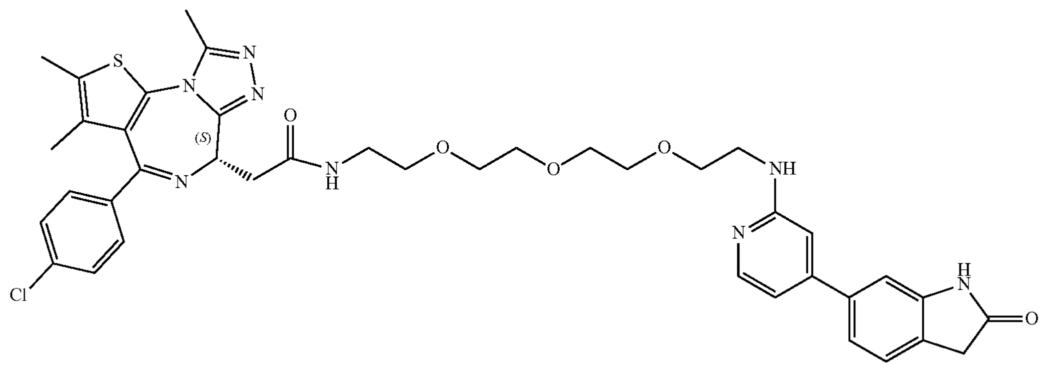 |
| 114 | 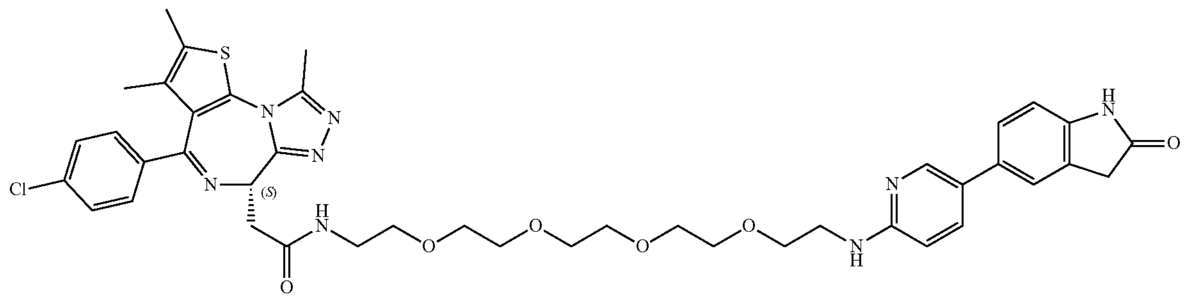 |
| 115 | 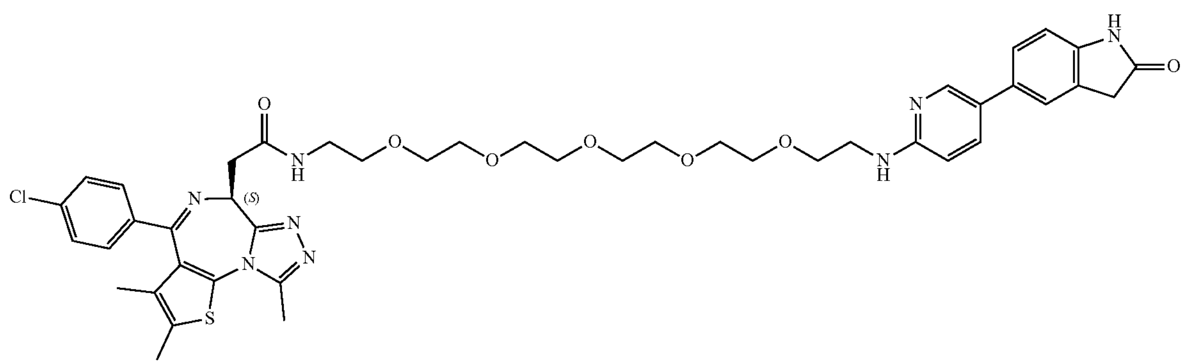 |

TABLE 1-continued
| Compound ID | Structure |
|---|---|
| 116 | 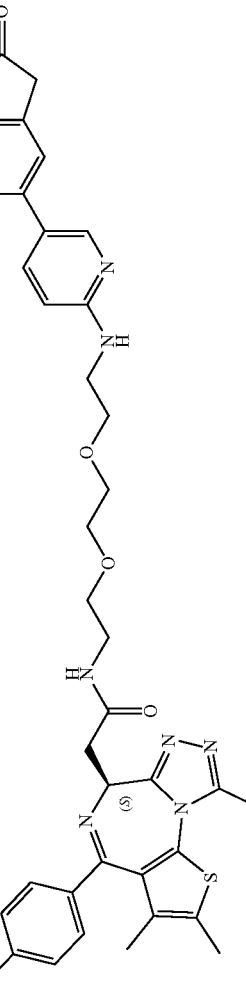 |
| 117 | 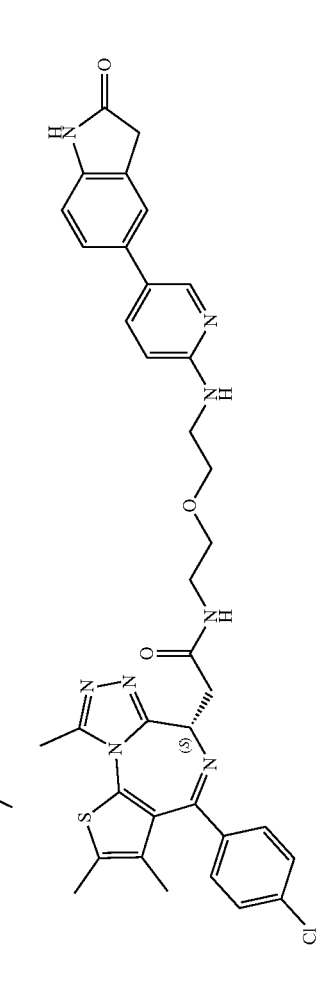 |
| 118 | 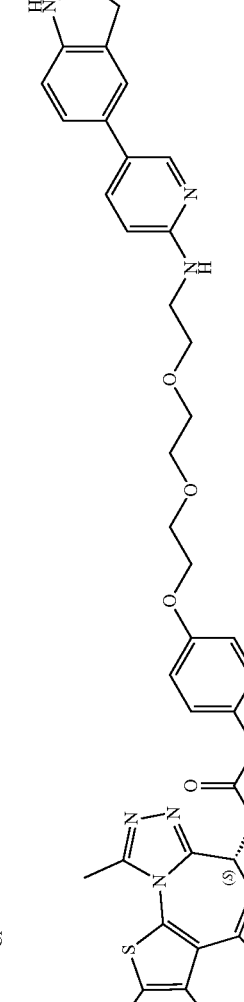 |

TABLE 1-continued
| Compound ID | Structure |
|---|---|
| 119 | 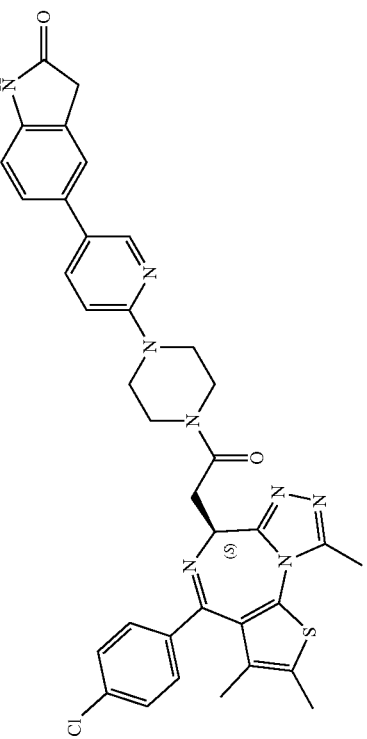 |
| 120 | 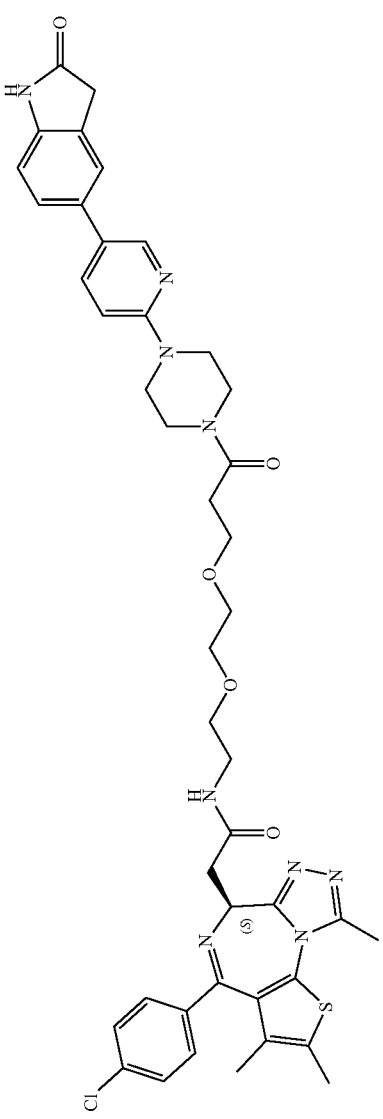 |

TABLE 1-continued

| Compound ID | Structure |
|---|---|
| 121 | 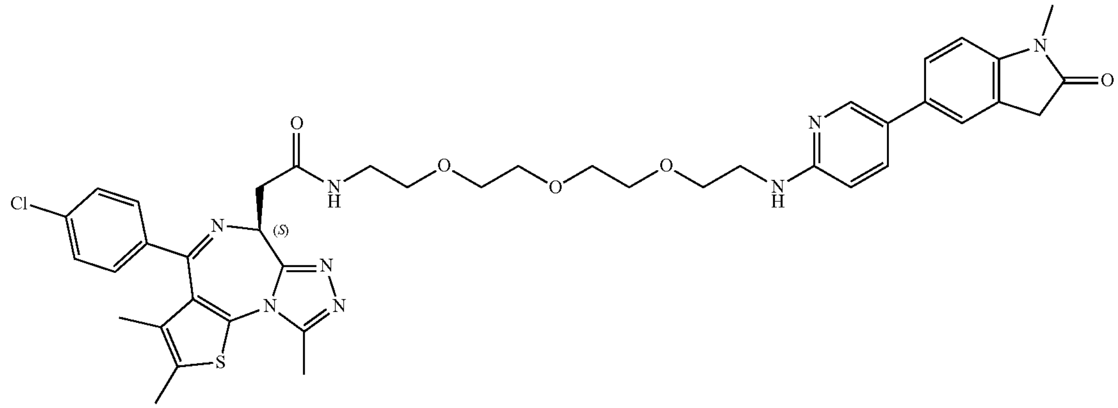 |
| 122 | 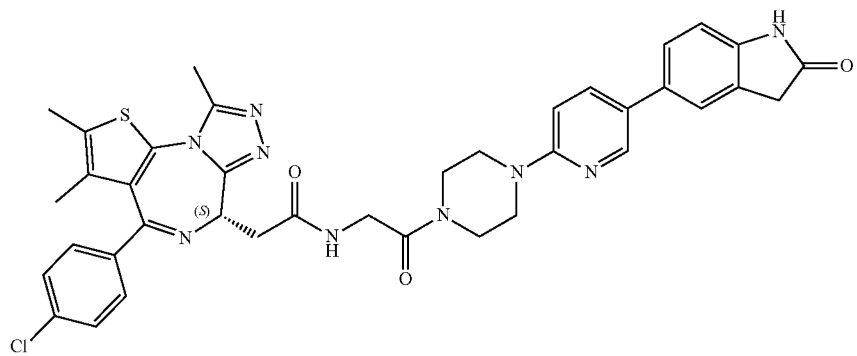 |

TABLE 1-continued

| Compound ID | Structure |
|---|---|
| 123 | 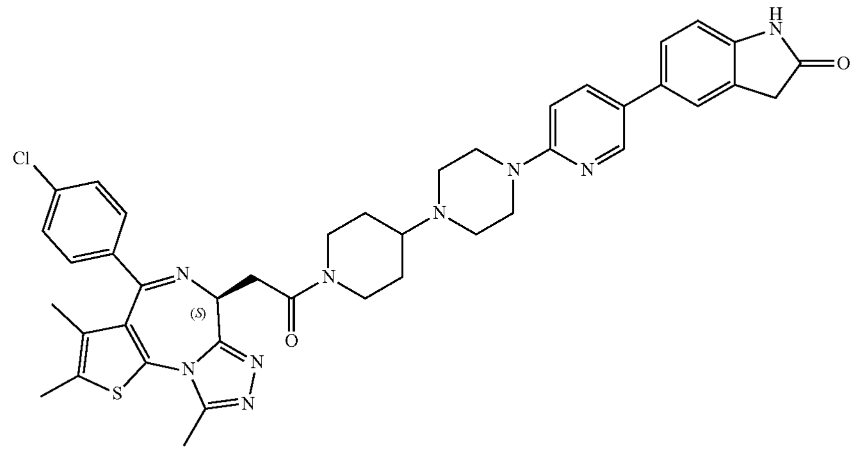 |
| 124 | 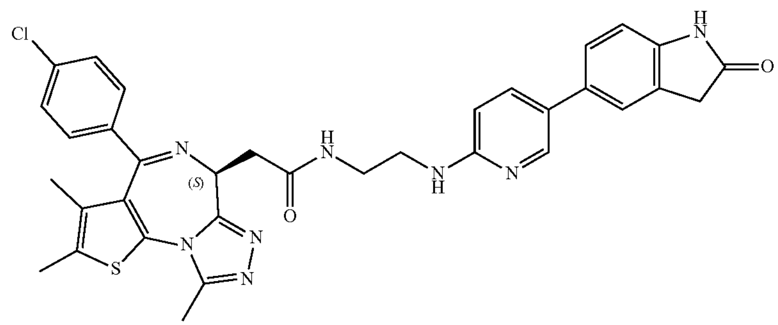 |

TABLE 1-continued

| Compound ID | Structure |
|---|---|
| 125 | 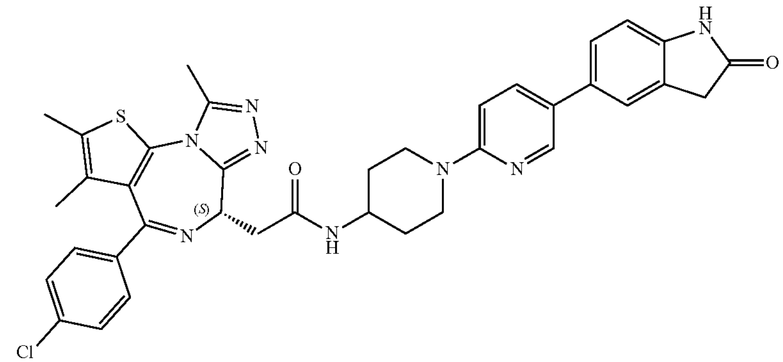 |
| 126 | 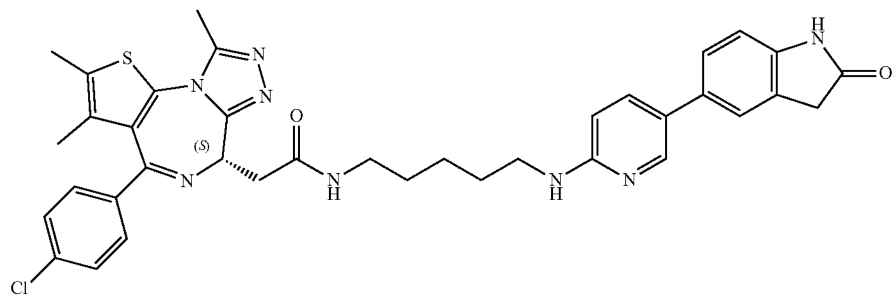 |
| 127 | 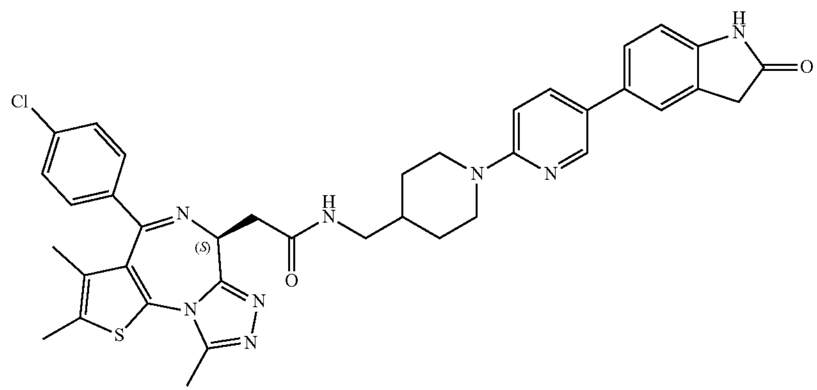 |

TABLE 1-continued
| Compound ID | Structure |
|---|---|
| 128 | 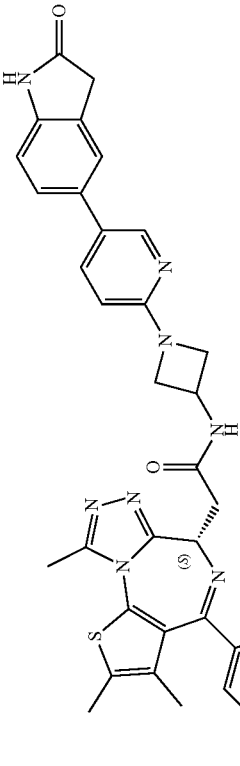 |
| 129 | 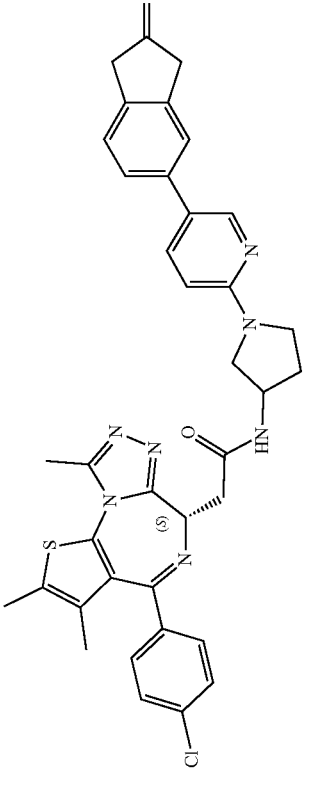 |
| 130 | 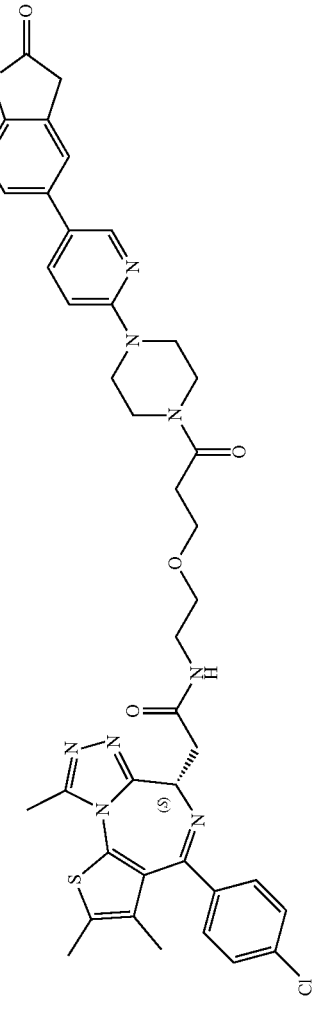 |

TABLE 1-continued
| Compound ID | Structure |
|---|---|
| 131 | 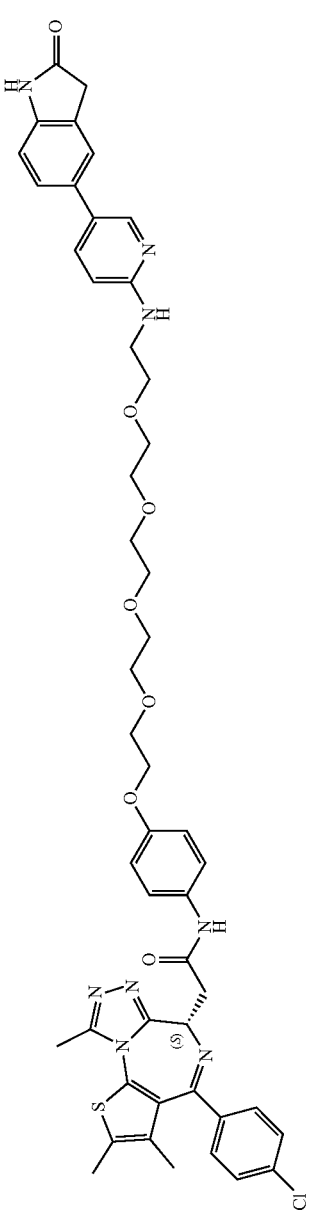 |
| 132 | 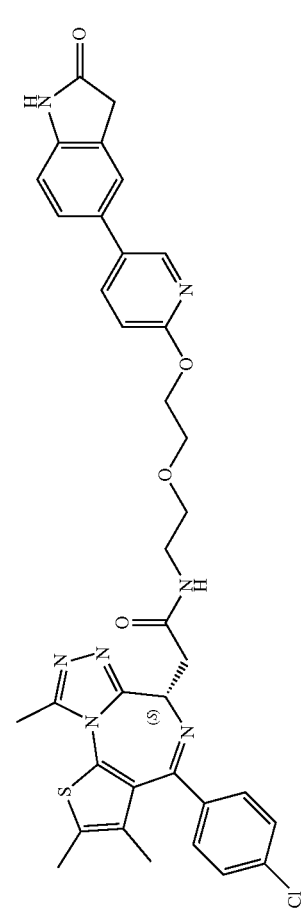 |
| 133 | 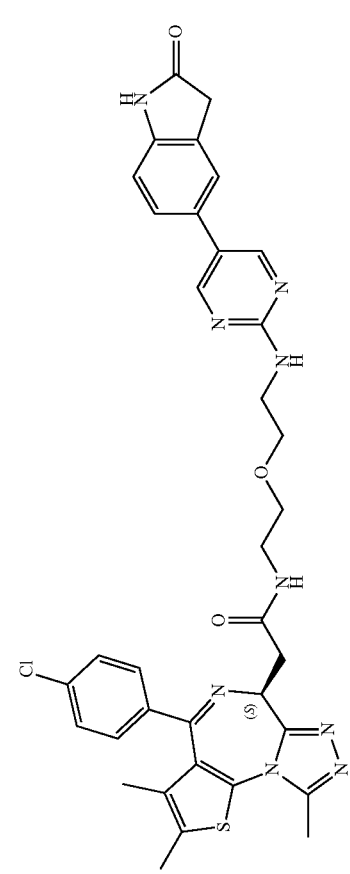 |

TABLE 1-continued

| Compound ID | Structure |
|---|---|
| 134 | 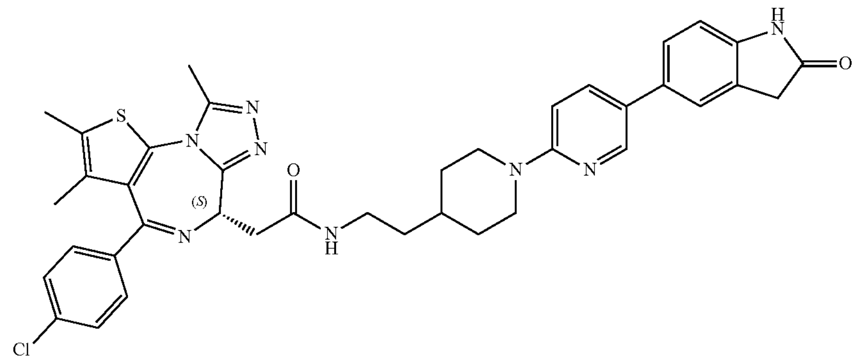 |
| 135 | 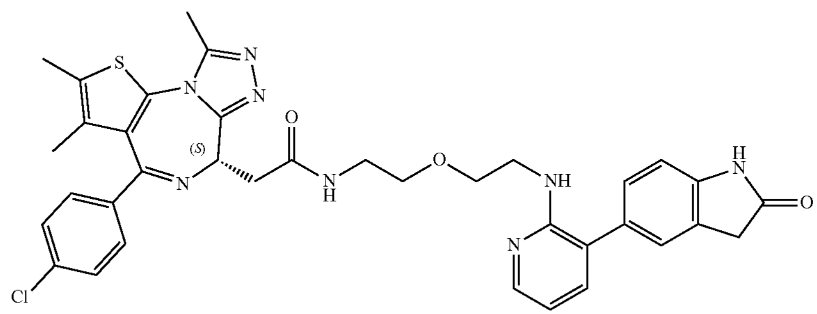 |

TABLE 1-continued

| Compound ID | Structure |
|---|---|
| 136 | (structure) |
| 137 | (structure) |

TABLE 1-continued
| Compound ID | Structure |
|---|---|
| 138 | 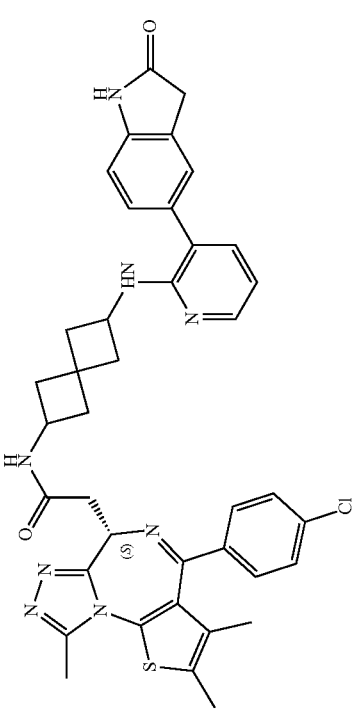 |
| 139 | 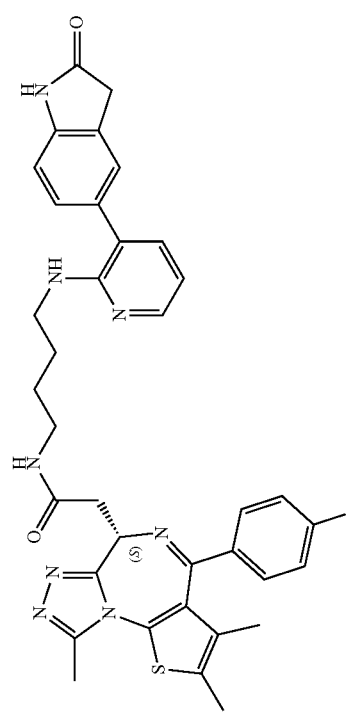 |

TABLE 1-continued

| Compound ID | Structure |
|---|---|
| 140 | 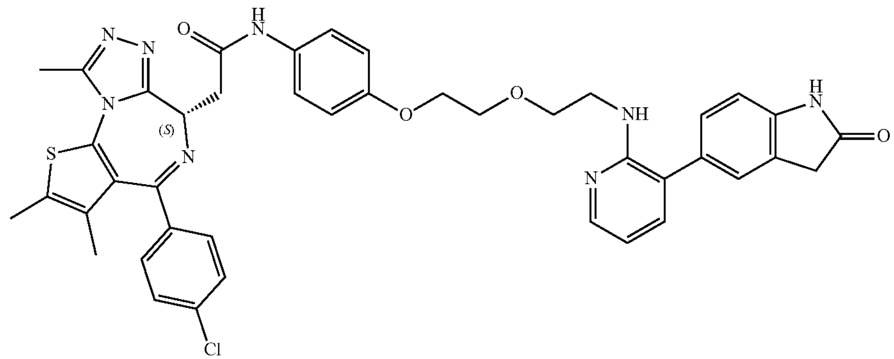 |
| 141 | 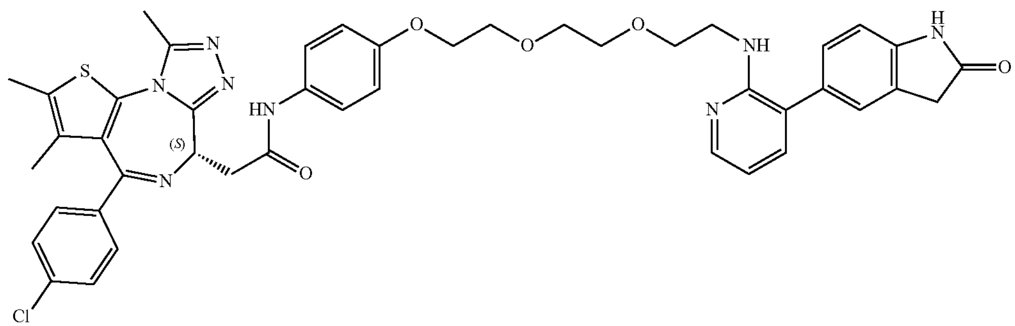 |

TABLE 1-continued

| Compound ID | Structure |
|---|---|
| 142 | 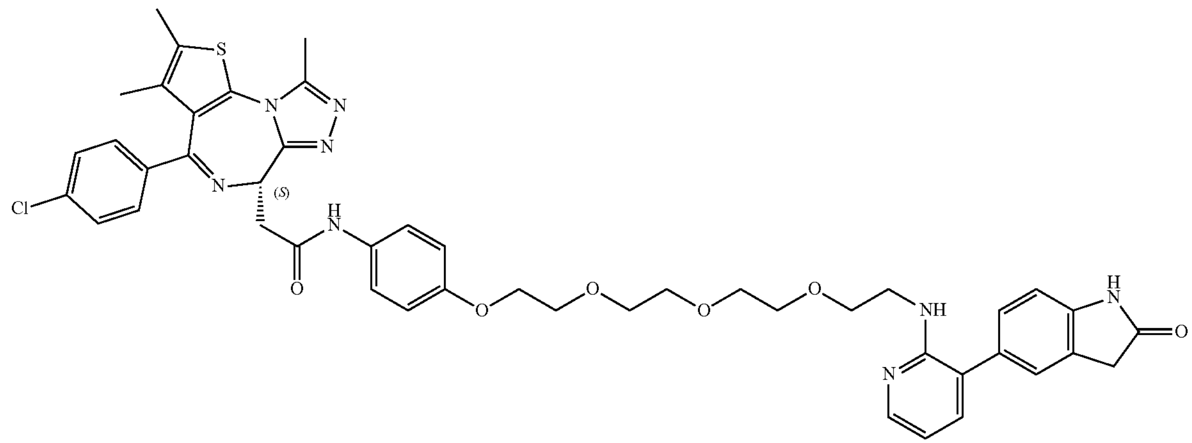 |
| 143 | 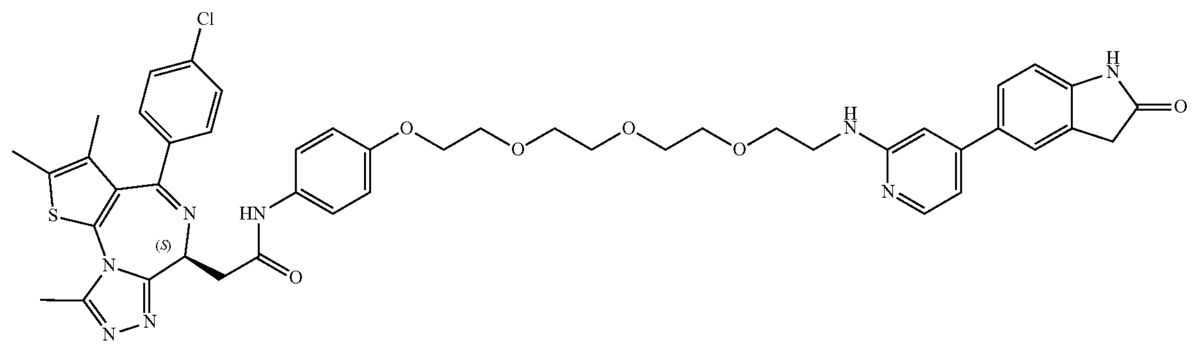 |

TABLE 1-continued

| Compound ID | Structure |
|---|---|
| 144 | 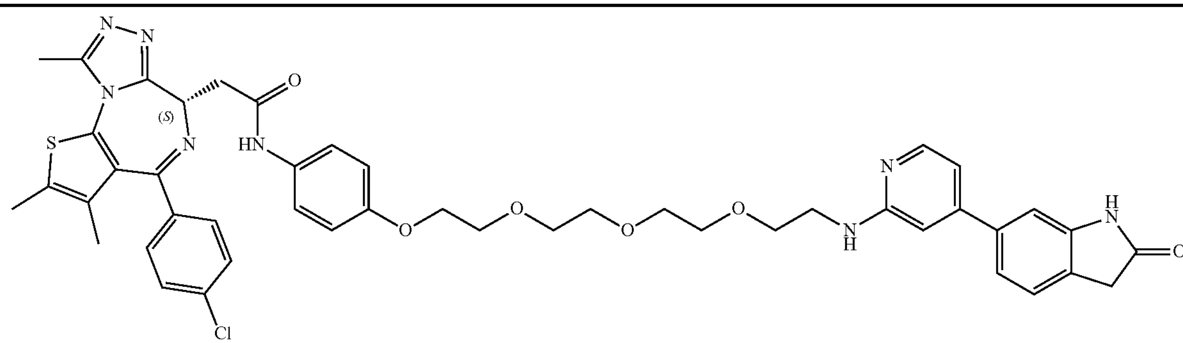 |
| 145 | 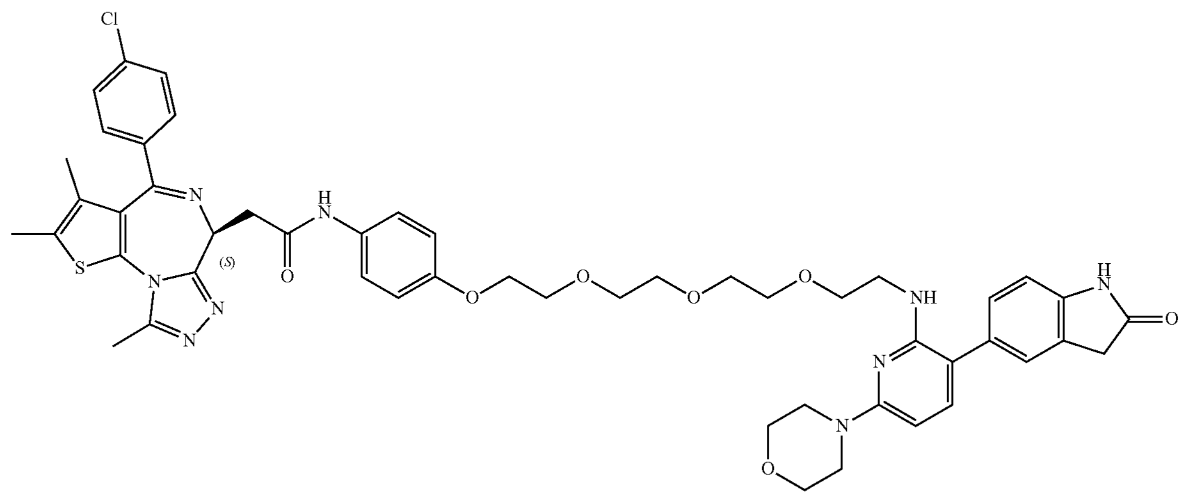 |

TABLE 1-continued

| Compound ID | Structure |
|---|---|
| 146 | 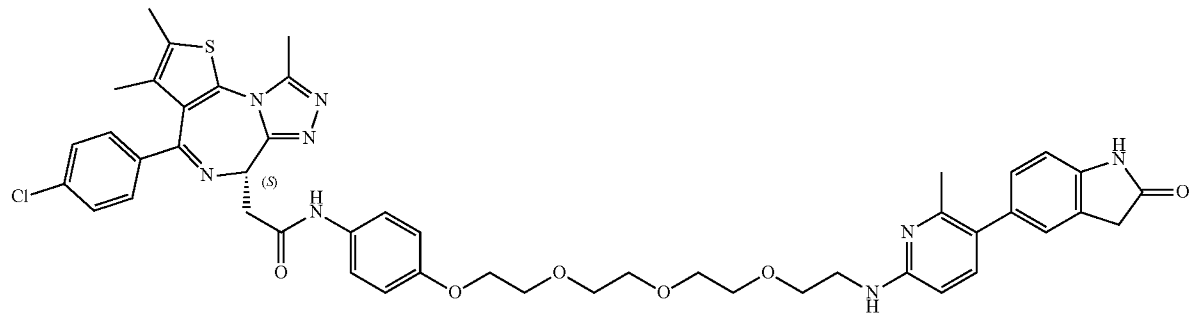 |
| 147 | 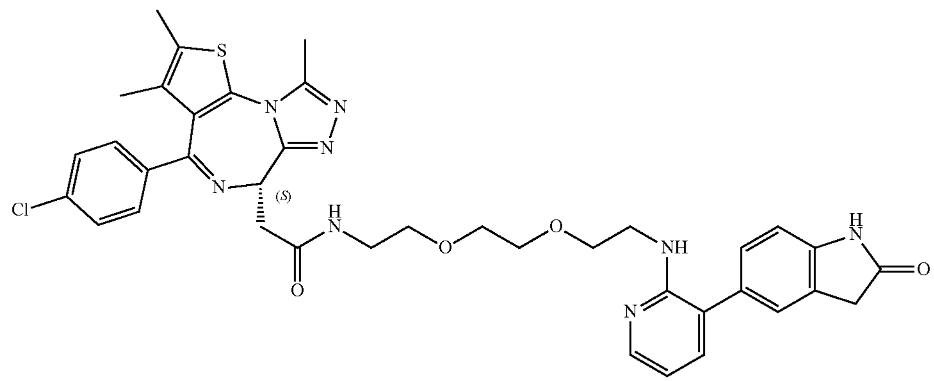 |
| 148 | 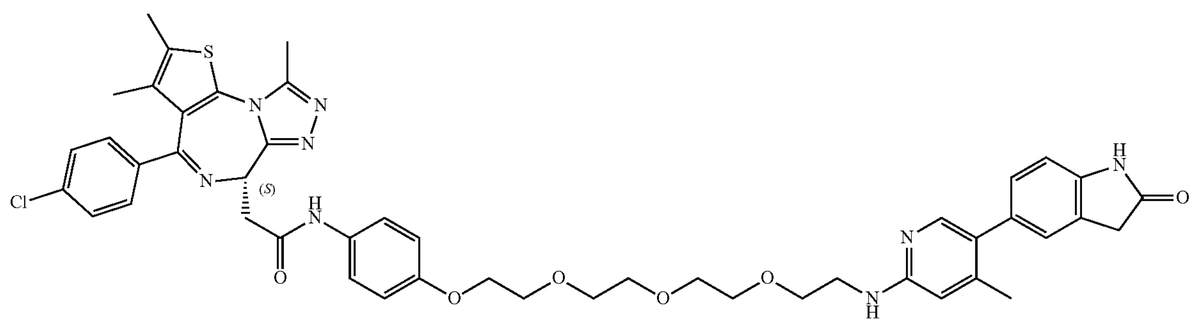 |

TABLE 1-continued

| Compound ID | Structure |
|---|---|
| 149 | 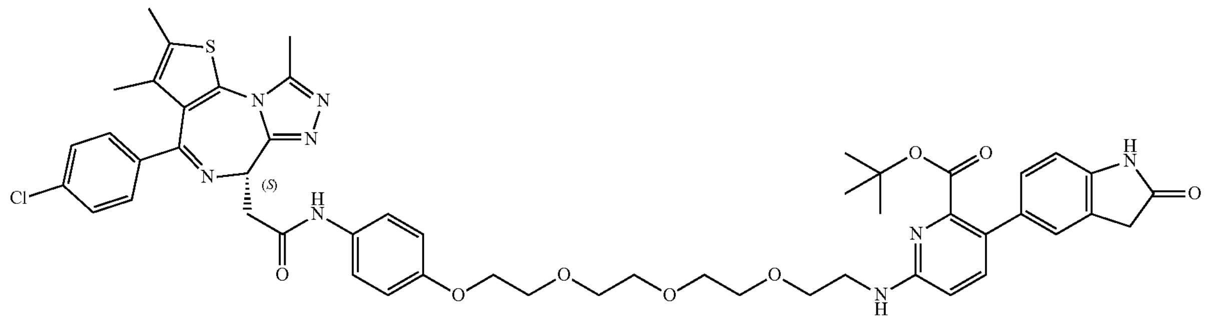 |
| 150 | 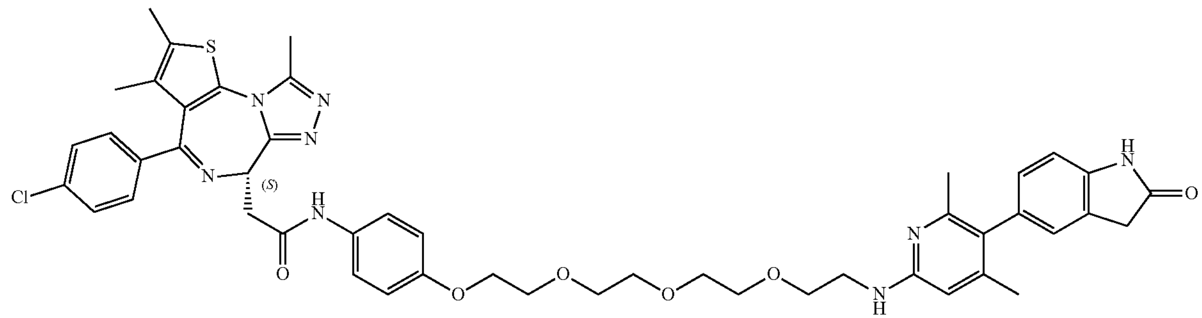 |
| 151 | 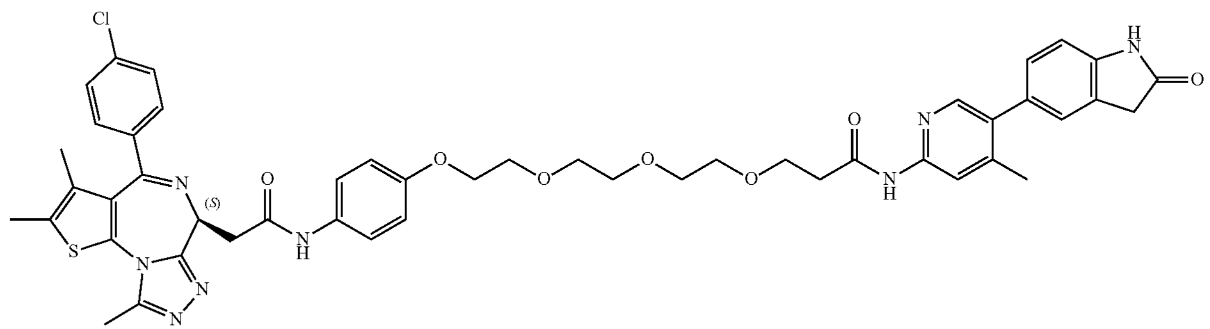 |

TABLE 1-continued
| Compound ID | Structure |
|---|---|
| 152 | 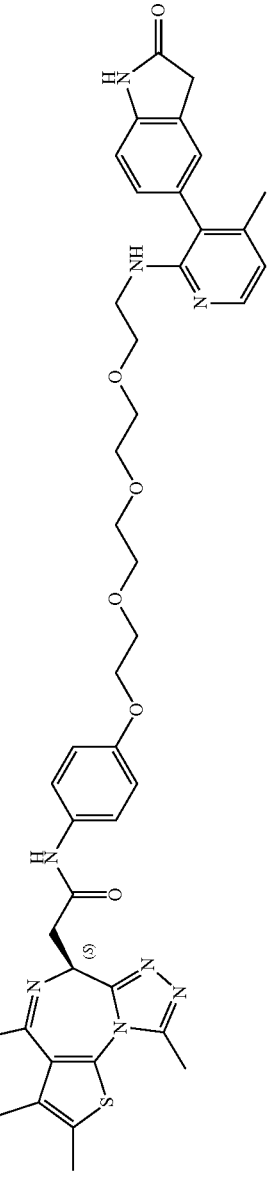 |
| 153 | 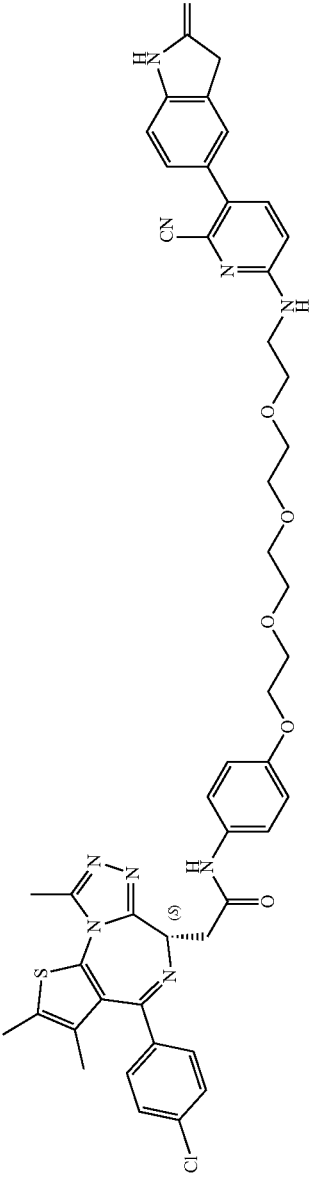 |
| 154 | 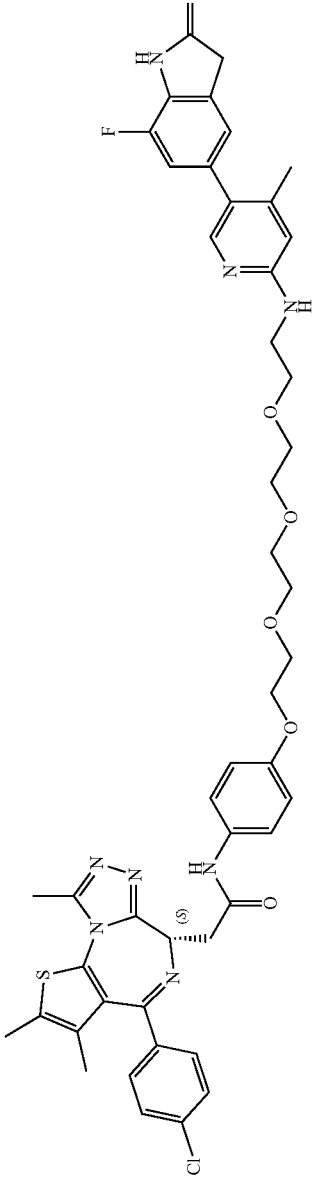 |

TABLE 1-continued

| Compound ID | Structure |
|---|---|
| 155 | 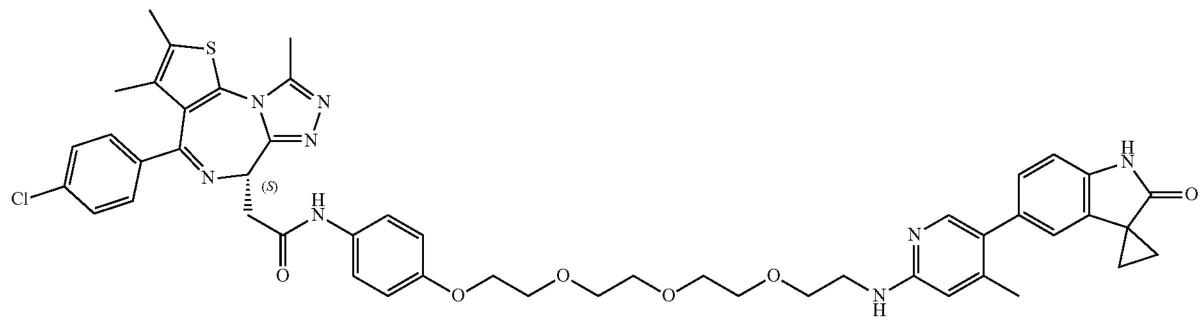 |
| 156 | 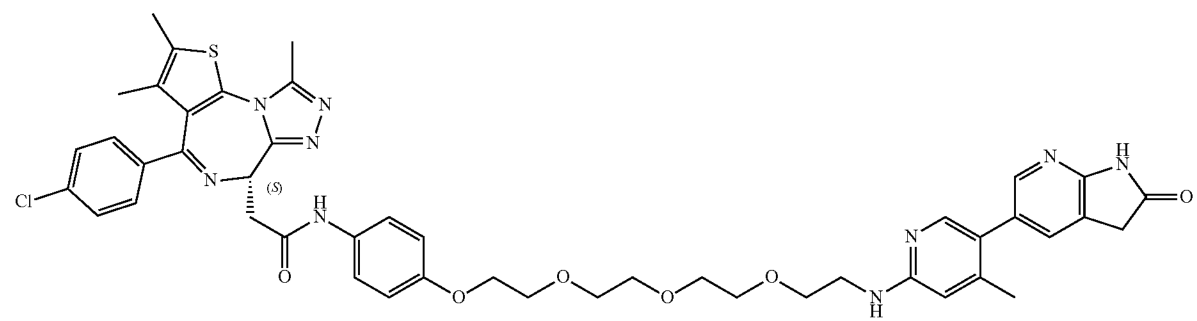 |
| 157 | 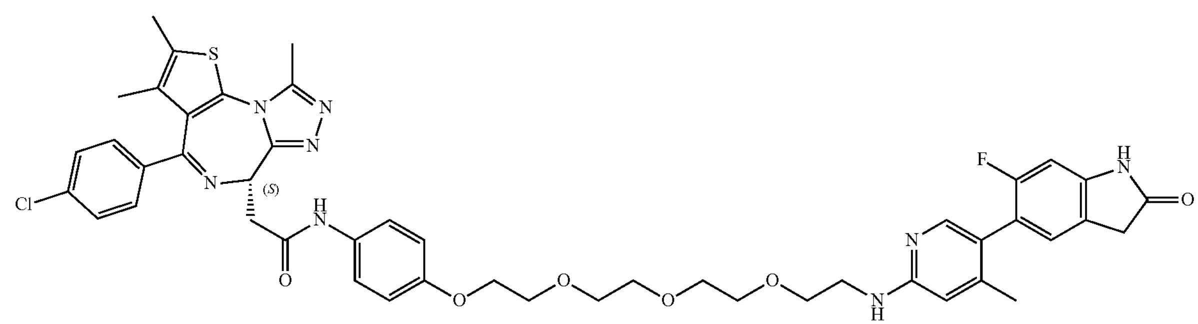 |

TABLE 1-continued

| Compound ID | Structure |
|---|---|
| 158 | 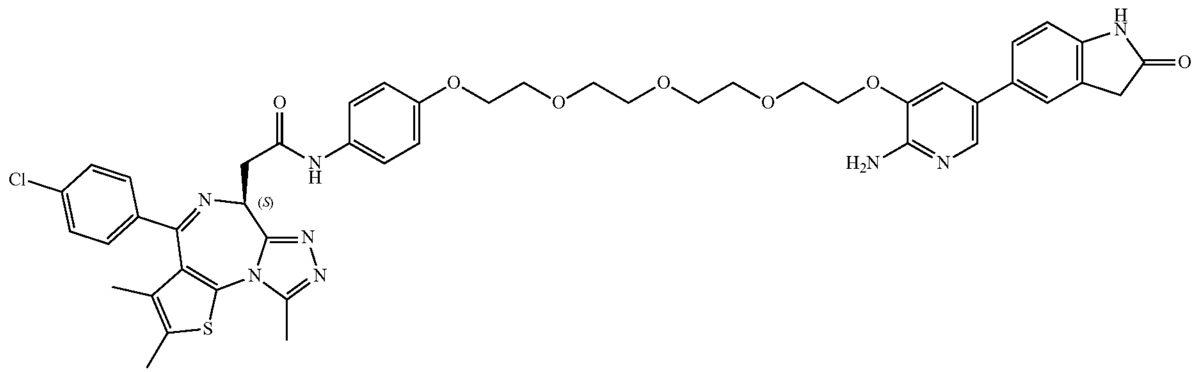 |
| 159 | 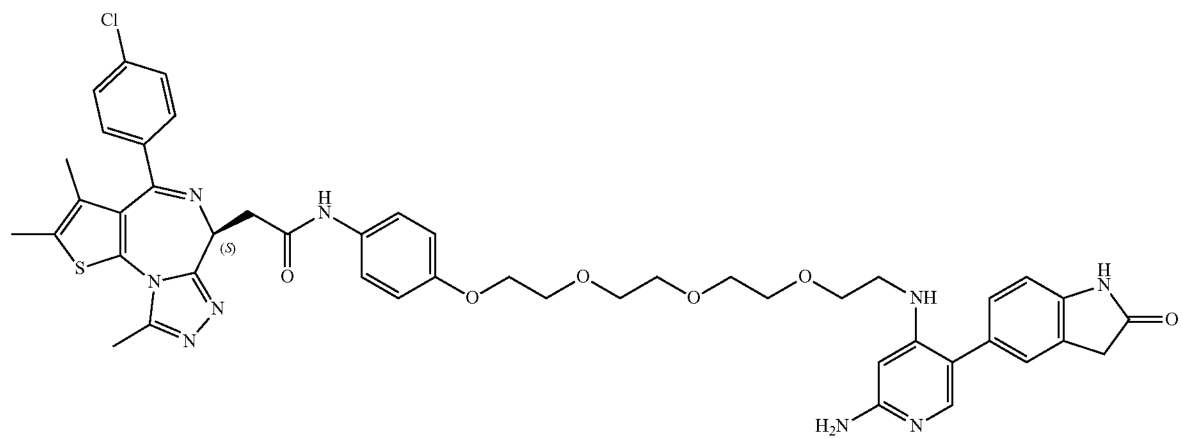 |

TABLE 1-continued
| Compound ID | Structure |
|---|---|
| 160 | 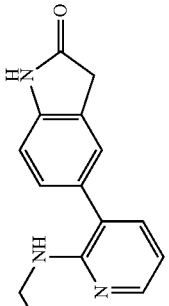 |
| 161 | 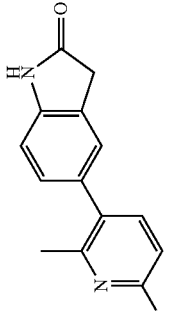 |
| 162 | 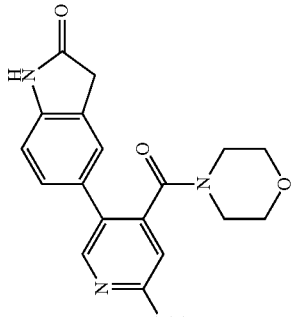 |

TABLE 1-continued

| Compound ID | Structure |
|---|---|
| 163 | 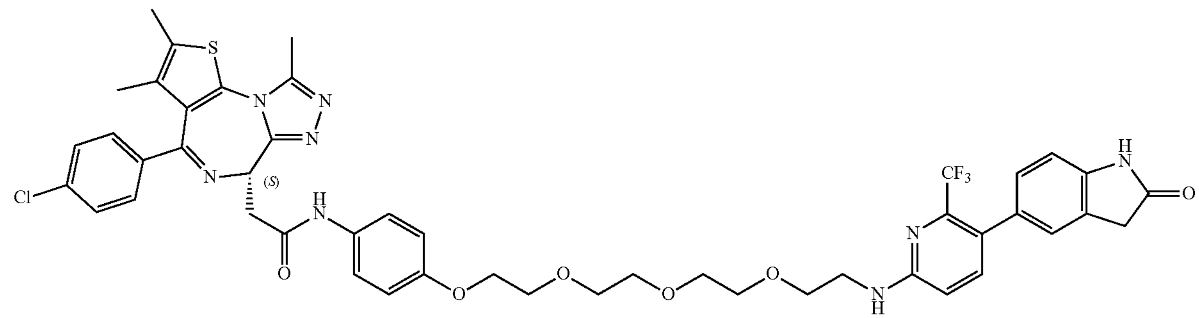 |
| 164 | 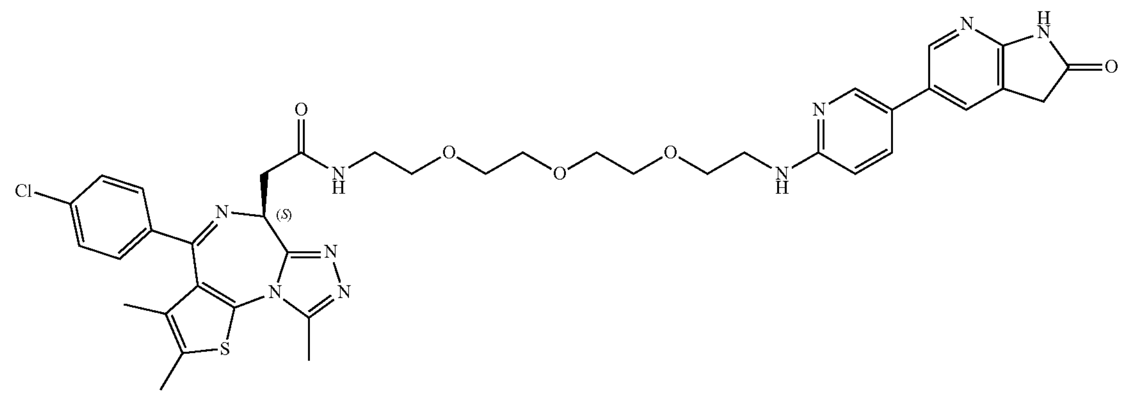 |
| 165 | 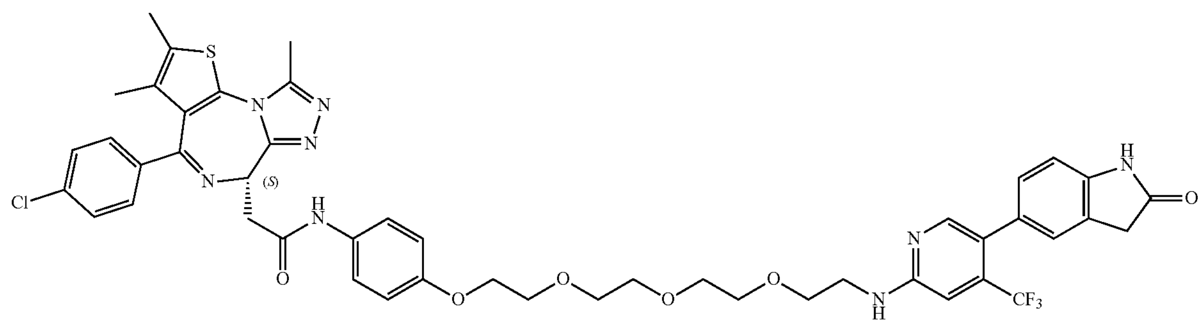 |

TABLE 1-continued
| Compound ID | Structure |
|---|---|
| 166 | 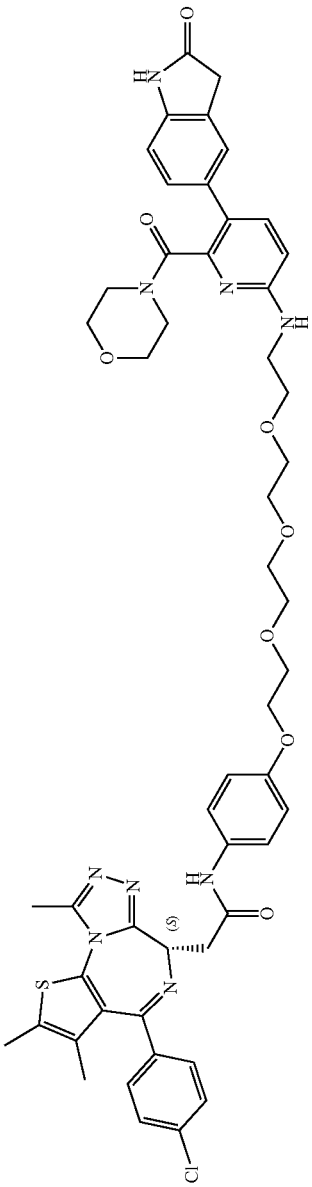 |
| 167 | 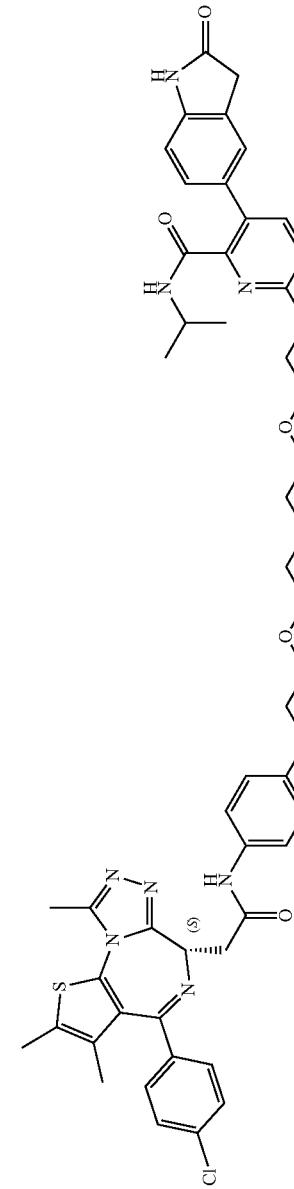 |
| 168 | 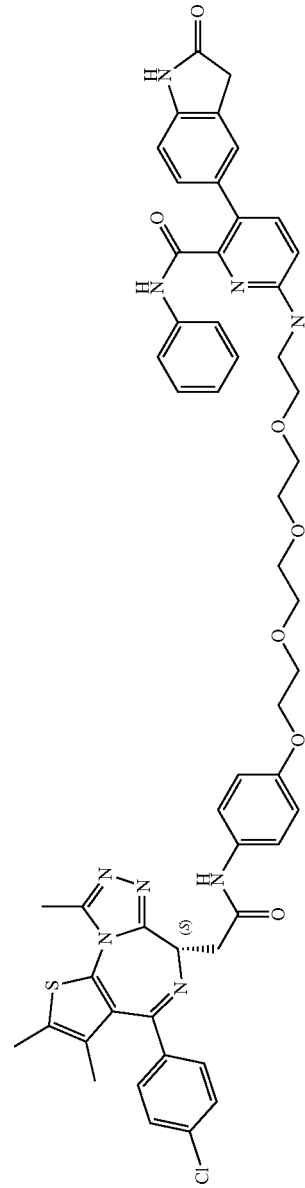 |

TABLE 1-continued
| Compound ID | Structure |
|---|---|
| 169 | 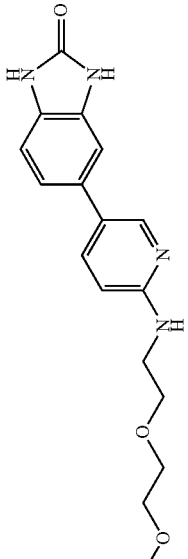 |
| 170 | 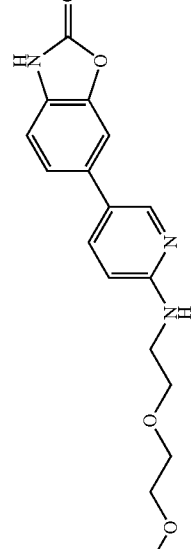 |

In various embodiments, the present disclosure also relates to a compound of Formula (XI) or a pharmaceutically acceptable salt, solvate, stereoisomer or prodrug thereof:

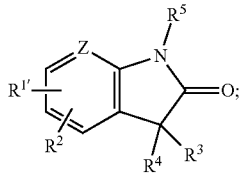
(XI)

wherein $R^{1'}$ is selected from optionally substituted heterocyclyl, optionally substituted aryl, optionally substituted heteroaryl, optionally substituted aminoacyl, optionally substituted acylamino, and optionally substituted acyl;

$R^2$ is selected from H, halogen and methyl;

$R^3$ and $R^4$ are independently selected from H and methyl; and $R^5$ is selected from H and methyl;

wherein $R^{1'}$ is located at either a 5' or 6' position of the oxindole ring.

Compounds of Formula (XI) can be used as the ubiquitination moiety as disclosed herein.

In some embodiments, $R^{1'}$ is selected from optionally substituted phenyl, optionally substituted pyridinyl, optionally substituted pyrazolyl, optionally substituted indolyl, optionally substituted azaindolyl, optionally substituted aminoacyl, optionally substituted acylamino, optionally substituted heterocyclylacyl and optionally substituted piperidinyl.

In some embodiments, $R^3$, $R^4$ and $R^5$ are independently selected from H and methyl.

The compound of Formula (XI) may be represented as Formula (XI') or (XI''):

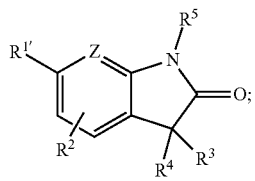
(XI')

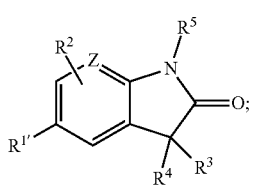
(XI'')

wherein $R^{1'}$, $R^2$, $R^3$, $R^4$ and $R^5$ are as defined herein. In this regard, compounds of Formula (II') have $RR^{1'}$ located at a 6' position of the oxindole ring and compounds of Formula (II'') have $RR^{1'}$ located at a 5' position of the oxindole ring.

The compound of Formula (XI) may also be represented as Formulae (XI'a) or (II''a):

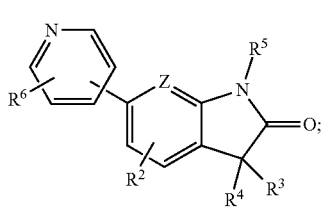
(XI'a)

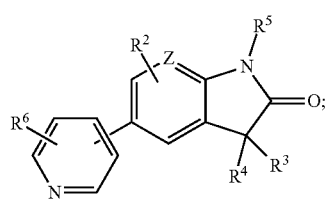
(XI''a)

wherein $R^2$, $R^3$, $R^4$ and $R^5$ are as defined herein, and $R^6$ is selected from halogen, optionally substituted alkyl, optionally substituted cycloalkyl, optionally substituted heterocyclyl, optionally substituted alkoxy, optionally substituted amino, optionally substituted oxyacyl, optionally substituted acyl, optionally substituted aminoacyl and optionally substituted acylamino.

In some embodiments, $R^6$ is selected from optionally substituted amino, optionally substituted aminoacyl and optionally substituted acylamino.

In some embodiments, $R^6$ is optionally substituted spirocycloalkyl.

Exemplary compounds of the invention include a fragment of use as a ubiquitination moiety, e.g., XI, XI', XI'', XI'a, XI'a, which is substituted as shown in the Formulae set forth herein and which is selected from the fragments in Table 2:

TABLE 2

| Compound ID | Structure |
|---|---|
| 001 | 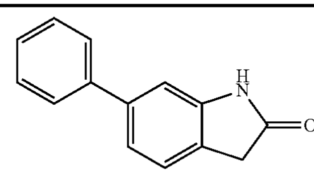 |
| 002 | 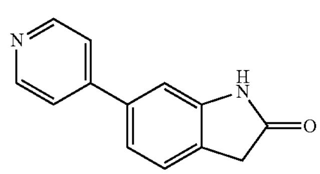 [SMILES: O=C1Cc2ccc(-c3ccncc3)cc2N1] |
| 003 | 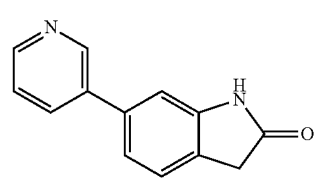 [SMILES: O=C1Cc2ccc(-c3cccnc3)cc2N1] |

TABLE 2-continued
| Compound ID | Structure |
|---|---|
| 004 | 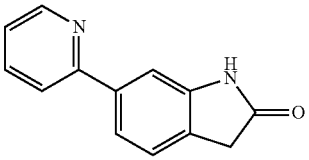 |
| 005 | 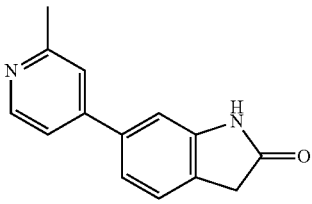 [SMILES: Cc1cc(-c2ccc3c(c2)NC(=O)C3)ccn1] |
| 006 | 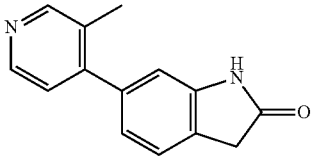 [SMILES: Cc1cnccc1-c1ccc2c(c1)NC(=O)C2] |
| 007 | 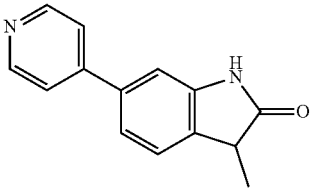 [SMILES: CC1C(=O)Nc2cc(-c3ccncc3)ccc21] |
| 008 | 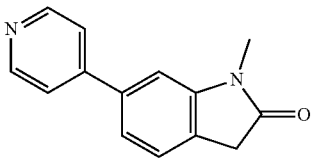 [SMILES: CN1C(=O)Cc2ccc(-c3ccncc3)cc21] |
| 009 | 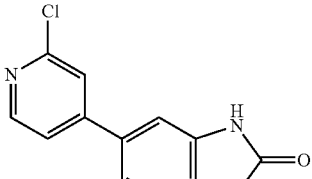 |
| 010 | 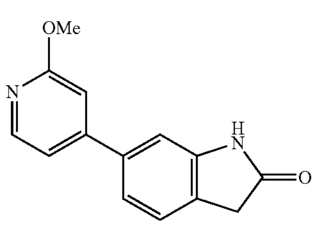 [SMILES: COc1cc(-c2ccc3c(c2)NC(=O)C3)ccn1] |
| 011 | 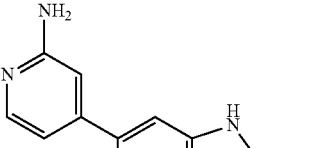 |
| 012 | 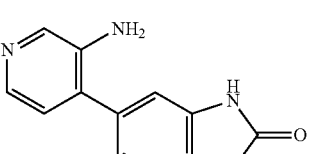 |
| 013 | 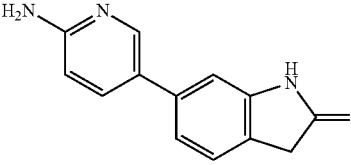 |
| 014 | 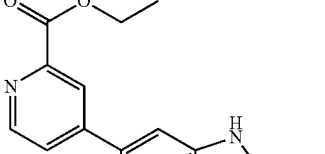 |
| 015 | 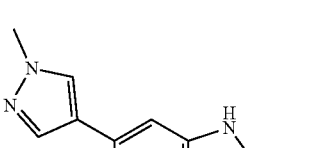 |
| 016 | 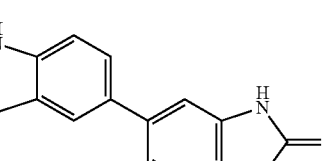 |
| 017 | 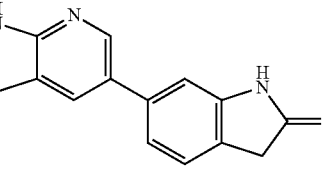 |
| 018 | 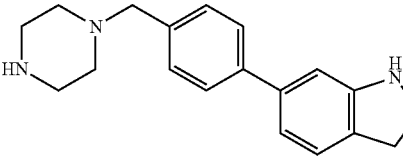 |

TABLE 2-continued
| Compound ID | Structure |
|---|---|
| 019 | 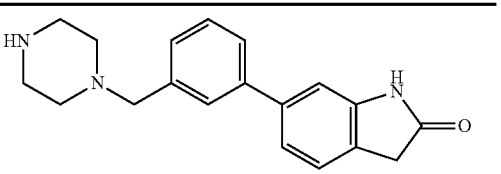 |
| 020 | 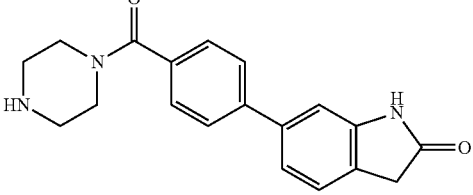 |
| 021 | 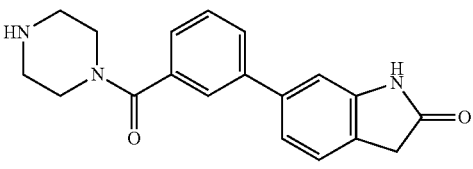 [SMILES: O=C1Cc2ccc(-c3cccc(C(=O)N4CCNCC4)c3)cc2N1] |
| 022 | 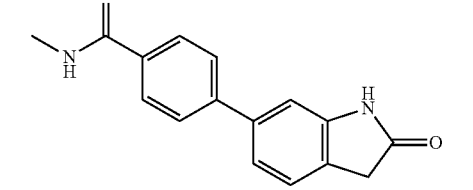 |
| 023 | 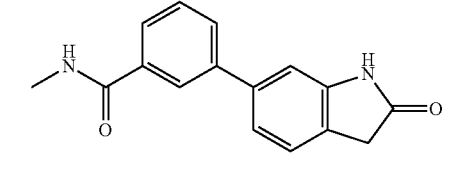 [SMILES: CNC(=O)c1cccc(-c2ccc3c(c2)NC(=O)C3)c1] |
| 024 | 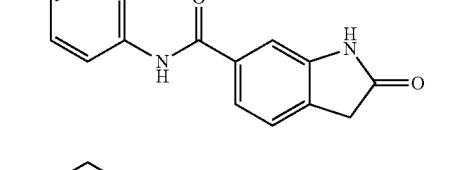 |
| 025 | 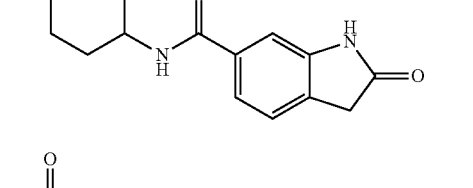 |
| 026 | 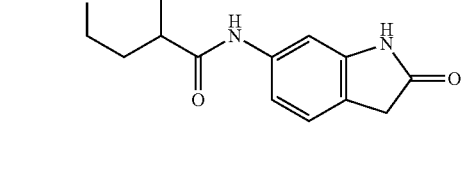 |
| 027 | 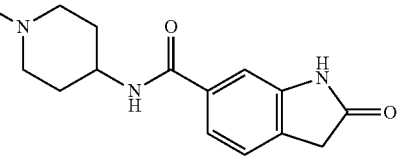 |
| 028 | 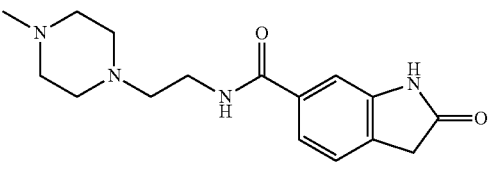 [SMILES: CN1CCN(CCNC(=O)c2ccc3c(c2)NC(=O)C3)CC1] |
| 029 | 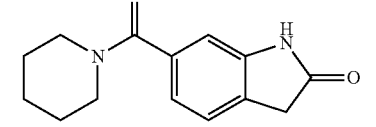 |
| 030 | 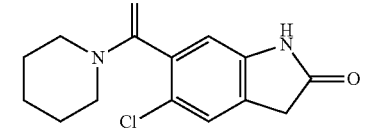 |
| 031 | 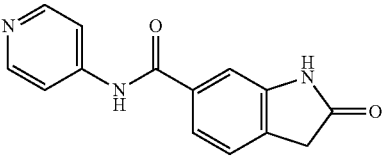 [SMILES: O=C1Cc2ccc(C(=O)Nc3ccncc3)cc2N1] |
| 032 | 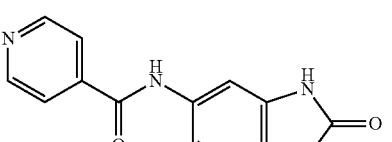 |
| 033 | 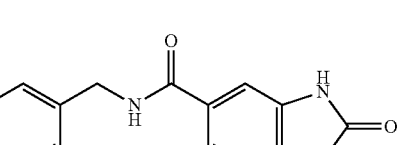 |
| 034 | 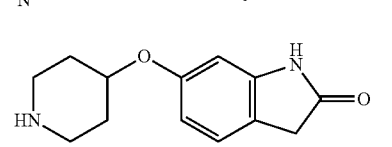 |
| 035 | 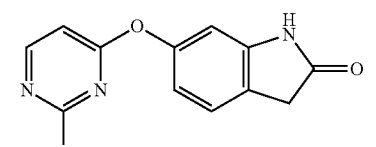 |

TABLE 2-continued

| Compound ID | Structure |
|---|---|
| 036 | (structure) |
| 037 | (structure) |
| 038 | (structure) |
| 039 | (structure) |
| 040 | (structure) |
| 041 | (structure) |
| 042 | (structure) |
| 043 | (structure) |
| 044 | (structure) |
| 045 | (structure) |
| 046 | (structure) |
| 047 | (structure) |
| 048 | (structure) |
| 049 | (structure) |

TABLE 2-continued

| Compound ID | Structure |
|---|---|
| 050 | 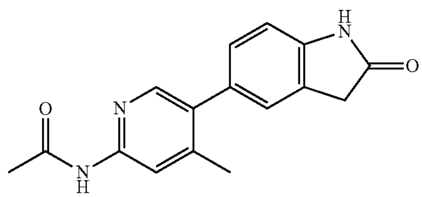 [SMILES: CC(=O)Nc1cc(C)c(-c2ccc3c(c2)CC(=O)N3)cn1] |
| 051 | 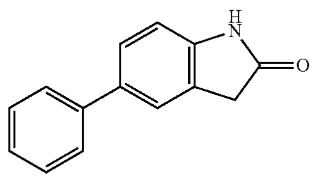 [SMILES: O=C1Cc2cc(-c3ccccc3)ccc2N1] |
| 052 | 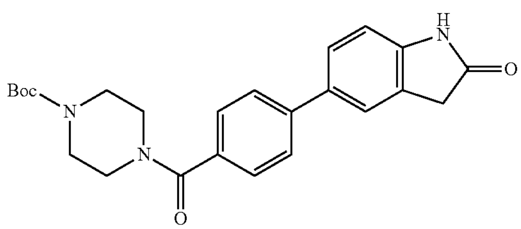 [SMILES: CC(C)(C)OC(=O)N1CCN(C(=O)c2ccc(-c3ccc4c(c3)CC(=O)N4)cc2)CC1] |
| 053 | 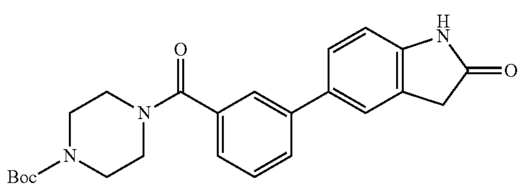 [SMILES: CC(C)(C)OC(=O)N1CCN(C(=O)c2cccc(-c3ccc4c(c3)CC(=O)N4)c2)CC1] |
| 054 | 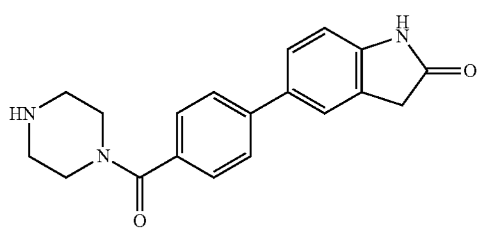 [SMILES: O=C1Cc2cc(-c3ccc(C(=O)N4CCNCC4)cc3)ccc2N1] |
| 055 | 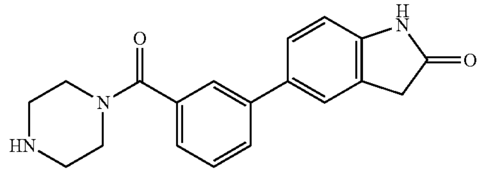 [SMILES: O=C1Cc2cc(-c3cccc(C(=O)N4CCNCC4)c3)ccc2N1] |
| 056 | 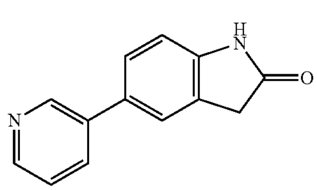 [SMILES: O=C1Cc2cc(-c3cccnc3)ccc2N1] |
| 057 | |
| 058 | |
| 059 | |
| 060 | |
| 061 | |
| 062 | |
| 063 | |

TABLE 2-continued

| Compound ID | Structure |
|---|---|
| 064 | 6-(6-(piperidin-1-yl)pyridin-3-yl)indolin-2-one |
| 065 | 6-(6-(piperazin-1-yl)pyridin-3-yl)indolin-2-one |
| 066 | ethyl 4-(2-oxoindolin-6-yl)picolinate |
| 067 | 5-(4-methylpiperazine-1-carbonyl)indolin-2-one |
| 068 | 5-(4-phenylpiperidine-1-carbonyl)indolin-2-one |
| 069 | 5-(4-benzylpiperidine-1-carbonyl)indolin-2-one |
| 070 | 6-(6-fluoropyridin-3-yl)indolin-2-one |
| 071 | N-(2-oxoindolin-6-yl)nicotinamide |
| 072 | N-(2-oxoindolin-5-yl)nicotinamide |
| 073 | 5-(pyridin-4-yl)-1H-pyrrolo[2,3-c]pyridin-2(3H)-one |
| 074 | 6-(pyridin-4-yl)-1H-pyrrolo[3,2-c]pyridin-2(3H)-one |
| 075 | 6-(pyridin-4-yl)-1H-pyrrolo[3,2-b]pyridin-2(3H)-one |
| 076 | 2-fluoro-N-(2-oxoindolin-5-yl)isonicotinamide |
| 077 | 6-(4-aminopiperidine-1-carbonyl)indolin-2-one |
| 078 | 5-(4-aminopiperidine-1-carbonyl)indolin-2-one |
| 079 | methyl 2-(2-oxoindolin-6-yl)benzoate |

TABLE 2-continued

| Compound ID | Structure |
|---|---|
| 080 | (3-aminopiperidin-1-yl)(2-oxoindolin-6-yl)methanone |
| 081 | (3-aminopiperidin-1-yl)(2-oxoindolin-5-yl)methanone |
| 082 | 3-isopropyl-5-(pyridin-4-yl)indolin-2-one |
| 083 | 1-methyl-5-(piperidine-1-carbonyl)indolin-2-one |

The fragments of Table 2, the moieties identified as linkers and X can be combined in any useful combination.

The present disclosure also relates to a compound of Formula (III) or a pharmaceutically acceptable salt, solvate, stereoisomer or prodrug thereof:

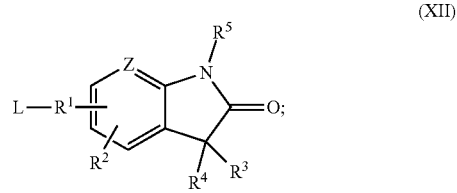

(XII)

wherein $R^1$, $R^2$, $R^3$, $R^4$ and $R^5$ are as defined herein; $R^1$ is located at either a 5' or 6' position of the oxindole ring; and L is an optionally substituted linker having 2 to 18 atoms in the chain length.

In some embodiments, L is a linker selected from optionally substituted alkyl, optionally substituted heteroalkyl, optionally substituted cycloalkyl (such as spirocycloalkyl) and optionally substituted heterocyclyl, each having 2 to 18 atoms in the chain length. In other embodiments, L is a linker having 2 to 15 atoms in the chain length.

Fragments containing a linker covalently attached to a ubiquitination moiety may be formed using compound of Formula (XII). Exemplary compounds (and the fragments inferred from these compounds are set forth in Table 3.

TABLE 3

| Compound ID | Structure |
|---|---|
| 084 | azido-PEG3-amide-pyridine-oxindole compound |
| 085 | azido-PEG3-amino-pyridine-oxindole compound |
| 086 | azido-PEG3-amino-pyridine-carboxamide-oxindole compound |

TABLE 3-continued
| Compound ID | Structure |
|---|---|
| 087 | 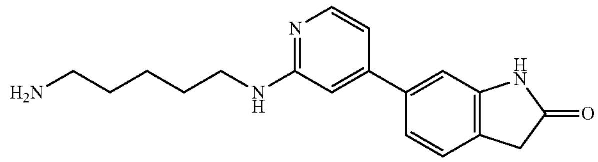 [SMILES: NCCCCCNc1cc(-c2ccc3c(c2)NC(=O)C3)ccn1] |
| 088 | 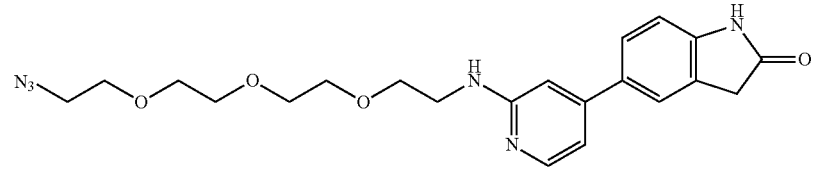 [SMILES: [N-]=[N+]=NCCOCCOCCOCCNc1cc(-c2ccc3c(c2)CC(=O)N3)ccn1] |
| 089 | 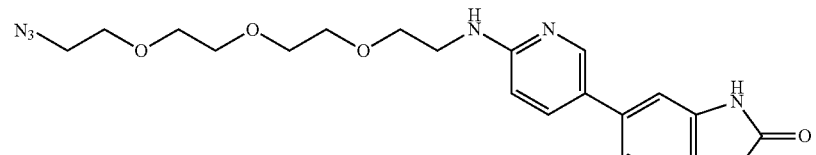 |
| 090 | 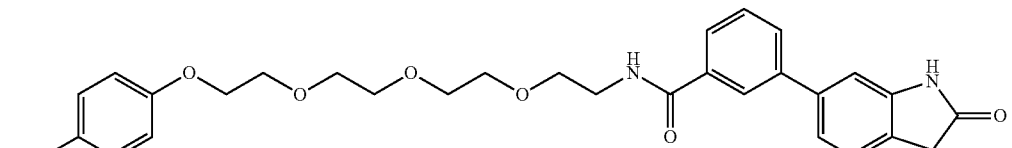 |
| 091 | 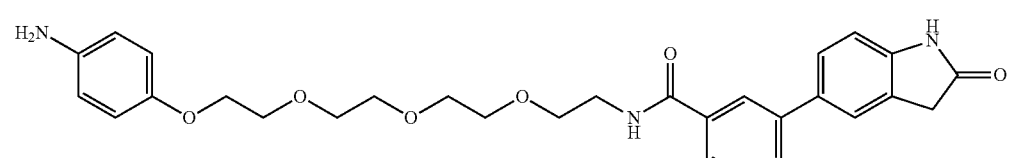 |
| 092 | 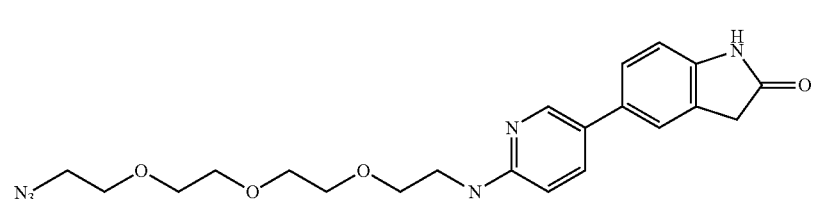 |
| 093 | 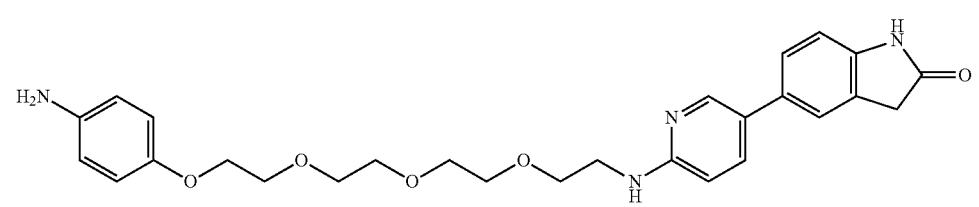 [SMILES: Nc1ccc(OCCOCCOCCOCCNc2ccc(-c3ccc4c(c3)CC(=O)N4)cn2)cc1] |
| 094 | 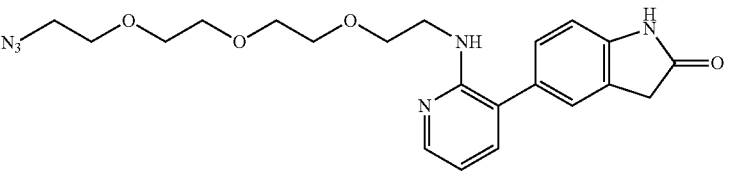 [SMILES: [N-]=[N+]=NCCOCCOCCOCCNc1ncccc1-c1ccc2c(c1)CC(=O)N2] |

TABLE 3-continued

| Compound ID | Structure |
|---|---|
| 095 | 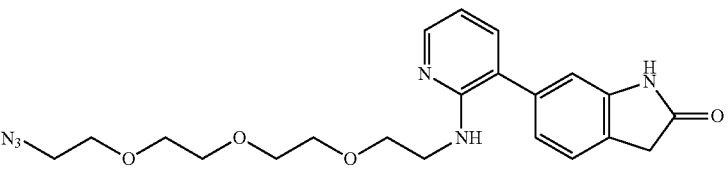 [SMILES: [N-]=[N+]=NCCOCCOCCOCCNc1ncccc1-c1ccc2c(c1)NC(=O)C2] |

The exemplars in Table 3 are based on a linker based on repeat ethylene glycol subunits. As will be apparent to those of skill in the art, any of the species discussed herein in the context of linkers may be substituted for the linkers of Table 3.

In another aspect, the present disclosure relates to a pharmaceutical composition comprising an effective amount of compound set forth in a Formula herein or a pharmaceutically acceptable salt, solvate, stereoisomer or prodrug thereof. The pharmaceutical composition may optionally be in combination with a pharmaceutically acceptable carrier, excipient or diluent.

In another aspect, the present disclosure relates to a method of inducing degradation of an overexpressed protein in a cell, including a step of contacting a compound set forth in a Formula herein with the cell to induce degradation of the overexpressed protein in the cell.

In another aspect, the present disclosure relates to a method of treating a disease or condition associated with an overexpressed protein, comprising administering a compound of a Formula set forth herein or a pharmaceutically acceptable salt, solvate, stereoisomer or prodrug thereof in a subject in need thereof.

In another aspect, the present disclosure relates to a compound of a Formula set forth herein or a pharmaceutically acceptable salt, solvate, stereoisomer or prodrug thereof for use as a medicament.

In another aspect, the present disclosure relates to a compound of Formula (I) or a pharmaceutically acceptable salt, solvate, stereoisomer or prodrug thereof for use in the treatment of a disease or condition associated with an overexpressed protein.

In another aspect, the present disclosure relates to a use of a compound of the invention or a pharmaceutically acceptable salt, solvate, stereoisomer or prodrug thereof in the manufacture of a medicament for the treatment of a disease or condition associated with an overexpressed protein.

The overexpressed or malfunctioning protein can be selected from BRD4, transcriptional enhanced associate domain (TEAD), Polycomb Repressive Complex 2 (PRC2), focal adhesion kinase (FAK), BCR-ABL, Hippo pathway protein and transcription factor. The disease or condition can be selected from hyperplasia and cancer (such as multiple myeloma, glioblastoma, uveal melanoma, liposarcoma, hepatocellular carcinoma, midline carcinoma, acute myeloid leukemia, Burkitt lymphoma and prostate cancer). The diseases can also be a protein accumulation disease, for example Alzheimer's disease and amyotrophic lateral sclerosis.

The compound of the invention can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of the compound the invention is also within the scope and spirit of the invention. Thus the compound of the invention can be administered to a subject in the form of a pharmaceutically acceptable pro-drug. The term "pro-drug" is used in its broadest sense and encompasses those derivatives that are converted in vivo to the compound of the invention. Such derivatives would readily occur to those skilled in the art. Other texts which generally describe prodrugs (and the preparation thereof) include: *Design of Prodrugs*, 1985, H. Bundgaard (Elsevier); *The Practice of Medicinal Chemistry*, 1996, Camille G. Wermuth et al., Chapter 31 (Academic Press); and *A Textbook of Drug Design and Development*, 1991, Bundgaard et al., Chapter 5, (Harwood Academic Publishers). For example, the N atom on the oxindole ring may be reacted with an acid (for example acetic acid) to form N-acetyloxindole.

The compound of the invention may be in crystalline form either as the free compound or as a solvate (e.g. hydrate) and it is intended that both forms are within the scope of the present invention. Methods of solvation are generally known within the art.

The compound of the invention, or a pharmaceutically acceptable salt, solvate or prodrug thereof is administered to the patient in a therapeutically effective amount.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages may lie within the range of about 0.1 ng per kg of body weight to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The compound, composition or combinations of the invention may also be suitable for intravenous administration. For example, a compound of the invention or a pharmaceutically acceptable salt, solvate or prodrug thereof may be administered intravenously at a dose of up to 16 mg/m$^2$.

Suitable dosage amounts and dosing regimens can be determined by the attending physician and may depend on the severity of the condition as well as the general age, health and weight of the patient to be treated.

The compound of the invention may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier is pharmaceutically "acceptable" in the sense of being compatible with the other ingredients of the composition and not injurious to the patient. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Injectables for such use can be prepared in conventional forms, either as a liquid solution or suspension or in a solid form suitable for preparation as a solution or suspension in a liquid prior to injection, or as an emulsion. Carriers can include, for example, water, saline (e.g., normal saline (NS), phosphate-buffered saline (PBS), balanced saline solution (BSS)), sodium lactate Ringer's solution, dextrose, glycerol, ethanol, and the like; and if desired, minor amounts of auxiliary substances, such as wetting or emulsifying agents, buffers, and the like can be added. Proper fluidity can be maintained, for example, by using a coating such as lecithin, by maintaining the required particle size in the case of dispersion and by using surfactants.

In an exemplary embodiment, the compound of the invention is administered to the eye of a subject in need of treatment with a compound of the invention. By way of example, the compound, composition or combination can be dissolved in a pharmaceutically effective carrier and be injected into the vitreous of the eye with a fine gauge hollow bore needle (e.g., 30 gauge, ½ or ⅜ inch needle) using a temporal approach (e.g., about 3 to about 4 mm posterior to the limbus for human eye to avoid damaging the lens). The compound may be injected directly to the eye, and in particular the vitreous of the eye. The compound, composition or combination of the invention can be administered to the vitreous of the eye using any intravitreal or transscleral administration technique. For example, the compound, composition or combination can be administered to the vitreous of the eye by intravitreal injection. Intravitreal injection typically involves administering a compound of the invention or a pharmaceutically acceptable salt, solvate or prodrug in a total amount between 0.1 ng to 10 mg per dose.

A person skilled in the art will appreciate that other means for injecting and/or administering the compound, composition or combinations to the vitreous of the eye can also be used. These other means can include, for example, intravitreal medical delivery devices. These devices and methods can include, for example, intravitreal medicine delivery devices, and biodegradable polymer delivery members that are inserted in the eye for long term delivery of medicaments. These devices and methods can further include transscleral delivery devices.

As used herein, a therapeutically effective amount is intended to include at least partially attaining the desired effect, or delaying the onset of, or inhibiting the progression of, or halting or reversing altogether the onset or progression of macular degeneration.

Other modes of administration including topical or intravenous administration are also of use. For example, solutions or suspensions of the compound, composition or combinations of the invention may be formulated as eye drops, or as a membranous ocular patch, which is applied directly to the surface of the eye. Topical application typically involves administering the compound of the invention in an amount between 0.1 ng and 10 mg.

The compound, composition or combinations of the invention may also be suitable for oral administration and may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste. In another embodiment, the compound of formula (I) or a pharmaceutically acceptable salt, solvate or prodrug is orally administrable.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The compound, composition or combinations of the invention may be suitable for topical administration in the mouth including lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

The compound, composition or combinations of the invention may be suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

The compound, composition or combination of the invention may be suitable for parenteral administration include aqueous and non-aqueous isotonic sterile injection solutions which may contain anti-oxidants, buffers, bactericides and solutes which render the compound, composition or combination isotonic with the blood of the intended recipient; and aqueous and non-aqueous sterile suspensions which may include suspending agents and thickening agents. The compound, composition or combination may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage composition or combinations are those containing a daily dose or unit, daily sub-dose, as herein above described, or an appropriate fraction thereof, of the active ingredient.

It should be understood that in addition to the active ingredients particularly mentioned above, the composition or combination of this invention may include other agents conventional in the art having regard to the type of composition or combination in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

It will be appreciated that many further modifications and permutations of various aspects of the described embodiments are possible. Accordingly, the described aspects are intended to embrace all such alterations, modifications, and variations that fall within the spirit and scope of the appended statements.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1

Identification of the Ubiquitination Moiety

Using state-of-the-art biophysical fragment screening techniques, fragments were identified which bind to CRBN. Protein NMR studies and ligand competition assays were performed to analyse the fragments and one fragment binding to the thalidomide binding region of CRBN was identified as the most viable option, after balancing the various factors such as affinity, pharmacokinetics and toxicity. These fragments were then further modified and optimized to generate more potent CRBN binders.

Example 2

2.1 Synthesis of Oxindole Fragments (1)

2.1a General Procedure for Suzuki Reaction:

A stirred mixture of aryl halide (1.0 equiv.), boronic acid/ester (1.2 equiv.) and potassium phosphate (3.0 equiv.) in 1,4-Dioxane and water (4:1) was degassed for 15 min with nitrogen. Tetrakis(triphenylphosphine)palladium(0) or Pd(dppf)Cl$_2$.DCM (0.05-0.15 equiv.) was added to the reaction mixture and heated to reflux for 1-18 h. After completion of starting material, the reaction mixture was concentrated under vacuum. Water was added to the residue and extracted with ethyl acetate. The combined organic layers were washed with brine, dried with Na$_2$SO$_4$ and concentrated under vacuum. The crude compound was purified by column chromatography and/or reversed phase chromatography to afford the purified product.

2.1b General Procedure for Amide Coupling:

To a mixture of acid (1.0 equiv.), amine (1.1 equiv.) in DMF was added triethylamine (4.0 equiv.), followed by HATU (1.2 equiv.). The reaction was stirred at room temperature for 0.5-1 h. After completion of starting material, dichloromethane was added and the organic layer was washed with water and brine, dried with Na$_2$SO$_4$ and concentrated under vacuum. The crude compound was purified by column chromatography and/or reversed phase chromatography to afford the purified product.

2.1c De-Protection of Boc Protecting Group:

To a solution of N-Boc intermediate (1.0 equiv.) in dichloromethane was added triflouroacetic acid (10.0 equiv.). The reaction mixture was stirred at room temperature for 1-2 h. After completion of starting material as confirmed by LCMS, the crude product was concentrated under vacuum and purified by reversed phase chromatography to afford the purified product.

2.1.1 Synthesis of 5-phenylindolin-2-one (001)

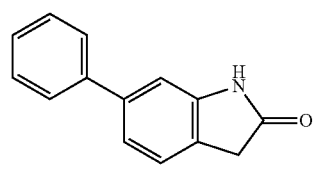 [SMILES: O=C1Cc2ccc(-c3ccccc3)cc2N1]

$^1$H NMR (400 MHz, DMSO-d$_6$) δ (ppm): 10.45 (s, 1H), 7.61-7.58 (m, 2H), 7.47-7.34 (m, 3H), 7.28 (d, J=8.0 Hz, 1H), 7.21-7.19 (dd, J=8.0, 1.2 Hz, 1H), 7.02 (d, J=1.2 Hz, 1H), 3.51 (s, 2H). LC-MS m/z [M+H]$^+$: 210.0 with a purity of 99%.

2.1.2 Synthesis of 6-(pyridin-4-yl)indolin-2-one (002)

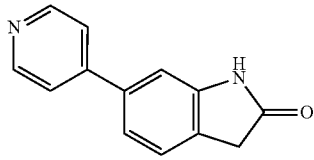

$^1$H NMR (400 MHz, CDCl$_3$) δ (ppm): 9.32 (s, 1H), 8.66 (d, J=6.0 Hz, 2H), 7.47 (d, J=6.0 Hz, 2H), 7.35-7.28 (m, 2H), 7.16 (bs, 1H), 3.61 (s, 2H). LC-MS m/z [M+H]$^+$: 211.1 with a purity of >99%.

2.1.3 Synthesis of 6-(pyridin-3-yl)indolin-2-one (003)

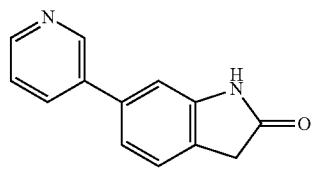 [SMILES: O=C1Cc2ccc(-c3cccnc3)cc2N1]

$^1$H NMR (400 MHz, CDCl$_3$) δ (ppm): 9.02 (s, 1H), 8.84 (s, 1H), 8.61 (d, J=3.6 Hz, 1H), 7.91-7.89 (m, 1H), 7.43-7.40 (m, 1H), 7.34 (d, J=7.6 Hz, 1H), 7.23 (dd, J=7.6, 1.6 Hz, 1H), 7.12 (bs, 1H), 3.62 (s, 2H). LC-MS m/z [M+H]$^+$: 211.1 with a purity of >99%.

2.1.4 Synthesis of 6-(pyridin-2-yl)indolin-2-one (004)

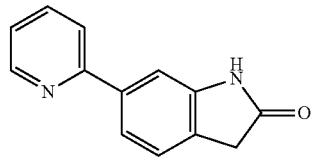

$^1$H NMR (400 MHz, DMSO-d$_6$) δ (ppm): 10.45 (s, 1H), 8.65-8.63 (m, 1H), 7.91-7.84 (m, 2H), 7.65 (dd, J=8.0, 1.6 Hz, 1H), 7.56 (d, J=1.2 Hz, 1H), 7.35-7.33 (m, 2H), 3.53 (s, 2H). LC-MS m/z [M+H]$^+$: 211.1 with a purity of 98%.

2.1.5 Synthesis of 6-(2-methylpyridin-4-yl)indolin-2-one (005)

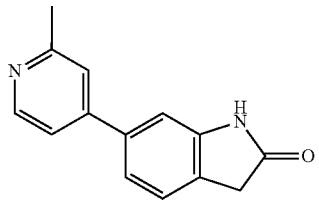 [SMILES: Cc1cc(-c2ccc3c(c2)NC(=O)C3)ccn1]

$^1$H NMR (400 MHz, DMSO-d$_6$) δ (ppm): 10.53 (s, 1H), 8.48 (d, J=5.2 Hz, 1H), 7.50 (s, 1H), 7.42 (dd, J=5.2, 1.6 Hz, 1H), 7.33 (bs, 2H), 7.11 (bs, 1H), 3.54 (s, 2H), 3.34 (s, 3H). LC-MS m/z [M+H]$^+$: 225.1 with a purity of 97%.

2.1.6 Synthesis of 6-(3-methylpyridin-4-yl)indolin-2-one (006)

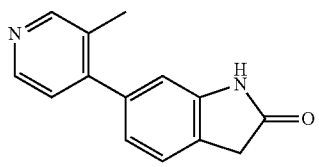 [SMILES: Cc1cnccc1-c1ccc2c(c1)NC(=O)C2]

$^1$H NMR (400 MHz, DMSO-d$_6$) δ (ppm): 10.45 (s, 1H), 8.49 (s, 1H), 8.43 (d, J=4.8 Hz, 1H), 7.31 (d, J=7.6 Hz, 1H), 7.21 (d, J=5.2 Hz, 1H), 6.95 (dd, J=7.6, 1.2 Hz, 1H), 6.78 (bs, 1H), 3.54 (s, 2H), 2.25 (s, 3H). LC-MS m/z [M+H]$^+$: 225.1 with a purity of 98%.

2.1.7 Synthesis of 3-methyl-6-(pyridin-4-yl)indolin-2-one (007)

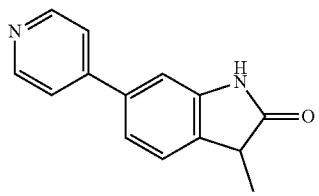 [SMILES: CC1C(=O)Nc2cc(-c3ccncc3)ccc21]

$^1$H NMR (400 MHz, DMSO-d$_6$) δ (ppm): 10.50 (s, 1H), 8.62 (d, J=6.0 Hz, 2H), 7.64 (dd, J=7.6, 1.2 Hz, 2H), 7.41-7.36 (m, 2H), 7.14 (s, 1H), 3.49-3.46 (m, 1H), 1.36 (d, J=7.6 Hz, 3H). LC-MS m/z [M+H]$^+$: 225.1 with a purity of 95%.

2.1.8 Synthesis of 1-methyl-6-(pyridin-4-yl)indolin-2-one (008)

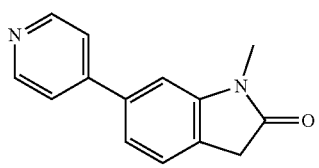 [SMILES: CN1C(=O)Cc2ccc(-c3ccncc3)cc21]

¹H NMR (400 MHz, DMSO-d₆) δ (ppm): 8.64 (d, J=6.0 Hz, 2H), 7.76 (dd, J=4.4, 1.6 Hz, 2H), 7.45 (dd, J=7.6, 1.6 Hz, 1H), 7.41-7.38 (m, 2H), 3.61 (s, 2H), 3.21 (s, 3H). LC-MS m/z [M+H]⁺: 225.1 with a purity of 98%.

2.1.9 Synthesis of 6-(2-chloropyridin-4-yl)indolin-2-one (009)

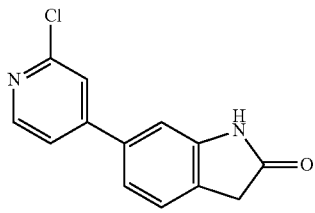

¹H NMR (400 MHz, DMSO-d₆) δ (ppm): 10.57 (s, 1H), 8.45 (d, J=5.2 Hz, 1H), 7.77 (d, J=1.2 Hz, 1H), 7.68 (dd, J=5.2, 1.2 Hz, 1H), 7.43-7.33 (m, 2H), 7.16 (d, J=1.2 Hz, 1H), 3.55 (s, 2H). LC-MS m/z [M+H]⁺: 245.0 with a purity of 98%.

2.1.10 Synthesis of 6-(2-methoxypyridin-4-yl)indolin-2-one (010)

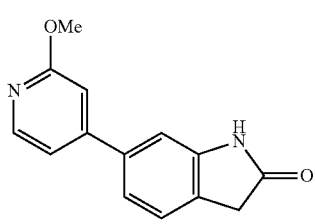

¹H NMR (400 MHz, DMSO-d₆) δ (ppm): 10.50 (s, 1H), 8.21 (d, J=5.2 Hz, 1H), 7.32 (bs, 2H), 7.24 (dd, J=5.2, 1.6 Hz, 1H), 7.09 (bs, 1H), 7.01 (bs, 1H), 3.89 (s, 3H), 3.53 (s, 2H). LC-MS m/z [M+H]⁺: 244.1 with a purity of 98%.

2.1.11 Synthesis of 6-(2-aminopyridin-4-yl)indolin-2-one (011)

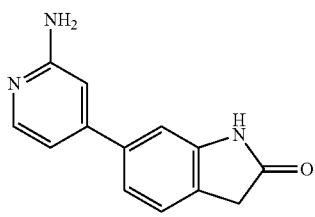

¹H NMR (400 MHz, DMSO-d₆) δ (ppm): 10.50 (s, 1H), 7.94 (d, J=5.2 Hz, 1H), 7.29 (d, J=7.6 Hz, 1H), 7.19 (d, J=7.6 Hz, 1H), 7.00 (s, 1H), 6.71 (d, J=5.2 Hz, 1H), 6.50 (bs, 1H), 5.97 (s, 2H), 3.52 (s, 2H). LC-MS m/z [M+H]⁺: 226.1 with a purity of 99%.

2.1.12 Synthesis of 6-(3-aminopyridin-4-yl)indolin-2-one (012)

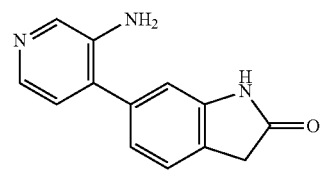 [SMILES: Nc1cnccc1-c1ccc2c(c1)NC(=O)C2]

¹H NMR (400 MHz, DMSO-d₆) δ (ppm): 10.43 (s, 1H), 7.94 (d, J=4.4 Hz, 1H), 7.30-7.27 (m, 2H), 6.96 (d, J=7.6 Hz, 1H), 6.85 (s, 1H), 6.65-6.62 (m, 1H), 5.54 (s, 2H), 3.50 (s, 2H). LC-MS m/z [M+H]⁺: 226.1 with a purity of >99%.

2.1.13 Synthesis of 6-(6-aminopyridin-3-yl)indolin-2-one (013)

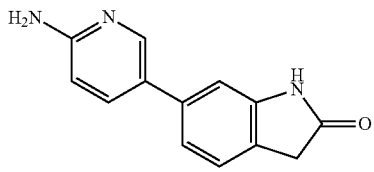

¹H NMR (400 MHz, DMSO-d₆) δ (ppm): 10.40 (s, 1H), 8.17 (s, 1H), 7.62 (d, J=8.8 Hz, 1H), 7.22 (d, J=7.6 Hz, 1H), 7.10 (d, J=7.6 Hz, 1H), 6.92 (s, 1H), 6.51 (d, J=8.8 Hz, 1H), 6.04 (s, 2H), 3.47 (s, 2H). LC-MS m/z [M+H]⁺: 226.1 with a purity of >99%.

2.1.14 Synthesis of ethyl 4-(2-oxoindolin-6-yl)picolinate (014)

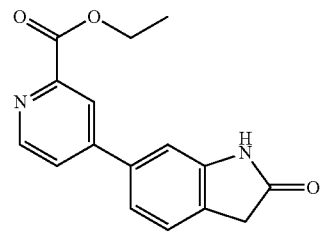 [SMILES: CCOC(=O)c1cc(-c2ccc3c(c2)NC(=O)C3)ccn1]

¹H NMR (400 MHz, DMSO-d₆) δ (ppm): 10.54 (s, 1H), 8.75 (d, J=4.8 Hz, 1H), 8.22 (d, J=1.6 Hz, 1H), 7.92 (dd, J=4.8, 1.6 Hz, 1H), 7.45-7.35 (m, 2H), 7.18 (d, J=1.2 Hz, 1H), 4.38 (q, J=7.2 Hz, 2H), 3.56 (s, 2H), 1.36 (t, J=7.2 Hz, 3H). LC-MS m/z [M+H]⁺: 283.1 with a purity of 97%.

2.1.15 Synthesis of 6-(1-methyl-1H-pyrazol-4-yl)indolin-2-one (015)

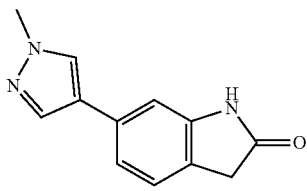 [SMILES: Cn1cc(-c2ccc3c(c2)NC(=O)C3)cn1]

$^1$H NMR (400 MHz, DMSO-d$_6$) δ (ppm): 10.45 (s, 1H), 8.07 (s, 1H), 7.78 (s, 1H), 7.17-7.10 (m, 2H), 6.93 (bs, 1H), 3.85 (s, 3H), 3.44 (s, 2H). LC-MS m/z [M+H]$^+$: 214.1 with a purity of 98%.

2.1.16 Synthesis of 6-(1H-indol-5-yl)indolin-2-one (016)

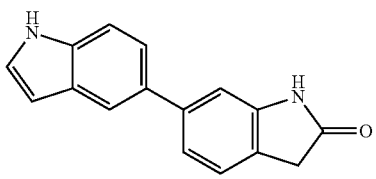 [SMILES: O=C1Cc2ccc(-c3ccc4[nH]ccc4c3)cc2N1]

$^1$H NMR (400 MHz, DMSO-d$_6$) δ (ppm): 11.13 (s, 1H), 10.41 (s, 1H), 7.63-7.56 (m, 2H), 7.41-7.36 (m, 1H), 7.29-7.20 (m, 3H), 7.05 (s, 1H), 6.44 (t, J=2.0 Hz, 1H), 3.50 (s, 2H). LC-MS m/z [M+H]$^+$: 249.1 with a purity of >99%.

2.1.17 Synthesis of 6-(1H-pyrrolo[2,3-b]pyridin-5-yl)indolin-2-one (017)

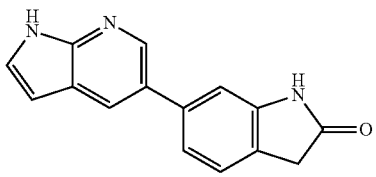 [SMILES: O=C1Cc2ccc(-c3cnc4[nH]ccc4c3)cc2N1]

$^1$H NMR (400 MHz, DMSO-d$_6$) δ (ppm): 11.69 (s, 1H), 10.46 (s, 1H), 8.44 (d, J=2.0 Hz, 1H), 8.13 (d, J=2.0 Hz, 1H), 7.53-7.48 (m, 1H), 7.29 (d, J=7.6 Hz, 1H), 7.25 (dd, J=7.6, 1.6 Hz, 1H), 7.06 (d, J=0.8 Hz, 1H), 6.50 (dd, J=3.6, 1.6 Hz, 1H), 3.52 (s, 2H). LC-MS m/z [M+H]$^+$: 250.1 with a purity of 95%.

2.1.18 Synthesis of 6-(4-(piperazin-1-ylmethyl)phenyl)indolin-2-one (018)

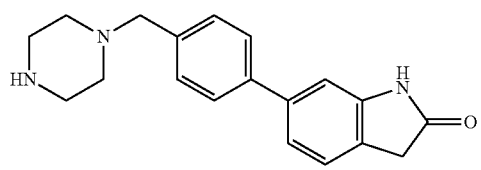

$^1$H NMR (400 MHz, DMSO-d$_6$) δ (ppm): 10.46 (s, 1H), 8.28 (s, 1H), 7.56 (d, J=8.0 Hz, 2H), 7.39-7.36 (m, 2H), 7.27 (d, J=7.6 Hz, 1H), 7.20 (d, J=7.6 Hz, 1H), 7.02 (bs 1H), 3.53-3.50 (m, 4H), 2.93-2.91 (m, 4H), 2.49-2.47 (m, 4H). LC-MS m/z [M+H]$^+$: 308.2 with a purity of 98%.

2.1.19 Synthesis of 6-(3-(piperazin-1-ylmethyl)phenyl)indolin-2-one (019)

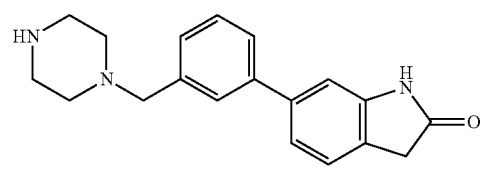 [SMILES: O=C1Cc2ccc(-c3cccc(CN4CCNCC4)c3)cc2N1]

$^1$H NMR (400 MHz, MeOD) δ (ppm): 7.60 (s, 1H), 7.54 (d, J=7.6 Hz, 1H), 7.44 (t, J=7.6 Hz, 1H), 7.36-7.34 (m, 2H), 7.27 (dd, J=7.6, 1.2 Hz, 1H), 7.14 (bs, 1H), 3.70 (s, 2H), 3.58 (s, 2H), 3.25-3.23 (m, 4H), 2.75-2.71 (m, 4H). LC-MS m/z [M+H]$^+$: 308.2 with a purity of 99%.

2.1.20 Synthesis of 6-(4-(piperazine-1-carbonyl)phenyl)indolin-2-one (020)

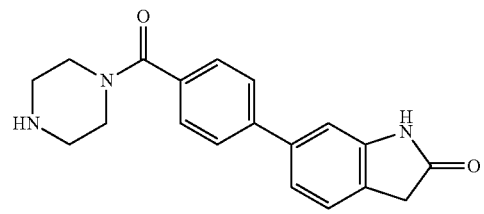 [SMILES: O=C1Cc2ccc(-c3ccc(C(=O)N4CCNCC4)cc3)cc2N1]

$^1$H NMR (400 MHz, MeOD) δ (ppm): 7.73 (d, J=8.2 Hz, 2H), 7.56 (d, J=8.2 Hz, 2H), 7.37-7.29 (m, 2H), 7.18 (bs, 1H), 3.91-3.74 (m, 4H), 3.32 (s, 2H), 3.25-3.13 (m, 4H), LC-MS m/z [M+H]$^+$: 322.2 with a purity of 95%.

2.1.21 Synthesis of 6-(3-(piperazine-1-carbonyl)phenyl)indolin-2-one (021)

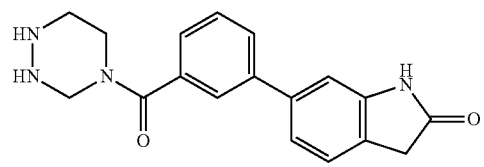

$^1$H NMR (400 MHz, DMSO-d$_6$) δ (ppm): 10.51 (s, 1H), 7.70-7.25 (m, 7H), 7.06 (bs, 1H), 3.52-3.47 (m, 6H), 3.30-2.81 (m, 4H). LC-MS m/z [M+H]$^+$: 322.2 with a purity of 94%.

2.1.22 Synthesis of N-methyl-4-(2-oxoindolin-6-yl)benzamide (022)

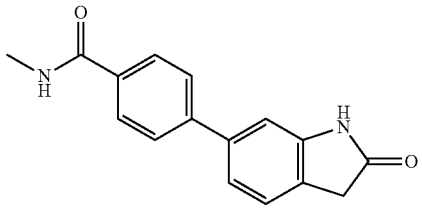 [SMILES: CNC(=O)c1ccc(-c2ccc3c(c2)NC(=O)C3)cc1]

$^1$H NMR (400 MHz, DMSO-d$_6$) δ (ppm): 10.45 (s, 1H), 10.01 (s, 1H), 7.65 (d, J=7.6 Hz, 2H), 7.53 (d, J=7.6 Hz, 2H), 7.25 (d, J=7.6 Hz, 1H), 7.18 (dd, J=7.6, 1.2 Hz, 1H), 7.00 (d, J=1.2 Hz, 1H), 3.49 (s, 2H), 2.06 (s, 3H). LC-MS m/z [M+H]$^+$: 267.1 with a purity of >99%.

2.1.23 Synthesis of N-methyl-3-(2-oxoindolin-6-yl)benzamide (023)

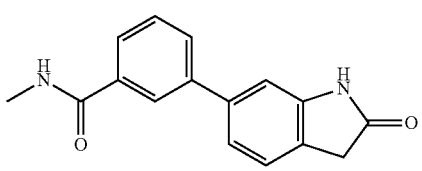 [SMILES: CNC(=O)c1cccc(-c2ccc3c(c2)NC(=O)C3)c1]

$^1$H NMR (400 MHz, DMSO-d$_6$) δ (ppm): 10.47 (s, 1H), 10.02 (s, 1H), 7.54 (d, J=8.4 Hz, 1H), 7.36 (t, J=7.6 Hz, 1H), 7.27 (m, 2H), 7.17 (dd, J=7.6, 1.6 Hz, 1H), 7.00 (d, J=1.2 Hz, 1H), 6.99 (d, J=1.2 Hz, 1H), 3.51 (s, 2H), 2.06 (s, 3H). LC-MS m/z [M+H]$^+$: 267.1 with a purity of 93%.

2.1.24 Synthesis of 2-oxo-N-phenylindoline-6-carboxamide (024)

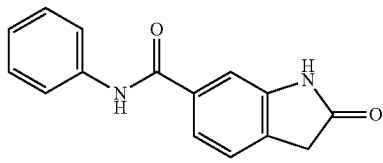 [SMILES: O=C1Cc2ccc(C(=O)Nc3ccccc3)cc2N1]

$^1$H NMR (400 MHz, DMSO-d$_6$) δ (ppm): 10.58 (s, 1H), 10.21 (s, 1H), 7.76 (d, J=7.6 Hz, 2H), 7.57 (dd, J=7.6, 1.2 Hz, 1H), 7.36-7.32 (m, 4H), 7.11-7.07 (m, 1H), 3.60 (s, 2H). LC-MS m/z [M+H]$^+$: 253.0 with a purity of 98%.

2.1.25 Synthesis of N-cyclohexyl-2-oxoindoline-6-carboxamide (025)

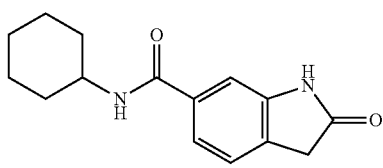 [SMILES: O=C1Cc2ccc(C(=O)NC3CCCCC3)cc2N1]

$^1$H NMR (400 MHz, DMSO-d$_6$) δ (ppm): 10.49 (s, 1H), 8.14 (d, J=7.6 Hz, 1H), 7.43 (dd, J=8.0, 1.2 Hz, 1H), 7.25-7.23 (m, 2H), 3.85-3.76 (m, 1H), 3.51 (s, 2H), 1.79-1.27 (m, 10H). LC-MS m/z [M+H]$^+$: 259.1 with a purity of 98%.

2.1.26 Synthesis of N-(1-acetylpiperidin-4-yl)-2-oxoindoline-6-carboxamide (026)

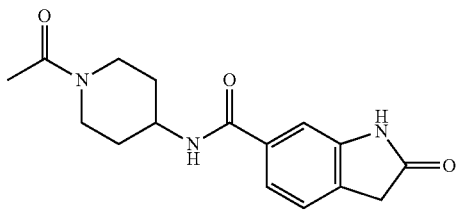 [SMILES: CC(=O)N1CCC(NC(=O)c2ccc3c(c2)NC(=O)C3)CC1]

$^1$H NMR (400 MHz, DMSO-d$_6$) δ (ppm): 10.34 (s, 1H), 9.86 (s, 1H), 7.34 (d, J=1.2 Hz, 1H), 7.08 (d, J=8.0 Hz, 1H), 7.02 (dd, J=8.0, 1.6 Hz, 1H), 4.40 (d, J=12.8 Hz, 1H), 3.86 (d, J=12.8 Hz, 1H), 3.38 (s, 2H), 3.08-3.01 (m, 1H), 2.59-2.56 (m, 2H), 2.00 (s, 3H), 1.81-1.24 (m, 4H). LC-MS m/z [M+H]$^+$: 302.1 with a purity of 96%.

2.1.27 Synthesis of N-(1-methylpiperidin-4-yl)-2-oxoindoline-6-carboxamide (027)

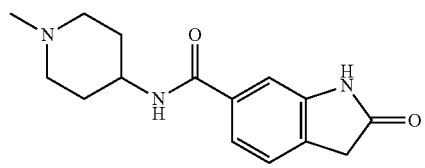 [SMILES: CN1CCC(NC(=O)c2ccc3c(c2)NC(=O)C3)CC1]

$^1$H NMR (400 MHz, MeOD) δ (ppm): 8.49 (s, 1H), 7.49 (dd, J=7.6, 1.6 Hz, 1H), 7.34 (d, J=7.6 Hz, 2H), 4.11-4.05 (m, 1H), 3.39-3.36 (m, 4H), 2.92 (t, J=11.6 Hz, 2H), 2.74 (s, 3H), 2.16 (d, J=11.6 Hz, 2H), 1.91-1.85 (m, 2H). LC-MS m/z [M+H]$^+$: 274.1 with a purity of 99%.

2.1.28 Synthesis of N-(2-(1-methylpiperidin-4-yl)ethyl)-2-oxoindoline-6-carboxamide (028)

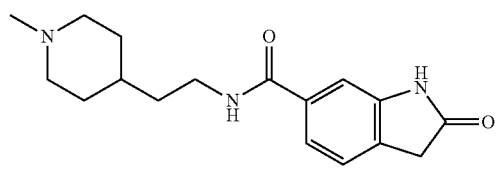 [SMILES: CN1CCC(CCNC(=O)c2ccc3c(c2)NC(=O)C3)CC1]

$^1$H NMR (400 MHz, DMSO-d$_6$) δ (ppm): 10.52 (s, 1H), 8.31 (t, J=5.6 Hz, 1H), 7.41 (dd, J=7.6, 1.2 Hz, 1H), 7.26 (d, J=7.6 Hz, 1H), 7.24 (s, 1H), 3.52 (s, 2H), 3.36-3.34 (m, 3H), 2.45-2.30 (m, 10H), 2.13 (s, 3H). LC-MS m/z [M+H]$^+$: 303.1 with a purity of 97%.

2.1.29 Synthesis of 6-(piperidine-1-carbonyl)indolin-2-one (029)

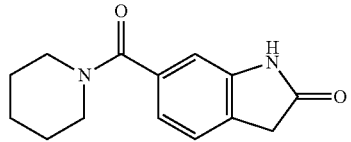 [SMILES: O=C1Cc2ccc(C(=O)N3CCCCC3)cc2N1]

$^1$H NMR (400 MHz, DMSO-d$_6$) δ (ppm): 10.43 (s, 1H), 7.24 (d, J=7.6, 1H), 6.90 (dd, J=7.6, 1.2 Hz, 1H), 6.74 (d, J=0.4 Hz, 1H), 3.50-3.31 (m, 6H), 1.61-1.48 (m, 6H). LC-MS m/z [M+H]$^+$: 245.1 with a purity of 99%.

2.1.30 Synthesis of 5-chloro-6-(piperidine-1-carbonyl)indolin-2-one (030)

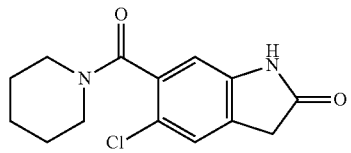 [SMILES: O=C1Cc2cc(Cl)c(C(=O)N3CCCCC3)cc2N1]

$^1$H NMR (400 MHz, DMSO-d$_6$) δ (ppm): 10.57 (s, 1H), 7.15 (s, 1H), 6.85 (s, 1H), 6.74 (d, J=0.4 Hz, 1H), 3.66-3.49 (m, 4H), 3.14-3.10 (m, 2H), 1.59-1.53 (m, 6H). LC-MS m/z [M+H]$^+$: 279.0 with a purity of 98%.

2.1.31 Synthesis of 2-oxo-N-(pyridin-4-yl)indoline-6-carboxamide (031)

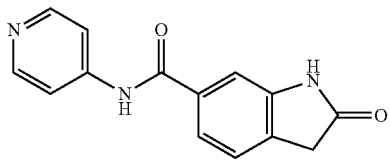 [SMILES: O=C1Cc2ccc(C(=O)Nc3ccncc3)cc2N1]

$^1$H NMR (400 MHz, DMSO-d$_6$) δ (ppm): 10.61 (s, 1H), 10.56 (s, 1H), 8.46 (d, J=1.6 Hz, 2H), 7.78 (dd, J=4.8, 1.2 Hz, 2H), 7.59 (dd, J=7.6, 1.6 Hz, 1H), 7.38-7.35 (m, 2H), 3.58 (s, 2H). LC-MS m/z [M+H]$^+$: 254.0 with a purity of 95%.

2.1.32 Synthesis of N-(2-oxoindolin-6-yl)isonicotinamide (032)

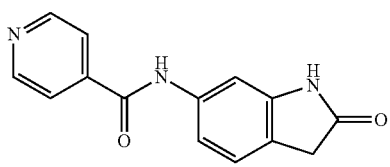 [SMILES: O=C1Cc2ccc(NC(=O)c3ccncc3)cc2N1]

$^1$H NMR (400 MHz, DMSO-d$_6$) δ (ppm): 10.44 (s, 2H), 8.78 (dd, J=8.4, 1.6 Hz, 2H), 7.84 (dd, J=8.4, 1.6 Hz, 2H), 7.47 (d, J=1.6 Hz, 1H), 7.28 (dd, J=8.0, 1.6 Hz, 1H), 7.17 (d, J=8.0 Hz, 1H), 3.44 (s, 2H). LC-MS m/z [M+H]$^+$: 254.0 with a purity of 97%.

2.1.33 Synthesis of 2-oxo-N-(pyridin-3-ylmethyl)indoline-6-carboxamide (033)

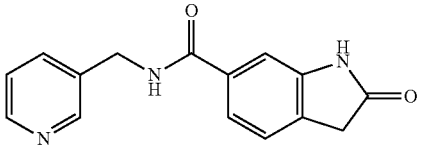 [SMILES: O=C1Cc2ccc(C(=O)NCc3cccnc3)cc2N1]

$^1$H NMR (400 MHz, DMSO-d$_6$) δ (ppm): 10.53 (s, 1H), 9.04 (t, J=5.2 Hz, 1H), 8.54 (d, J=2.0 Hz, 1H), 8.46-8.44 (m, 1H), 7.70 (d, J=7.6 Hz, 1H), 7.48 (dd, J=7.6, 1.6 Hz, 1H), 7.36-7.27 (m, 3H), 4.46 (d, J=5.6 Hz, 2H), 3.53 (s, 2H). LC-MS m/z [M+H]$^+$: 268.1 with a purity of 97%.

2.1.34 Synthesis of 6-(piperidin-4-yloxy)indolin-2-one (034)

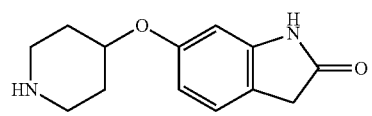 [SMILES: O=C1Cc2ccc(OC3CCNCC3)cc2N1]

$^1$H NMR (400 MHz, DMSO-d$_6$) δ (ppm): 10.25 (s, 1H), 7.05 (d, J=8.4 Hz, 1H), 6.47 (dd, J=8.0, 1.6 Hz, 1H), 6.38 (d, J=1.6 Hz, 1H), 4.34-4.31 (m, 1H), 4.46 (d, J=5.6 Hz, 2H), 3.35-3.32 (m, 3H), 2.95-2.92 (m, 2H), 2.59-2.51 (m, 2H), 1.90-1.87 (m, 4H). LC-MS m/z [M+H]$^+$: 233.1 with a purity of 99%.

2.1.35 Synthesis of 6-((2-chloropyrimidin-4-yl)oxy)indolin-2-one (035)

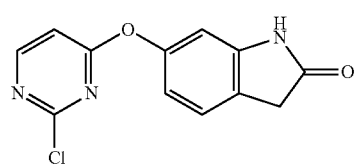 [SMILES: O=C1Cc2ccc(Oc3ccnc(Cl)n3)cc2N1]

$^1$H NMR (400 MHz, DMSO-d$_6$) δ (ppm): 10.52 (s, 1H), 8.60 (d, J=2.0 Hz, 1H), 7.28 (d, J=8.0 Hz, 1H), 7.14 (d, J=5.6 Hz, 1H), 6.78 (dd, J=8.0, 2.4 Hz, 1H), 6.70 (d, J=2.4 Hz, 1H), 3.51 (s, 2H). LC-MS m/z [M+H]$^+$: 262.0 with a purity of 98%.

2.1.36 Synthesis of methyl 2-((2-oxoindolin-6-yl)oxy)acetate (036)

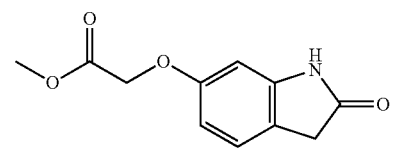 [SMILES: COC(=O)COc1ccc2c(c1)NC(=O)C2]

¹H NMR (400 MHz, DMSO-d₆) δ (ppm): 10.30 (s, 1H), 7.07 (d, J=8.0 Hz, 1H), 6.46 (dd, J=8.0, 2.4 Hz, 1H), 6.37 (d, J=2.4 Hz, 1H), 4.75 (s, 2H), 3.69 (s, 3H), 3.37 (s, 2H). LC-MS m/z [M+H]⁺: 222.0 with a purity of 98%.

2.1.37 Synthesis of 7-(pyridin-4-yl)indolin-2-one (037)

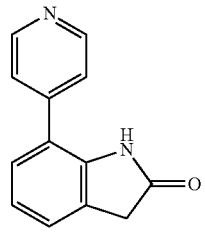 [SMILES: O=C1Cc2cccc(-c3ccncc3)c2N1]

¹H NMR (400 MHz, CDCl₃) δ (ppm): 8.71 (d, J=5.6 Hz, 2H), 7.83 (bs, 1H), 7.36 (d, J=5.6 Hz, 2H), 7.30-7.25 (m, 2H), 7.16-7.12 (m, 1H), 3.62 (s, 2H). LC-MS m/z [M+H]⁺: 211.1 with a purity of >99%.

2.1.38 Synthesis of 4-(pyridin-4-yl)indolin-2-one (038)

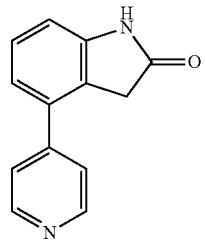 [SMILES: O=C1Cc2c(cccc2-c2ccncc2)N1]

¹H NMR (400 MHz, DMSO-d₆) δ (ppm): 10.51 (s, 1H), 8.64 (d, J=4.4 Hz, 2H), 7.60 (dd, J=4.4, 1.6 Hz, 2H), 7.33 (t, J=7.6 Hz, 1H), 7.11 (d, J=7.6 Hz, 1H), 6.91 (d, J=7.6 Hz, 1H), 3.65 (s, 2H). LC-MS m/z [M+H]⁺: 211.1 with a purity of 97%.

2.1.39 Synthesis of 5-(pyridin-4-yl)indolin-2-one (039)

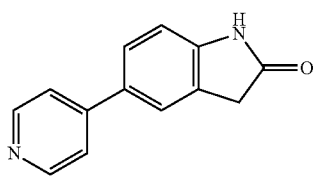

¹H NMR (400 MHz, DMSO-d₆) δ (ppm): 10.56 (s, 1H), 8.56 (d, J=6.0 Hz, 2H), 7.68-7.63 (m, 4H), 6.94 (d, J=8.0 Hz, 1H), 3.56 (s, 2H). LC-MS m/z [M+H]⁺: 211.1 with a purity of 97%.

2.1.40 Synthesis of 5-(2-aminopyridin-4-yl)indolin-2-one (040)

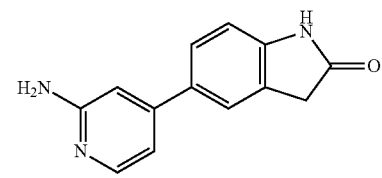 [SMILES: Nc1cc(-c2ccc3c(c2)CC(=O)N3)ccn1]

¹H NMR (400 MHz, DMSO-d₆) δ (ppm): 10.51 (s, 1H), 8.13 (s, 1H), 7.91 (dd, J=5.2 Hz, 1H), 7.49 (s, 1H), 6.90 (d, J=8.0 Hz, 1H), 6.74 (dd, J=5.6, 1.6 Hz, 1H), 6.66 (bs, 1H), 5.95 (s, 2H), 3.54 (s, 2H). LC-MS m/z [M+H]⁺: 225.9 with a purity of 98%.

2.1.41 Synthesis of 5-(2-methoxypyridin-4-yl)indolin-2-one (041)

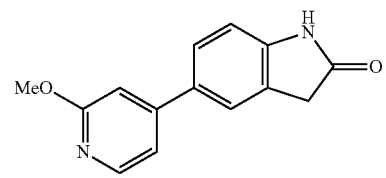 [SMILES: COc1cc(-c2ccc3c(c2)CC(=O)N3)ccn1]

¹H NMR (400 MHz, DMSO-d₆) δ (ppm): 10.54 (s, 1H), 8.16 (d, J=5.2 Hz, 1H), 7.65-7.61 (m, 2H), 7.25 (dd, J=5.2, 1.2 Hz, 1H), 7.02 (s, 1H), 6.92 (d, J=8.0 Hz, 1H), 3.88 (s, 3H), 3.55 (s, 2H). LC-MS m/z [M+H]⁺: 241.1 with a purity of 97%.

2.1.42 Synthesis of 5-(2-aminopyridin-3-yl)indolin-2-one (042)

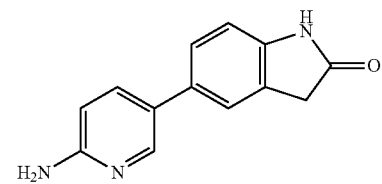 [SMILES: Nc1ccc(-c2ccc3c(c2)CC(=O)N3)cn1]

¹H NMR (400 MHz, DMSO-d₆) δ (ppm): 10.37 (s, 1H), 8.15-8.13 (m, 1H), 7.62 (dd, J=8.4, 2.4 Hz, 1H), 7.39 (s, 1H), 7.32 (dd, J=8.0, 1.6 Hz, 1H), 6.83 (d, J=8.0 Hz, 1H), 6.49 (d, J=8.4 Hz, 1H), 5.96 (s, 2H), 3.50 (s, 2H). LC-MS m/z [M+H]⁺: 225.9 with a purity of 98%.

2.1.43 Synthesis of 5-(6-amino-4-methylpyridin-3-yl)indolin-2-one (043)

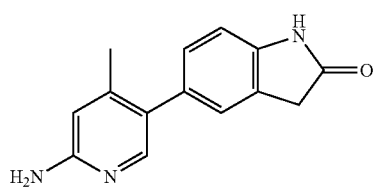 [SMILES: Cc1cc(N)ncc1-c1ccc2c(c1)CC(=O)N2]

¹H NMR (400 MHz, DMSO-d₆) δ (ppm): 10.33 (s, 1H), 7.07-7.01 (m, 2H), 6.82-6.79 (m, 1H), 6.45-6.41 (m, 2H), 4.97 (s, 2H), 3.47 (s, 2H), 2.10 (s, 3H). LC-MS m/z [M+H]⁺: 240.1 with a purity of >99%.

2.1.44 Synthesis of 5-(6-amino-2-methylpyridin-3-yl)indolin-2-one (044)

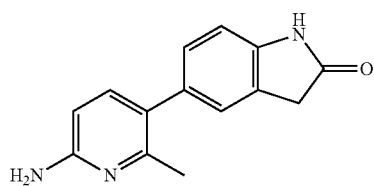 [SMILES: Cc1nc(N)ccc1-c1ccc2c(c1)CC(=O)N2]

¹H NMR (400 MHz, DMSO-d₆) δ (ppm): 10.37 (s, 1H), 7.17 (d, J=8.0 Hz, 1H), 7.11 (s, 1H), 7.06 (d, J=8.0 Hz, 1H), 6.82 (d, J=8.0 Hz, 1H), 6.32 (d, J=8.0 Hz, 1H), 5.82 (s, 2H), 3.49 (s, 2H), 2.22 (s, 3H). LC-MS m/z [M+H]⁺: 240.1 with a purity of >99%.

2.1.45 Synthesis of 5-(2-aminopyridin-3-yl)indolin-2-one 045)

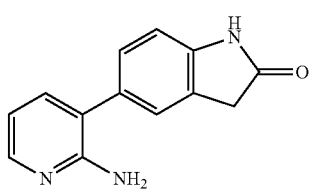 [SMILES: Nc1ncccc1-c1ccc2c(c1)CC(=O)N2]

¹H NMR (400 MHz, DMSO-d₆) δ (ppm): 10.45 (s, 1H), 7.91 (d, J=4.4 Hz, 1H), 7.28-7.26 (m, 2H), 7.21 (d, J=8.0 Hz, 1H), 6.89 (d, J=8.0 Hz, 1H), 6.64 (d, J=5.2 Hz, 1H), 5.50 (s, 2H), 3.51 (s, 2H). LC-MS m/z [M+H]⁺: 226.1 with a purity of >99%.

2.1.46 Synthesis of 5-(6-(methylamino)pyridin-3-yl)indolin-2-one (046)

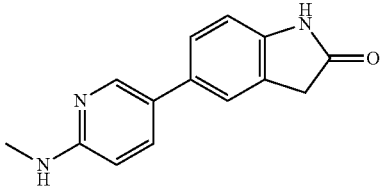 [SMILES: CNc1ccc(-c2ccc3c(c2)CC(=O)N3)cn1]

¹H NMR (400 MHz, DMSO-d₆) δ (ppm): 10.36 (s, 1H), 8.23 (s, 1H), 8.13 (s, 1H), 7.62 (d, J=8.0 Hz, 1H), 7.40 (s, 1H), 7.34 (d, J=8.0 Hz, 1H), 6.84 (d, J=8.0 Hz, 1H), 6.49 (d, J=8.0 Hz, 1H), 3.50 (s, 2H), 2.79 (d, J=4.4 Hz, 3H). LC-MS m/z [M+H]⁺: 240.1 with a purity of 99%.

2.1.47 Synthesis of 5-(2-(methylamino)pyridin-4-yl)indolin-2-one 047)

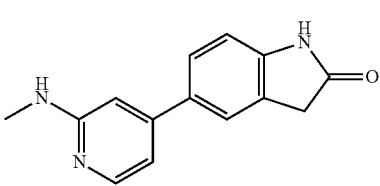 [SMILES: CNc1cc(-c2ccc3c(c2)CC(=O)N3)ccn1]

¹H NMR (400 MHz, DMSO-d₆) δ (ppm): 10.51 (s, 1H), 7.99 (d, J=5.2 Hz, 1H), 7.50-7.48 (m, 2H), 6.90 (d, J=8.0 Hz, 1H), 6.71 (d, J=5.2 Hz, 1H), 6.61 (s, 1H), 6.41 (d, J=4.4 Hz, 1H), 3.54 (s, 2H), 2.79 (d, J=4.4 Hz, 3H). LC-MS m/z [M+H]⁺: 240.1 with a purity of >99%.

2.1.48 Synthesis of N-(3-methyl-5-(2-oxoindolin-5-yl)pyridin-2-yl)acetamide (048)

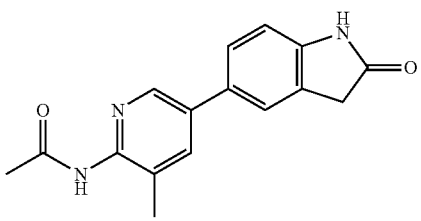 [SMILES: CC(=O)Nc1ncc(-c2ccc3c(c2)CC(=O)N3)cc1C]

¹H NMR (400 MHz, DMSO-d₆) δ (ppm): 10.48 (s, 1H), 9.97 (s, 1H), 8.47 (s, 1H), 7.88 (s, 1H), 7.58 (s, 1H), 7.52 (d, J=8.0 Hz, 1H), 6.91 (d, J=8.0 Hz, 1H), 3.54 (s, 2H), 2.20 (s, 3H), 2.06 (s, 3H). LC-MS m/z [M+H]⁺: 282.1 with a purity of 99%.

2.1.49 Synthesis of N-(6-methyl-5-(2-oxoindolin-5-yl)pyridin-2-yl)acetamide (049)

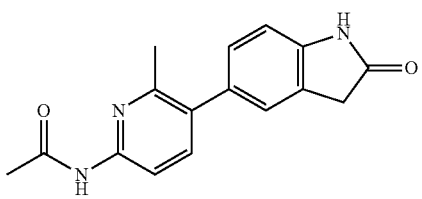 [SMILES: CC(=O)Nc1ccc(-c2ccc3c(c2)CC(=O)N3)c(C)n1]

$^1$H NMR (400 MHz, DMSO-d$_6$) δ (ppm): 10.48 (s, 1H), 10.44 (s, 1H), 7.94 (d, J=8.4 Hz, 1H), 7.54 (d, J=8.4 Hz, 1H), 7.21 (s, 1H), 7.16 (d, J=8.0 Hz, 1H), 6.87 (d, J=8.0 Hz, 1H), 3.55 (s, 2H), 2.31 (s, 3H), 2.09 (s, 3H). LC-MS m/z [M+H]$^+$: 282.1 with a purity of 98%.

2.1.50 Synthesis of N-(4-methyl-5-(2-oxoindolin-5-yl)pyridin-2-yl)acetamide (050)

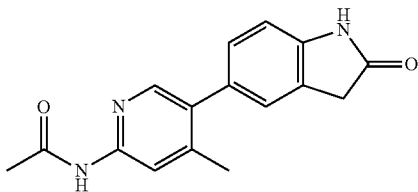 [SMILES: CC(=O)Nc1cc(C)c(-c2ccc3c(c2)CC(=O)N3)cn1]

$^1$H NMR (400 MHz, DMSO-d$_6$) δ (ppm): 10.45 (s, 1H), 10.42 (s, 1H), 8.06 (s, 1H), 8.00 (s, 1H), 7.23 (s, 1H), 7.16 (d, J=8.0 Hz, 1H), 6.89 (d, J=8.0 Hz, 1H), 3.52 (s, 2H), 2.25 (s, 3H), 2.09 (s, 3H). LC-MS m/z [M+H]$^+$: 282.1 with a purity of 99%.

2.1.51 Synthesis of 5-phenylindolin-2-one (051)

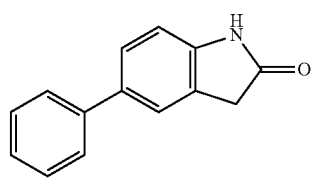 [SMILES: O=C1Cc2cc(-c3ccccc3)ccc2N1]

$^1$H NMR (400 MHz, DMSO-d$_6$) δ (ppm): 10.44 (s, 1H), 7.60-7.57 (m, 2H), 7.57-7.40 (m, 4H), 7.30 (t, J=8.0 Hz, 1H), 6.89 (d, J=8.0 Hz, 1H), 3.53 (s, 2H). LC-MS m/z [M+H]$^+$: 210.0 with a purity of 99%.

2.1.52 Synthesis of tert-butyl 4-(4-(2-oxoindolin-5-yl)benzoyl)piperazine-1-carboxylate (052)

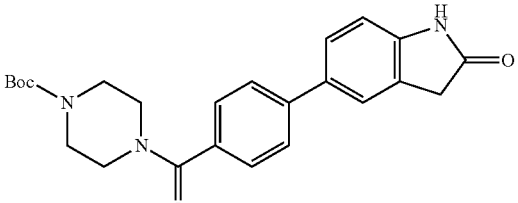

$^1$H NMR (400 MHz, DMSO-d$_6$) δ (ppm): 10.45 (s, 1H), 7.66 (d, J=8.0 Hz, 2H), 7.56 (s, 1H), 7.52 (d, J=8.0 Hz, 1H), 7.46 (d, J=8.0 Hz, 2H), 6.91 (d, J=8.0 Hz, 1H), 3.54-3.38 (m, 10H), 1.41 (s, 9H). LC-MS m/z [M+H]$^+$: 422.2 with a purity of 97%.

2.1.53 Synthesis of tert-butyl 4-(3-(2-oxoindolin-5-yl)benzoyl)piperazine-1-carboxylate (053)

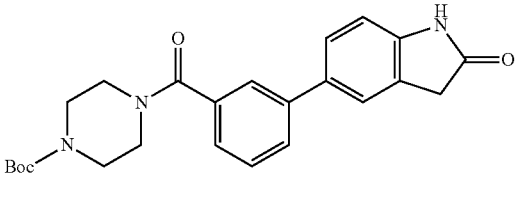 [SMILES: CC(C)(C)OC(=O)N1CCN(C(=O)c2cccc(-c3ccc4c(c3)CC(=O)N4)c2)CC1]

$^1$H NMR (400 MHz, DMSO-d$_6$) δ (ppm): 10.46 (s, 1H), 7.68 (d, J=8.0 Hz, 1H), 7.59 (s, 1H), 7.56 (s, 1H), 7.52-7.49 (m, 2H), 7.32 (d, J=8.0 Hz, 1H), 6.90 (d, J=8.0 Hz, 1H), 3.53-3.37 (m, 10H), 1.41 (s, 9H). LC-MS m/z [M+H]$^+$: 422.2 with a purity of >99%.

2.1.54 Synthesis of 5-(4-(piperazine-1-carbonyl)phenyl)indolin-2-one (054)

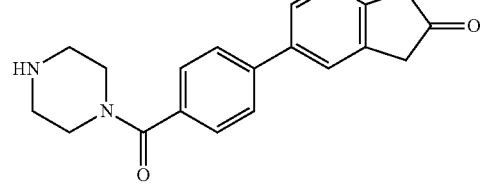

$^1$H NMR (400 MHz, MeOD) δ (ppm): 7.72 (d, J=8.4 Hz, 2H), 7.58-7.53 (m, 4H), 7.01 (d, J=8.0 Hz, 1H), 3.87-3.59 (m, 4H), 3.33-3.26 (m, 6H). LC-MS m/z [M+H]$^+$: 322.1 with a purity of 96%.

21.56 Synthesis of 5-(3-(piperazine-1-carbonyl)phenyl)indolin-2-one (055)

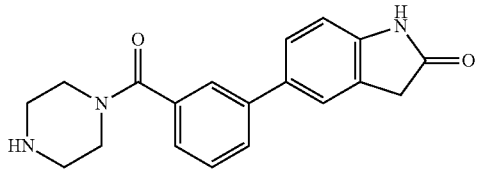 [SMILES: O=C1Cc2cc(-c3cccc(C(=O)N4CCNCC4)c3)ccc2N1]

$^1$H NMR (400 MHz, DMSO-d$_6$) δ (ppm): 10.50 (s, 1H), 7.70-7.35 (m, 6H), 6.92 (d, J=6.8 Hz, 1H), 3.61-3.02 (m, 11H). LC-MS m/z [M+H]$^+$: 322.1 with a purity of >99%.

2.1.57 Synthesis of 5-(pyridin-3-yl)indolin-2-one (056)

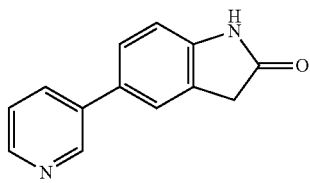 [SMILES: O=C1Cc2cc(-c3cccnc3)ccc2N1]

$^1$H NMR (400 MHz, DMSO-d$_6$) δ (ppm): 10.50 (s, 1H), 8.83 (d, J=2.4 Hz, 1H), 8.51 (dd, J=4.8, 1.6 Hz, 1H), 8.01-7.98 (m, 1H), 7.58-7.52 (m, 2H), 7.44 (dd, J=8.0, 4.8 Hz, 1H), 6.93 (d, J=8.0 Hz, 1H), 3.55 (s, 2H). LC-MS m/z [M+H]$^+$: 211.1 with a purity of >99%.

2.1.58 Synthesis of 5-(6-(piperidin-1-yl)pyridin-3-yl)indolin-2-one (057)

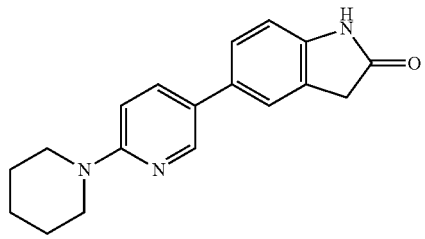 [SMILES: O=C1Cc2cc(-c3ccc(N4CCCCC4)nc3)ccc2N1]

$^1$H NMR (400 MHz, DMSO-d$_6$) δ (ppm): 10.34 (s, 1H), 8.33 (d, J=2.4 Hz, 1H), 7.74 (dd, J=8.0, 2.4 Hz, 1H), 7.44 (s, 1H), 7.39 (d, J=8.0 Hz, 1H), 6.93 (d, J=8.0 Hz, 2H), 3.54-3.50 (m, 6H), 1.61-1.54 (m, 6H). LC-MS m/z [M+H]$^+$: 294.1 with a purity of 99%.

2.1.59 Synthesis of 5-(piperidine-1-carbonyl)indolin-2-one (058)

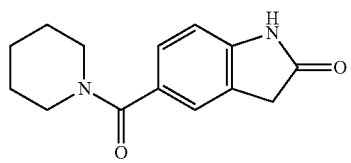 [SMILES: O=C1Cc2cc(C(=O)N3CCCCC3)ccc2N1]

$^1$H NMR (400 MHz, DMSO-d$_6$) δ (ppm): 10.51 (s, 1H), 7.20 (d, J=2.4 Hz, 2H), 6.83 (d, J=8.0 Hz, 1H), 3.50 (s, 2H), 3.43-3.31 (m, 4H), 1.61-1.49 (m, 6H). LC-MS m/z [M+H]$^+$: 245.1 with a purity of 98%.

2.1.60 Synthesis of N-(2-oxoindolin-5-yl)isonicotinamide (059)

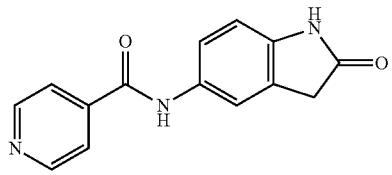 [SMILES: O=C1Cc2cc(NC(=O)c3ccncc3)ccc2N1]

$^1$H NMR (400 MHz, DMSO-d$_6$) δ (ppm): 10.38-10.35 (m, 2H), 8.77 (d, J=6.0 Hz, 2H), 7.84 (d, J=6.0 Hz, 2H), 7.65 (s, 1H), 7.52 (d, J=8.4 Hz, 1H), 6.80 (d, J=8.4 Hz, 1H), 3.50 (s, 2H). LC-MS m/z [M+H]$^+$: with a purity of 94%.

2.1.60 Synthesis of 1-acetyl-N-(2-oxoindolin-5-yl)piperidine-4-carboxamide (060)

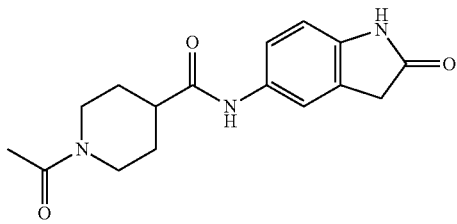 [SMILES: CC(=O)N1CCC(C(=O)Nc2ccc3c(c2)CC(=O)N3)CC1]

$^1$H NMR (400 MHz, DMSO-d$_6$) δ (ppm): 10.26 (s, 1H), 9.74 (s, 1H), 7.50 (s, 1H), 7.33 (dd, J=8.4, 2.0 Hz, 1H), 6.71 (d, J=8.4 Hz, 1H), 4.39 (d, J=13.2 Hz, 1H), 3.86 (d, J=13.2 Hz, 1H), 3.44 (s, 2H), 3.08-3.02 (m, 1H), 2.60-2.52 (m, 2H), 2.00 (s, 3H), 1.80-1.38 (m, 4H). LC-MS m/z [M+H]$^+$: 302.1 with a purity of 99%.

2.1.61 Synthesis of 3,3-difluoro-6-(pyridin-4-yl)indolin-2-one (061)

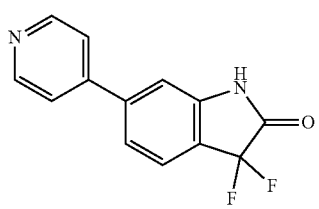 [SMILES: O=C1Nc2cc(-c3ccncc3)ccc2C1(F)F]

$^1$H NMR (400 MHz, DMSO-d$_6$) δ (ppm): 8.68 (d, J=5.6 Hz, 2H), 7.80 (d, J=7.6 Hz, 1H), 7.71 (d, J=5.6 Hz, 2H), 7.55 (d, J=7.6 Hz, 1H), 7.28 (s, 1H). LC-MS m/z [M+H]$^+$: 247.0 with a purity of 98%.

2.1.62 Synthesis of 3,3-dimethyl-6-(pyridin-4-yl)indolin-2-one (062)

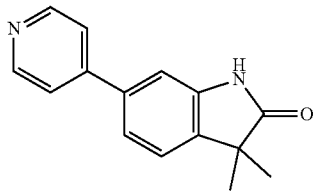 [SMILES: CC1(C)C(=O)Nc2cc(-c3ccncc3)ccc21]

$^1$H NMR (400 MHz, DMSO-$d_6$) δ (ppm): 10.49 (s, 1H), 8.62 (d, J=5.6 Hz, 2H), 7.64 (d, J=5.6 Hz, 2H), 7.44-7.36 (m, 2H), 7.15 (d, J=1.6 Hz, 1H), 1.29 (s, 6H). LC-MS m/z [M+H]$^+$: 239.1 with a purity of 99%.

2.1.63 Synthesis of benzyl 4-(2-oxoindolin-6-yl)-3,6-dihydropyridine-1(2H)-carboxylate (063)

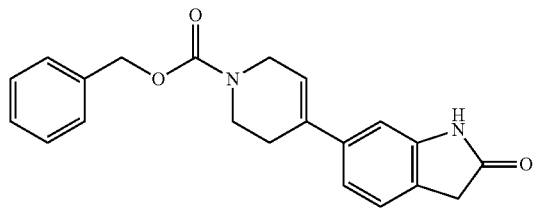 [SMILES: O=C1Cc2ccc(C3=CCN(C(=O)OCc4ccccc4)CC3)cc2N1]

$^1$H NMR (400 MHz, DMSO-$d_6$) δ (ppm): 10.37 (s, 1H), 7.35-7.31 (m, 5H), 7.16 (d, J=8.0 Hz, 1H), 7.00 (dd, J=8.0, 1.6 Hz, 1H), 6.82 (s, 1H), 6.09 (s, 1H), 5.12 (s, 2H), 4.07 (bs, 2H), 3.61 (bs, 2H), 3.44 (s, 2H), 2.46 (bs, 2H). LC-MS m/z [M+H]$^+$: 349.1 with a purity of 99%.

2.1.64 Synthesis of 6-(6-(piperidin-1-yl)pyridin-3-yl)indolin-2-one (064)

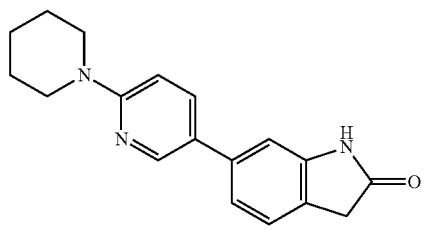 [SMILES: O=C1Cc2ccc(-c3ccc(N4CCCCC4)nc3)cc2N1]

$^1$H NMR (400 MHz, DMSO-$d_6$) δ (ppm): 10.44 (s, 1H), 8.38 (d, J=2.4 Hz, 1H), 8.26 (s, 1H), 7.81 (dd, J=8.8, 2.4 Hz, 1H), 7.24 (d, J=7.6 Hz, 1H), 7.16 (dd, J=7.6, 1.2 Hz, 1H), 6.97 (s, 1H), 6.91 (d, J=8.4 Hz, 1H), 3.59-3.57 (m, 4H), 3.48 (s, 2H), 3.00-2.98 (m, 4H). LC-MS m/z [M+H]$^+$: 294.2 with a purity of 99%.

21.65 Synthesis of 6-(6-(piperazin-1-yl)pyridin-3-yl)indolin-2-one (065)

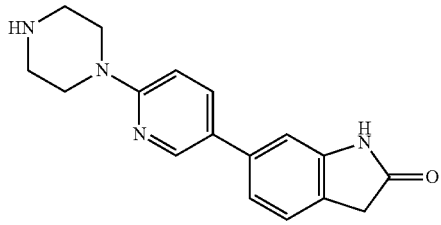 [SMILES: O=C1Cc2ccc(-c3ccc(N4CCNCC4)nc3)cc2N1]

$^1$H NMR (400 MHz, DMSO-$d_6$) δ (ppm): 10.44 (s, 1H), 8.38 (d, J=2.4 Hz, 1H), 8.26 (s, 1H), 7.81 (dd, J=8.8, 2.4 Hz, 1H), 7.24 (d, J=7.6 Hz, 1H), 7.16 (dd, J=7.6, 1.2 Hz, 1H), 6.97 (s, 1H), 6.91 (d, J=8.4 Hz, 1H), 3.59-3.57 (m, 4H), 3.48 (s, 2H), 3.00-2.98 (m, 4H). LC-MS m/z [M+H]$^+$: 295.1 with a purity of 96%.

2.1.66 Synthesis of ethyl 4-(2-oxoindolin-6-yl)picolinate (066)

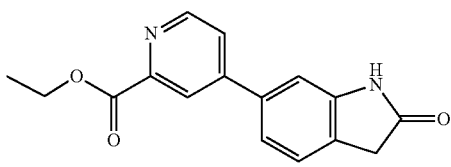 [SMILES: CCOC(=O)c1cc(-c2ccc3c(c2)NC(=O)C3)ccn1]

$^1$H NMR (400 MHz, DMSO-$d_6$) δ (ppm): 10.54 (s, 1H), 8.75 (d, J=4.8 Hz, 1H), 8.22 (d, J=1.6 Hz, 1H), 7.92 (dd, J=4.8, 1.6 Hz, 1H), 7.45-7.35 (m, 2H), 7.18 (d, J=1.2 Hz, 1H), 4.38 (q, J=7.2 Hz, 2H), 3.56 (s, 2H), 1.36 (t, J=7.2 Hz, 3H). LC-MS m/z [M+H]$^+$: 283.1 with a purity of 97%.

2.1.67 Synthesis of 5-(4-methylpiperazine-1-carbonyl)indolin-2-one (067)

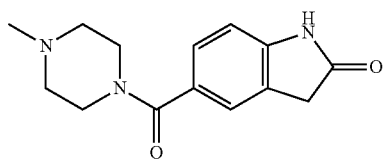 [SMILES: CN1CCN(C(=O)c2ccc3c(c2)CC(=O)N3)CC1]

$^1$H NMR (400 MHz, DMSO-$d_6$) δ (ppm): 10.53 (s, 1H), 7.23-7.21 (m, 2H), 6.83 (d, J=8.0 Hz, 1H), 3.50 (s, 2H), 3.49-3.40 (m, 4H), 2.30-2.28 (m, 4H), 2.19 (s, 3H). LC-MS m/z [M+H]$^+$: 260.1 with a purity of 99%.

2.1.68 Synthesis of 5-(4-phenylpiperidine-1-carbonyl)indolin-2-one (068)

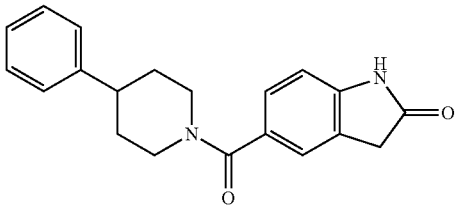 [SMILES: O=C1Cc2cc(C(=O)N3CCC(c4ccccc4)CC3)ccc2N1]

$^1$H NMR (400 MHz, DMSO-d$_6$) δ (ppm): 10.50 (s, 1H), 7.28-7.18 (m, 7H), 6.84 (d, J=8.0 Hz, 1H), 3.51 (s, 2H), 2.98-2.76 (m, 4H), 1.80-1.55 (m, 5H). LC-MS m/z [M+H]$^+$: 321.1 with a purity of 99%.

2.1.69 Synthesis of 5-(4-benzylpiperidine-1-carbonyl)indolin-2-one (069)

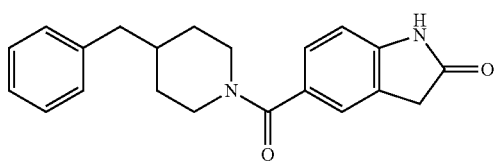 [SMILES: O=C1Cc2cc(C(=O)N3CCC(Cc4ccccc4)CC3)ccc2N1]

$^1$H NMR (400 MHz, DMSO-d$_6$) δ (ppm): 10.27 (s, 1H), 7.28-7.15 (m, 7H), 6.82 (d, J=7.6 Hz, 1H), 4.03 (d, J=13.6 Hz, 2H), 3.47 (s, 2H), 2.87-2.80 (m, 2H), 2.55-2.53 (m, 2H), 1.85-1.76 (m, 1H), 1.61-1.13 (m, 4H). LC-MS m/z [M+H]$^+$: 335.1 with a purity of 99%.

2.1.70 Synthesis of 6-(6-fluoropyridin-3-yl)indolin-2-one (070)

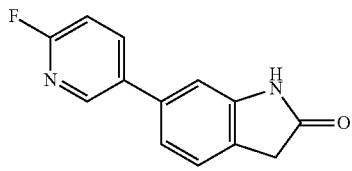 [SMILES: O=C1Cc2ccc(-c3ccc(F)nc3)cc2N1]

$^1$H NMR (400 MHz, DMSO-d$_6$) δ (ppm): 10.52 (s, 1H), 8.48 (d, J=2.8 Hz, 1H), 8.24-8.20 (m, 1H), 7.32 (d, J=7.6 Hz, 1H), 7.28-7.23 (m, 2H), 7.05 (s, 1H), 3.53 (s, 2H). LC-MS m/z [M+H]$^+$: 229.0 with a purity of 99%.

2.1.71 Synthesis of N-(2-oxoindolin-6-yl)nicotinamide (071)

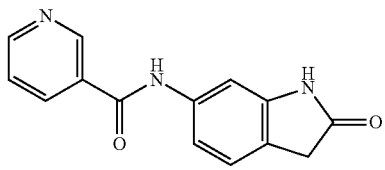 [SMILES: O=C1Cc2ccc(NC(=O)c3cccnc3)cc2N1]

$^1$H NMR (400 MHz, DMSO-d$_6$) δ (ppm): 10.44 (s, 1H), 10.39 (s, 1H), 9.08 (d, J=1.6 Hz, 1H), 8.75-8.74 (m, 1H), 8.29-8.26 (m, 1H), 7.58-7.54 (m, 1H), 7.47 (d, J=1.6 Hz, 1H), 7.27 (d, J=8.0, 1.6 Hz, 1H), 7.17 (d, J=8.0 Hz, 1H), 3.44 (s, 2H). LC-MS m/z [M+H]$^+$: 254.0 with a purity of 99%.

21.72 Synthesis of N-(2-oxoindolin-5-yl)nicotinamide (072)

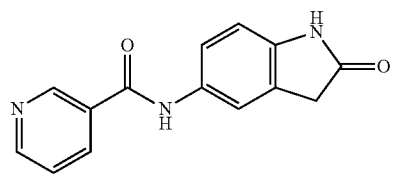 [SMILES: O=C1Cc2cc(NC(=O)c3cccnc3)ccc2N1]

$^1$H NMR (400 MHz, DMSO-d$_6$) δ (ppm): 10.34 (s, 1H), 10.30 (s, 1H), 9.08 (d, J=1.6 Hz, 1H), 8.75 (dd, J=4.8, 1.6 Hz, 1H), 8.28-8.25 (m, 1H), 7.65 (s, 1H), 7.57-7.51 (m, 2H), 6.80 (d, J=8.4 Hz, 1H), 3.53 (s, 2H). LC-MS m/z [M+H]$^+$: 254.0 with a purity of 98%.

2.1.73 Synthesis of 5-(pyridin-4-yl)-1,3-dihydro-2H-pyrrolo[2,3-c]pyridin-2-one (073)

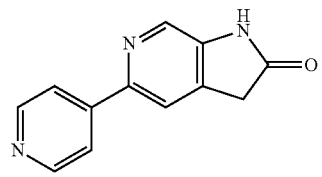

$^1$H NMR (400 MHz, DMSO-d$_6$) δ (ppm): 10.34 (s, 1H), 10.30 (s, 1H), 9.08 (d, J=1.6 Hz, 1H), 8.75 (dd, J=4.8, 1.6 Hz, 1H), 8.28-8.25 (m, 1H), 7.65 (s, 1H), 7.57-7.51 (m, 2H), 6.80 (d, J=8.4 Hz, 1H), 4.29 (s, 2H). LC-MS m/z [M+H]$^+$: 212.1 with a purity of 90%.

2.1.74 Synthesis of 6-(pyridin-4-yl)-1,3-dihydro-2H-pyrrolo[3,2-c]pyridin-2-one (074)

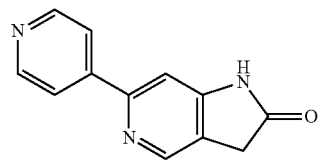

$^1$H NMR (400 MHz, DMSO-d$_6$) δ (ppm): 10.98 (s, 1H), 8.67 (d, J=6.0 Hz, 2H), 8.41 (s, 1H), 7.98 (dd, J=4.4, 1.6 Hz, 2H), 7.44 (s, 1H), 3.63 (s, 2H). LC-MS m/z [M+H]$^+$: 212.1 with a purity of 95%.

21.75 Synthesis of 6-(pyridin-4-yl)-1,3-dihydro-2H-pyrrolo[3,2-b]pyridin-2-one (075)

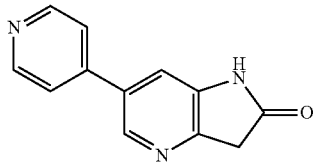 [SMILES: O=C1Cc2ncc(-c3ccncc3)cc2N1]

$^1$H NMR (400 MHz, DMSO-d$_6$) δ (ppm): 10.98 (s, 1H), 8.67 (d, J=6.0 Hz, 2H), 8.75 (d, J=4.4, 1.6 Hz, 2H), 8.41 (s, 1H), 7.44 (s, 1H), 3.63 (s, 2H). LC-MS m/z [M+H]$^+$: 212.1 with a purity of 95%.

21.76 Synthesis of 2-fluoro-N-(2-oxoindolin-5-yl)isonicotinamide (076)

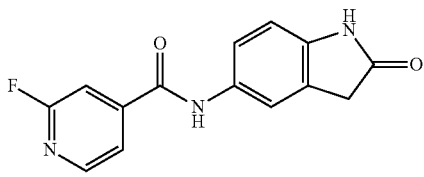 [SMILES: O=C1Cc2cc(NC(=O)c3ccnc(F)c3)ccc2N1]

$^1$H NMR (400 MHz, DMSO-d$_6$) δ (ppm): 10.42 (s, 1H), 10.37 (s, 1H), 8.44 (d, J=5.2 Hz, 1H), 7.84-7.80 (m, 1H), 7.75-7.63 (m, 2H), 7.51 (dd, J=8.4, 2.0 Hz, 1H), 6.81 (d, J=8.4 Hz, 1H), 3.51 (s, 2H). LC-MS m/z [M+H]$^+$: 272.1 with a purity of 99%.

21.77 Synthesis of 6-(4-aminopiperidine-1-carbonyl)indolin-2-one (077)

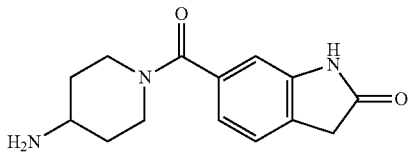 [SMILES: NC1CCN(C(=O)c2ccc3c(c2)NC(=O)C3)CC1]

$^1$H NMR (400 MHz, DMSO-d$_6$) δ (ppm): 10.50 (s, 1H), 7.26 (d, J=7.6 Hz, 1H), 6.91 (dd, J=7.6, 1.2 Hz, 1H), 6.74 (bs, 1H), 3.52 (s, 2H), 3.31-3.16 (m, 7H), 1.90-1.35 (m, 4H). LC-MS m/z [M+H]$^+$: 260.1 with a purity of 90%.

21.78 Synthesis of 5-(4-aminopiperidine-1-carbonyl)indolin-2-one (078)

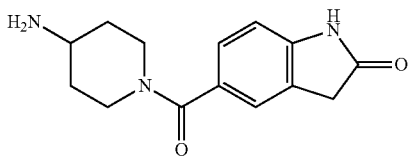 [SMILES: NC1CCN(C(=O)c2ccc3c(c2)CC(=O)N3)CC1]

$^1$H NMR (400 MHz, DMSO-d$_6$) δ (ppm): 10.56 (s, 1H), 7.22-6.84 (m, 2H), 6.85 (d, J=8.0 Hz, 1H), 3.52 (s, 2H), 3.30-3.16 (m, 7H), 1.95-1.38 (m, 4H). LC-MS m/z [M+H]$^+$: 260.1 with a purity of 90%.

21.79 Synthesis of methyl 2-(2-oxoindolin-6-yl)benzoate (079)

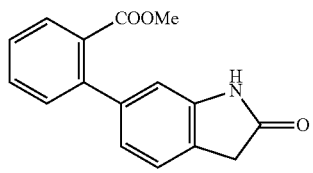 [SMILES: COC(=O)c1ccccc1-c1ccc2c(c1)NC(=O)C2]

$^1$H NMR (400 MHz, DMSO-d$_6$) δ (ppm): 10.39 (s, 1H), 7.71-7.59 (m, 2H), 7.50-7.42 (m, 2H), 7.24 (d, J=7.6 Hz, 1H), 6.85 (dd, J=7.6, 1.6 Hz, 1H), 6.71 (d, J=1.2 Hz, 1H), 3.62 (s, 3H), 3.52 (s, 2H). LC-MS m/z [M+H]$^+$: 268.1 with a purity of 98%.

21.80 Synthesis of 6-(3-aminopiperidine-1-carbonyl)indolin-2-one (080)

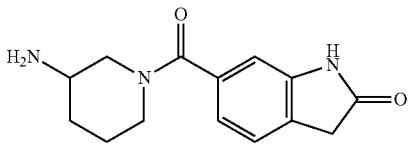 [SMILES: NC1CCCN(C(=O)c2ccc3c(c2)NC(=O)C3)C1]

$^1$H NMR (400 MHz, DMSO-d$_6$) δ (ppm): 10.50 (s, 1H), 7.27 (d, J=7.6 Hz, 1H), 6.97 (d, J=7.6 Hz, 1H), 6.83 (s, 1H), 3.53 (s, 2H), 3.31-3.17 (m, 7H), 2.02-1.43 (m, 4H). LC-MS m/z [M+H]$^+$: 260.1 with a purity of 90%.

21.81 Synthesis of 5-(3-aminopiperidine-1-carbonyl)indolin-2-one (081)

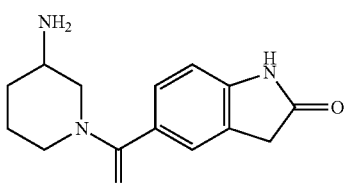

$^1$H NMR (400 MHz, DMSO-d$_6$) δ (ppm): 10.57 (s, 1H), 7.28-7.26 (m, 2H), 6.85 (d, J=8.0 Hz, 1H), 3.52 (s, 2H), 3.35-3.06 (m, 7H), 2.00-1.49 (m, 4H). LC-MS m/z [M+H]$^+$: 260.1 with a purity of 90%.

21.82 Synthesis of 3-isopropyl-5-(pyridin-4-yl)indolin-2-one (082)

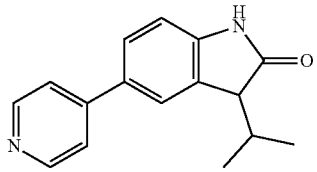 [SMILES: CC(C)C1C(=O)Nc2ccc(-c3ccncc3)cc21]

$^1$H NMR (400 MHz, DMSO-d$_6$) δ (ppm): 10.53 (s, 1H), 8.57 (d, J=4.4 Hz, 2H), 7.68-7.65 (m, 4H), 6.95 (dd, J=8.0, 1.6 Hz, 1H), 3.46-3.44 (m, 1H), 2.44-2.40 (m, 1H), 1.00-0.92 (m, 6H). LC-MS m/z [M+H]$^+$: 252.9 with a purity of 98%.

21.83 Synthesis of 1-methyl-5-(piperidine-1-carbonyl)indolin-2-one (083)

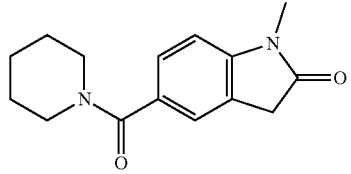 [SMILES: CN1C(=O)Cc2cc(C(=O)N3CCCCC3)ccc21]

$^1$H NMR (400 MHz, DMSO-d$_6$) δ (ppm): 7.31 (dd, J=8.0, 1.2 Hz, 1H), 7.27 (d, J=1.2 Hz, 1H), 7.00 (d, J=8.0 Hz, 1H), 3.58 (s, 2H), 3.55-3.44 (m, 4H), 3.13 (s, 3H), 1.61-1.49 (m, 6H). LC-MS m/z [M+H]$^+$: 258.9 with a purity of 99%.

2.2 Synthesis of Oxindole Compounds (II)

General Procedures:

2.2a Step 1 (SNAr reaction): To a thick wall vial/pressure tube was added pyridyl halide (1.0 equiv.), amine (1.2 equiv.), N-methylpyrrolidine and trimethylamine. The reaction mixture was stirred at 80-110° C. for 2-12 h. The reaction mixture was diluted with ethyl acetate and washed with water and brine. The organic phase was dried with anhydrous Na$_2$SO$_4$ and concentrated under vacuum. The crude product was purified by column chromatography to afford the purified product as pale yellow solid/oil with a yield of 30-80%.

2.2b Step 2 (Suzuki reaction): A mixture of compound from step 1 (1.0 equiv.), boronic acid/ester (1.2 equiv.) and potassium phosphate (3.0 equiv.) in 1,4-dioxane and water (4:1) was degassed for 15 min with nitrogen. Tetrakis(triphenylphosphine)palladium(0) or Pd(dppf)Cl$_2$.DCM (0.05-0.15 equiv.) was added and the reaction mixture was heated to reflux for 3-18 h. After completion of starting material, the reaction mixture was concentrated under vacuum. Water was added to the residue and extracted with ethyl acetate. The combined organic layers were washed with brine, dried with Na$_2$SO$_4$ and concentrated under vacuum. The crude compound was purified by column chromatography and/or reversed phase chromatography to afford the purified product.

2.2c Step 3 (Hydrogenation): Compound from step 2 (1.0 equiv.), 10% Pd/C in MeOH was stirred at room temperature for 5 h under hydrogen atmosphere. After LCMS confirmed the completion of the reaction, the mixture was filtered and the solid was washed with MeOH. The filtrate was concentrated under vacuum to afford the desired amine product as an oil. It was used in next step without further purification.

2.2d Step 4 (Amide coupling): To a mixture of acid (1.0 equiv.), amine from step 3 (1.1 equiv.) in DMF was added triethylamine (4.0 equiv.), followed by HATU (1.2 equiv.). The reaction was stirred at room temperature for 0.5-1 h. After completion of starting material, dichloromethane was added and the organic layer was washed with water and brine, dried with Na$_2$SO$_4$ and concentrated under vacuum. The crude compound was purified by column chromatography and/or reversed phase chromatography to afford the purified product.

2.2.1 Synthesis of N-(2-(2-(2-(2-azidoethoxy)ethoxy)ethoxy)ethyl)-4-(2-oxoindolin-6-yl)picolinamide (084)

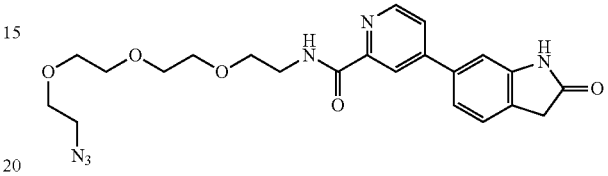

$^1$H NMR (400 MHz, DMSO-d$_6$) δ (ppm): 10.54 (s, 1H), 8.75 (t, J=5.6 Hz, 1H), 8.68 (d, J=5.2 Hz, 1H), 8.23 (s, 1H), 7.87 (d, J=5.2 Hz, 1H), 7.45-7.35 (m, 2H), 7.19 (s, 1H), 3.63-3.46 (m, 16H), 3.40-3.34 (m, 2H). LC-MS m/z [M+H]$^+$: 455.1 with a purity of 98%.

2.2.2 Synthesis of 6-(2-((2-(2-(2-(2-azidoethoxy)ethoxy)ethoxy)ethyl)amino)pyridin-4-yl)indolin-2-one (085)

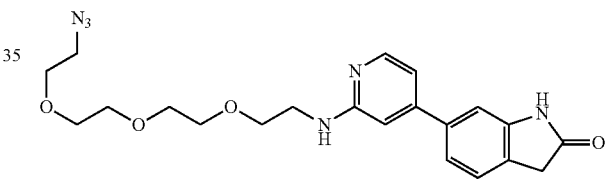

$^1$H NMR (400 MHz, DMSO-d$_6$) δ (ppm): 10.49 (s, 1H), 8.04-7.97 (m, 1H), 7.29 (d, J=7.6 Hz, 1H), 7.20 (dd, J=7.6, 1.6 Hz, 1H), 7.00 (d, J=1.2 Hz, 1H), 6.74-6.68 (m, 2H), 6.58 (t, J=6.0 Hz, 1H), 3.61-3.53 (m, 12H), 3.52 (s, 2H), 3.48-3.42 (m, 2H), 3.39-3.35 (m, 2H). LC-MS m/z [M+H]$^+$: 427.1 with a purity of 98%.

22.3 Synthesis of 6-((2-(2-(2-(2-azidoethoxy)ethoxy)ethoxy)ethyl)amino)-N-(2-oxoindolin-5-yl)nicotinamide (086)

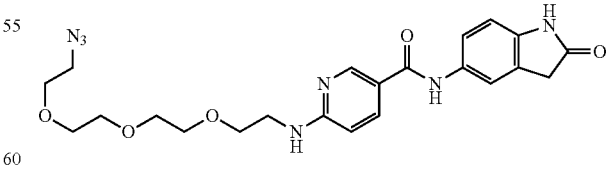

$^1$H NMR (400 MHz, DMSO-d$_6$) δ (ppm): 10.29 (s, 1H), 9.77 (s, 1H), 8.60 (d, J=2.4 Hz, 1H), 7.88 (dd, J=8.8, 2.4 Hz, 1H), 7.61 (s, 1H), 7.47 (dd, J=8.4, 2.0 Hz, 1H), 7.17 (t, J=5.6 Hz, 1H), 6.75 (d, J=8.4 Hz, 1H), 6.54 (d, J=8.8 Hz, 1H), 3.63-3.52 (m, 12H), 3.52-3.44 (m, 4H), 3.42-3.35 (m, 2H). LC-MS m/z [M+H]$^+$: 470.1 with a purity of 98%.

2.2.4 Synthesis of 6-(2-((5-aminopentyl)amino)pyridin-4-yl)indolin-2-one (087)

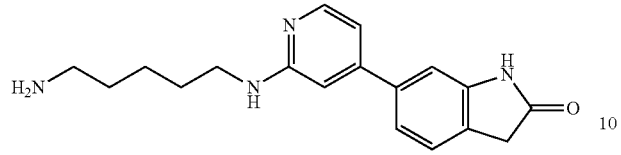

$^1$H NMR (400 MHz, DMSO-d$_6$) δ (ppm): 10.46 (bs, 1H), 7.99 (d, J=5.2 Hz, 1H), 7.29 (d, J=7.6 Hz, 1H), 7.20 (dd, J=7.6, 1.6 Hz, 1H), 7.00 (d, J=0.8 Hz, 1H), 6.68 (dd, J=5.2, 1.6 Hz, 1H), 6.64 (s, 1H), 6.54 (t, J=5.6 Hz, 1H), 3.52 (s, 2H), 3.29-3.20 (m, 2H), 2.65-2.50 (m, 2H), 1.60-1.30 (m, 6H). LC-MS m/z [M+H]$^+$: 311.1 with a purity of 99%.

2.2.5 Synthesis of 5-(2-((2-(2-(2-(2-azidoethoxy)ethoxy)ethoxy)ethyl)amino)pyridin-4-yl)indolin-2-one (088)

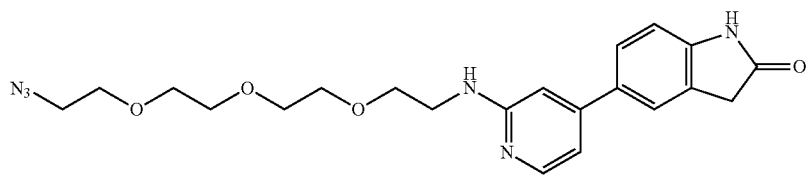 [SMILES: [N-]=[N+]=NCCOCCOCCOCCNc1cc(-c2ccc3c(c2)CC(=O)N3)ccn1]

$^1$H NMR (400 MHz, DMSO-d$_6$) δ (ppm): 10.49 (s, 1H), 7.97 (d, J=5.2 Hz, 1H), 7.56-7.47 (m, 2H), 6.89 (d, J=8.0 Hz, 1H), 6.73-6.69 (m, 2H), 6.44 (t, J=5.2, 1 H), 3.72-3.36 (m, 18H). LC-MS m/z [M+H]$^+$: 427.1 with a purity of 98%.

22.6 Synthesis of 6-(6-((2-(2-(2-(2-azidoethoxy)ethoxy)ethoxy)ethyl)amino)pyridin-3-yl)indolin-2-one (089)

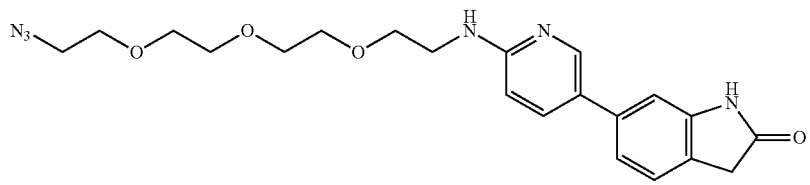 [SMILES: [N-]=[N+]=NCCOCCOCCOCCNc1ccc(-c2ccc3c(c2)NC(=O)C3)cn1]

$^1$H NMR (400 MHz, DMSO-d$_6$) δ (ppm): 10.40 (s, 1H), 8.23 (d, J=2.4 Hz, 1H), 7.62 (dd, J=8.8, 2.4 Hz, 1H), 7.21 (d, J=7.6 Hz, 1H), 7.10 (dd, J=7.6, 1.6 Hz, 1H), 6.92 (d, J=1.2 Hz, 1H), 6.67 (t, J=5.6 Hz, 1H), 6.58 (d, J=8.8 Hz, 1H), 3.62-3.52 (m, 12H), 3.51-3.42 (m, 4H), 3.38 (d, J=4.8 Hz, 2H). LC-MS m/z [M+H]$^+$: 427.2 with a purity of 99%.

2.2.7 Synthesis of N-(2-(2-(2-(2-(4-aminophenoxy)ethoxy)ethoxy)ethoxy)ethyl)-3-(2-oxoindolin-6-yl)benzamide (090)

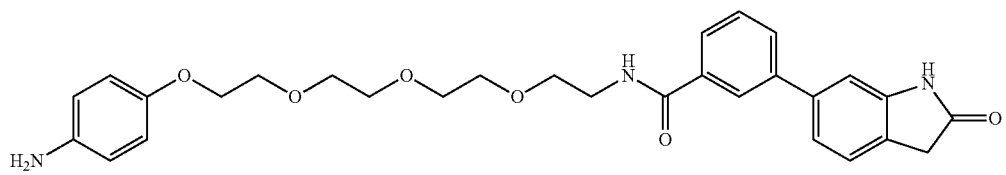 [SMILES: Nc1ccc(OCCOCCOCCOCCNC(=O)c2cccc(-c3ccc4c(c3)NC(=O)C4)c2)cc1]

¹H NMR (400 MHz, DMSO-d₆) δ (ppm): 10.49 (s, 1H), 8.65 (t, J=5.6 Hz, 1H), 8.07 (s, 1H), 7.83 (d, J=7.6 Hz, 1H), 7.75 (d, J=7.6 Hz, 1H), 7.53 (t, J=7.6 Hz, 1H), 7.32-7.28 (m, 2H), 7.08 (s, 1H), 6.62 (d, J=8.4 Hz, 2H), 6.48 (d, J=8.4 Hz, 2H), 3.88 (t, J=4.8 Hz, 2H), 3.62-3.43 (m, 18H). LC-MS m/z [M+H]⁺: 520.2 with a purity of 90%.

2.2.8 Synthesis of N-(2-(2-(2-(2-(4-aminophenoxy)ethoxy)ethoxy)ethoxy)ethyl)-3-(2-oxoindolin-5-yl)benzamide (091)

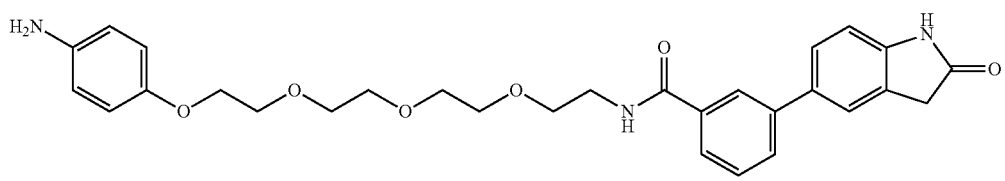 [SMILES: Nc1ccc(OCCOCCOCCOCCNC(=O)c2cccc(-c3ccc4c(c3)CC(=O)N4)c2)cc1]

¹H NMR (400 MHz, DMSO-d₆) δ (ppm): 10.47 (s, 1H), 8.61 (t, J=5.6 Hz, 1H), 8.07 (s, 1H), 7.78-7.73 (m, 2H), 7.59 (s, 1H), 7.55-7.48 (m, 2H), 6.91 (d, J=8.0 Hz, 1H), 6.62 (d, J=8.4 Hz, 2H), 6.48 (d, J=8.4 Hz, 2H), 3.88 (t, J=4.8 Hz, 2H), 3.63-3.42 (m, 18H). LC-MS m/z [M+H]⁺: 520.2 with a purity of 90%.

22.9 Synthesis of 5-(6-((2-(2-(2-(2-azidoethoxy)ethoxy)ethoxy)ethyl)amino)pyridin-3-yl)indolin-2-one (092)

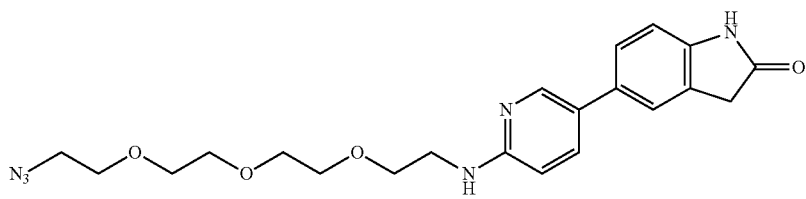 [SMILES: [N-]=[N+]=NCCOCCOCCOCCNc1ccc(-c2ccc3c(c2)CC(=O)N3)cn1]

¹H NMR (400 MHz, DMSO-d₆) δ (ppm): 10.37 (s, 1H), 8.21 (d, J=2.4 Hz, 1H), 7.61 (dd, J=8.8, 2.4 Hz, 1H), 7.40 (s, 1H), 7.34 (d, J=8.0 Hz, 1H), 6.83 (d, J=8.0 Hz, 1H), 6.63-6.52 (m, 2H), 3.63-3.52 (m, 12H), 3.50 (s, 2H), 3.48-3.36 (m, 4H). LC-MS m/z [M+H]⁺: 427.1 with a purity of 98%.

2.2.10 Synthesis of 5-(6-((2-(2-(2-(2-(4-aminophenoxy)ethoxy)ethoxy)ethoxy)ethyl)amino)-pyridin-3-yl)indolin-2-one (093)

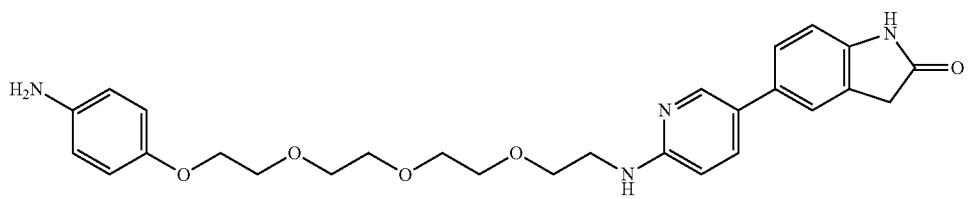 [SMILES: Nc1ccc(OCCOCCOCCOCCNc2ccc(-c3ccc4c(c3)CC(=O)N4)cn2)cc1]

¹H NMR (400 MHz, DMSO-d₆) δ (ppm): 10.37 (s, 1H), 8.21 (d, J=2.0 Hz, 1H), 7.59 (dd, J=8.8, 3.0 Hz, 1H), 7.39 (s, 1H), 7.34 (d, J=8.0 Hz, 1H), 6.83 (d, J=8.0 Hz, 1H), 6.68-6.61 (m, 2H), 6.60-6.53 (m, 2H), 6.52-6.46 (m, 2H), 4.58 (s, 2H), 3.94-3.89 (m, 2H), 3.69-3.63 (m, 2H), 3.60-3.51 (m, 10H), 3.50 (s, 2H), 3.48-3.40 (m, 2H). LC-MS m/z [M+H]⁺: 493.2 with a purity of 96%.

2.2.11 Synthesis of 5-(2-((2-(2-(2-(2-azidoethoxy)ethoxy)ethoxy)ethyl)amino)pyridin-3-yl)indolin-2-one (094)

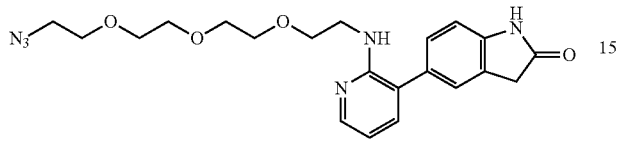

¹H NMR (400 MHz, DMSO-d₆) δ (ppm): 10.47 (s, 1H), 7.99 (dd, J=4.8, 1.6 Hz, 1H), 7.24-7.17 (m, 3H), 6.90 (d, J=8.0 Hz, 1H), 6.61 (dd, J=7.2, 4.0 Hz, 1H), 5.47 (t, J=5.2 Hz, 1H), 3.57-3.50 (m, 16H), 3.49-3.35 (m, 2H). LC-MS: m/z [M+H]⁺: 427.1 with a purity of 97%.

22.12 Synthesis of 6-(2-((2-(2-(2-(2-azidoethoxy)ethoxy)ethoxy)ethyl)amino)pyridin-3-yl)indolin-2-one (095)

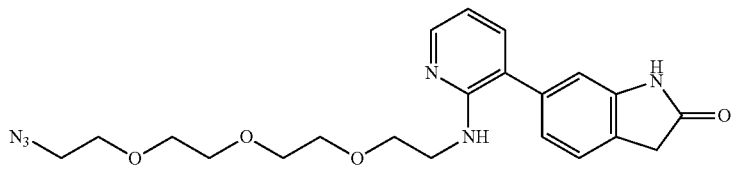 [SMILES: [N-]=[N+]=NCCOCCOCCOCCNc1ncccc1-c1ccc2c(c1)NC(=O)C2]

¹H NMR (400 MHz, DMSO-d₆) δ (ppm): 10.45 (s, 1H), 8.01 (dd, J=4.8, 1.6 Hz, 1H), 7.30-7.25 (m, 2H), 6.93 (dd, J=7.6, 1.6 Hz, 1H), 6.78 (dd, J=4.0, 1.2 Hz, 1H), 6.64-6.61 (m, 1H), 5.53 (t, J=5.2 Hz, 1H), 3.57-3.51 (m, 16H), 3.49-3.32 (m, 2H). LC-MS: m/z [M+H]⁺: 427.1 with a purity of 99%.

2.2.13 Synthesis of (S)-2-(4-(4-chlorophenyl)-2,3,9-trimethyl-6H-thieno[3,2-f][1,2,4]triazolo[4,3-a][1,4]diazepin-6-yl)-N-(5-((4-(2-oxoindolin-6-yl)pyridin-2-yl)amino)pentyl)acetamide (096)

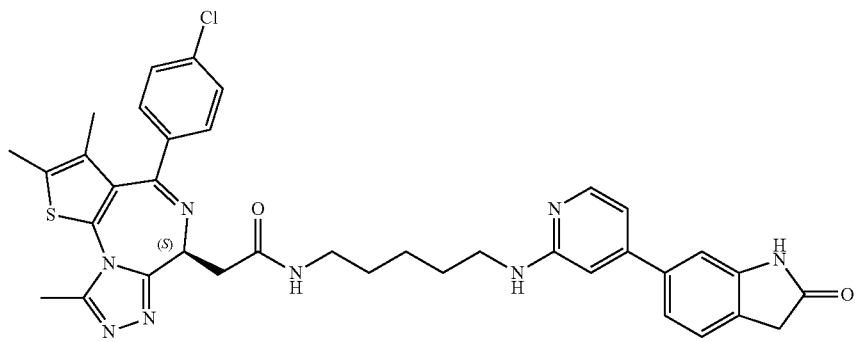

¹H NMR (400 MHz, DMSO-d₆) δ (ppm): 10.48 (s, 1H), 8.19 (t, J=5.2 Hz, 1H), 7.99 (d, J=5.2 Hz, 1H), 7.47 (d, J=8.8 Hz, 2H), 7.41 (d, J=8.4 Hz, 2H), 7.29 (d, J=7.6 Hz, 1H), 7.19 (dd, J=7.6, 1.2 Hz, 1H), 6.99 (d, J=0.8 Hz, 1H), 6.68 (dd, J=5.2, 1.6 Hz, 1H), 6.64 (s, 1H), 6.53 (t, J=5.2 Hz, 1H), 4.57-4.46 (m, 1H), 3.51 (s, 2H), 3.26-3.03 (m, 6H), 2.59 (s, 3H), 2.39 (s, 3H), 1.60 (s, 3H), 1.59-1.32 (m, 6H). LC-MS m/z [M+H]⁺: 693.2 with a purity of 98%.

22.14 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((4-(2-oxoindolin-5-yl)pyridin-2-yl)amino)ethoxy)ethoxy)ethoxy)ethyl)acetamide (097)

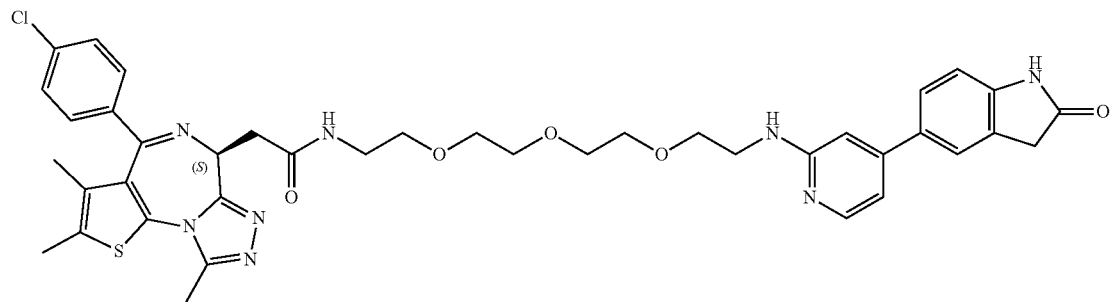

¹H NMR (400 MHz, DMSO-d₆) δ (ppm): 10.48 (s, 1H), 8.24 (t, J=5.6 Hz, 1H), 7.96 (d, J=5.6 Hz, 1H), 7.54-7.38 (m, 6H), 6.89 (d, J=8.0 Hz, 1H), 6.75-6.66 (m, 2H), 6.43 (t, J=5.6 Hz, 1H), 4.51 (t, J=7.2 Hz, 1H), 3.58-3.51 (m, 12H), 3.49-3.41 (m, 4H), 3.26-3.17 (m, 4H), 2.59 (s, 3H), 2.40 (s, 3H), 1.61 (s, 3H). LC-MS m/z [M+H]⁺: 784.2 with a purity of 98%.

2.2.15 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((5-(2-oxoindolin-5-yl)pyridin-2-yl)amino)ethoxy)ethoxy)ethoxy)ethoxy)phenyl)acetamide (098)

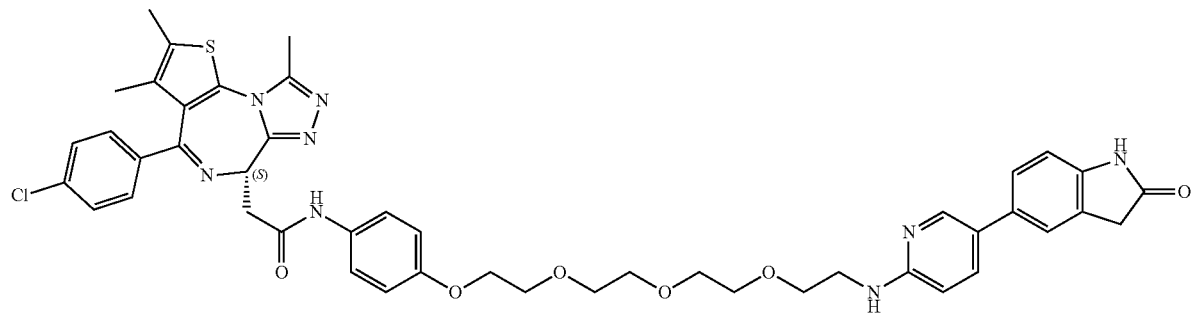

¹H NMR (400 MHz, DMSO-d₆) δ (ppm): 10.36 (s, 1H), 10.16 (s, 1H), 8.21 (t, J=2.4 Hz, 1H), 7.59 (dd, J=8.8, 2.4 Hz, 1H), 7.56-7.50 (m, 2H), 7.41 (d, J=7.2 Hz, 2H), 7.45-7.37 (m, 3H), 7.33 (d, J=8.0 Hz, 1H), 6.93-6.86 (m, 2H), 6.83 (d, J=8.0 Hz, 1H), 6.60-6.52 (m, 2H), 4.59 (t, J=7.2 Hz, 1H), 4.08-4.00 (m, 2H), 3.76-3.68 (m, 2H), 3.60-3.52 (m, 10H), 3.51-3.41 (m, 6H), 2.60 (s, 3H), 2.41 (s, 3H), 1.62 (s, 3H). LC-MS m/z [M+H]⁺: 873.1 with a purity of 96%.

22.16 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((5-(2-oxoindolin-5-yl)pyridin-2-yl)amino)ethoxy)ethoxy)ethoxy)ethyl)acetamide (099)

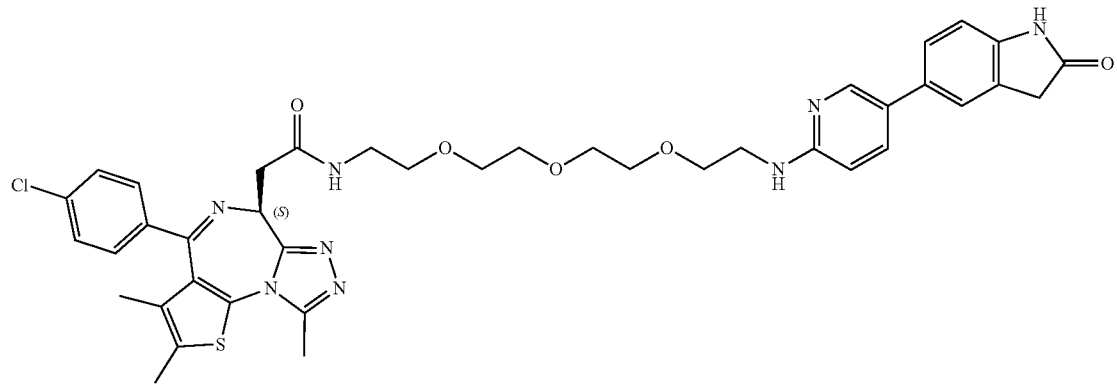

¹H NMR (400 MHz, DMSO-d₆) δ (ppm): 10.36 (s, 1H), 8.28 (t, J=5.6 Hz, 1H), 8.20 (d, J=2.4 Hz, 1H), 7.59 (dd, J=8.4, 2.4 Hz, 1H), 7.53-7.38 (m, 5H), 7.33 (d, J=8.0 Hz, 1H), 6.83 (d, J=8.0 Hz, 1H), 6.60-6.52 (m, 2H), 4.50 (dd, J=8.0, 6.4 Hz, 1H), 3.62-3.40 (m, 18H), 3.27-3.17 (m, 2H), 2.59 (s, 3H), 2.40 (s, 3H), 1.61 (s, 3H). LC-MS m/z [M+H]⁺: 783.3 with a purity of 97%.

2.2.17 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((5-(2-oxoindolin-6-yl)pyridin-2-yl)amino)ethoxy)ethoxy)ethoxy)ethyl)acetamide (100)

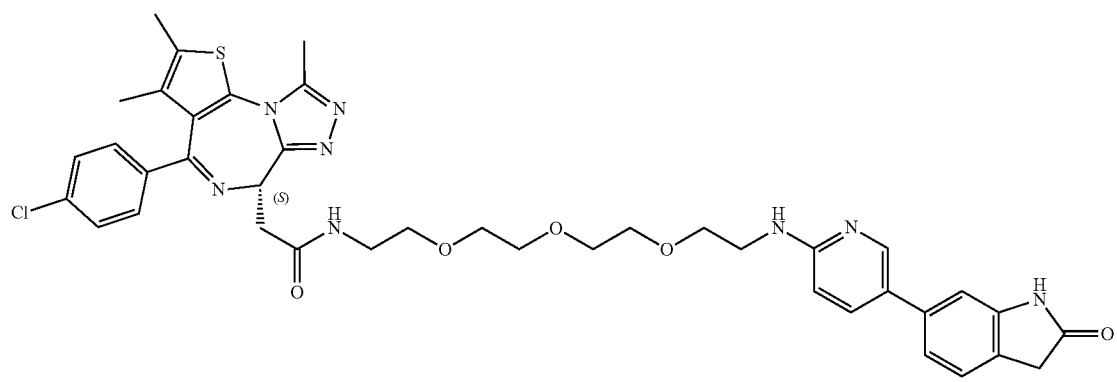

¹H NMR (400 MHz, DMSO-d₆) δ (ppm): 10.39 (s, 1H), 8.26 (t, J=5.6 Hz, 1H), 8.22 (d, J=2.0 Hz, 1H), 7.61 (dd, J=8.4, 2.4 Hz, 1H), 7.47 (d, J=8.4 Hz, 2H), 7.41 (d, J=8.8 Hz, 2H), 7.21 (d, J=8.0 Hz, 1H), 7.09 (dd, J=7.6, 1.6 Hz, 1H), 6.92 (s, 1H), 6.66 (t, J=5.6 Hz, 1H), 6.57 (d, J=8.4 Hz, 1H), 4.50 (dd, J=7.6, 6.0 Hz, 1H), 3.59-3.52 (m, 10H), 3.50-3.42 (m, 6H), 3.28-3.16 (m, 4H), 2.59 (s, 3H), 2.40 (s, 3H), 1.61 (s, 3H). LC-MS m/z [M+H]⁺: 783.2 with a purity of 99%.

2.2.18 Synthesis of (S)-6-((1-(4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yl)amino)-N-(2-oxoindolin-5-yl)nicotinamide (101)

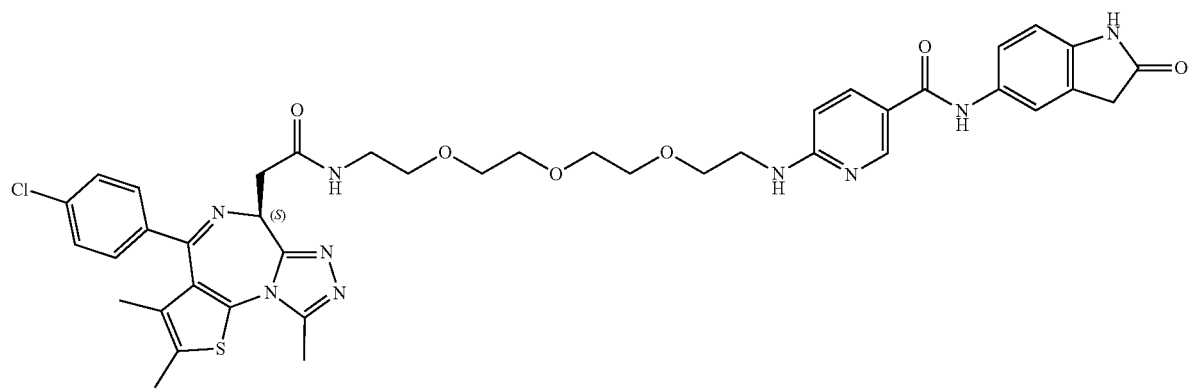

¹H NMR (400 MHz, DMSO-d₆) δ (ppm): 10.28 (s, 1H), 9.76 (s, 1H), 8.60 (t, J=2.4 Hz, 1H), 8.26 (t, J=5.6 Hz, 1H), 7.87 (dd, J=8.8, 2.4 Hz, 1H), 7.61 (s, 1H), 7.53-7.37 (m, 5H), 7.17 (t, J=5.6 Hz, 1H), 6.75 (d, J=8.4 Hz, 1H), 6.54 (d, J=8.8 Hz, 1H), 4.50 (dd, J=7.6, 6.0 Hz, 1H), 3.57-3.53 (m, 10H), 3.52-3.43 (m, 6H), 3.29-3.16 (m, 4H), 2.67 (s, 3H), 2.40 (s, 3H), 1.61 (s, 3H). LC-MS m/z [M+H]⁺: 826.2 with a purity of 99%.

2.2.19 Synthesis of (S)—N-(2-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)-3-(2-oxoindolin-6-yl)benzamide (102)

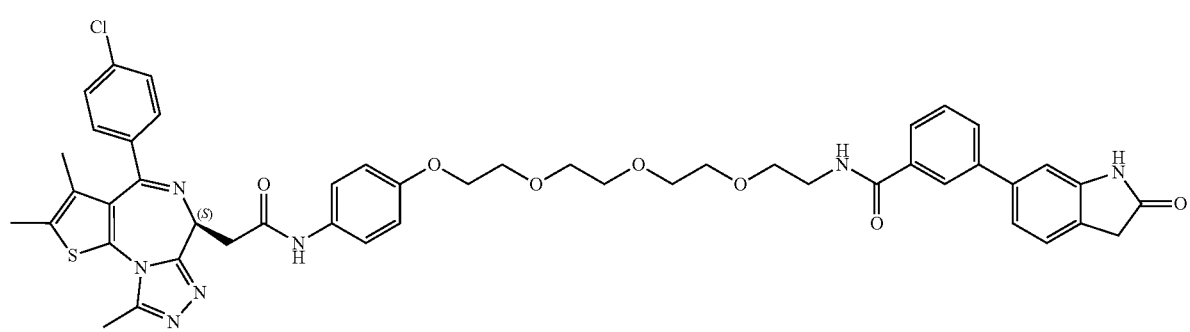

¹H NMR (400 MHz, DMSO-d₆) δ (ppm): 10.48 (s, 1H), 10.15 (s, 1H), 8.65 (t, J=2.4 Hz, 1H), 8.07 (s, 1H), 7.82 (d, J=7.6 Hz, 1H), 7.74 (d, J=7.6 Hz, 1H), 7.54-7.46 (m, 5H), 7.41 (d, J=8.4 Hz, 2H), 7.29-7.28 (m, 2H), 7.08 (s, 1H), 6.87 (d, J=8.8 Hz, 2H), 4.59 (t, J=7.2 Hz, 1H), 4.02-4.00 (m, 2H), 3.69-3.67 (m, 2H), 3.57-3.38 (m, 16H), 2.60 (s, 3H), 2.41 (s, 3H), 1.62 (s, 3H). LC-MS m/z [M+H]⁺: 902.2 with a purity of 99%.

2.2.20 Synthesis of (S)—N-(2-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)-3-(2-oxoindolin-5-yl)benzamide (103)

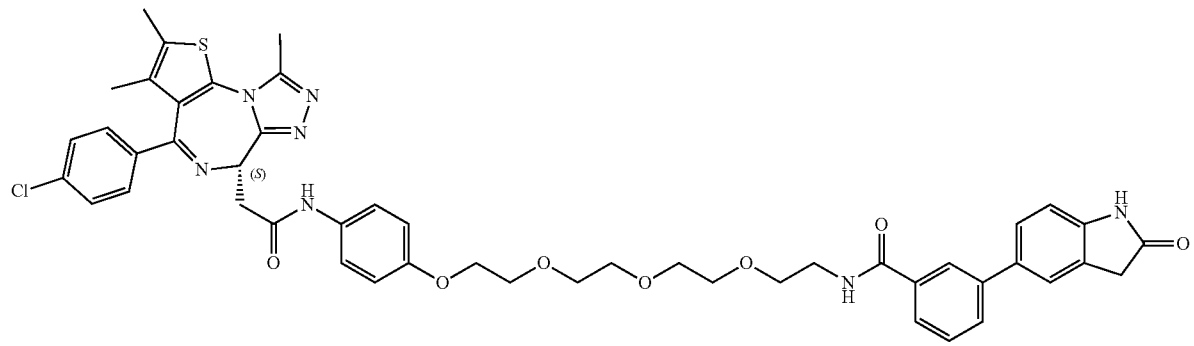

$^1$H NMR (400 MHz, DMSO-d$_6$) δ (ppm): 10.49 (s, 1H), 10.15 (s, 1H), 8.60 (t, J=5.6 Hz, 1H), 8.06 (s, 1H), 7.76 (d, J=7.6 Hz, 1H), 7.73 (d, J=7.6 Hz, 1H), 7.59 (s, 1H), 7.55-7.46 (m, 6H), 7.41 (d, J=8.4 Hz, 2H), 6.92-6.86 (m, 3H), 4.59 (t, J=7.2 Hz, 1H), 4.02-4.00 (m, 2H), 3.69-3.67 (m, 2H), 3.57-3.42 (m, 16H), 2.60 (s, 3H), 2.41 (s, 3H), 1.62 (s, 3H). LC-MS m/z [M+H]$^+$: 902.2 with a purity of 99%.

2.2.21 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-(2-oxoindolin-5-yl)phenyl)amino)ethoxy)ethoxy)ethoxy)ethoxy)phenyl)acetamide (104)

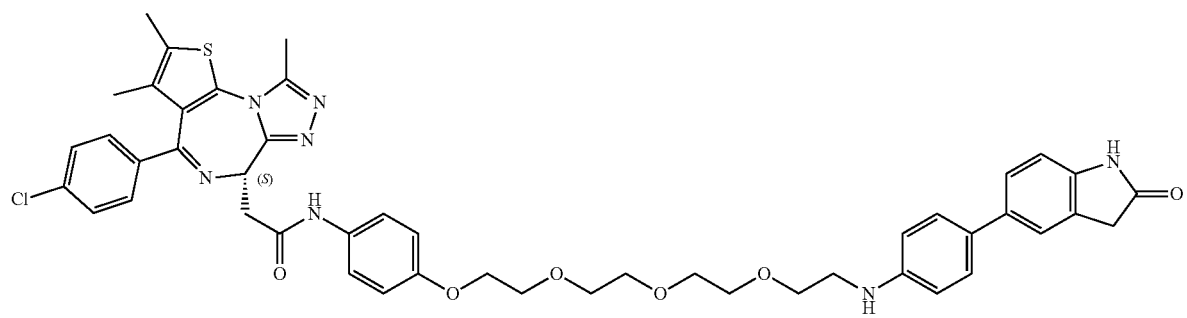

$^1$H NMR (400 MHz, DMSO-d$_6$) δ (ppm): 10.33 (s, 1H), 10.17 (s, 1H), 7.54 (d, J=9.0 Hz, 2H), 7.48 (d, J=8.7 Hz, 2H), 7.44-7.36 (m, 3H), 7.35-7.29 (m, 3H), 6.90 (d, J=9.0 Hz, 2H), 6.81 (d, J=8.0 Hz, 2H), 6.64 (d, J=8.7 Hz, 2H), 5.61 (t, J=5.7 Hz, 1H), 4.60 (t, J=7.2 Hz, 1H), 4.08-4.02 (m, 2H), 3.77-3.70 (m, 2H), 3.63-3.54 (m, 9H), 3.51-3.44 (m, 4H), 3.25-3.17 (m, 2H), 2.61 (s, 3H), 2.42 (s, 3H), 1.63 (s, 3H). LC-MS m/z [M+H]$^+$: 874.1 with a purity of 96%.

2.2.22 Synthesis of (S)-2-(4-(4-chlorophenyl)-2,3,9-trimethyl-6H-thieno[3,2-f][1,2,4]triazolo[4,3-a][1,4]diazepin-6-yl)-N-(5-((3-(2-oxoindolin-5-yl)pyridin-2-yl)amino)pentyl)acetamide (105)

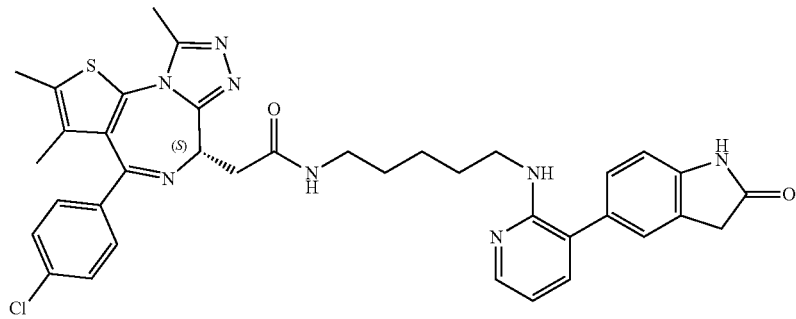

¹H NMR (400 MHz, MEOD) δ (ppm): 7.92 (dd, J=5.4, 1.8 Hz, 1H), 7.46-7.33 (m, 5H), 7.26 (bs, 1H), 7.21 (dd, J=8.2, 1.6 Hz, 1H), 6.98 (d, J=8.0 Hz, 1H), 6.70 (dd, J=7.2, 5.5 Hz, 1H), 4.60 (dd, J=8.8, 5.4 Hz, 1H), 3.54 (bs, 2H), 3.43-3.34 (m, 3H), 3.29-3.22 (m, 3H), 2.69 (s, 3H), 2.44 (s, 3H), 1.68 (s, 3H), 1.65-1.55 (m, 4H), 1.47-1.38 (m, 2H) LC-MS m/z [M+H]⁺: 693.5 with a purity of 99%.

2.2.23 Synthesis of (S)—N-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethyl)-3-(2-oxoindolin-5-yl)benzamide (106)

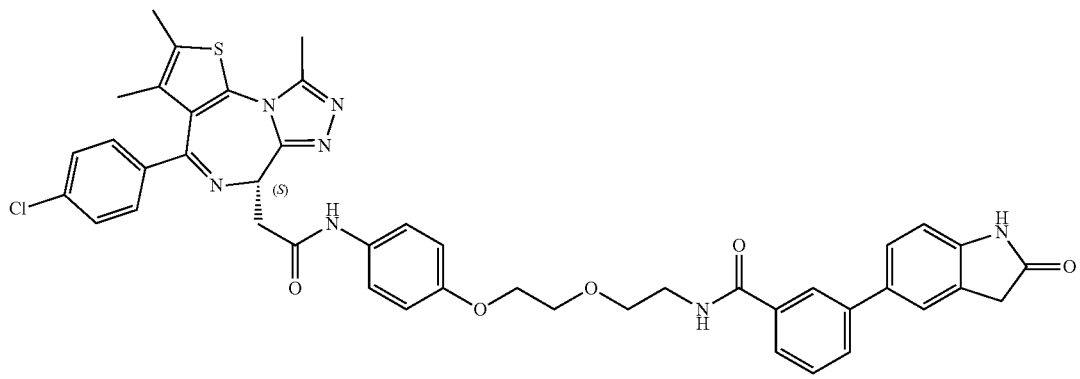

¹H NMR (400 MHz, DMSO-d₆) δ (ppm): 10.48 (s, 1H), 10.15 (s, 1H), 8.66 (t, J=5.2 Hz, 1H), 8.07 (s, 1H), 7.78-7.74 (m, 2H), 7.60 (s, 1H), 7.56-7.48 (m, 8H), 6.93-6.87 (m, 3H), 4.59 (t, J=7.2 Hz, 1H), 4.07 (t, J=4.4 Hz, 2H), 3.76 (t, J=4.4 Hz, 2H), 3.63-3.45 (m, 8H), 2.61 (s, 3H), 2.43 (s, 3H), 1.64 (s, 3H). LC-MS m/z [M+H]⁺: 814.1 with a purity of 99%.

2.2.24 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((3-(2-oxoindolin-5-yl)pyridin-2-yl)amino)ethoxy)ethoxy)ethoxy)ethyl)acetamide (107)

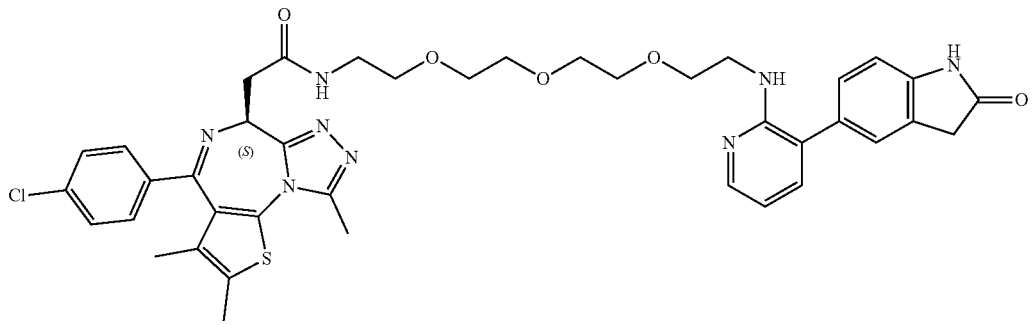

¹H NMR (400 MHz, DMSO-d₆) δ (ppm): 10.47 (s, 1H), 8.25 (t, J=5.6 Hz, 1H), 7.99 (dd, J=2.5, 1.8 Hz, 1H), 7.47 (d, J=8.6 Hz, 2H), 7.42 (d, J=8.6 Hz, 2H), 7.28-7.14 (m, 3H), 6.90 (d, J=7.9 Hz, 1H), 6.60 (d, J=5.0, 3.6 Hz, 1H), 5.48 (t, J=5.3 Hz, 1H), 4.49 (dd, J=8.0, 6.2 Hz, 1H), 3.53-3.41 (m, 16H), 3.28-3.16 (m, 4H), 2.59 (s, 3H), 2.40 (s, 3H), 1.61 (s, 3H). LC-MS m/z [M+H]⁺: 783.1 with a purity of 99%.

2.2.25 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((3-(2-oxoindolin-6-yl)pyridin-2-yl)amino)ethoxy)ethoxy)ethoxy)ethyl)acetamide (108)

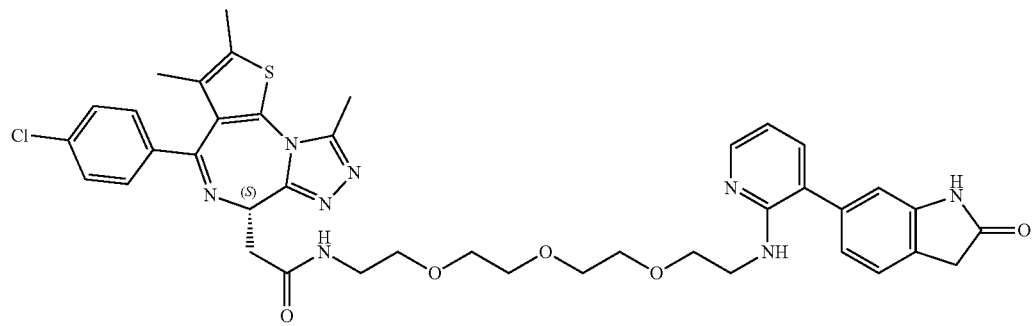

¹H NMR (400 MHz, DMSO-d₆) δ (ppm): 10.45 (s, 1H), 8.25 (t, J=5.5 Hz, 1H), 8.01 (dd, J=2.5, 1.8 Hz, 1H), 7.48 (d, J=8.7 Hz, 2H), 7.42 (d, J=8.6 Hz, 2H), 7.33-7.21 (m, 2H), 6.94 (dd, J=3.8, 1.4 Hz, 1H), 6.79 (s, 1H), 6.62 (dd, J=7.2, 5.0 Hz, 1H), 5.55 (t, J=5.3 Hz, 1H), 4.49 (dd, J=8.0, 6.2 Hz, 1H), 3.52-3.41 (m, 16H), 3.25-3.18 (m, 4H), 2.59 (s, 3H), 2.40 (s, 3H), 1.61 (s, 3H). LC-MS m/z [M+H]⁺: 783.1 with a purity of 98%.

2.2.26 Synthesis of (S)-3-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-(1-(2-oxoindoline-5-carbonyl)piperidin-4-yl)propanamide (109)

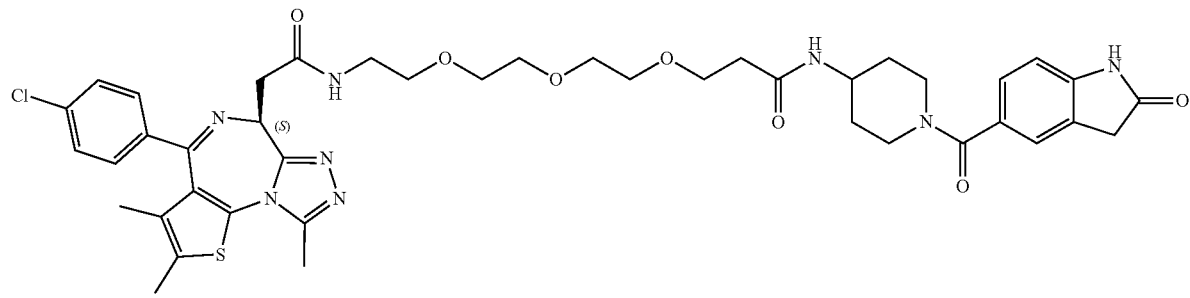

¹H NMR (400 MHz, DMSO-d₆) δ (ppm): 10.53 (s, 1H), 8.26 (t, J=5.6 Hz, 1H), 7.82 (d, J=7.6 Hz, 1H), 7.48 (d, J=8.4 Hz, 2H), 7.42 (d, J=8.4 Hz, 2H), 7.21-7.19 (m, 2H), 6.83 (d, J=7.6 Hz, 1H), 4.50 (t, J=5.3 Hz, 1H), 3.80-3.78 (m, 1H), 3.61-3.30 (m, 20H), 3.05-2.99 (m, 2H), 2.59 (s, 3H), 2.41 (s, 3H), 2.39-2.28 (m, 2H), 1.85-1.74 (m, 2H), 1.62 (s, 3H), 1.39-1.28 (m, 2H). LC-MS m/z [M+H]⁺: 845.2 with a purity of 99%.

2.2.27 Synthesis of (S)-3-(2-(2-(2-(2-(4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-(1-(2-oxoindoline-6-carbonyl)piperidin-4-yl)propanamide (110)

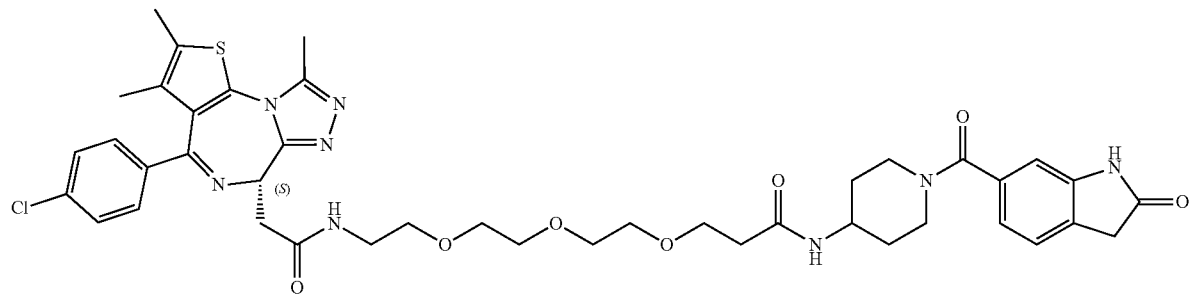

¹H NMR (400 MHz, DMSO-d₆) δ (ppm): 10.46 (s, 1H), 8.26 (t, J=5.6 Hz, 1H), 7.83 (d, J=7.6 Hz, 1H), 7.48 (d, J=8.4 Hz, 2H), 7.42 (d, J=8.4 Hz, 2H), 7.25 (d, J=7.6 Hz, 1H), 6.90 (dd, J=7.6, 1.2 Hz, 1H), 6.75 (s, 1H), 4.51 (t, J=5.3 Hz, 1H), 3.85-3.75 (m, 1H), 3.61-3.43 (m, 20H), 3.20-3.17 (m, 2H), 2.59 (s, 3H), 2.42 (s, 3H), 2.30-2.20 (m, 2H), 1.84-1.74 (m, 2H), 1.63 (s, 3H), 1.35-1.23 (m, 2H). LC-MS m/z [M+H]⁺: 845.2 with a purity of 99%.

2.2.28 Synthesis of 3-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-(1-(2-oxoindoline-6-carbonyl)piperidin-3-yl)propanamide (111)

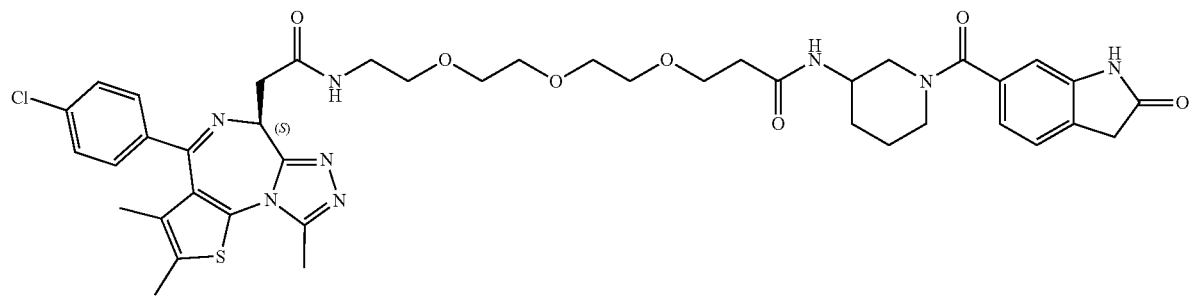

¹H NMR (400 MHz, DMSO-d₆) δ (ppm): 10.46 (s, 1H), 8.26 (t, J=5.6 Hz, 1H), 7.85 (bs, 1H), 7.48 (d, J=8.4 Hz, 2H), 7.42 (d, J=8.4 Hz, 2H), 7.22 (d, J=7.2 Hz, 1H), 6.93 (d, J=7.2 Hz, 1H), 6.77 (bs, 1H), 4.51 (t, J=5.3 Hz, 1H), 3.80-3.20 (m, 21H), 3.20-3.17 (m, 2H), 2.59 (s, 3H), 2.42 (s, 3H), 2.30-2.20 (m, 2H), 1.84-1.74 (m, 2H), 1.63 (s, 3H), 1.35-1.23 (m, 2H). LC-MS m/z [M+H]⁺: 845.2 with a purity of 99%.

2.2.29 Synthesis of 3-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-(1-(2-oxoindoline-5-carbonyl)piperidin-3-yl)propanamide (112)

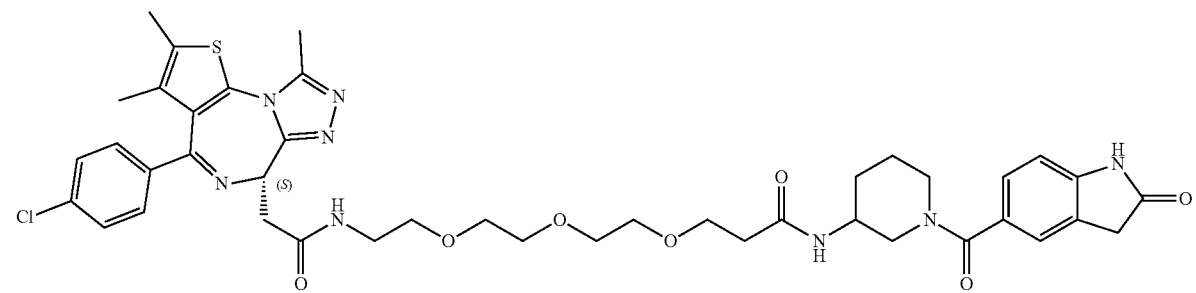

¹H NMR (400 MHz, DMSO-d₆) δ (ppm): 10.53 (s, 1H), 8.26 (t, J=5.6 Hz, 1H), 7.84 (bs, 1H), 7.83 (d, J=7.6 Hz, 1H), 7.48 (d, J=8.4 Hz, 2H), 7.42 (d, J=8.4 Hz, 2H), 7.26-7.22 (m, 2H), 6.82 (d, J=8.0 Hz, 1H), 4.52-4.49 (m, 1H), 3.57-3.44 (m, 16H), 3.20-3.17 (m, 2H), 2.59 (s, 3H), 2.42 (s, 3H), 1.62 (s, 3H). LC-MS m/z [M+H]⁺: 845.2 with a purity of 99%.

2.2.30 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((4-(2-oxoindolin-6-yl)pyridin-2-yl)amino)ethoxy)ethoxy)ethoxy)ethyl)acetamide (113)

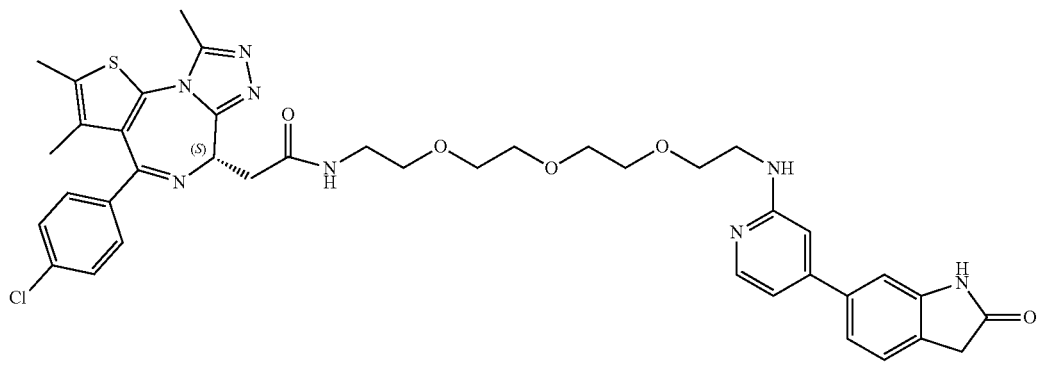

¹H NMR (400 MHz, DMSO-d₆) δ (ppm): 10.49 (s, 1H), 8.27 (t, J=5.6 Hz, 1H), 8.02-7.97 (m, 1H), 7.48 (d, J=8.8 Hz, 2H), 7.42 (d, J=8.6 Hz, 2H), 7.29 (d, J=7.7 Hz, 1H), 7.20 (dd, J=7.7, 1.6 Hz, 1H), 7.00 (d, J=1.3 Hz, 1H), 6.75-6.66 (m, 2H), 6.59 (t, J=5.6 Hz, 1H), 4.50 (dd, J=8.0, 6.2 Hz, 1H), 3.56-3.50 (m, 12H), 3.47-3.43 (m, 4H), 3.30-3.18 (m, 4H), 2.59 (s, 3H), 2.40 (s, 3H), 1.61 (s, 3H). LC-MS m/z [M+H]⁺: 783.3 with a purity of 95%.

2.2.31 Synthesis of (S)-2-(4-(4-chlorophenyl)-2,3,9-trimethyl-6H-thieno[3,2-f][1,2,4]triazolo[4,3-a][1,4]diazepin-6-yl)-N-(14-((5-(2-oxoindolin-5-yl)pyridin-2-yl)amino)-3,6,9,12-tetraoxatetradecyl)acetamide (114)

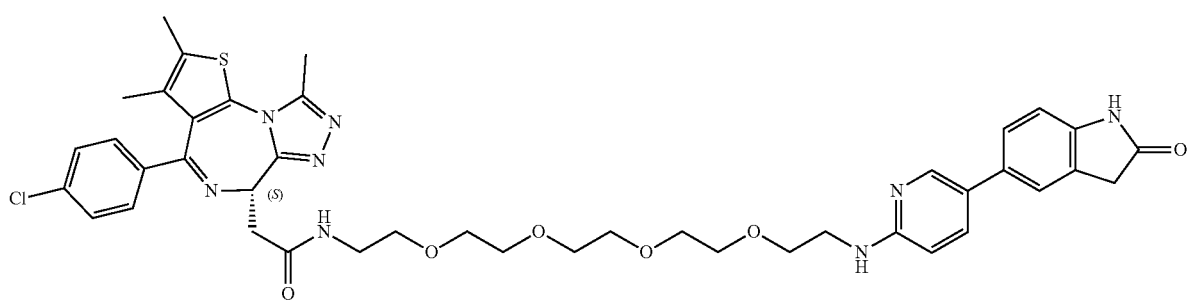

¹H NMR (400 MHz, DMSO-d₆) δ (ppm): 10.37 (s, 1H), 8.27 (t, J=5.5 Hz, 1H), 8.21 (d, J=2.4 Hz, 1H), 7.60 (dd, J=8.7, 2.5 Hz, 1H), 7.48 (d, J=8.8 Hz, 2H), 7.45-7.38 (m, 3H), 7.34 (dd, J=8.1, 1.8 Hz, 1H), 6.83 (d, J=8.1 Hz, 1H), 6.62-6.52 (m, 2H), 4.50 (dd, J=8.0, 6.1 Hz, 1H), 3.55-3.40 (m, 20H), 3.31-3.16 (m, 4H), 2.59 (s, 3H), 2.40 (s, 3H), 1.61 (s, 3H). LC-MS m/z [M+H]⁺: 827.3 with a purity of 98%.

2.2.32 Synthesis of (S)-2-(4-(4-chlorophenyl)-2,3,9-trimethyl-6H-thieno[3,2-f][1,2,4]triazolo[4,3-a][1,4]diazepin-6-yl)-N-(17-((5-(2-oxoindolin-5-yl)pyridin-2-yl)amino)-3,6,9,12,15-pentaoxaheptadecyl)acetamide (115)

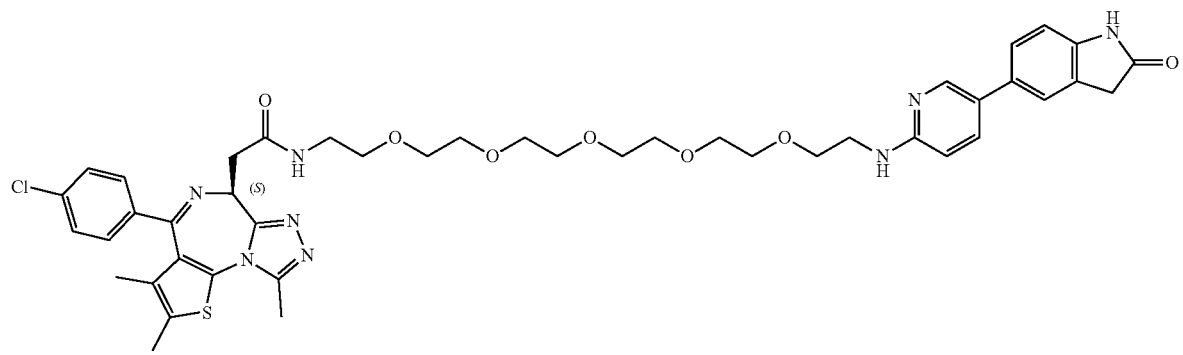

$^1$H NMR (400 MHz, DMSO-d$_6$) δ (ppm): 10.37 (s, 1H), 8.27 (t, J=5.5 Hz, 1H), 8.21 (d, J=2.3 Hz, 1H), 7.60 (dd, J=8.7, 2.5 Hz, 1H), 7.48 (d, J=8.8 Hz, 2H), 7.45-7.38 (m, 3H), 7.34 (dd, J=8.1, 1.8 Hz, 1H), 6.83 (d, J=8.1 Hz, 1H), 6.62-6.52 (m, 2H), 4.50 (dd, J=8.0, 6.1 Hz, 1H), 3.55-3.40 (m, 24H), 3.31-3.16 (m, 4H), 2.59 (s, 3H), 2.40 (s, 3H), 1.61 (s, 3H). LC-MS m/z [M+H]$^+$: 871.3 with a purity of 99%.

2.2.32 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-((5-(2-oxoindolin-5-yl)pyridin-2-yl)amino)ethoxy)ethoxy)ethyl)acetamide (116)

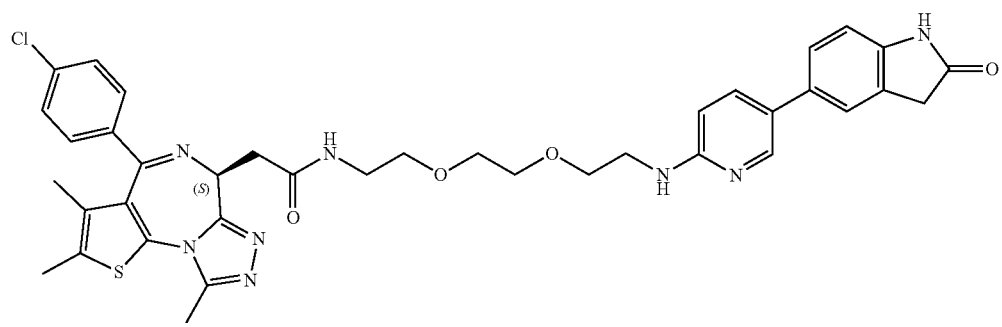

$^1$H NMR (400 MHz, DMSO-d$_6$) δ (ppm): 10.39 (s, 1H), 8.28 (t, J=5.5 Hz, 1H), 8.18 (d, J=2.3 Hz, 1H), 7.67 (d, J=7.2 Hz, 1H), 7.47 (d, J=8.8 Hz, 2H), 7.44-7.40 (m, 3H), 7.35 (d, J=8.0 Hz, 1H), 6.83 (d, J=8.0 Hz, 1H), 6.64-6.60 (m, 2H), 4.50 (dd, J=8.0, 6.1 Hz, 1H), 3.58-3.45 (m, 12H), 3.31-3.22 (m, 4H), 2.58 (s, 3H), 2.40 (s, 3H), 1.61 (s, 3H). LC-MS m/z [M+H]$^+$: 738.5 with a purity of 99%.

2.2.33 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-((5-(2-oxoindolin-5-yl)pyridin-2-yl)amino)ethoxy)ethyl)acetamide (117)

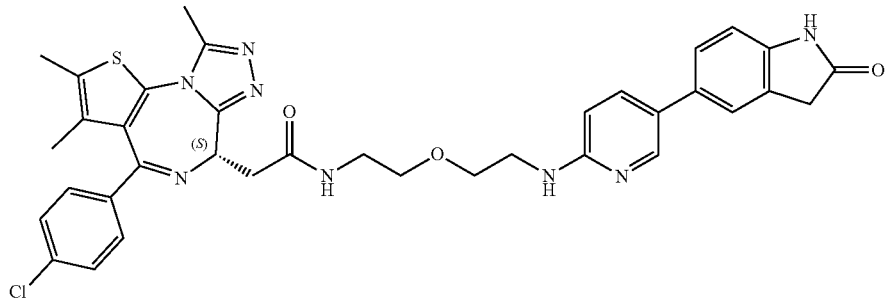

$^1$H NMR (400 MHz, DMSO-d$_6$) δ (ppm): 10.37 (s, 1H), 8.30 (t, J=5.5 Hz, 1H), 8.20 (d, J=2.3 Hz, 1H), 7.59 (dd, J=8.7, 2.5 Hz, 1H), 7.48 (d, J=8.8 Hz, 2H), 7.44-7.39 (m, 3H), 7.33 (dd, J=8.0, 2.0 Hz, 1H), 6.83 (d, J=8.0 Hz, 1H), 6.60-6.55 (m, 2H), 4.51 (dd, J=8.0, 6.1 Hz, 1H), 3.58-3.44 (m, 8H), 3.31-3.22 (m, 4H), 2.59 (s, 3H), 2.38 (s, 3H), 1.59 (s, 3H). LC-MS m/z [M+H]$^+$: 694.6 with a purity of 99%.

2.2.34 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-((5-(2-oxoindolin-5-yl)pyridin-2-yl)amino)ethoxy)ethoxy)ethoxy)phenyl)acetamide (118)

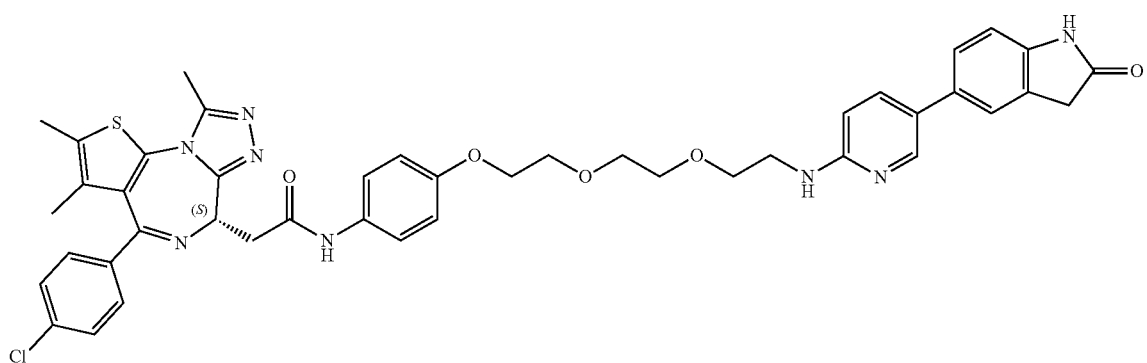

$^1$H NMR (400 MHz, DMSO-d$_6$) δ (ppm): 10.37 (s, 1H), 10.17 (s, 1H), 8.21 (d, J=2.4 Hz, 1H), 7.59 (dd, J=8.4, 2.4 Hz, 1H), 7.53 (d, J=8.4 Hz, 2H), 7.48 (d, J=8.4 Hz, 2H), 7.39-7.35 (m, 3H), 7.33 (d, J=1.6 Hz, 1H), 6.89 (d, J=8.8 Hz, 2H), 6.81 (d, J=8.0 Hz, 1H), 6.60-6.58 (m, 2H), 4.59 (t, J=7.2 Hz, 1H), 4.06-4.03 (m, 2H), 3.74-3.72 (m, 2H), 3.61-3.55 (m, 6H), 3.49-3.44 (m, 6H), 2.61 (s, 3H), 2.42 (s, 3H), 1.63 (s, 3H). LC-MS m/z [M+H]$^+$: 830.4 with a purity of 98%.

2.2.35 Synthesis of (S)-5-(6-(4-(2-(4-(4-chlorophenyl)-2,3,9-trimethyl-6H-thieno[3,2-f][1,2,4]triazolo[4,3-a][1,4]diazepin-6-yl)acetyl)piperazin-1-yl)pyridin-3-yl)indolin-2-one (119)

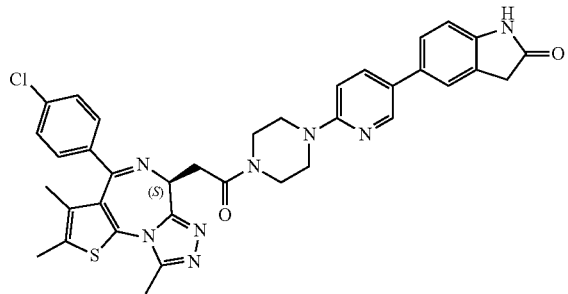

$^1$H NMR (400 MHz, DMSO-d$_6$) δ (ppm): 10.41 (s, 1H), 8.40 (d, J=2.4 Hz, 1H), 7.82 (dd, J=8.4, 2.4 Hz, 1H), 7.48-7.42 (m, 6H), 7.94 (d, J=4.8 Hz, 1H), 6.87 (d, J=8.0 Hz, 1H), 4.61 (t, J=7.2 Hz, 1H), 3.81-3.80 (m, 2H), 3.70-3.61 (m, 6H), 3.53-3.44 (m, 4H), 2.61 (s, 3H), 2.42 (s, 3H), 1.63 (s, 3H). LC-MS m/z [M+H]$^+$: 676.5 with a purity of 96%.

2.2.36 Synthesis of (S)-2-(4-(4-chlorophenyl)-2,3,6,9-tetramethyl-6H-thieno[3,2-f][1,2,4]triazolo[4,3-a][1,4]diazepin-6-yl)-N-(2-(2-(3-oxo-3-(4-(5-(2-oxoindolin-5-yl)pyridin-2-yl)piperazin-1-yl)propoxy)ethoxy)ethyl)acetamide (120)

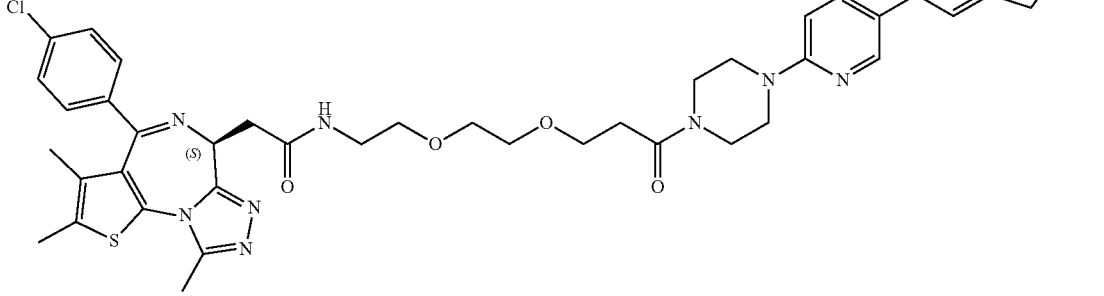

$^1$H NMR (400 MHz, DMSO-d$_6$) δ (ppm): 10.40 (s, 1H), 8.37 (d, J=2.4 Hz, 1H), 8.26 (t, J=5.6 Hz, 1H), 7.78 (dd, J=8.4, 2.4 Hz, 1H), 7.49-7.39 (m, 6H), 6.90-6.88 (m, 2H), 4.50 (t, J=7.2 Hz, 1H), 3.66 (t, J=6.4 Hz, 2H), 3.56-3.43 (m, 16H), 3.31-3.21 (m, 4H), 2.65-2.63 (m, 2H), 2.62 (s, 3H), 2.40 (s, 3H), 1.61 (s, 3H). LC-MS m/z [M+H]$^+$: 835.3 with a purity of 99%.

22.37 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((5-(1-methyl-2-oxoindolin-5-yl)pyridin-2-yl)amino)ethoxy)ethoxy)ethoxy)ethyl)acetamide (121)

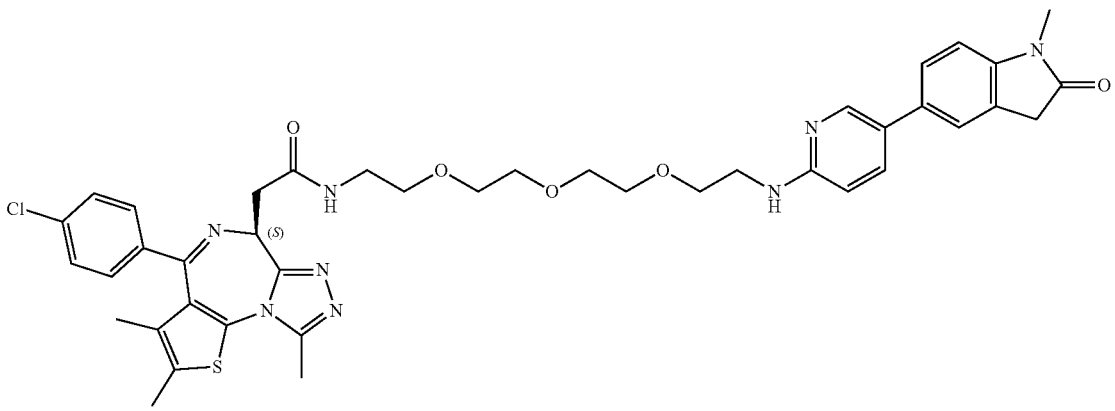

$^1$H NMR (400 MHz, DMSO-d$_6$) δ (ppm): 8.27 (t, J=5.5 Hz, 1H), 8.24 (J=2.4 Hz, 1H), 7.64 (dd, J=8.8, 2.8 Hz, 1H), 7.48-7.40 (m, 6H), 6.99 (d, J=8.8 Hz, 1H), 6.61-6.59 (m, 2H), 4.51 (t, J=4.7 Hz, 1H), 3.56-3.43 (m, 16H), 3.29-3.21 (m, 4H), 3.12 (s, 3H), 2.59 (s, 3H), 2.40 (s, 3H), 1.60 (s, 3H) LC-MS m/z [M+H]$^+$: 798.5 with a purity of 99%.

2.2.38 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-oxo-2-(4-(5-(2-oxoindolin-5-yl)pyridin-2-yl)piperazin-1-yl)ethyl)acetamide (122)

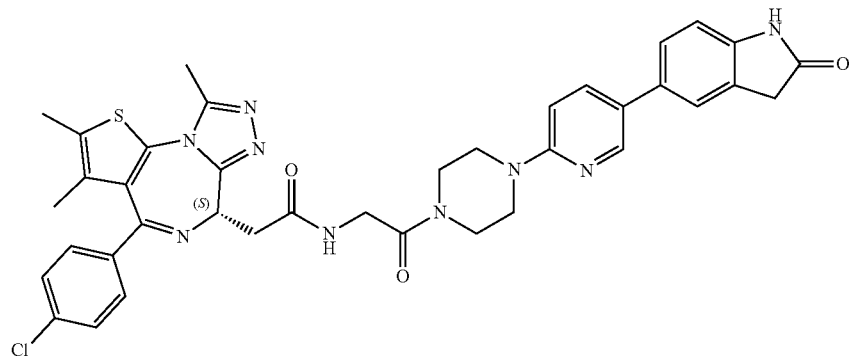

$^1$H NMR (400 MHz, DMSO-d$_6$) δ (ppm): 10.41 (s, 1H), 8.38 (t, J=2.4 Hz, 2H), 7.80 (dd, J=8.8, 2.4 Hz, 1H), 7.46-7.40 (m, 6H), 6.91 (d, J=8.8 Hz, 1H), 6.86 (d, J=8.0 Hz, 1H), 4.53 (dd, J=8.0, 1.6 Hz, 1H), 4.14-4.02 (m, 2H), 3.57-3.24 (m, 12H), 2.59 (s, 3H), 2.41 (s, 3H), 1.62 (s, 3H). LC-MS m/z [M+H]$^+$: 735.5 with a purity of 99%.

2.2.39 Synthesis of (S)-5-(6-(4-(1-(2-(4-(4-chlorophenyl)-2,3,9-trimethyl-6H-thieno[3,2-f][1,2,4]triazolo[4,3-a][1,4]diazepin-6-yl)acetyl)piperidin-4-yl)piperazin-1-yl)pyridin-3-yl)indolin-2-one (123)

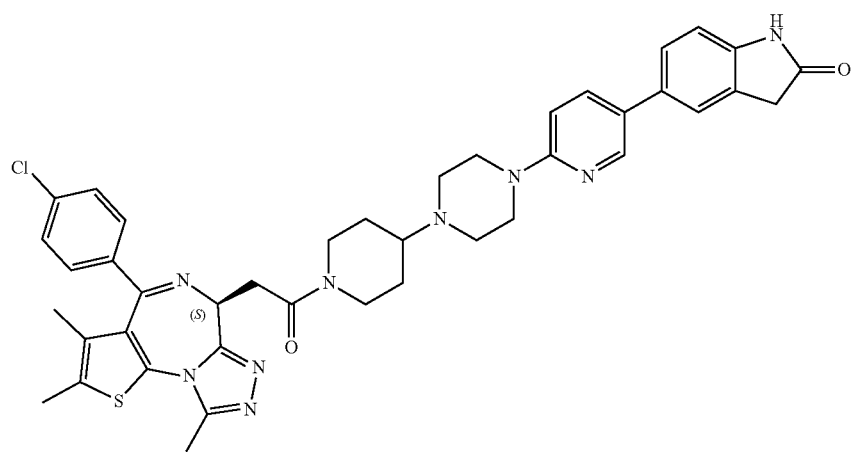

$^1$H NMR (400 MHz, DMSO-d$_6$) δ (ppm): 10.40 (s, 1H), 8.36 (d, J=2.4 Hz, 1H), 7.77 (dd, J=8.8, 2.4 Hz, 1H), 7.50-7.39 (m, 6H), 6.92 (d, J=8.4 Hz, 1H), 6.86 (d, J=8.0 Hz, 1H), 4.57 (t, J=8.0 Hz, 1H), 4.41-4.39 (m, 2H), 3.63-3.61 (m, 3H), 3.43-3.37 (m, 8H), 2.87-2.81 (m, 4H), 2.60 (s, 3H), 2.41 (s, 3H), 2.00-1.85 (m, 2H), 1.62 (s, 3H), 1.55-1.45 (m, 2H). LC-MS m/z [M+H]$^+$: 761.5 with a purity of 99%.

2.2.40 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-((5-(2-oxoindolin-5-yl)pyridin-2-yl)amino)ethyl)acetamide (124)

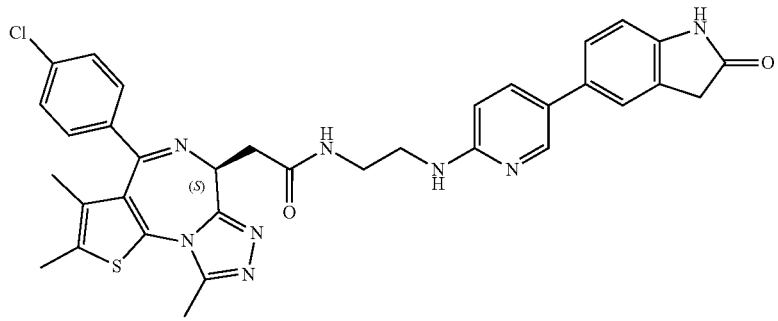

$^1$H NMR (400 MHz, DMSO-d$_6$) δ (ppm): 10.38 (s, 1H), 8.35 (t, J=2.4 Hz, 1H), 8.22 (d, J=2.0 Hz, 1H), 7.63 (dd, J=8.8, 2.4 Hz, 1H), 7.49-7.34 (m, 6H), 6.84 (d, J=8.0 Hz, 1H), 6.61-6.53 (m, 2H), 4.52 (t, J=7.2 Hz, 1H), 3.50-3.20 (m, 8H), 2.59 (s, 3H), 2.41 (s, 3H), 1.62 (s, 3H). LC-MS m/z [M+H]$^+$: 650.6 with a purity of 98%.

2.2.41 Synthesis of (S)-2-(4-(4-chlorophenyl)-2,3,9-trimethyl-6H-thieno[3,2-f][1,2,4]triazolo[4,3-a][1,4]diazepin-6-yl)-N-(1-(5-(2-oxoindolin-5-yl)pyridin-2-yl)piperidin-4-yl)acetamide (125)

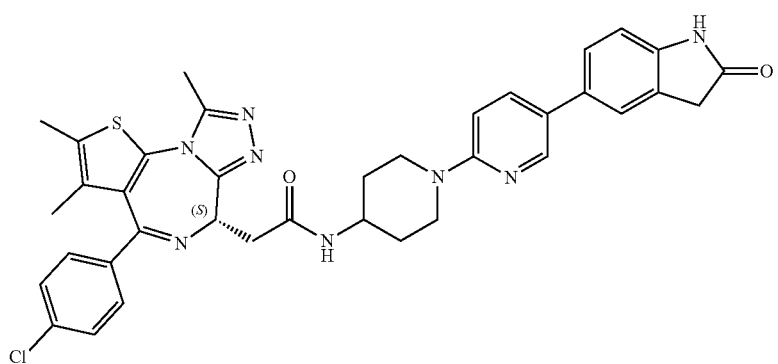

$^1$H NMR (400 MHz, DMSO-d$_6$) δ (ppm): 10.40 (s, 1H), 8.37 (d, J=2.4 Hz, 1H), 8.20 (t, J=8.0 Hz, 1H), 7.77 (dd, J=9.2, 2.8 Hz, 1H), 7.51-7.39 (m, 6H), 6.93 (d, J=8.8 Hz, 1H), 6.86 (d, J=8.0 Hz, 1H), 4.51 (dd, J=8.4, 2.0 Hz, 1H), 4.25-4.15 (m, 2H), 3.90-3.80 (m, 1H), 3.51 (s, 2H), 3.29-2.99 (m, 4H), 2.59 (s, 3H), 2.41 (s, 3H), 1.90-1.80 (m, 2H), 1.62 (s, 3H), 1.55-1.45 (m, 2H). LC-MS m/z [M+H]$^+$: 690.5 with a purity of 98%.

2.2.42 Synthesis of (S)-2-(4-(4-chlorophenyl)-2,3,9-trimethyl-6H-thieno[3,2-f][1,2,4]triazolo[4,3-a][1,4]diazepin-6-yl)-N-(5-((5-(2-oxoindolin-5-yl)pyridin-2-yl)amino)pentyl)acetamide (126)

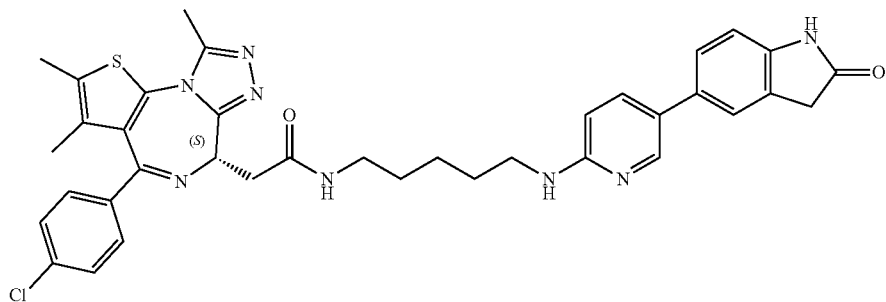

$^1$H NMR (400 MHz, DMSO-d$_6$) δ (ppm): 10.37 (s, 1H), 8.24-8.15 (m, 2H), 7.58 (dd, J=8.8, 2.8 Hz, 1H), 7.48 (d, J=8.8 Hz, 2H), 7.45-7.37 (m, 3H), 7.33 (dd, J=8.0, 1.8 Hz, 1H), 6.83 (d, J=8.1 Hz, 1H), 6.53 (t, J=5.3 Hz, 1H), 6.50 (d, J=8.7 Hz, 1H), 4.51 (dd, J=8.2, 5.9 Hz, 1H), 3.53-3.48 (m, 2H), 3.24-3.02 (m, 6H), 2.59 (s, 3H), 2.39 (s, 3H), 1.60 (s, 3H), 1.59-1.52 (m, 2H), 1.52-1.45 (m, 2H), 1.43-1.35 (m, 2H). LC-MS m/z [M+H]$^+$: 692.6 with a purity of 96%.

2.2.43 Synthesis of (S)-2-(4-(4-chlorophenyl)-2,3,9-trimethyl-6H-thieno[3,2-f][1,2,4]triazolo[4,3-a][1,4]diazepin-6-yl)-N-((1-(5-(2-oxoindolin-5-yl)pyridin-2-yl)piperidin-4-yl)methyl)acetamide (127)

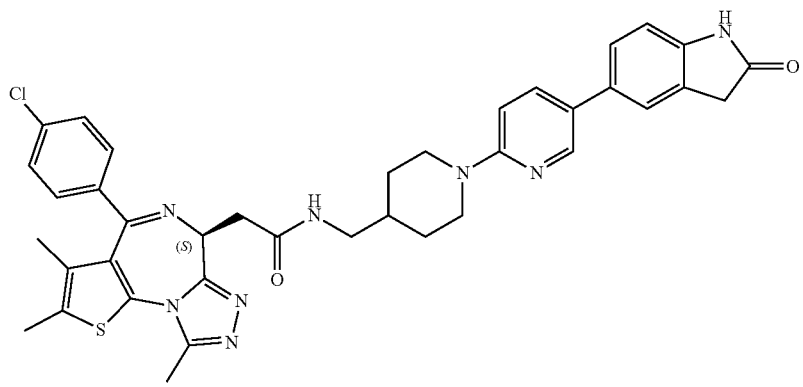

$^1$H NMR (400 MHz, DMSO-d$_6$) δ (ppm): 10.40 (s, 1H), 8.92 (d, J=6.9 Hz, 1H), 8.35 (d, J=2.0 Hz, 1H), 7.78 (dd, J=8.6, 2.5 Hz, 1H), 7.78 (dd, J=8.6, 2.5 Hz, 1H), 7.49-7.38 (m, 6H), 6.86 (d, J=8.0 Hz, 1H), 6.51 (d, J=8.6 Hz, 1H), 4.70-4.60 (m, 1H), 4.52 (t, J=7.2 Hz, 1H), 4.32-4.21 (m, 2H), 3.88-3.79 (m, 2H), 3.52 (s, 2H), 3.30-3.21 (m, 2H), 2.59 (s, 3H), 2.41 (s, 3H), 1.62 (s, 3H) LC-MS m/z [M+H]$^+$: 704.6 with a purity of 96%.

2.2.44 Synthesis of (S)-2-(4-(4-chlorophenyl)-2,3,9-trimethyl-6H-thieno[3,2-f][1,2,4]triazolo[4,3-a][1,4]diazepin-6-yl)-N-(1-(5-(2-oxoindolin-5-yl)pyridin-2-yl)azetidin-3-yl)acetamide (128)

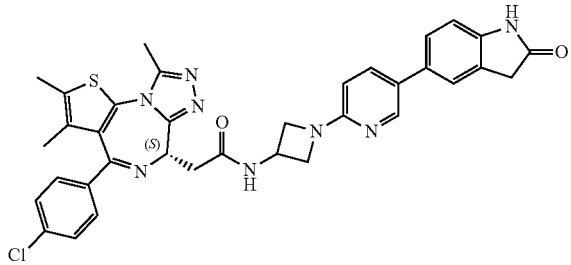

$^1$H NMR (400 MHz, DMSO-d$_6$) δ (ppm): 10.40 (s, 1H), 8.34 (d, J=2.4 Hz, 1H), 8.25 (t, J=5.8 Hz, 1H), 7.76 (d, J=7.6 Hz, 1H), 7.51-7.38 (m, 6H), 6.90 (d, J=8.8 Hz, 1H), 6.86 (d, J=8.0 Hz, 1H), 4.51 (dd, J=8.6, 5.7 Hz, 1H), 4.32 (d, J=12.5 Hz, 2H), 3.51 (s, 2H), 3.23-3.15 (m, 1H), 3.14-2.97 (m, 2H), 2.81 (t, J=12.3 Hz, 2H), 2.59 (s, 3H), 2.41 (s, 3H), 1.62 (s, 3H). LC-MS m/z [M+H]$^+$: 662.6 with a purity of 99%.

2.2.45 Synthesis of 2-((S)-4-(4-chlorophenyl)-2,3,9-trimethyl-6H-thieno[3,2-f][1,2,4]triazolo[4,3-a][1,4]diazepin-6-yl)-N-(1-(5-(2-oxoindolin-5-yl)pyridin-2-yl)pyrrolidin-3-yl)acetamide (129)

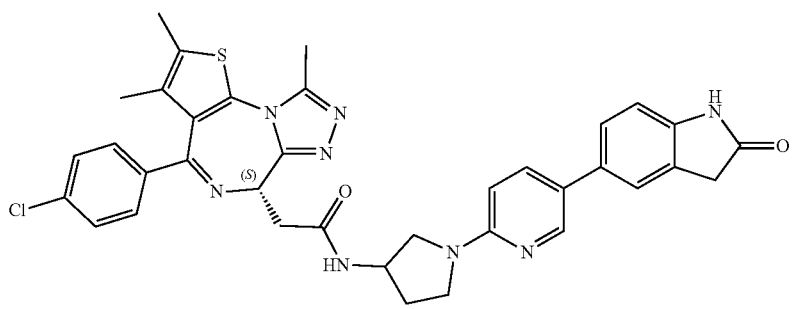

$^1$H NMR (400 MHz, DMSO-d$_6$) δ (ppm): 10.39 (s, 1H), 8.57 (d, J=6.6 Hz, 1H), 8.37 (d, J=2.4 Hz, 1H), 7.77 (dd, J=8.8, 2.5 Hz, 1H), 7.44 (bs, 1H), 7.41-7.37 (m, 1H), 7.35-7.31 (m, 4H), 6.86 (d, J=8.0 Hz, 1H), 6.56 (d, J=8.8 Hz, 1H), 4.51 (dd, J=8.9, 5.3 Hz, 1H), 4.44-4.38 (m, 1H), 3.70-3.42 (m, 8H), 3.19-3.10 (m, 2H), 2.59 (s, 3H), 2.41 (s, 3H), 1.62 (s, 3H). LC-MS m/z [M+H]$^+$: 676.6 with a purity of 98%.

2.2.46 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(3-oxo-3-(4-(5-(2-oxoindolin-5-yl)pyridin-2-yl)piperazin-1-yl)propoxy)ethyl)acetamide (130)

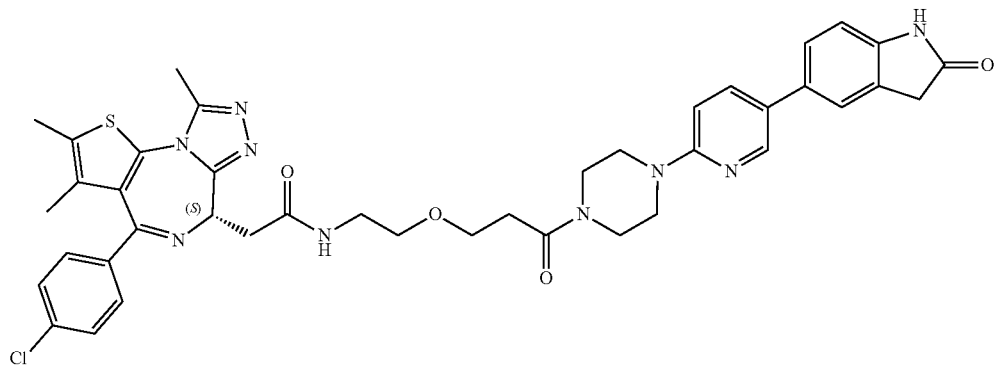

¹H NMR (400 MHz, DMSO-d₆) δ (ppm): 10.41 (s, 1H), 8.37 (d, J=2.3 Hz, 1H), 8.26 (t, J=5.3 Hz, 1H), 7.79 (dd, J=8.8, 2.5 Hz, 1H), 7.51-7.38 (m, 6H), 6.93-6.82 (m, 2H), 4.50 (dd, J=8.0, 6.2 Hz, 1H), 3.69 (t, J=6.6 Hz, 2H), 3.62-3.43 (m, 14H), 3.27-3.18 (m, 2H), 2.65 (t, J=6.4 Hz, 2H), 2.59 (s, 3H), 2.40 (s, 3H), 1.61 (s, 3H). LC-MS m/z [M+H]⁺: 791.5 with a purity of 99%.

2.2.47 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-((14-((5-(2-oxoindolin-5-yl)pyridin-2-yl)amino)-3,6,9,12-tetraoxatetradecyl)oxy)phenyl)acetamide (131)

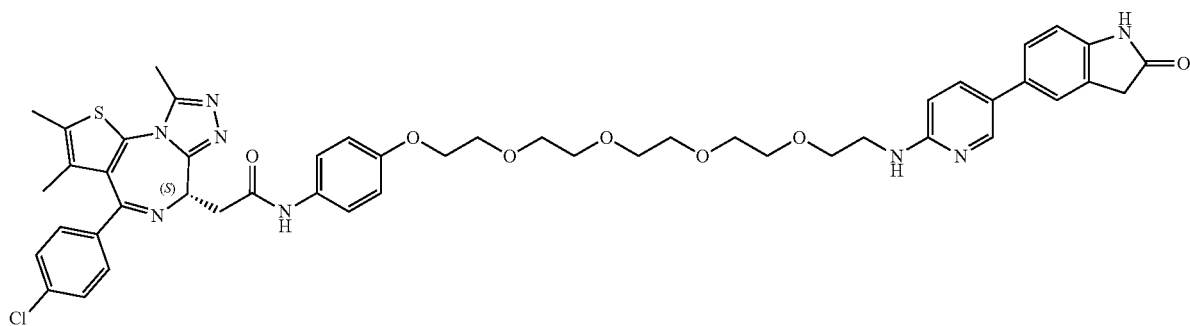

¹H NMR (400 MHz, DMSO-d₆) δ (ppm): 10.36 (s, 1H), 10.16 (s, 1H), 8.20 (d, J=2.4 Hz, 1H), 7.59 (dd, J=8.4, 2.4 Hz, 1H), 7.53 (d, J=2.0 Hz, 2H), 7.51 (d, J=2.0 Hz, 2H), 7.48-7.38 (m, 3H), 7.33 (dd, J=8.0, 2.0 Hz, 1H), 6.91-6.88 (m, 2H), 6.83 (d, J=8.0, 1H), 6.58-6.54 (m, 2H), 4.58 (t, J=6.2 Hz, 1H), 4.05-4.02 (m, 2H), 3.72-3.71 (m, 2H), 3.57-3.42 (m, 20H), 2.60 (s, 3H), 2.41 (s, 3H), 1.62 (s, 3H). LC-MS m/z [M+H]⁺: 918.5 with a purity of 97%.

2.2.48 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-((5-(2-oxoindolin-5-yl)pyridin-2-yl)oxy)ethoxy)ethyl)acetamide (132)

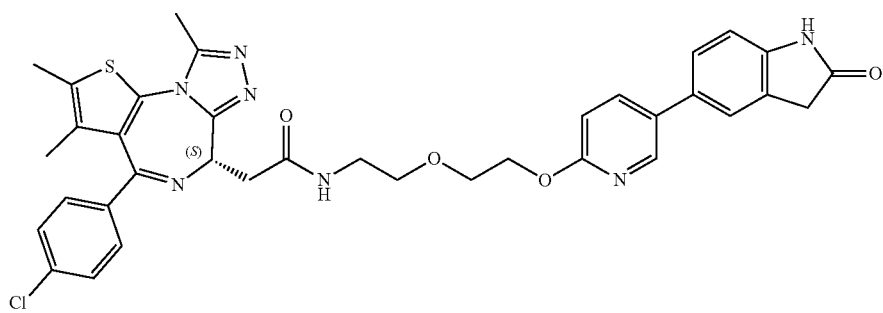

¹H NMR (400 MHz, DMSO-d₆) δ (ppm): 10.45 (s, 1H), 8.37 (d, J=2.2 Hz, 1H), 8.31 (t, J=5.6 Hz, 1H), 7.92 (dd, J=8.6, 2.6 Hz, 1H), 7.51-7.40 (m, 6H), 6.88 (d, J=8.2 Hz, 2H), 4.51 (dd, J=8.2, 5.9 Hz, 1H), 4.45-4.40 (m, 2H), 3.78 (t, J=4.8 Hz, 2H), 3.56-3.52 (m, 4H), 3.37-3.14 (m, 4H), 2.59 (s, 3H), 2.40 (s, 3H), 1.61 (s, 3H). LC-MS m/z [M+H]⁺: 695.5 with a purity of 98%.

22.49 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-((5-(2-oxoindolin-5-yl)pyrimidin-2-yl)amino)ethoxy)ethyl)acetamide (133)

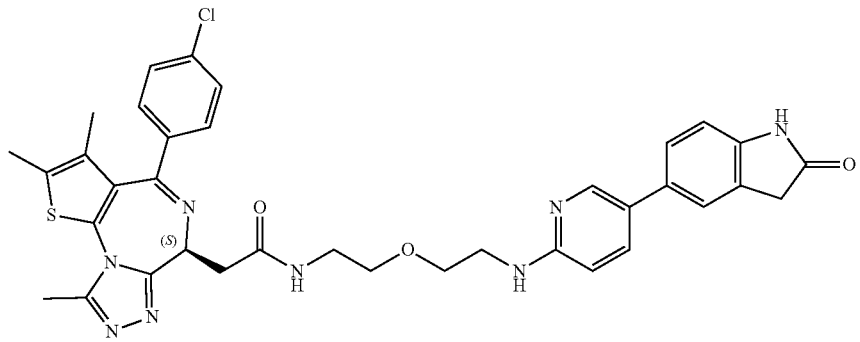

$^{1}$H NMR (400 MHz, DMSO-d$_{6}$) δ (ppm): 10.42 (s, 1H), 8.52 (s, 2H), 8.31 (t, J=5.5 Hz, 1H), 7.49-7.36 (m, 6H), 7.19 (t, J=5.6 Hz, 1H), 6.86 (d, J=8.0 Hz, 1H), 4.53 (dd, J=8.4, 5.8 Hz, 1H), 3.61-3.56 (m, 2H), 3.53-3.46 (m, 6H), 3.40-3.35 (m, 1H), 3.30-3.17 (m, 3H), 2.59 (s, 3H), 2.38 (s, 3H), 1.60 (s, 3H). LC-MS m/z [M+H]$^{+}$: 695.5 with a purity of 99%.

2.2.50 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(1-(5-(2-oxoindolin-5-yl)pyridin-2-yl)piperidin-4-yl)ethyl)acetamide (134)

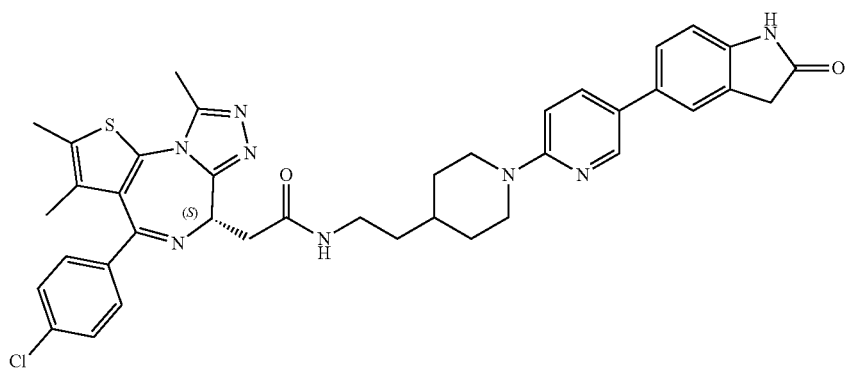

$^{1}$H NMR (400 MHz, MeOD) δ (ppm): 8.73 (t, J=5.2 Hz, 1H), 8.22 (d, J=2.3 Hz, 1H), 7.90 (dd, J=9.1, 2.4 Hz, 1H), 7.50-7.38 (m, 6H), 7.02 (d, J=9.2 Hz, 1H), 6.96 (d, J=8.1 Hz, 1H), 4.65 (dd, J=8.4, 5.8 Hz, 1H), 4.29-4.19 (m, 2H), 3.59 (bs, 2H), 3.45-3.33 (m, 4H), 3.01-2.90 (m, 2H), 2.69 (s, 3H), 2.44 (s, 3H), 1.89 (d, J=12.5 Hz, 2H), 1.70 (bs, 4H), 1.56 (dd, J=13.5, 6.8 Hz, 2H), 1.36-1.23 (m, 2H). LC-MS m/z [M+H]$^{+}$: 718.6 with a purity of 96%.

22.51 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-((3-(2-oxoindolin-5-yl)pyridin-2-yl)amino)ethoxy)ethyl)acetamide (135)

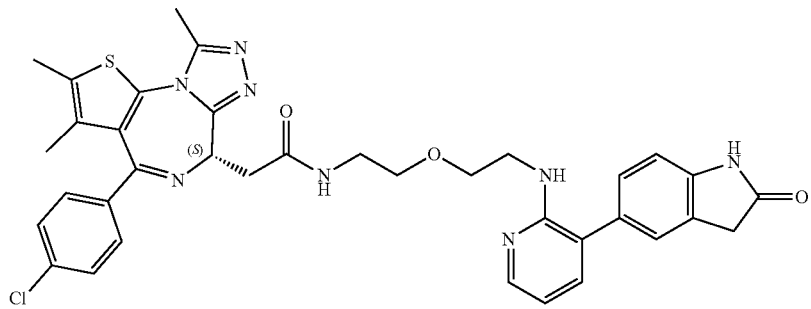

¹H NMR (400 MHz, MeOD) δ (ppm): 7.95 (dd, J=5.5, 1.7 Hz, 1H), 7.50-7.34 (m, 5H), 7.28 (bs, 1H), 7.24 (d, J=8.0 Hz, 1H), 6.98 (d, J=8.0 Hz, 1H), 6.73 (dd, J=7.2, 5.4 Hz, 1H), 4.59 (dd, J=8.7, 5.4 Hz, 1H), 3.66 (t, J=5.2 Hz, 2H), 3.61-3.51 (m, 6H), 3.43-3.39 (m, 2H), 3.38-3.34 (m, 1H), 3.23 (dd, J=15.1, 5.4 Hz, 1H), 2.69 (s, 3H), 2.44 (s, 3H), 1.67 (s, 3H). LC-MS m/z [M+H]⁺: 695.6 with a purity of 98%.

2.2.52 Synthesis of (S)-2-(4-(4-chlorophenyl)-2,3,9-trimethyl-6H-thieno[3,2-f][1,2,4]triazolo[4,3-a][1,4]diazepin-6-yl)-N-(1-(3-(2-oxoindolin-5-yl)pyridin-2-yl)piperidin-4-yl)acetamide (136)

¹H NMR (400 MHz, DMSO-d₆) δ (ppm): 10.48 (s, 1H), 8.18-8.10 (m, 2H), 7.53-7.38 (m, 7H), 6.97 (dd, J=7.4, 2.6 Hz, 1H), 6.89 (d, J=8.0 Hz, 1H), 4.49 (dd, J=8.3, 4.5 Hz, 1H), 3.74-3.63 (m, 1H), 3.56 (s, 2H), 3.52-3.39 (m, 3H), 3.28-3.12 (m, 2H), 2.73-2.64 (m, 2H), 2.59 (s, 3H), 2.41 (s, 3H), 1.75-1.69 (m, 1H), 1.61 (s, 3H), 1.49-1.32 (m, 2H). LC-MS m/z [M+H]⁺: 690.6 with a purity of 98%.

22.53 Synthesis of (S)-2-(4-(4-chlorophenyl)-2,3,9-trimethyl-6H-thieno[3,2-f][1,2,4]triazolo[4,3-a][1,4]diazepin-6-yl)-N-(1-(3-(2-oxoindolin-5-yl)pyridin-2-yl)piperidin-4-yl)acetamide (137)

¹H NMR (400 MHz, DMSO-d₆) δ (ppm): 10.49-10.34 (m, 1H), 8.15-8.03 (m, 1H), 7.57-7.34 (m, 5H), 7.26-7.12 (m, 2H), 6.92-6.71 (m, 2H), 4.53 (t, J=5.0 Hz, 1H), 3.88-3.35 (m, 8H), 3.28-3.20 (m, 3H), 3.13-2.97 (m, 2H), 2.63-2.57 (m, 3H), 2.46-2.38 (m, 3H), 1.99-1.92 (m, 1H), 1.89-1.71 (m, 3H), 1.68-1.60 (m, 3H). LC-MS m/z [M+H]⁺: 716.5 with a purity of 99%.

2.2.54 Synthesis of (S)-2-(4-(4-chlorophenyl)-2,3,9-trimethyl-6H-thieno[3,2-f][1,2,4]triazolo[4,3-a][1,4]diazepin-6-yl)-N-(6-((3-(2-oxoindolin-5-yl)pyridin-2-yl)amino)spiro[3.3]heptan-2-yl)acetamide (138)

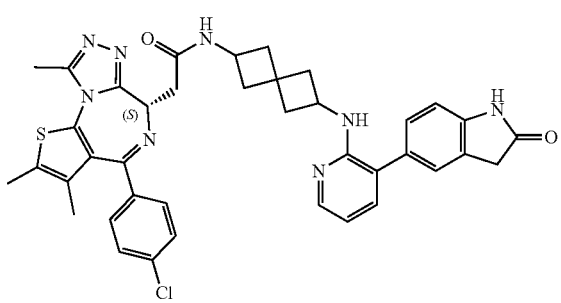

$^1$H NMR (400 MHz, MeOD) δ (ppm): 7.97-7.92 (m, 1H), 7.45-7.37 (m, 4H), 7.33-7.30 (m, 1H), 7.28 (bs, 1H), 7.25-7.21 (m, 1H), 7.03-6.79 (m, 1H), 6.68 (dd, J=7.2, 5.3 Hz, 1H), 4.60 (dd, J=8.9, 5.3 Hz, 1H), 4.36-4.19 (m, 2H), 3.62-3.56 (m, 2H), 3.37 (dd, J=15.0, 9.0 Hz, 1H), 3.27-3.20 (m, 1H), 2.69 (s, 3H), 2.61-2.49 (m, 2H), 2.47-2.39 (m, 4H), 2.37-2.23 (m, 1H), 2.15-1.97 (m, 2H), 1.92-1.81 (m, 2H), 1.72-1.67 (m, 3H). LC-MS m/z [M+H]$^+$: 717.5 with a purity of 99%.

22.55 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-((3-(2-oxoindolin-5-yl)pyridin-2-yl)amino)butyl)acetamide (139)

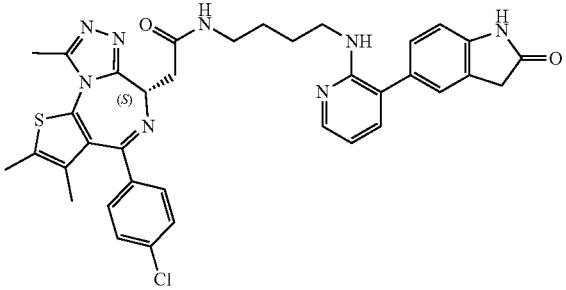

$^1$H NMR (400 MHz, DMSO-d$_6$) δ (ppm): 10.46 (s, 1H), 8.18 (t, J=5.5 Hz, 1H), 7.98 (dd, J=5.0, 1.8 Hz, 1H), 7.48-7.38 (m, 4H), 7.27-7.14 (m, 3H), 6.89 (d, J=7.9 Hz, 1H), 6.59 (t, J=6.5 Hz, 1H), 4.49 (dd, J=8.1, 6.1 Hz, 1H), 3.49 (bs, 2H), 3.27-3.05 (m, 6H), 2.58 (s, 3H), 2.40 (s, 3H), 1.60 (s, 3H), 1.58-1.50 (m, 2H), 1.50-1.37 (m, 2H). LC-MS m/z [M+H]$^+$: 678.6 with a purity of 97%.

2.2.56 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-((3-(2-oxoindolin-5-yl)pyridin-2-yl)amino)ethoxy)ethoxy)phenyl)acetamide (140)

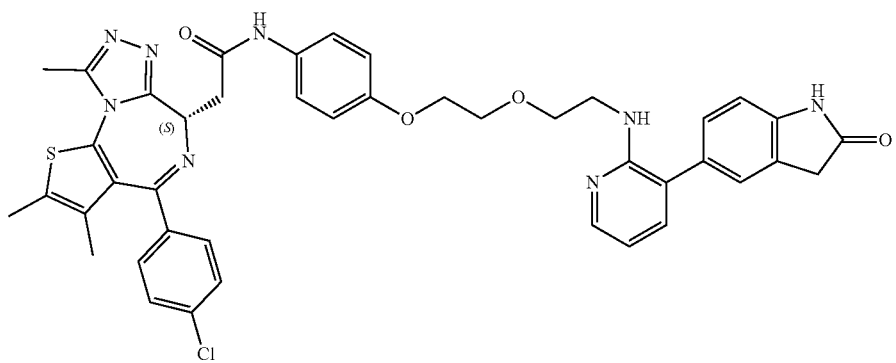

$^1$H NMR (400 MHz, MeOD) δ (ppm): 7.96 (dd, J=5.2, 1.8 Hz, 1H), 7.48-7.42 (m, 4H), 7.41-7.35 (m, 2H), 7.29 (dd, J=7.2, 1.8 Hz, 1H), 7.22 (bs, 1H), 7.21-7.17 (m, 1H), 6.84 (d, J=7.9 Hz, 1H), 6.81-6.75 (m, 2H), 6.68 (dd, J=7.2, 5.2, 1H), 4.73 (dd, J=8.7, 5.5 Hz, 1H), 4.05-3.99 (m, 2H), 3.81-3.75 (m, 2H), 3.74-3.68 (m, 2H), 3.65-3.54 (m, 3H), 3.53-3.43 (m, 3H), 2.71 (s, 3H), 2.44 (s, 3H), 1.70 (s, 3H). LC-MS m/z [M+H]$^+$: 787.5 with a purity of 99%.

22.57 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-((3-(2-oxoindolin-5-yl)pyridin-2-yl)amino)ethoxy)ethoxy)ethoxy)phenyl)acetamide (141)

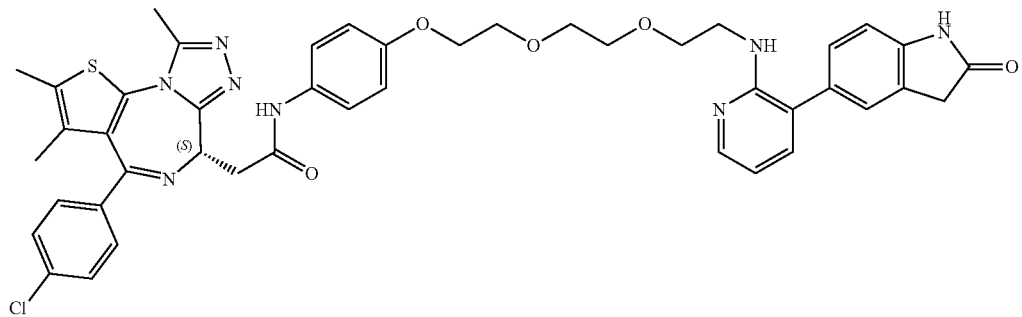

$^1$H NMR (400 MHz, MeOD) δ (ppm): 7.96 (dd, J=5.2, 1.8 Hz, 1H), 7.48-7.42 (m, 4H), 7.41-7.35 (m, 2H), 7.29 (dd, J=7.2, 1.8 Hz, 1H), 7.22 (bs, 1H), 7.21-7.17 (m, 1H), 6.84 (d, J=7.9 Hz, 1H), 6.81-6.75 (m, 2H), 6.68 (dd, J=7.2, 5.2, 1H), 4.73 (dd, J=8.7, 5.5 Hz, 1H), 4.01-3.98 (m, 2H), 3.73-3.70 (m, 2H), 3.65-3.59 (m, 7H), 3.53-3.43 (m, 5H), 2.71 (s, 3H), 2.44 (s, 3H), 1.70 (s, 3H). LC-MS m/z [M+H]$^+$: 787.5 with a purity of 99%.

2.2.58 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((3-(2-oxoindolin-5-yl)pyridin-2-yl)amino)ethoxy)ethoxy)ethoxy)ethoxy)phenyl)acetamide (142)

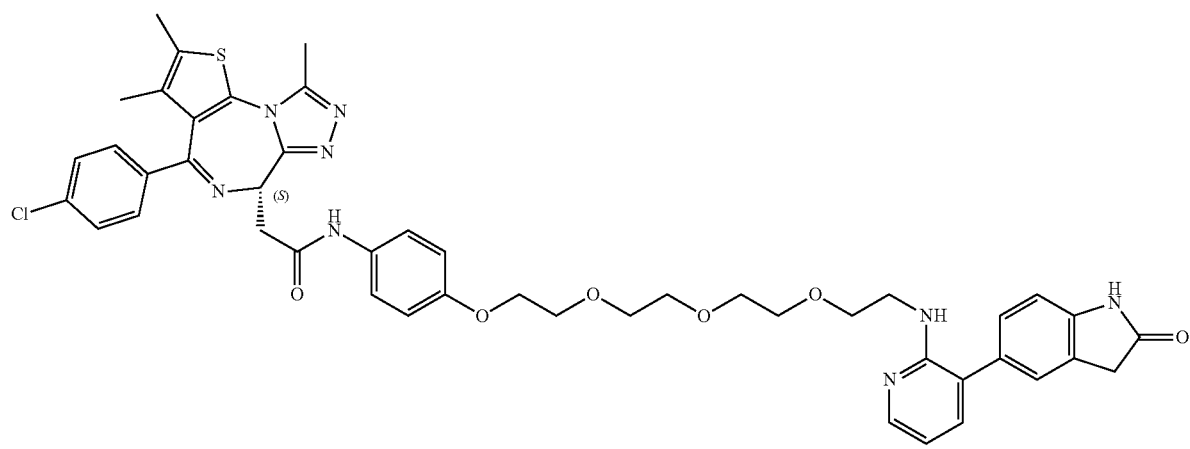

$^1$H NMR (400 MHz, MeOD) δ (ppm): 7.95 (dd, J=5.3, 1.8 Hz, 1H), 7.50-7.42 (m, 4H), 7.41-7.36 (m, 2H), 7.31 (dd, J=7.2, 1.8 Hz, 1H), 7.29-7.26 (m, 1H), 7.25-7.20 (m, 1H), 6.97 (d, J=8.0 Hz, 1H), 6.89-6.84 (m, 2H), 6.68 (dd, J=7.2, 5.3 Hz, 1H), 4.69 (dd, J=8.8, 5.4 Hz, 1H), 4.09-4.02 (m, 2H), 3.80-3.74 (m, 2H), 3.63-3.59 (m, 4H), 3.59-3.54 (m, 8H), 3.54-3.43 (m, 4H), 2.70 (s, 3H), 2.45 (s, 3H), 1.69 (s, 3H). LC-MS m/z [M+H]$^+$: 874.4 with a purity of 99%.

22.59 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-(2-oxoindolin-5-yl)pyridin-2-yl)amino)ethoxy)ethoxy)ethoxy)ethoxy)phenyl)acetamide (143)

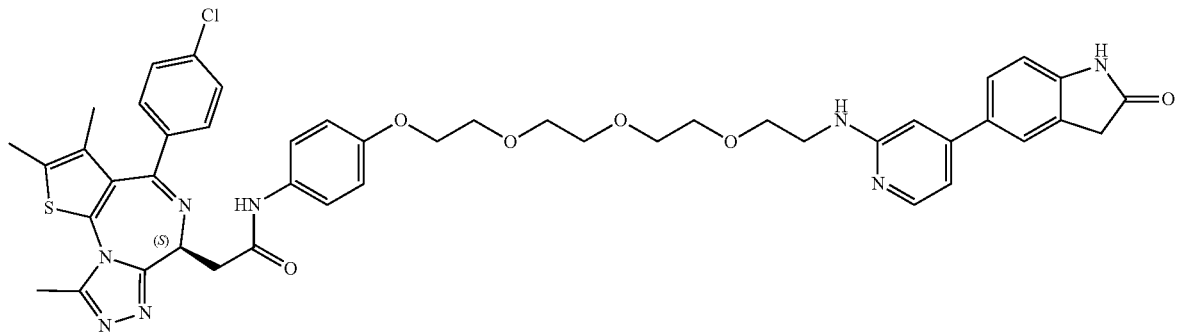

$^1$H NMR (400 MHz, MeOD) δ (ppm) 7.91 (d, J=5.6 Hz, 1H), 7.57-7.49 (m, 2H), 7.48-7.41 (m, 4H), 7.41-7.36 (m, 2H), 6.95 (d, J=8.1 Hz, 1H), 6.90-6.82 (m, 4H), 4.70 (dd, J=8.7, 5.6 Hz, 1H), 4.09-4.04 (m, 2H), 3.83-3.78 (m, 2H), 3.72-3.64 (m, 10H), 3.62-3.42 (m, 6H), 2.70 (s, 3H), 2.44 (s, 3H), 1.68 (s, 3H). LC-MS m/z [M+H]$^+$: 874.4 with a purity of 98%.

2.2.60 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-(2-oxoindolin-6-yl)pyridin-2-yl)amino)ethoxy)ethoxy)ethoxy)ethoxy)phenyl)acetamide (144)

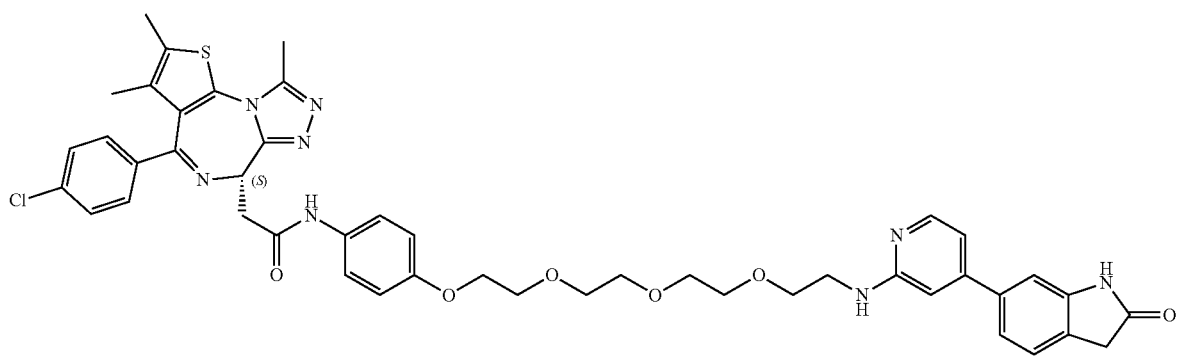

$^1$H NMR (400 MHz, MeOD) δ (ppm) 7.88 (d, J=6.8 Hz, 1H), 7.49-7.36 (m, 7H), 7.35-7.30 (m, 1H), 7.13 (s, 2H), 7.05 (dd, J=7.8, 1.6 Hz, 1H), 6.84-6.79 (m, 2H), 4.80 (dd, J=8.4, 6.2 Hz, 1H), 4.07-4.03 (m, 2H), 3.84-3.79 (m, 2H), 3.79-3.75 (m, 2H), 3.73-3.66 (m, 8H), 3.63-3.57 (m, 3H), 3.57-3.54 (m, 2H), 3.53-3.46 (m, 1H), 2.78 (s, 3H), 2.47 (s, 3H), 1.70 (s, 3H). LC-MS m/z [M+H]$^+$: 874.4 with a purity of 98%.

2.2.61 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((6-morpholino-3-(2-oxoindolin-5-yl)pyridin-2-yl)amino)ethoxy)ethoxy)ethoxy)ethoxy)phenyl)acetamide (145)

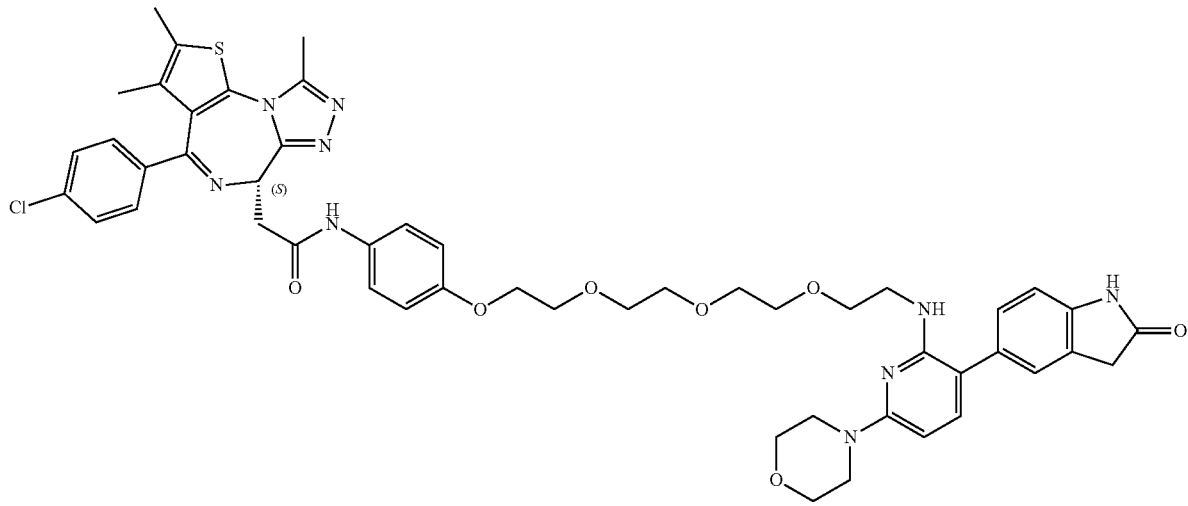

$^1$H NMR (400 MHz, DMSO-d$_6$) δ (ppm) 10.40 (s, 1H), 10.16 (s, 1H), 7.56-7.39 (m, 6H), 7.18-7.06 (m, 3H), 6.91-6.82 (m, 3H), 6.02 (d, J=8.1 Hz, 1H), 5.37 (t, J=5.1 Hz, 1H), 4.58 (t, J=7.0 Hz, 1H), 4.06-3.98 (m, 2H), 3.73-3.65 (m, 6H), 3.55-3.41 (m, 16H), 3.40-3.32 (m, 4H), 2.60 (s, 3H), 2.42 (s, 3H), 1.63 (s, 3H). LC-MS m/z [M+H]$^+$: 960.2 with a purity of 96%.

2.2.62 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((6-methyl-5-(2-oxoindolin-5-yl)pyridin-2-yl)amino)ethoxy)ethoxy)ethoxy)ethoxy)phenyl)acetamide (146)

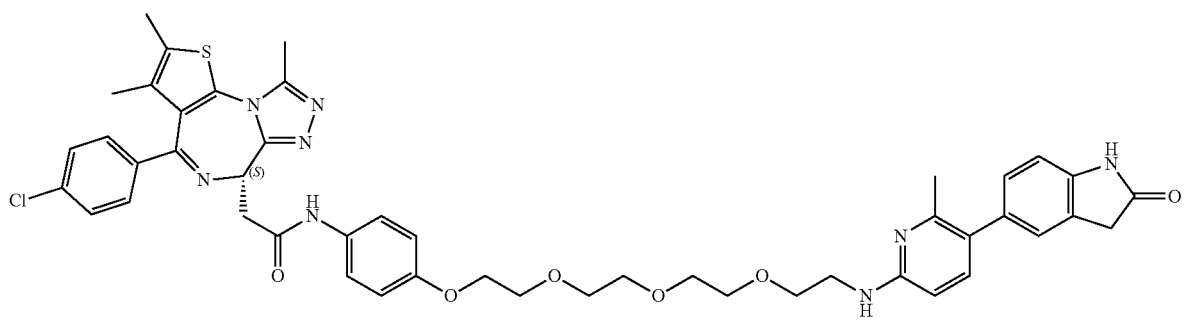

$^1$H NMR (400 MHz, DMSO-d$_6$) δ (ppm): 10.37 (s, 1H), 10.16 (s, 1H), 7.56-7.39 (m, 6H), 7.16 (d, J=8.4 Hz, 1H), 7.10 (s, 1H), 7.05 (d, J=7.9 Hz, 1H), 6.89 (d, J=8.9 Hz, 2H), 6.82 (d, J=7.9 Hz, 1H), 6.40-6.34 (m, 2H), 4.59 (t, J=7.1 Hz, 1H), 4.09-4.00 (m, 2H), 3.77-3.69 (m, 2H), 3.63-3.50 (m, 10H), 3.50-3.38 (m, 6H), 2.60 (s, 3H), 2.42 (s, 3H), 2.24 (s, 3H), 1.62 (s, 3H). LC-MS m/z [M+H]$^+$: 988.2 with a purity of 95%.

2.2.63 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-((3-(2-oxoindolin-5-yl)pyridin-2-yl)amino)ethoxy)ethoxy)ethyl)acetamide (147)

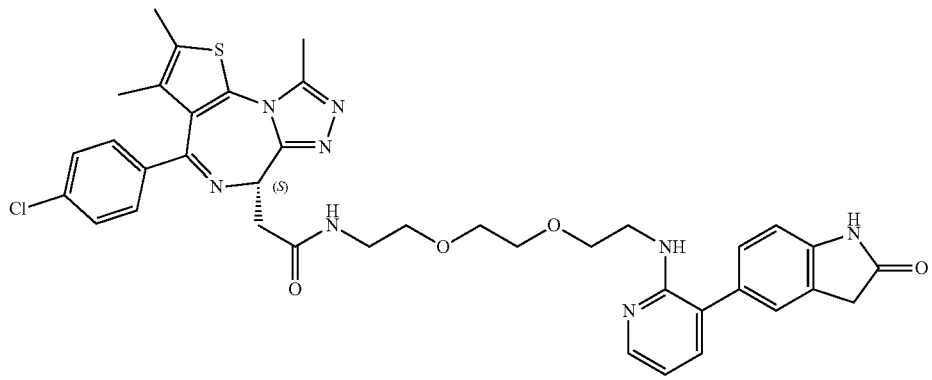

$^1$H NMR (400 MHz, MeOD) δ (ppm): 7.93 (d, J=5.0 Hz, 1H), 7.50-7.41 (m, 3H), 7.41-7.36 (m, 2H), 7.30 (s, 1H), 7.26 (d, J=8.0 Hz, 1H), 7.00 (d, J=7.9 Hz, 1H), 6.76 (t, J=6.3 Hz, 1H), 4.61 (dd, J=8.6, 5.8 Hz, 1H), 3.67 (t, J=5.0 Hz, 2H), 3.65-3.55 (m, 8H), 3.53 (t, J=5.4 Hz, 2H), 3.45-3.34 (m, 4H), 2.69 (s, 3H), 2.44 (s, 3H), 1.69 (s, 3H). LC-MS m/z [M+H]$^+$: 738.5 with a purity of 99%.

2.2.64 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-methyl-5-(2-oxoindolin-5-yl)pyridin-2-yl)amino)ethoxy)ethoxy)ethoxy)ethoxy)phenyl)acetamide (148)

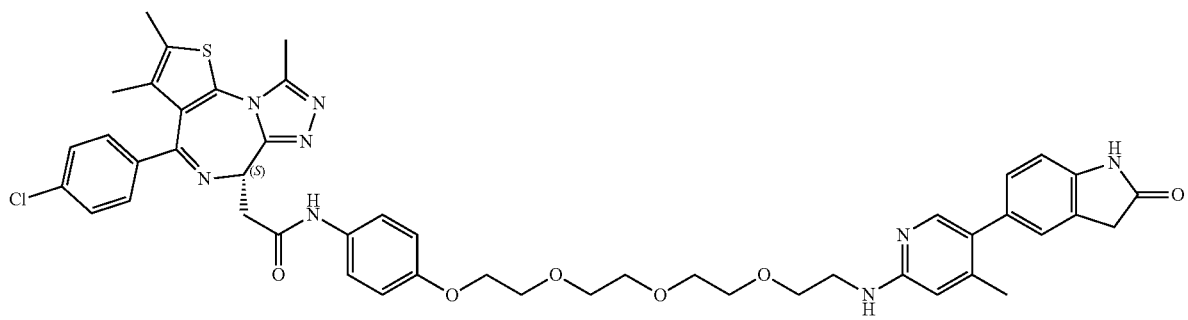

$^1$H NMR (400 MHz, DMSO-d$_6$) δ (ppm): 10.38 (s, 1H), 10.16 (s, 1H), 7.73 (s, 1H), 7.52 (d, J=9.0 Hz, 2H), 7.48 (d, J=8.6 Hz, 2H), 7.41 (d, J=8.4 Hz, 2H), 7.11 (s, 1H), 7.06 (d, J=8.5 Hz, 1H), 6.89 (d, J=9.0 Hz, 2H), 6.83 (d, J=8.0 Hz, 1H), 6.42-6.35 (m, 2H), 4.59 (t, J=7.1 Hz, 1H), 4.09-3.98 (m, 2H), 3.76-3.68 (m, 2H), 3.61-3.50 (m, 10H), 3.50-3.44 (m, 4H), 3.43-3.39 (m, 2H), 2.60 (s, 3H), 2.42 (s, 3H), 2.09 (s, 3H), 1.63 (s, 3H). LC-MS m/z [M+H]$^+$: 889.2 with a purity of 98%.

2.2.65 Synthesis of tert-butyl (S)-6-((2-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)amino)-3-(2-oxoindolin-5-yl)picolinate (149)

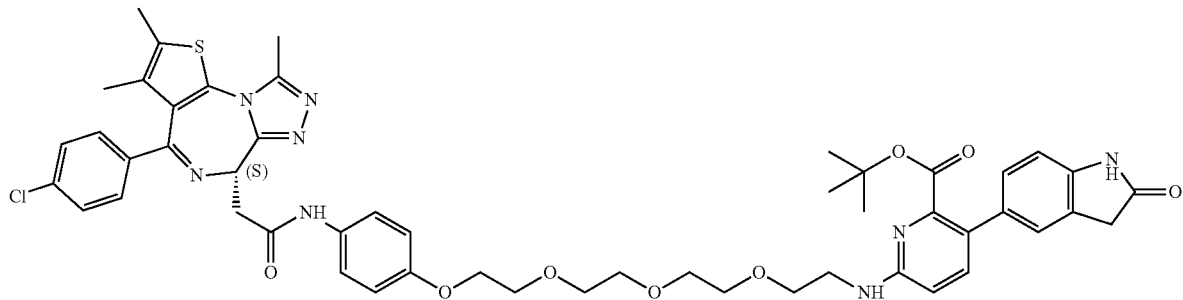

¹H NMR (400 MHz, DMSO-d$_6$) δ (ppm): 10.41 (s, 1H), 10.16 (s, 1H), 7.53 (d, J=8.9 Hz, 2H), 7.48 (d, J=8.6 Hz, 2H), 7.45-7.36 (m, 3H), 7.09 (s, 1H), 7.06 (d, J=8.1 Hz, 1H), 6.89 (d, J=8.9 Hz, 2H), 6.82 (d, J=7.9 Hz, 1H), 6.78 (t, J=6.0 Hz, 1H), 6.63 (d, J=8.6 Hz, 1H), 4.58 (t, J=7.0 Hz, 1H), 4.08-4.01 (m, 2H), 3.76-3.70 (m, 2H), 3.63-3.52 (m, 10H), 3.49-3.38 (m, 6H), 2.60 (s, 3H), 2.42 (s, 3H), 1.63 (s, 3H), 1.27 (s, 9H). LC-MS m/z [M+H]$^+$: 975.2 with a purity of 95%.

2.2.66 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4,6-dimethyl-5-(2-oxoindolin-5-yl)pyridin-2-yl)amino)ethoxy)ethoxy)ethoxy)ethoxy)phenyl)acetamide (150)

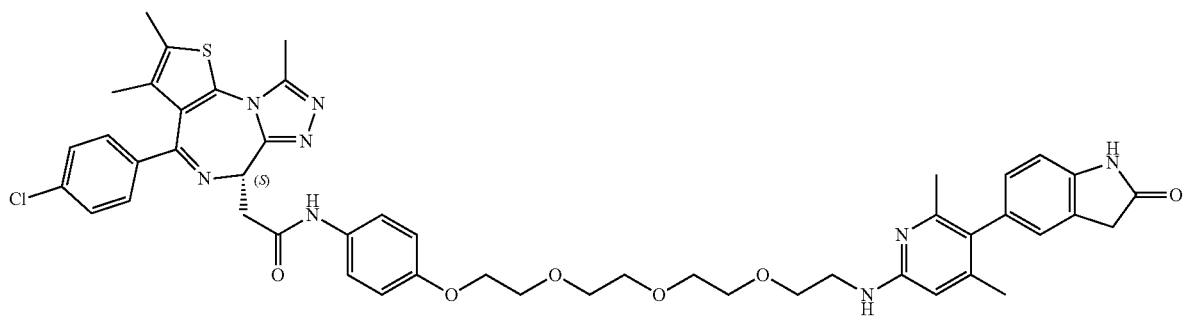

¹H NMR (400 MHz, DMSO-d$_6$) δ (ppm): 10.37 (s, 1H), 10.16 (s, 1H), 7.53 (d, J=9.2 Hz, 2H), 7.48 (d, J=8.4 Hz, 2H), 7.42 (d, J=8.4 Hz, 2H), 6.95 (s, 1H), 6.91-6.85 (m, 3H), 6.83 (d, J=7.6 Hz, 1H), 6.22 (s, 1H), 6.16 (t, J=5.6 Hz, 1H), 4.60 (t, J=7.2 Hz, 1H), 4.12-4.00 (m, 2H), 3.76-3.67 (m, 2H), 3.62-3.38 (m, 16H), 2.60 (s, 3H), 2.42 (s, 3H), 2.00 (s, 3H), 1.84 (s, 3H), 1.62 (s, 3H). LC-MS m/z [M+H]$^+$: 903.3 with a purity of 99%.

2.2.67 Synthesis of (S)-3-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)-N-(4-methyl-5-(2-oxoindolin-5-yl)pyridin-2-yl)propanamide (151)

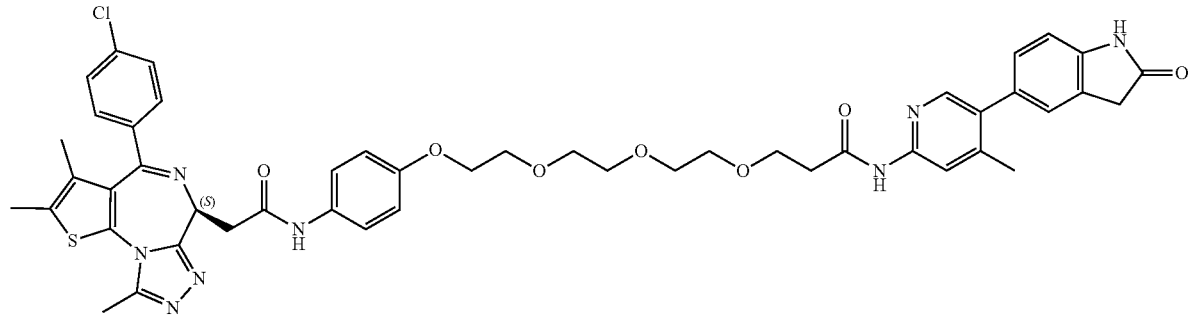

$^{1}$H NMR (400 MHz, DMSO-$d_6$) δ (ppm): 10.40 (s, 1H), 10.16 (s, 1H), 9.89 (s, 1H), 7.53-7.40 (m, 8H), 7.12 (s, 1H), 7.08-7.06 (m, 2H), 6.88 (d, J=8.4 Hz, 1H), 6.84 (d, J=8.0 Hz, 1H), 4.58 (t, J=7.2 Hz, 1H), 4.04-4.01 (m, 2H), 3.69-3.67 (m, 2H), 3.54-3.45 (m, 16H), 2.60 (s, 3H), 2.41 (s, 3H), 2.19 (s, 3H), 1.62 (s, 3H). LC-MS m/z [M+H]$^{+}$: 917.2 with a purity of 98%.

2.2.68 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-methyl-3-(2-oxoindolin-5-yl)pyridin-2-yl)amino)ethoxy)ethoxy)ethoxy)ethoxy)phenyl)acetamide (152)

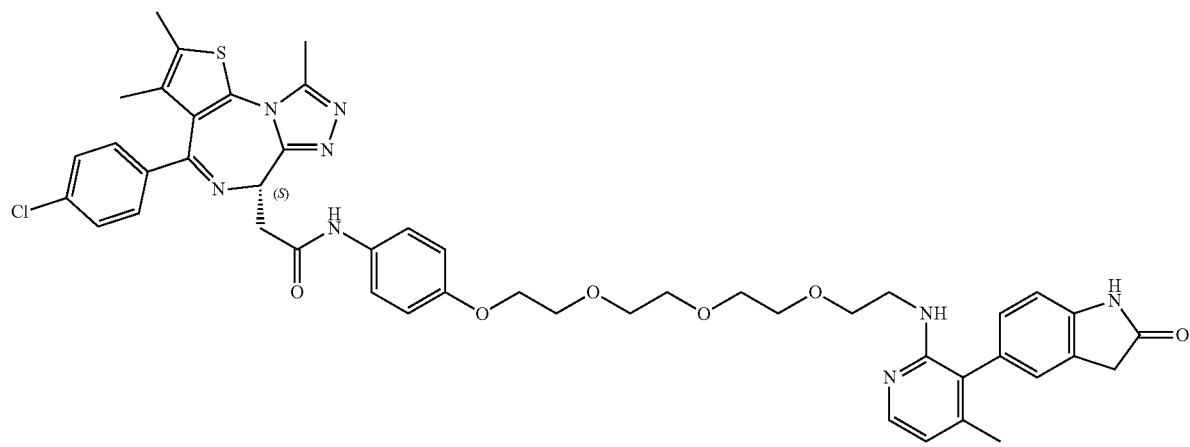

$^{1}$H NMR (400 MHz, DMSO-$d_6$) δ (ppm): 10.50 (s, 1H), 10.15 (s, 1H), 7.85 (d, J=5.2 Hz, 1H), 7.52-7.40 (m, 8H), 7.02-6.95 (m, 3H), 6.93 (d, J=7.6 Hz, 2H), 4.58 (t, J=7.2 Hz, 1H), 4.02-4.01 (m, 2H), 3.69-3.67 (m, 2H), 3.58-3.45 (m, 16H), 2.60 (s, 3H), 2.41 (s, 3H), 1.92 (s, 3H), 1.62 (s, 3H). LC-MS m/z [M+H]$^{+}$: 889.2 with a purity of 99%.

2.2.69 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((6-cyano-5-(2-oxoindolin-5-yl)pyridin-2-yl)amino)ethoxy)ethoxy)ethoxy)ethoxy)phenyl)acetamide (153)

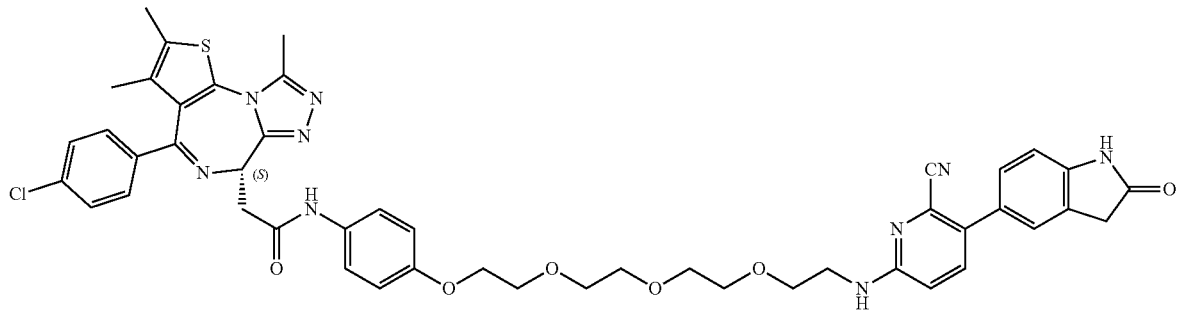

$^1$H NMR (400 MHz, DMSO-d$_6$) δ (ppm): 10.52 (s, 1H), 10.17 (s, 1H), 8.48 (s, 1H), 7.58-7.50 (m, 3H), 7.48 (d, J=8.4 Hz, 2H), 7.42 (d, J=8.4 Hz, 2H), 7.33-7.21 (m, 3H), 6.94-6.83 (m, 3H), 4.59 (t, J=6.8 Hz, 1H), 4.12-4.01 (m, 2H), 3.71-3.66 (m, 2H), 3.61-3.38 (m, 16H), 2.60 (s, 3H), 2.42 (s, 3H), 1.63 (s, 3H). LC-MS m/z [M+H]$^+$: 900.2 with a purity of 99%.

2.2.69 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((5-(7-fluoro-2-oxoindolin-5-yl)-4-methylpyridin-2-yl)amino)ethoxy)ethoxy)ethoxy)ethoxy)phenyl)acetamide (154)

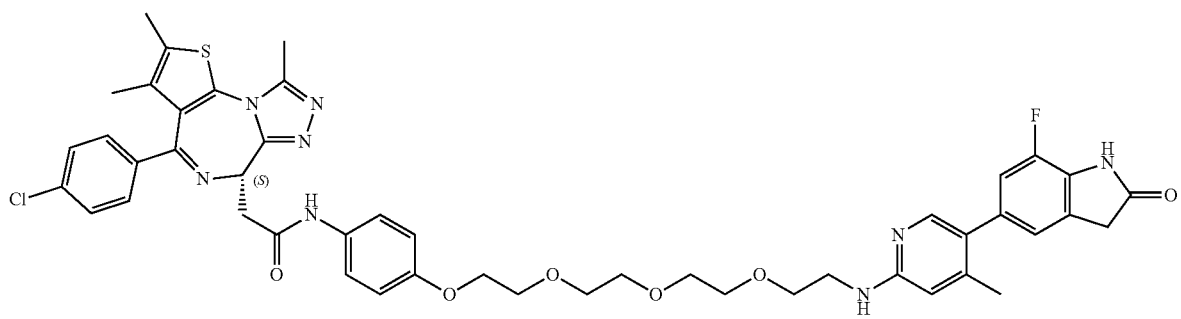

$^1$H NMR (400 MHz, DMSO-d$_6$) δ (ppm): 10.86 (s, 1H), 10.16 (s, 1H), 7.75 (s, 1H), 7.52 (d, J=8.4 Hz, 2H), 7.48 (d, J=8.0 Hz, 2H), 7.42 (d, J=8.4 Hz, 2H), 7.05-6.95 (m, 2H), 6.89 (d, J=8.0 Hz, 2H), 6.46 (t, J=5.2 Hz, 1H), 6.38 (s, 1H), 4.59 (t, J=7.2 Hz, 1H), 4.11-4.02 (m, 2H), 3.76-3.69 (m, 2H), 3.64-3.36 (m, 16H), 2.60 (s, 3H), 2.42 (s, 3H), 2.10 (s, 3H), 1.63 (s, 3H). LC-MS m/z [M+H]$^+$: 907.2 with a purity of 98%.

2.2.70 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-methyl-5-(2'-oxospiro[cyclopropane-1,3'-indolin]-5'-yl)pyridin-2-yl)amino)ethoxy)ethoxy)ethoxy)ethoxy)phenyl)acetamide (155)

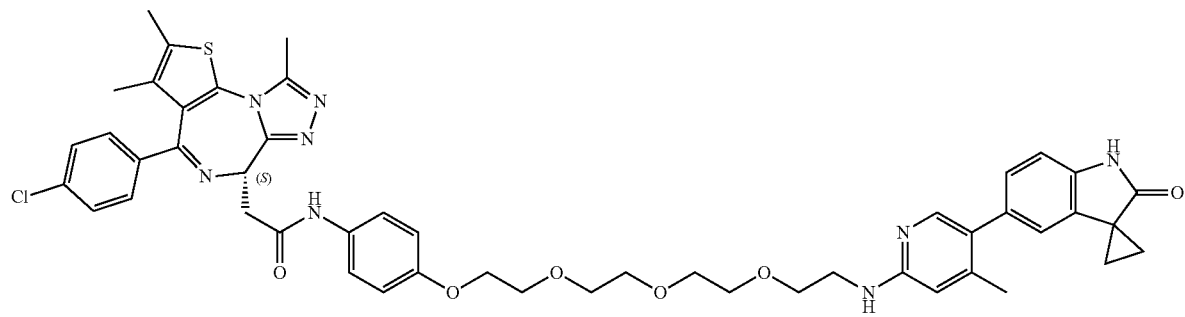

$^1$H NMR (400 MHz, DMSO-d$_6$) δ (ppm): 10.54 (s, 1H), 10.16 (s, 1H), 7.74 (s, 1H), 7.52 (d, J=8.4 Hz, 2H), 7.48 (d, J=8.4 Hz, 2H), 7.42 (d, J=8.4 Hz, 2H), 7.04 (d, J=7.6 Hz, 1H), 6.95-6.86 (m, 4H), 6.41-6.35 (m, 2H), 4.59 (t, J=7.2 Hz, 1H), 4.10-3.99 (m, 2H), 3.79-3.71 (m, 2H), 3.62-3.34 (m, 14H), 2.60 (s, 3H), 2.42 (s, 3H), 2.08 (s, 3H), 1.62 (s, 3H), 1.59-1.52 (m, 2H), 1.48-1.41 (m, 2H). LC-MS m/z [M+H]$^+$: 916.3 with a purity of 98%.

2.2.71 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-methyl-5-(2-oxo-2,3-dihydro-1H-pyrrolo[2,3-b]pyridin-5-yl)pyridin-2-yl)amino)ethoxy)ethoxy)ethoxy)ethoxy)phenyl)acetamide (156)

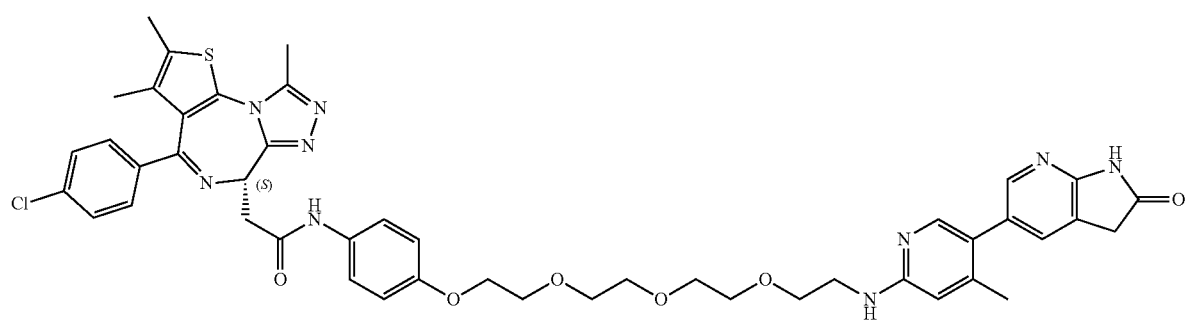

$^1$H NMR (400 MHz, DMSO-d$_6$) δ (ppm): 11.00 (s, 1H), 10.16 (s, 1H), 7.94 (s, 1H), 7.76 (s, 1H), 7.54-7.44 (m, 5H), 7.42 (d, J=8.0 Hz, 2H), 6.89 (d, J=8.4 Hz, 2H), 6.50 (t, J=4.8 Hz, 1H), 6.41 (s, 1H), 4.59 (t, J=6.8 Hz, 1H), 4.12-4.03 (m, 2H), 3.77-3.69 (m, 2H), 3.64-3.58 (m, 12H), 3.57-3.39 (m, 4H), 2.60 (s, 3H), 2.42 (s, 3H), 2.10 (s, 3H), 1.63 (s, 3H). LC-MS m/z [M+H]$^+$: 891.2 with a purity of 99%.

2.2.72 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((5-(6-fluoro-2-oxoindolin-5-yl)-4-methylpyridin-2-yl)amino)ethoxy)ethoxy)ethoxy)ethoxy)phenyl)acetamide (157)

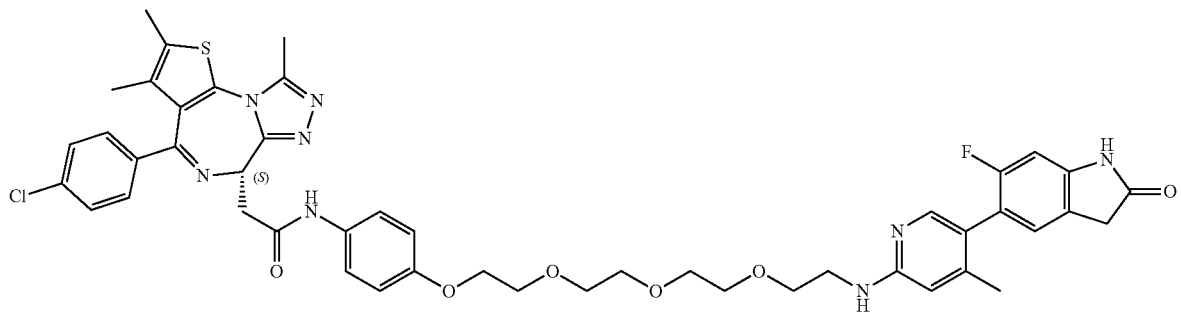

$^1$H NMR (400 MHz, DMSO-d$_6$) δ (ppm): 10.53 (s, 1H), 10.16 (s, 1H), 7.70 (s, 1H), 7.53 (d, J=8.4 Hz, 2H), 7.48 (d, J=8.4 Hz, 2H), 7.42 (d, J=8.4 Hz, 2H), 7.06 (d, J=7.2 Hz, 1H), 6.89 (d, J=8.8 Hz, 2H), 6.68 (d, J=10.0 Hz, 1H), 6.47 (t, J=4.8 Hz, 1H), 6.40 (s, 1H), 4.59 (t, J=6.8 Hz, 1H), 4.10-4.03 (m, 2H), 3.78-3.70 (m, 2H), 3.65-3.34 (m, 16H), 2.60 (s, 3H), 2.42 (s, 3H), 1.98 (s, 3H), 1.63 (s, 3H). LC-MS m/z [M+H]$^+$: 907.2 with a purity of 99%.

2.2.73 Synthesis of (S)—N-(4-(2-(2-(2-(2-((2-amino-5-(2-oxoindolin-5-yl)pyridin-3-yl)oxy)ethoxy)ethoxy)ethoxy)ethoxy)phenyl)-2-(4-(4-chlorophenyl)-2,3,9-trimethyl-6H-thieno[3,2-f][1,2,4]triazolo[4,3-a][1,4]diazepin-6-yl)acetamide (158)

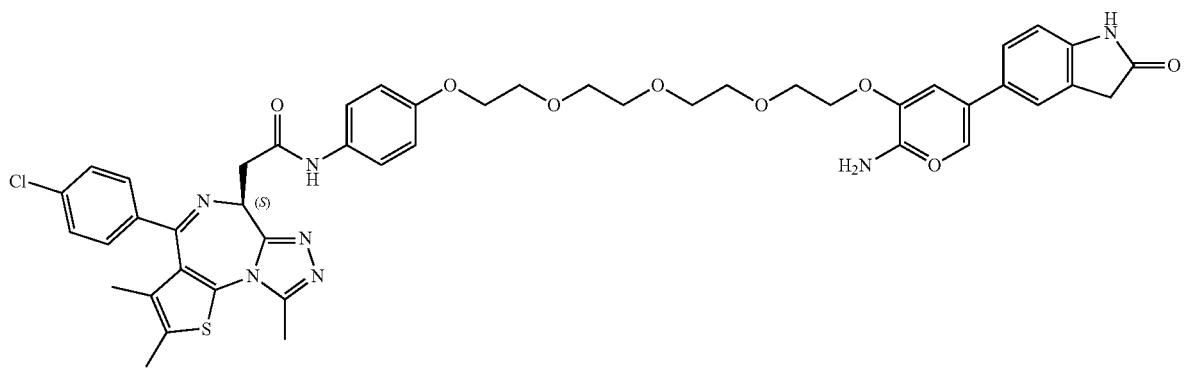

$^1$H NMR (400 MHz, DMSO-d$_6$) δ (ppm): 10.37 (s, 1H), 10.15 (s, 1H), 7.70 (s, 1H), 7.57-7.36 (m, 8H), 7.27 (s, 1H), 6.89 (d, J=8.4 Hz, 2H), 6.83 (d, J=8.4 Hz, 1H), 5.64 (s, 2H), 4.58 (t, J=6.8 Hz, 1H), 4.22-4.17 (m, 2H), 4.08-4.01 (m, 2H), 3.81-3.76 (m, 2H), 3.75-3.69 (m, 2H), 3.62-3.41 (m, 12H), 2.60 (s, 3H), 2.41 (s, 3H), 1.63 (s, 3H). LC-MS m/z [M+H]$^+$: 891.2 with a purity of 99%.

2.2.74 Synthesis of (S)—N-(4-(2-(2-(2-(2-((2-amino-5-(2-oxoindolin-5-yl)pyridin-4-yl)amino)ethoxy)ethoxy)ethoxy)ethoxy)phenyl)-2-(4-(4-chlorophenyl)-2,3,9-trimethyl-6H-thieno[3,2-f][1,2,4]triazolo[4,3-a][1,4]diazepin-6-yl)acetamide (159)

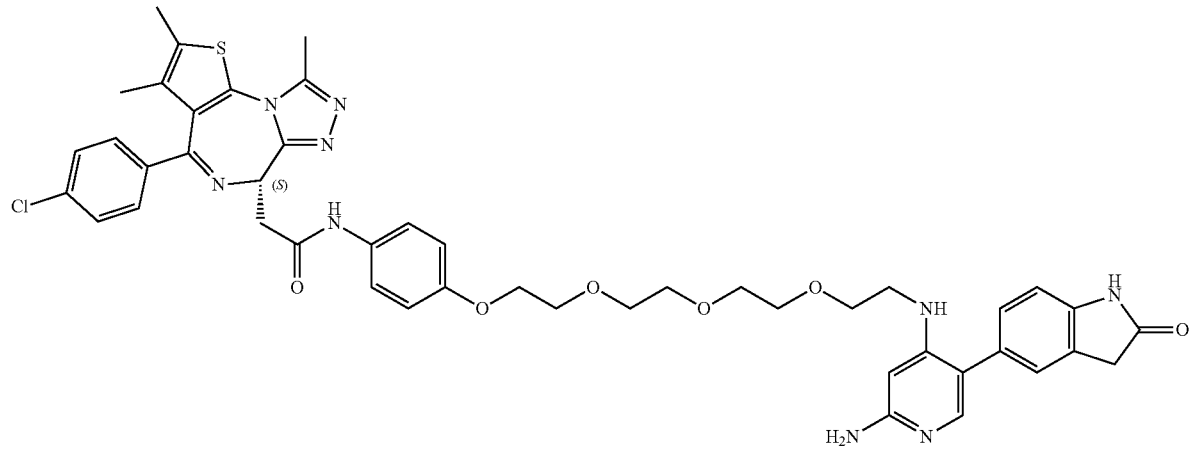

¹H NMR (400 MHz, DMSO-d₆) δ (ppm): 10.42 (s, 1H), 10.16 (s, 1H), 7.57-7.45 (m, 4H), 7.42 (d, J=8.4 Hz, 2H), 7.34 (s, 1H), 7.11 (s, 1H), 7.08 (d, J=8.0 Hz, 1H), 6.92-6.83 (m, 3H), 5.88-5.69 (m, 3H), 5.13-5.06 (m, 1H), 4.58 (t, J=6.8 Hz, 1H), 4.11-4.00 (m, 2H), 3.74-3.68 (m, 2H), 3.58-3.35 (m, 14H), 3.26-3.13 (m, 2H), 2.60 (s, 3H), 2.41 (s, 3H), 1.63 (s, 3H). LC-MS m/z [M+H]⁺: 890.2 with a purity of 98%.

2.2.75 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-((14-((3-(2-oxoindolin-5-yl)pyridin-2-yl)amino)-3,6,9,12-tetraoxatetradecyl)oxy)phenyl)acetamide (160)

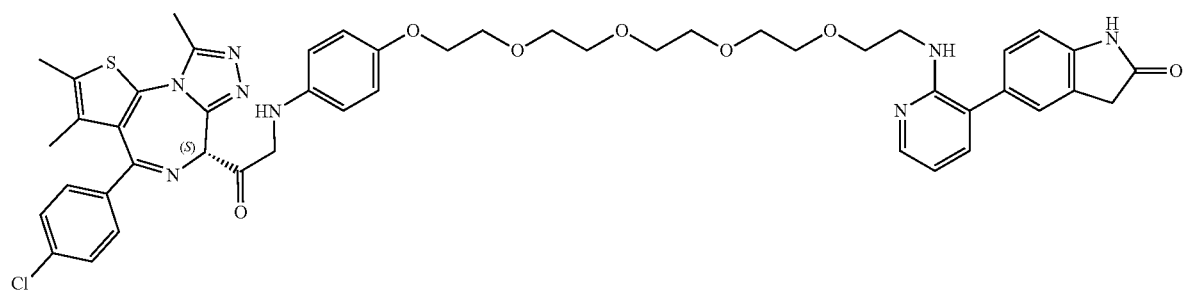

¹H NMR (400 MHz, MeOD) δ (ppm): 7.95 (dd, J=5.3, 1.8 Hz, 1H), 7.51-7.46 (m, 2H), 7.45-7.40 (m, 2H), 7.40-7.35 (m, 2H), 7.30 (dd, J=7.2, 1.8 Hz, 1H), 7.28-7.25 (m, 1H), 7.25-7.20 (m, 1H), 6.98 (d, J=8.0 Hz, 1H), 6.92-6.83 (m, 2H), 6.67 (dd, J=7.2, 5.3 Hz, 1H), 4.69 (dd, J=8.8, 5.4 Hz, 1H), 4.11-4.05 (m, 2H), 3.83-3.77 (m, 2H), 3.68-3.58 (m, 7H), 3.57-3.42 (m, 13H), 2.70 (s, 3H), 2.44 (s, 3H), 1.69 (s, 3H). LC-MS m/z [M+H]⁺: 918.4 with a purity of 99%.

2.2.76 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-((5-(2-(2-((6-methyl-5-(2-oxoindolin-5-yl)pyridin-2-yl)amino)ethoxy)ethoxy)pentyl)oxy)phenyl)acetamide (161)

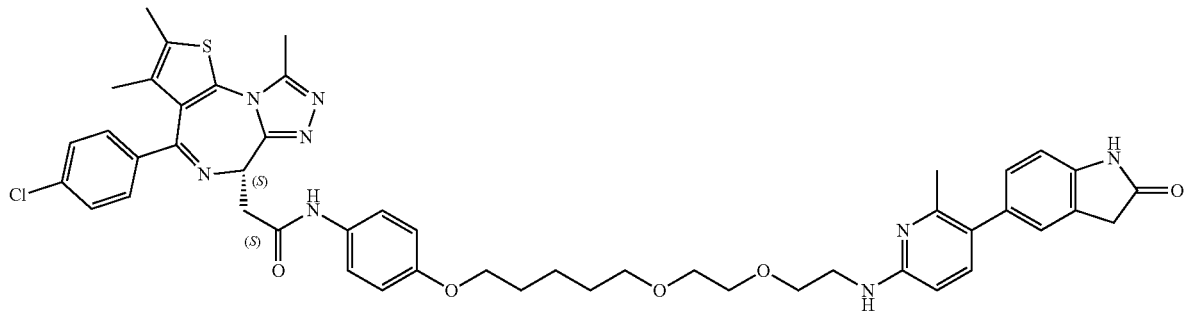

$^1$H NMR (400 MHz, DMSO-d$_6$) δ (ppm): 10.37 (s, 1H), 10.14 (s, 1H), 7.55-7.45 (m, 4H), 7.41 (d, J=8.0 Hz, 2H), 7.17 (d, J=8.4 Hz, 1H), 7.11 (s, 1H), 7.06 (d, J=8.4 Hz, 1H), 6.86 (d, J=8.8 Hz, 2H), 6.82 (d, J=8.0 Hz, 1H), 6.42-6.33 (m, 2H), 4.59 (t, J=7.2 Hz, 1H), 3.95-3.86 (m, 2H), 3.69-3.51 (m, 14H), 2.60 (s, 3H), 2.42 (s, 3H), 2.24 (s, 3H), 1.78-1.65 (m, 2H), 1.63 (s, 3H), 1.61-1.52 (m, 2H), 1.51-1.38 (m, 2H). LC-MS m/z [M+H]$^+$: 887.3 with a purity of 98%.

2.2.77 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((4-(morpholine-4-carbonyl)-5-(2-oxoindolin-5-yl)pyridin-2-yl)amino)ethoxy)ethoxy)ethoxy)ethoxy)phenyl)acetamide (162)

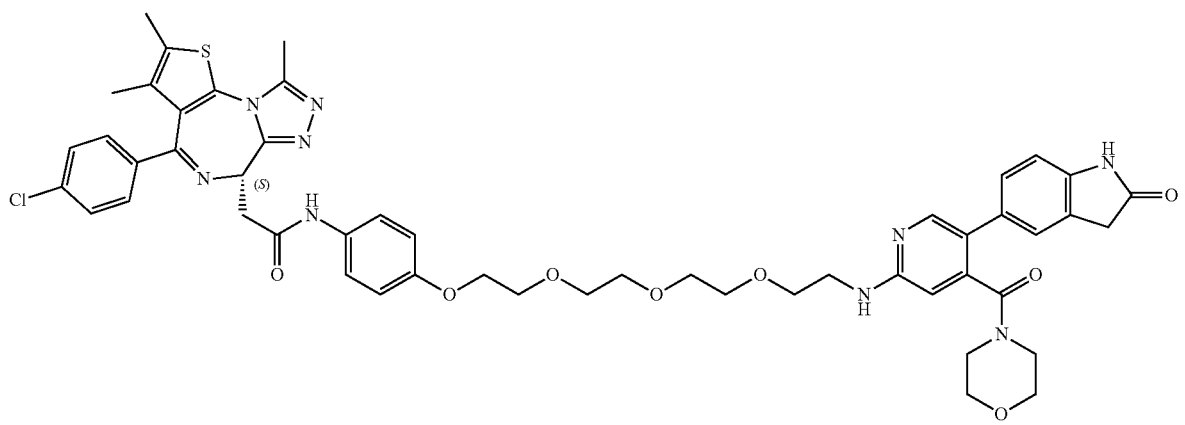

$^1$H NMR (400 MHz, DMSO-d$_6$) δ (ppm): 10.43 (s, 1H), 10.16 (s, 1H), 8.01 (s, 1H), 7.56-7.38 (m, 6H), 7.18-7.07 (m, 2H), 6.93-6.78 (m, 4H), 6.41 (s, 1H), 4.59 (t, J=7.0 Hz, 1H), 4.09-4.01 (m, 2H), 3.75-3.68 (m, 2H), 3.62-3.43 (m, 18H), 3.29-3.21 (m, 2H), 3.16-3.07 (m, 1H), 3.04-2.94 (m, 1H), 2.77-2.68 (m, 1H), 2.60 (s, 3H), 2.54-2.42 (m, 1H), 2.42 (s, 3H), 1.63 (s, 3H). LC-MS m/z [M+H]$^+$: 988.2 with a purity of 95%.

2.2.78 Synthesis of methyl (S)-2-(4-(4-chlorophenyl)-3,9-dimethyl-2-((4-(2-(2-(2-(2-((5-(2-oxoindolin-5-yl)-6-(trifluoromethyl)pyridin-2-yl)amino)ethoxy)ethoxy)ethoxy)ethoxy)phenyl)carbamoyl)-6H-thieno[3,2-f][1,2,4]triazolo[4,3-a][1,4]diazepin-6-yl)acetate (163)

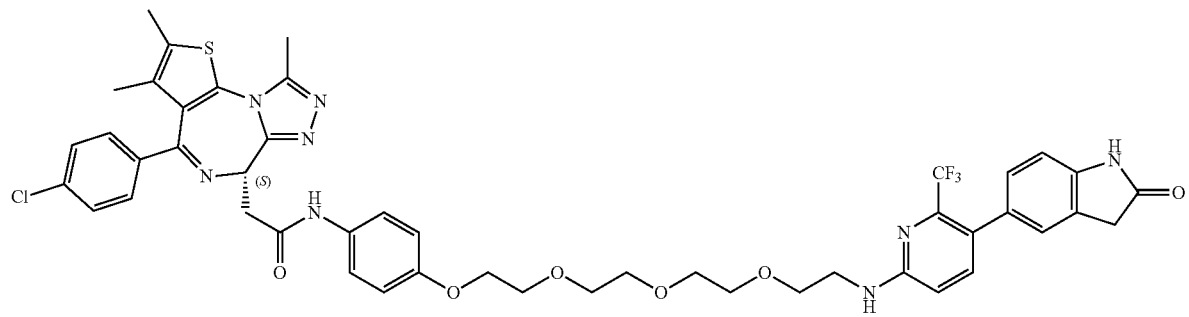

$^1$H NMR (400 MHz, DMSO-$d_6$) δ (ppm): 10.52 (s, 1H), 10.15 (s, 1H), 7.52-7.46 (m, 4H), 7.45-7.38 (m, 3H), 7.26 (s, 1H), 7.23 (d, J=8.4 Hz, 1H), 7.02 (d, J=7.2 Hz, 1H), 6.92 (d, J=8.0 Hz, 1H), 6.87 (d, J=8.8 Hz, 2H), 6.02 (t, J=5.2 Hz, 1H), 4.57 (t, J=7.2 Hz, 1H), 4.06-4.01 (m, 2H), 3.70-3.68 (m, 2H), 3.51-3.44 (m, 16H), 2.60 (s, 3H), 2.42 (s, 3H), 1.63 (s, 3H). LC-MS m/z [M+H]$^+$: 943.2 with a purity of 98%.

2.2.79 Synthesis of (S)-2-(4-(4-chlorophenyl)-2,3,9-trimethyl-6H-thieno[3,2-f][1,2,4]triazolo[4,3-a][1,4]diazepin-6-yl)-N-(2-(2-(2-(2-((5-(2-oxo-2,3-dihydro-1H-pyrrolo[2,3-b]pyridin-5-yl)pyridin-2-yl)amino)ethoxy)ethoxy)ethoxy)ethyl)acetamide (164)

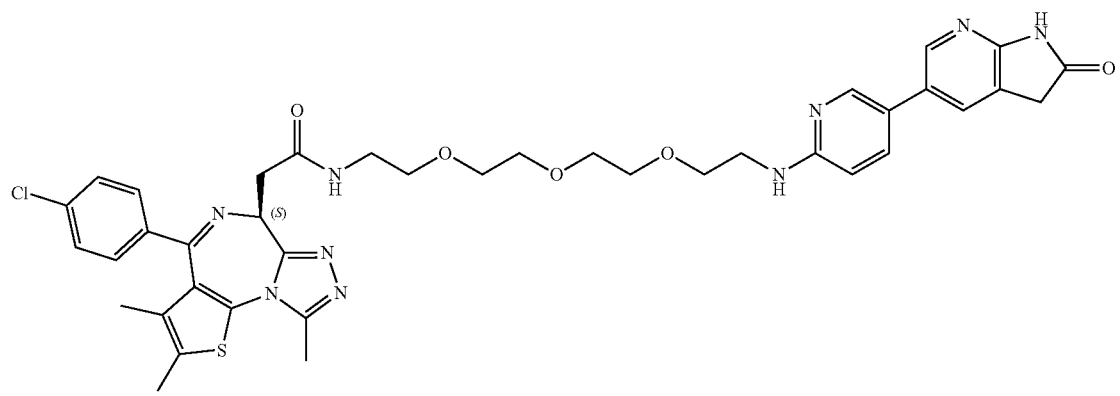

1H NMR (400 MHz, DMSO-$d_6$) δ (ppm): 10.98 (s, 1H), 8.28-8.22 (m, 3H), 7.75 (s, 1H), 7.64 (dd, J=8.4, 2.4 Hz, 1H), 7.47 (d, J=8.4 Hz, 2H), 7.41 (d, J=8.4 Hz, 2H), 6.67 (t, J=5.6 Hz, 1H), 6.57 (d, J=8.4 Hz, 1H), 4.50 (dd, J=7.6, 6.0 Hz, 1H), 3.57-3.43 (m, 18H), 3.26-3.17 (m, 2H), 2.59 (s, 3H), 2.40 (s, 3H), 1.61 (s, 3H). LC-MS m/z [M+H]$^+$: 783.5 with a purity of 95%.

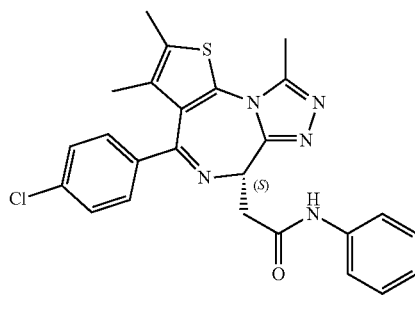 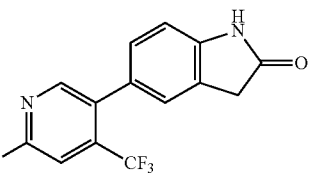

¹H NMR (400 MHz, DMSO-d₆) δ (ppm): 10.43 (s, 1H), 10.16 (s, 1H), 7.94 (s, 1H), 7.52 (d, J=8.8 Hz, 2H), 7.48 (d, J=8.4 Hz, 2H), 7.41 (d, J=8.4 Hz, 2H), 7.17 (t, J=5.6 Hz, 1H), 7.09 (s, 1H), 7.05 (d, J=8.0 Hz, 1H), 6.92-6.86 (m, 3H), 6.83 (d, J=7.6 Hz, 1H), 4.60 (t, J=7.2 Hz, 1H), 4.11-4.01 (m, 2H), 3.78-3.69 (m, 2H), 3.64-3.42 (m, 16H), 2.60 (s, 3H), 2.42 (s, 3H), 1.63 (s, 3H). LC-MS m/z [M+H]⁺: 943.2 with a purity of 97%.

2.2.81 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((6-(morpholine-4-carbonyl)-5-(2-oxoindolin-5-yl)pyridin-2-yl)amino)ethoxy)ethoxy)ethoxy)ethoxy)phenyl)acetamide (166)

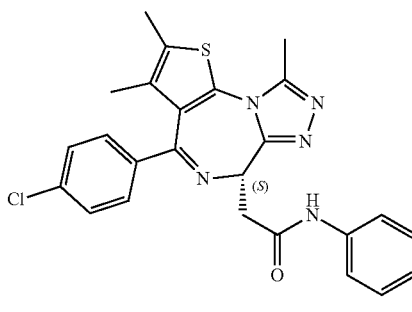 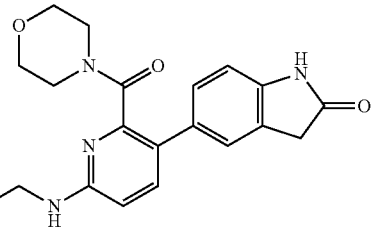

¹H NMR (400 MHz, DMSO-d₆) δ (ppm): 10.42 (s, 1H), 10.16 (s, 1H), 7.52 (d, J=9.0 Hz, 2H), 7.50-7.39 (m, 5H), 7.16 (s, 1H), 7.11 (d, J=8.2 Hz, 1H), 6.89 (d, J=9.0 Hz, 2H), 6.83 (d, J=8.0 Hz, 2H), 6.62 (d, J=8.7 Hz, 1H), 4.58 (t, J=7.1 Hz, 1H), 4.08-4.01 (m, 2H), 3.76-3.69 (m, 2H), 3.61-3.51 (m, 11H), 3.50-3.41 (m, 9H), 3.08-2.94 (m, 4H), 2.60 (s, 3H), 2.42 (s, 3H), 1.63 (s, 3H). LC-MS m/z [M+H]⁺: 988.2 with a purity of 97%.

2.2.82 Synthesis of (S)-6-((2-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)amino)-N-isopropyl-3-(2-oxoindolin-5-yl)picolinamide (167)

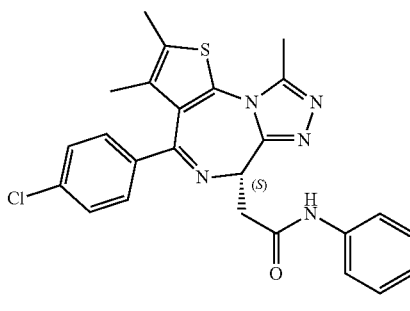 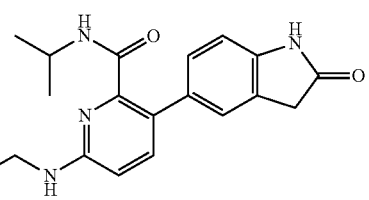

¹H NMR (400 MHz, DMSO-d₆) δ (ppm): 10.35 (s, 1H), 10.16 (s, 1H), 7.98 (d, J=7.8 Hz, 1H), 7.53 (d, J=8.8 Hz, 2H), 7.48 (d, J=8.5 Hz, 2H), 7.41 (d, J=8.5 Hz, 2H), 7.35 (d, J=8.6 Hz, 1H), 7.14 (s, 1H), 7.09 (d, J=8.0 Hz, 1H), 6.89 (d, J=8.8 Hz, 2H), 6.75 (d, J=7.9 Hz, 1H), 6.69 (t, J=5.5 Hz, 1H), 6.60 (d, J=8.6 Hz, 1H), 4.59 (t, J=7.0 Hz, 1H), 4.08-4.01 (m, 2H), 3.92-3.81 (m, 1H), 3.76-3.69 (m, 2H), 3.62-3.53 (m, 10H), 3.48-3.40 (m, 6H), 2.60 (s, 3H), 2.42 (s, 3H), 1.63 (s, 3H), 1.01 (d, J=6.6 Hz, 6H). LC-MS m/z [M+H]⁺: 960.2 with a purity of 97%.

2.2.83 Synthesis of (S)-6-((2-(2-(2-(2-(4-(2-(4-(4-chlorophenyl)-2,3,9-trimethyl-6H-thieno[3,2-f][1,2,4]triazolo[4,3-a][1,4]diazepin-6-yl)acetamido)phenoxy)ethoxy)ethoxy)ethoxy)ethyl)amino)-3-(2-oxoindolin-5-yl)-N-phenylpicolinamide (168)

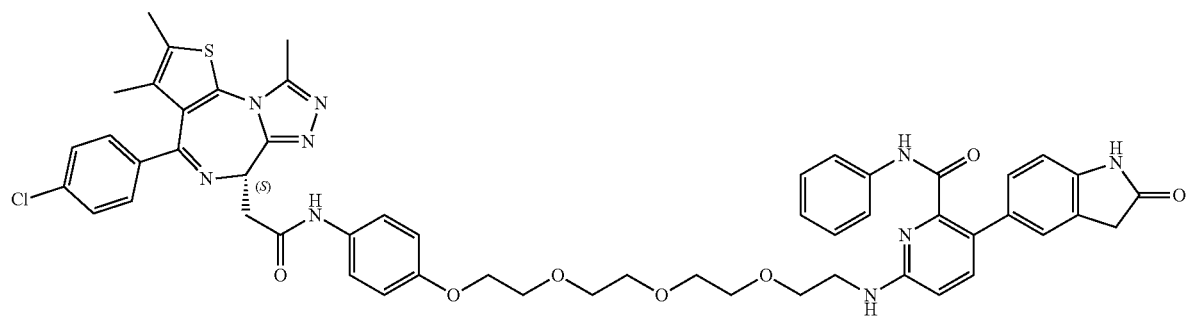

¹H NMR (400 MHz, DMSO-d₆) δ (ppm): 10.35 (s, 1H), 10.28 (s, 1H), 10.16 (s, 1H), 7.61 (d, J=8.0 Hz, 2H), 7.53 (d, J=8.8 Hz, 2H), 7.48 (d, J=8.4 Hz, 2H), 7.44-7.39 (m, 3H), 7.28 (t, J=8.0 Hz, 2H), 7.16 (s, 1H), 7.12 (d, J=8.0 Hz, 1H), 7.04 (t, J=7.6 Hz, 1H), 6.92-6.82 (m, 3H), 6.75 (d, J=8.0 Hz, 1H), 6.69 (d, J=8.8 Hz, 1H), 4.59 (t, J=7.2 Hz, 1H), 4.07-4.01 (m, 2H), 3.75-3.69 (m, 2H), 3.63-3.51 (m, 10H), 3.50-3.40 (m, 6H), 2.60 (s, 3H), 2.42 (s, 3H), 1.63 (s, 3H). LC-MS m/z [M+H]⁺: 994.57 with a purity of 97%.

2.2.84 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((5-(2-oxo-2,3-dihydro-1H-benzo[d]imidazol-5-yl)pyridin-2-yl)amino)ethoxy)ethoxy)ethoxy)ethoxy)phenyl)acetamide (169)

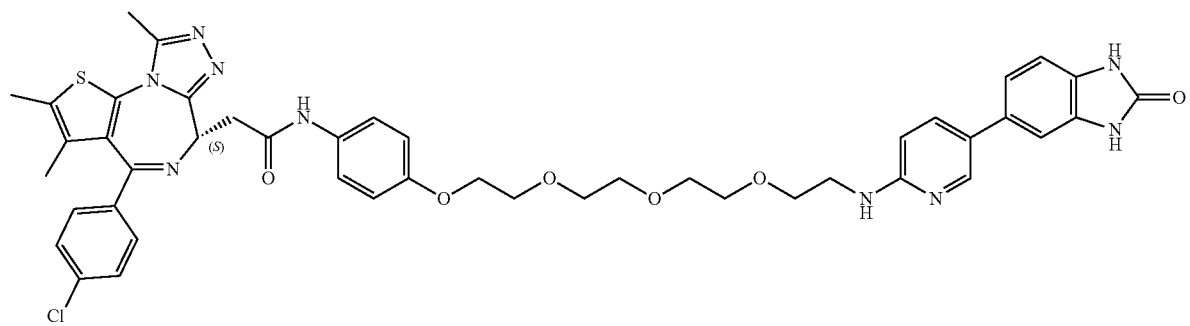

¹H NMR (400 MHz, DMSO-d₆) δ (ppm): 10.59 (d, J=13.0 Hz, 2H), 10.17 (s, 1H), 8.19 (d, J=1.5 Hz, 1H), 7.61 (d, J=8.3, 1H), 7.53 (d, J=8.8 Hz, 2H), 7.47 (d, J=8.6 Hz, 2H), 7.41 (d, J=8.4 Hz, 2H), 7.09 (d, J=8.1 Hz, 1H), 7.03 (s, 1H), 6.93 (d, J=8.0 Hz, 1H), 6.89 (d, J=8.9 Hz, 2H), 6.65-6.54 (m, 2H), 4.59 (t, J=7.1 Hz, 1H), 4.08-4.02 (m, 2H), 3.75-3.69 (m, 2H), 3.61-3.52 (m, 10H), 3.50-3.40 (m, 4H), 2.60 (s, 3H), 2.41 (s, 3H), 1.62 (s, 3H). LC-MS m/z [M+H]⁺: 876.2 with a purity of 98%.

2.2.85 Synthesis of (S)-2-(4-(4-chlorophenyl)-2,3,9-trimethyl-6H-thieno[3,2-f][1,2,4]triazolo[4,3-a][1,4]diazepin-6-yl)-N-(4-(2-(2-(2-(2-((5-(2-oxo-2,3-dihydrobenzo[d]oxazol-6-yl)pyridin-2-yl)amino)ethoxy)ethoxy)ethoxy)ethoxy)phenyl)acetamide (170)

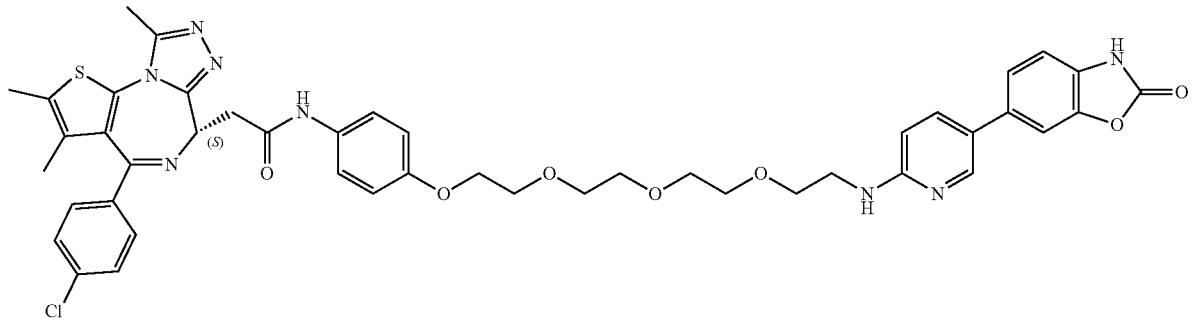

$^1$H NMR (400 MHz, DMSO-$d_6$) δ (ppm): 11.65 (s, 1H), 10.16 (s, 1H), 8.23 (bs, 1H), 7.55-7.42 (m, 9H), 7.35 (d, J=7.6 Hz, 1H), 7.11 (d, J=7.6 Hz, 1H), 6.89-6.87 (m, 3H), 4.59 (t, J=7.0 Hz, 1H), 4.08-4.01 (m, 2H), 3.76-3.69 (m, 2H), 3.62-3.52 (m, 14H), 2.60 (s, 3H), 2.42 (s, 3H), 1.62 (s, 3H). LC-MS m/z [M+H]$^+$: 877.2 with a purity of 99%.

Example 3

3.1 Affinity of Ubiquitination Moiety to E3-CEREBLON (CRBN)-Ubiquitin Ligase 3.1a Fluorescence Binding Assay Fluorescence quenching end point measurements were performed in black polystyrene 384-plates on Tecan Safire monochromator reader with the following settings: excitation 280 nm; excitation bandwidth 10.0 nm; emission collection 340 nm; emission bandwidth 20.0 nm; high sensitivity flash mode; integration time 40 µS; delay 0 µm. All measurements were done in duplicates; GraphPad Prism 5.03 was used for data evaluation, curve fitting, plotting and determination of IC$_{50}$ values.

Serial dilutions of each tested ligands were mixed with truncated CRBN (319-427) to a final volume of 25 µL in the assay buffer (20 mM sodium phosphate buffer, pH 6.5, with 150 mM sodium chloride). The final concentration of CRBN in all assay will be 5-10 µM with DMSO level at 4%. A control lanes were prepared with only tested ligands without the addition of CRBN, top up with assay buffer to 25 µL. Plates were incubated for 5 minutes and analyzed using the monochromator plate reader.

IC$_{50}$ is the compound concentration that causes 50% quenching of the desired activity.

3.1b Results

The affinity to CRBN is graded as follows:
A: 1 µM<IC$_{50}$<100 µM
B: 100 µM<IC$_{50}$<300 µM
C: IC$_{50}$>300 µM

| Compound ID | Structure | IC$_{50}$ µM (CRBN) |
|---|---|---|
| 001 | 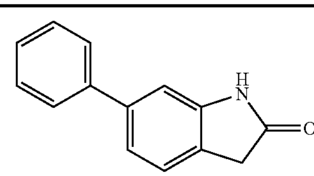 | C |
| 002 | 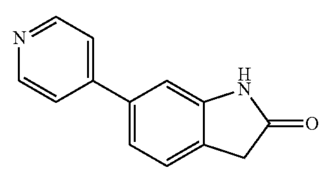 [SMILES: O=C1Cc2ccc(-c3ccncc3)cc2N1] | B |
| 003 | 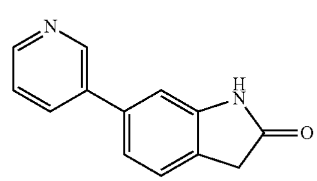 [SMILES: O=C1Cc2ccc(-c3cccnc3)cc2N1] | C |

-continued

| Compound ID | Structure | IC$_{50}$ μM (CRBN) |
|---|---|---|
| 004 | 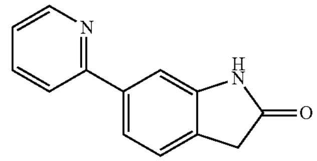 [SMILES: O=C1Cc2ccc(-c3ccccn3)cc2N1] | B |
| 005 | 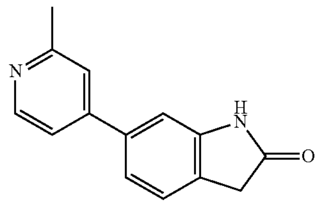 [SMILES: Cc1cc(-c2ccc3c(c2)NC(=O)C3)ccn1] | B |
| 006 | 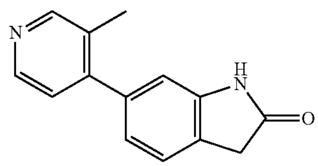 [SMILES: Cc1cnccc1-c1ccc2c(c1)NC(=O)C2] | C |
| 007 | 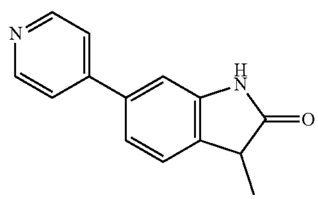 [SMILES: CC1C(=O)Nc2cc(-c3ccncc3)ccc21] | B |
| 008 | 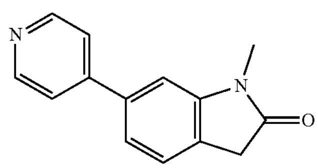 [SMILES: CN1C(=O)Cc2ccc(-c3ccncc3)cc21] | C |
| 009 | 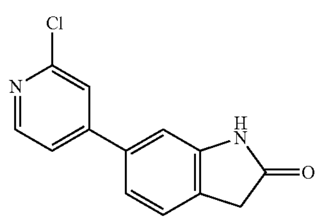 [SMILES: O=C1Cc2ccc(-c3ccnc(Cl)c3)cc2N1] | C |
| 010 | 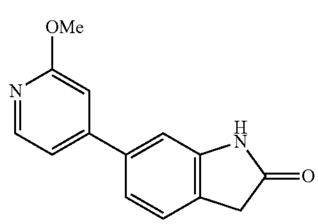 [SMILES: COc1cc(-c2ccc3c(c2)NC(=O)C3)ccn1] | B |

-continued

| Compound ID | Structure | IC$_{50}$ μM (CRBN) |
|---|---|---|
| 011 | 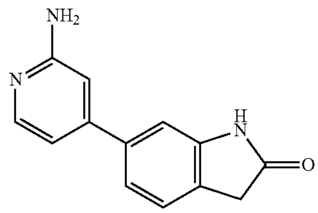 [SMILES: Nc1cc(-c2ccc3c(c2)NC(=O)C3)ccn1] | B |
| 012 | 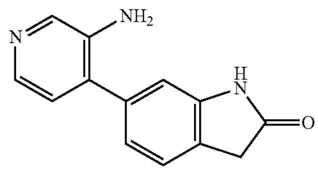 [SMILES: Nc1cnccc1-c1ccc2c(c1)NC(=O)C2] | C |
| 013 | 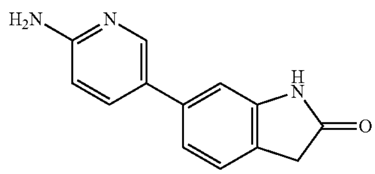 [SMILES: Nc1ccc(-c2ccc3c(c2)NC(=O)C3)cn1] | C |
| 014 | 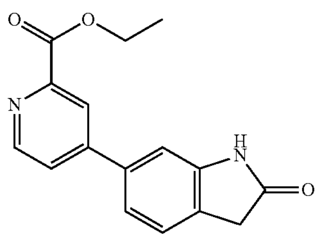 [SMILES: CCOC(=O)c1cc(-c2ccc3c(c2)NC(=O)C3)ccn1] | B |
| 015 | 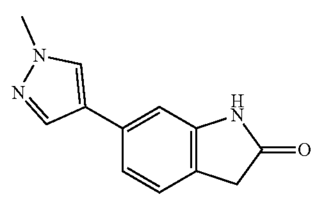 [SMILES: Cn1cc(-c2ccc3c(c2)NC(=O)C3)cn1] | C |
| 016 | 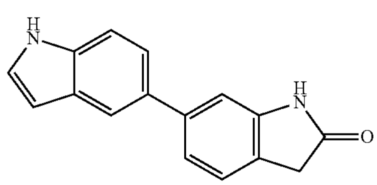 [SMILES: O=C1Cc2ccc(-c3ccc4[nH]ccc4c3)cc2N1] | C |
| 017 | 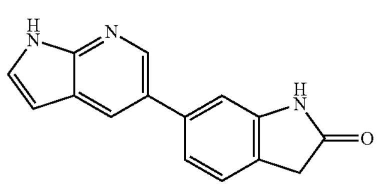 [SMILES: O=C1Cc2ccc(-c3cnc4[nH]ccc4c3)cc2N1] | C |
| 018 | 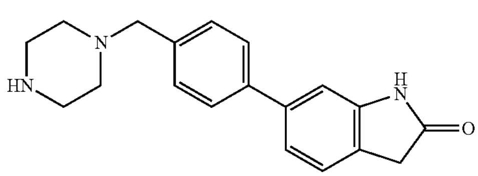 [SMILES: O=C1Cc2ccc(-c3ccc(CN4CCNCC4)cc3)cc2N1] | A |

-continued

| Compound ID | Structure | IC$_{50}$ μM (CRBN) |
|---|---|---|
| 019 | 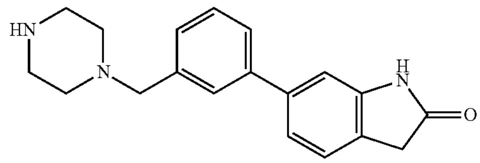 [SMILES: O=C1Cc2ccc(-c3cccc(CN4CCNCC4)c3)cc2N1] | C |
| 020 | 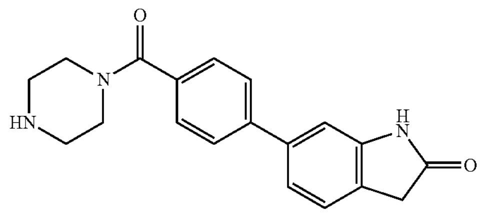 [SMILES: O=C1Cc2ccc(-c3ccc(C(=O)N4CCNCC4)cc3)cc2N1] | C |
| 021 | 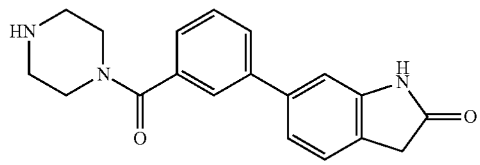 [SMILES: O=C1Cc2ccc(-c3cccc(C(=O)N4CCNCC4)c3)cc2N1] | C |
| 022 | 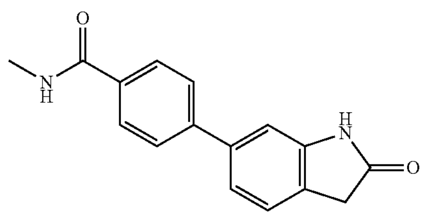 [SMILES: CNC(=O)c1ccc(-c2ccc3c(c2)NC(=O)C3)cc1] | A |
| 023 | 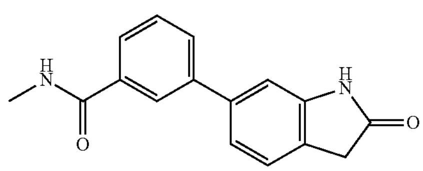 [SMILES: CNC(=O)c1cccc(-c2ccc3c(c2)NC(=O)C3)c1] | A |
| 024 | 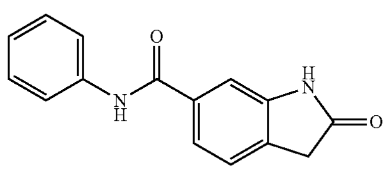 [SMILES: O=C1Cc2ccc(C(=O)Nc3ccccc3)cc2N1] | C |
| 025 | 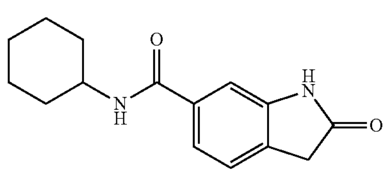 [SMILES: O=C1Cc2ccc(C(=O)NC3CCCCC3)cc2N1] | C |
| 026 | 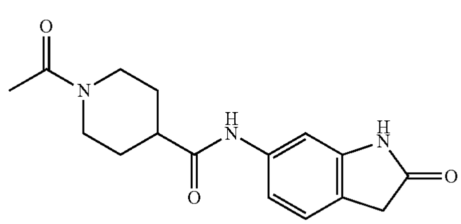 [SMILES: CC(=O)N1CCC(C(=O)Nc2ccc3c(c2)NC(=O)C3)CC1] | C |

-continued

| Compound ID | Structure | IC$_{50}$ μM (CRBN) |
|---|---|---|
| 027 | (1-methylpiperidin-4-yl)amide of 2-oxoindoline-6-carboxylic acid | C |
| 028 | N-(2-(4-methylpiperazin-1-yl)ethyl)-2-oxoindoline-6-carboxamide | C |
| 029 | piperidin-1-yl(2-oxoindolin-6-yl)methanone | C |
| 030 | (5-chloro-2-oxoindolin-6-yl)(piperidin-1-yl)methanone | C |
| 031 | N-(pyridin-4-yl)-2-oxoindoline-6-carboxamide | B |
| 032 | N-(2-oxoindolin-6-yl)isonicotinamide | B |
| 033 | N-(pyridin-3-ylmethyl)-2-oxoindoline-6-carboxamide | C |
| 034 | 6-(piperidin-4-yloxy)indolin-2-one | C |
| 035 | 6-((2-chloropyrimidin-4-yl)oxy)indolin-2-one | C |

-continued

| Compound ID | Structure | IC$_{50}$ μM (CRBN) |
|---|---|---|
| 036 | methyl 2-((2-oxoindolin-6-yl)oxy)acetate | C |
| 037 | 7-(pyridin-4-yl)indolin-2-one | C |
| 038 | 4-(pyridin-4-yl)indolin-2-one | C |
| 039 | 5-(pyridin-4-yl)indolin-2-one | B |
| 040 | 5-(2-aminopyridin-4-yl)indolin-2-one | B |
| 041 | 5-(2-methoxypyridin-4-yl)indolin-2-one | C |
| 042 | 5-(6-aminopyridin-3-yl)indolin-2-one | C |
| 043 | 5-(6-amino-4-methylpyridin-3-yl)indolin-2-one | B |

-continued
| Compound ID | Structure | IC$_{50}$ μM (CRBN) |
|---|---|---|
| 044 | 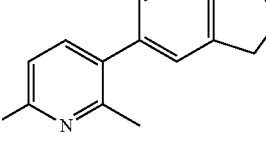 | B |
| 045 | 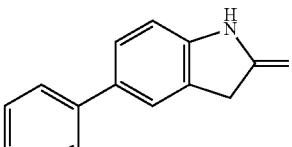 | B |
| 046 | 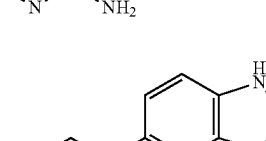 | B |
| 047 | 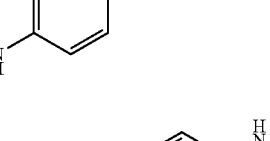 | B |
| 048 | 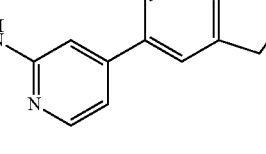 | B |
| 049 | 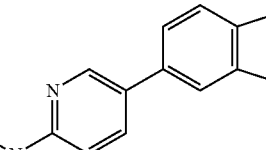 | C |
| 050 | 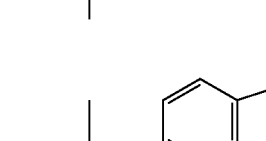 | A |

-continued
| Compound ID | Structure | IC$_{50}$ μM (CRBN) |
|---|---|---|
| 051 | 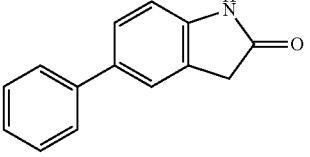 | C |
| 052 | 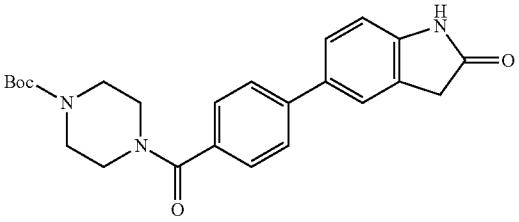 [SMILES: CC(C)(C)OC(=O)N1CCN(C(=O)c2ccc(-c3ccc4c(c3)CC(=O)N4)cc2)CC1] | C |
| 053 | 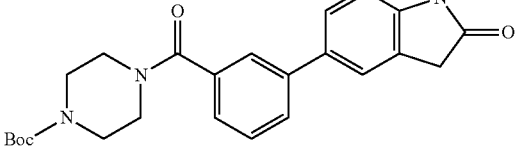 | A |
| 054 | 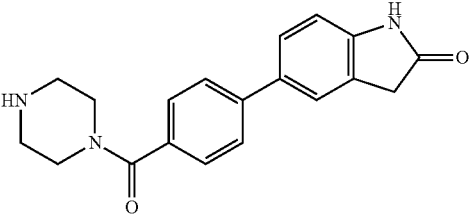 | B |
| 055 | 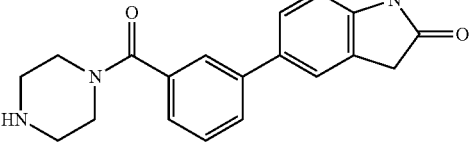 | B |
| 056 | 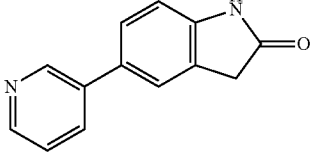 | B |
| 057 | 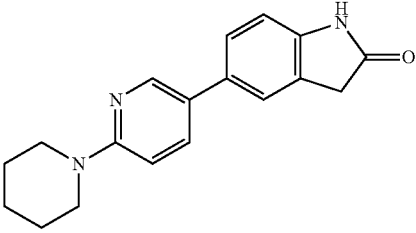 [SMILES: O=C1Cc2cc(-c3ccc(N4CCCCC4)nc3)ccc2N1] | C |

-continued

| Compound ID | Structure | IC$_{50}$ μM (CRBN) |
|---|---|---|
| 058 | 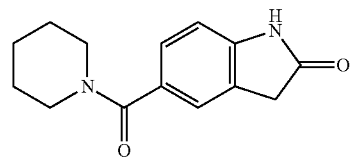 [SMILES: O=C1Cc2cc(C(=O)N3CCCCC3)ccc2N1] | B |
| 059 | 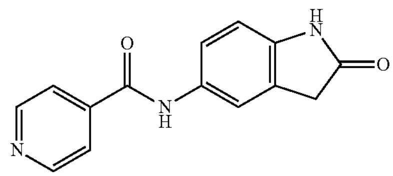 [SMILES: O=C1Cc2cc(NC(=O)c3ccncc3)ccc2N1] | B |
| 060 | 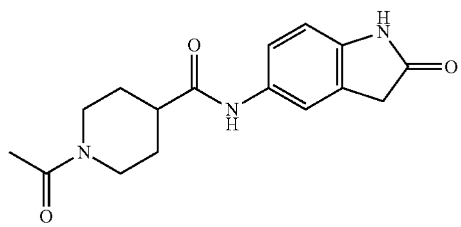 [SMILES: CC(=O)N1CCC(C(=O)Nc2ccc3c(c2)CC(=O)N3)CC1] | B |
| 061 | 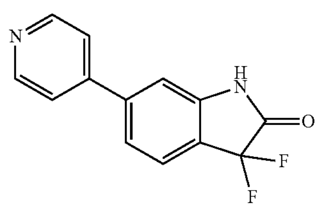 [SMILES: O=C1Nc2cc(-c3ccncc3)ccc2C1(F)F] | C |
| 062 | 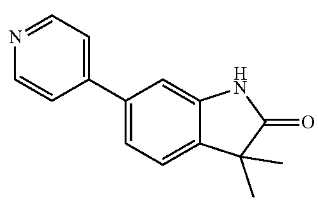 [SMILES: CC1(C)C(=O)Nc2cc(-c3ccncc3)ccc21] | C |
| 063 | 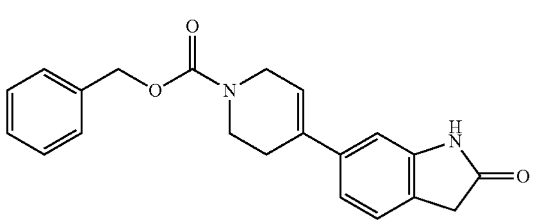 [SMILES: O=C1Cc2ccc(C3=CCN(C(=O)OCc4ccccc4)CC3)cc2N1] | C |
| 064 | 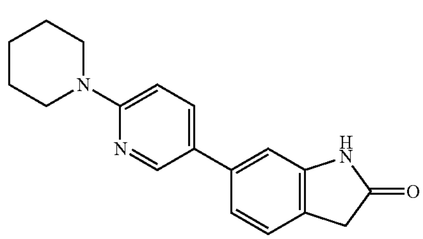 [SMILES: O=C1Cc2ccc(-c3ccc(N4CCCCC4)nc3)cc2N1] | C |

-continued

| Compound ID | Structure | IC$_{50}$ μM (CRBN) |
|---|---|---|
| 065 | 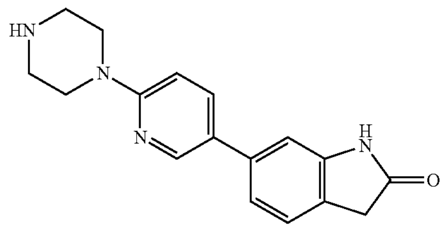 [SMILES: O=C1Cc2ccc(-c3ccc(N4CCNCC4)nc3)cc2N1] | C |
| 066 | 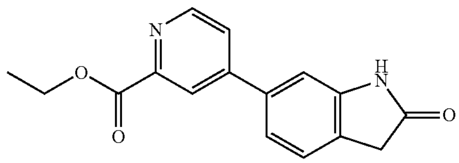 [SMILES: CCOC(=O)c1cc(-c2ccc3c(c2)NC(=O)C3)ccn1] | C |
| 067 | 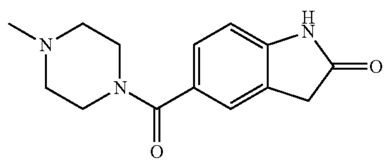 [SMILES: CN1CCN(C(=O)c2ccc3c(c2)CC(=O)N3)CC1] | C |
| 068 | 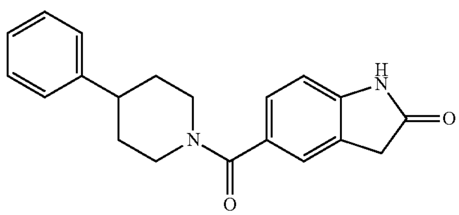 [SMILES: O=C1Cc2cc(C(=O)N3CCC(c4ccccc4)CC3)ccc2N1] | B |
| 069 | 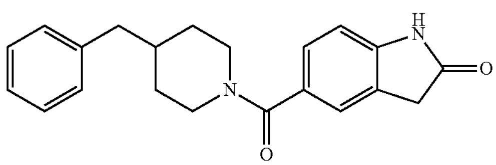 [SMILES: O=C1Cc2cc(C(=O)N3CCC(Cc4ccccc4)CC3)ccc2N1] | C |
| 070 | 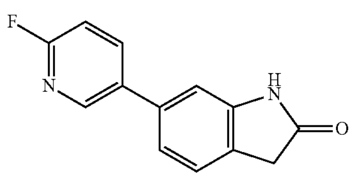 [SMILES: O=C1Cc2ccc(-c3ccc(F)nc3)cc2N1] | C |
| 071 | 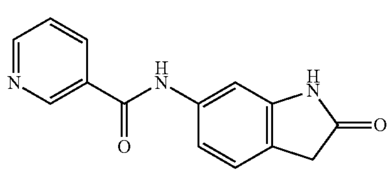 [SMILES: O=C1Cc2ccc(NC(=O)c3cccnc3)cc2N1] | B |
| 072 | 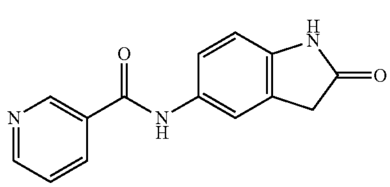 [SMILES: O=C1Cc2cc(NC(=O)c3cccnc3)ccc2N1] | B |

| Compound ID | Structure | IC$_{50}$ μM (CRBN) |
|---|---|---|
| 073 | 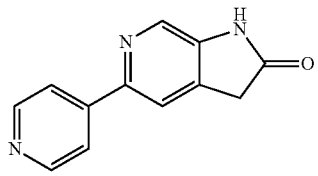 [SMILES: O=C1Cc2cc(-c3ccncc3)ncc2N1] | C |
| 074 | 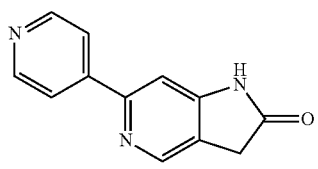 | B |
| 075 | 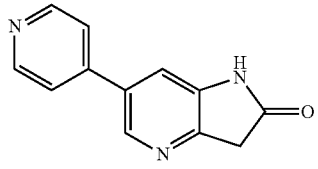 [SMILES: O=C1Cc2ncc(-c3ccncc3)cc2N1] | C |
| 076 | 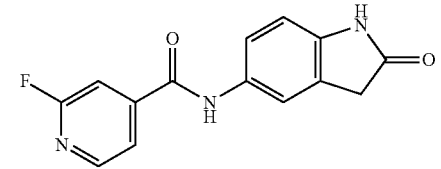 [SMILES: O=C1Cc2cc(NC(=O)c3ccnc(F)c3)ccc2N1] | B |
| 077 | 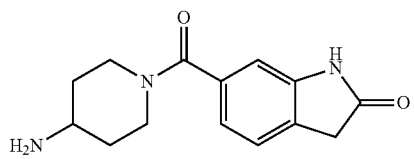 [SMILES: NC1CCN(C(=O)c2ccc3c(c2)NC(=O)C3)CC1] | C |
| 078 | 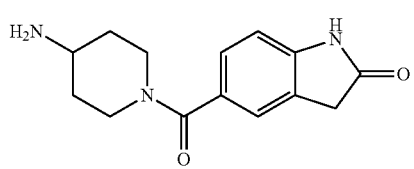 [SMILES: NC1CCN(C(=O)c2ccc3c(c2)CC(=O)N3)CC1] | C |
| 079 | 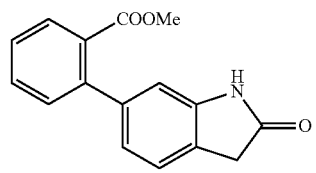 [SMILES: COC(=O)c1ccccc1-c1ccc2c(c1)NC(=O)C2] | C |
| 080 | 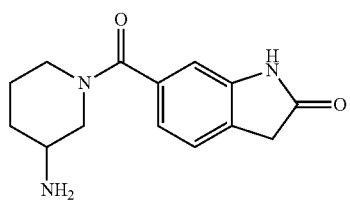 [SMILES: NC1CCCN(C(=O)c2ccc3c(c2)NC(=O)C3)C1] | C |

| Compound ID | Structure | IC₅₀ µM (CRBN) |
|---|---|---|
| 081 | [3-aminopiperidin-1-yl]-(2-oxoindolin-5-yl)methanone | C |
| 082 | 3-isopropyl-5-(pyridin-4-yl)indolin-2-one | C |
| 083 | (1-methyl-2-oxoindolin-5-yl)(piperidin-1-yl)methanone | C |

Affinity of ubiquitination moiety and linker to E3-CEREBLON (CRBN)-ubiquitin ligase The affinity to CRBN is graded as follows:

A: $1\ \mu M < IC_{50} < 100\ \mu M$
B: $100\ \mu M < IC_{50} < 300\ \mu M$
C: $IC_{50} > 300\ \mu M$

| Compound ID | Structure | IC₅₀ µM (CRBN) |
|---|---|---|
| 084 | azido-PEG3-NH-C(O)-pyridine-indolin-2-one | A |
| 085 | azido-PEG3-NH-pyridine-indolin-2-one | B |
| 086 | azido-PEG3-NH-pyridine-C(O)NH-indolin-2-one | A |

-continued
| Compound ID | Structure | IC$_{50}$ μM (CRBN) |
|---|---|---|
| 087 | 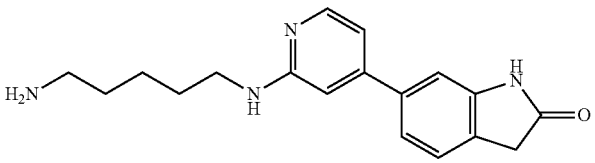 [SMILES: NCCCCCNc1cc(-c2ccc3c(c2)NC(=O)C3)ccn1] | C |
| 088 | 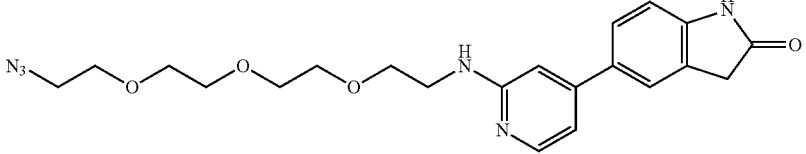 | B |
| 089 | 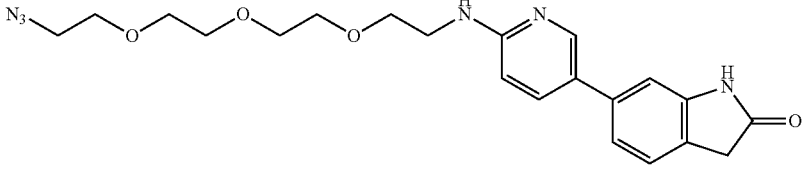 | B |
| 090 | 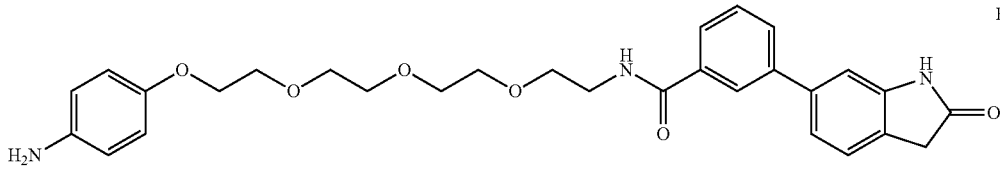 | B |
| 091 | 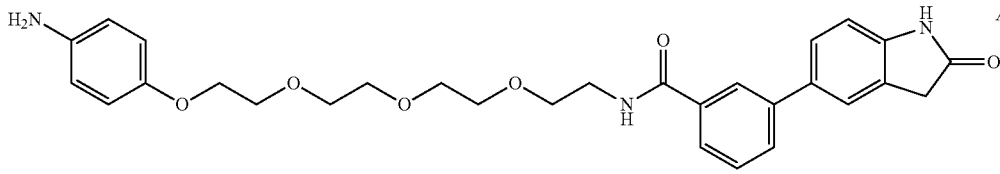 [SMILES: Nc1ccc(OCCOCCOCCOCCNC(=O)c2cccc(-c3ccc4c(c3)CC(=O)N4)c2)cc1] | A |
| 092 | 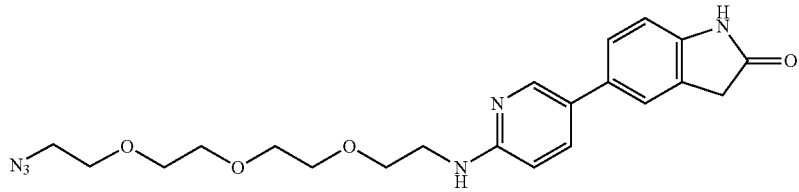 [SMILES: [N-]=[N+]=NCCOCCOCCOCCNc1ccc(-c2ccc3c(c2)CC(=O)N3)cn1] | A |
| 093 | 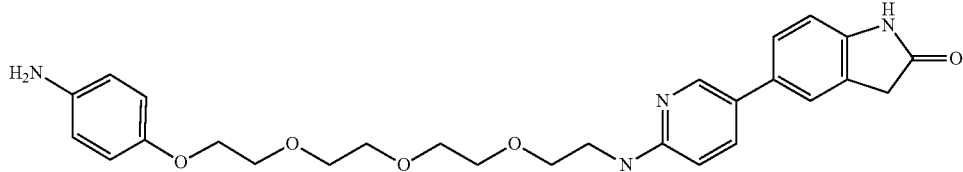 | A |
| 094 | 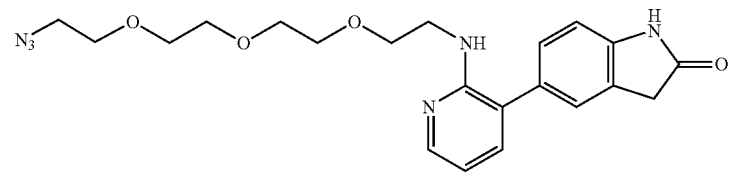 [SMILES: [N-]=[N+]=NCCOCCOCCOCCNc1ncccc1-c1ccc2c(c1)CC(=O)N2] | B |

-continued

| Compound ID | Structure | IC$_{50}$ µM (CRBN) |
|---|---|---|
| 095 | 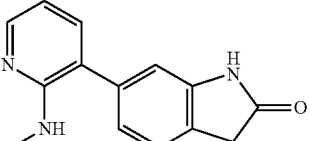 | C |

Example 4

4.1 NMR Binding Experiments Procedure

All the NMR experiments were carried out on a Bruker magnet with proton frequency of 600 MHz or 700 MHz equipped with a cryo-probe. The experiments were performed at 25° C. The $^1$H-$^{15}$N HSQC spectrum was collected using a standard pulse from the pulse library (Topspin version 2.1). To test whether a developed CRBN binder interacts with CRBN, titration of the compound to $^{15}$N-labeled CRBN was carried out. The $^1$H-$^{15}$N HSQC spectra of mixtures in which ligand to CRBN ratios are 0, 0.5, 1.0 and 1.5 were collected and compared. The data were collected using Topspin (ver 2.1) provided with equipment. The data were processed with topspin (ver 2.1), NMRPipe (Delaglio et al. 1995) and visualized using NMRView (Johnson 2004). The truncated CRBN: residues 319-427 was used in the NMR experiments.

Compounds 011, 012, 013, 040, 042, 045 show clear binding to CRBN in HSQC titration experiments, see FIG. 1 for results.

Example 5

5.1 Anti-Proliferation Assays

In cell growth experiments, cells were seeded in 96-well cell culture plates at a density of 3000 of RAMOS cells/well in 100 µL of culture medium. 100 µL of the diluted solution containing the tested compound was added to the appropriate wells of the cell plate. After addition of the tested compound, the cells were incubated at 37° C. in an atmosphere of 5% CO$_2$ for 3 days. CellTiter-Glo (CTG) reagent from the Promega CellTiter-Glo Luminescent Cell Viability Assay kit (#G7572) was added into an OptiPlate 96 (Perkin Elmer, White, Opaque, #6005299) in the dark, incubated for at least 2 hrs, and luminescence signal was read using Tecan Safire II Multi-Mode Plate Reader. The GI$_{50}$ was calculated by nonlinear regression analysis using GraphPad Prism5 software.

GI$_{50}$ is the concentration for 50% of maximal inhibition of cell proliferation.

The affinity to Burkitt's lymphoma cell line (RAMOS) is graded as follows:
D: 1 nM<GI$_{50}$<100 nM
E: 100 nM<GI$_{50}$<1 µM
F: GI$_{50}$>1 µM

| Compound ID | Structure | GI$_{50}$ μM (RAMOS) |
|---|---|---|
| 096 | 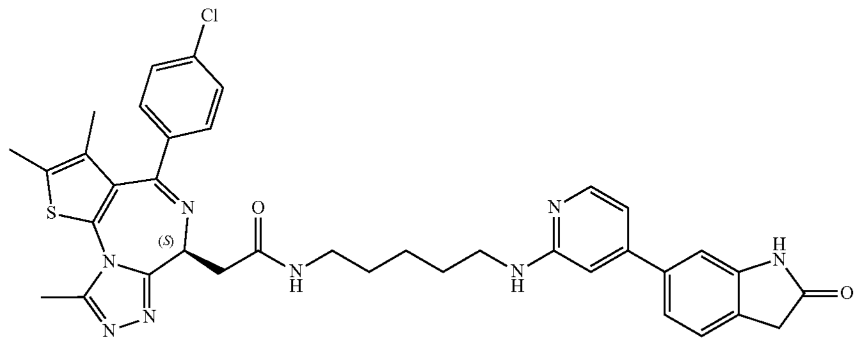 | E |
| 097 | 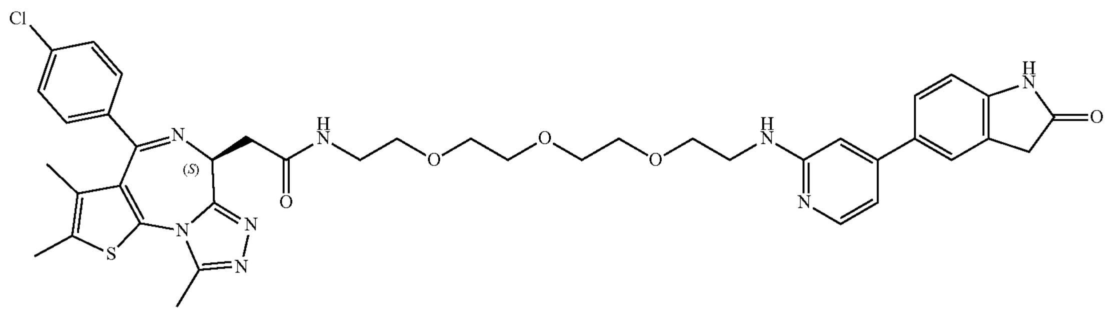 | F |
| 098 | 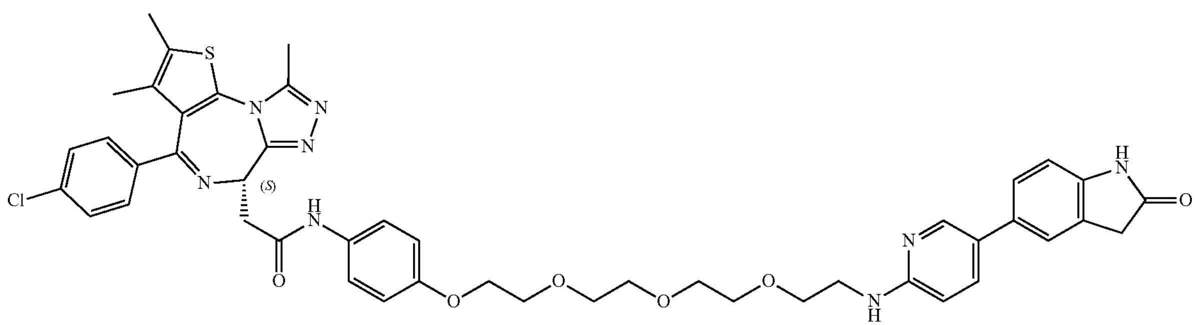 | D |

| Compound ID | Structure | GI$_{50}$ μM (RAMOS) |
|---|---|---|
| 099 | 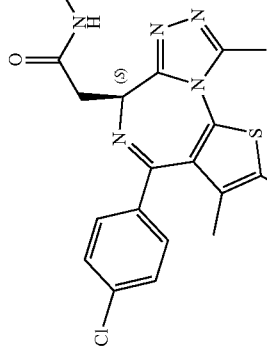 | D |
| 100 | 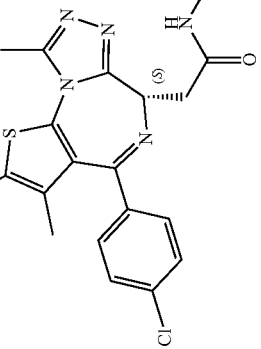 | E |

-continued
| Compound ID | Structure | GI$_{50}$ μM (RAMOS) |
|---|---|---|
| 101 | 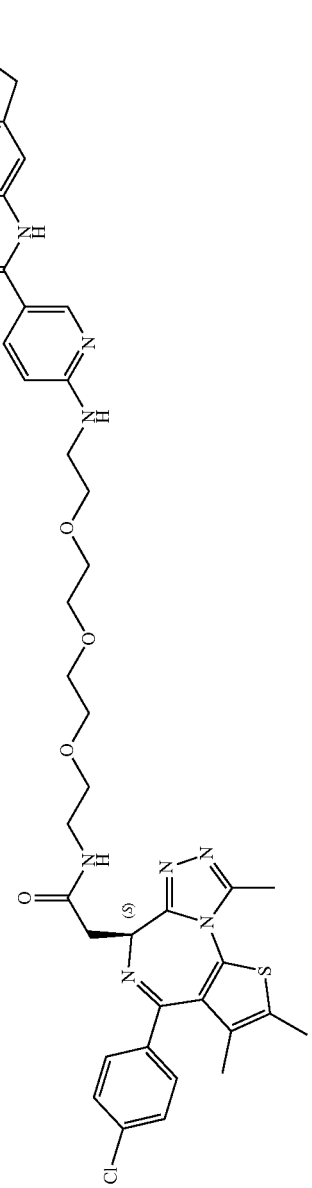 | E |
| 102 | 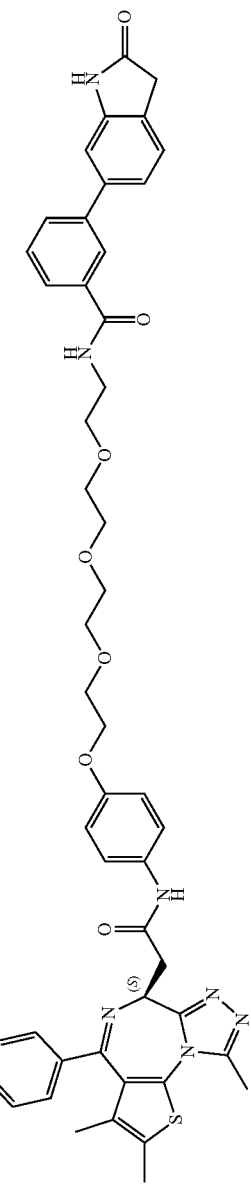 | E |

-continued
| Compound ID | Structure | GI₅₀ μM (RAMOS) |
|---|---|---|
| 103 | 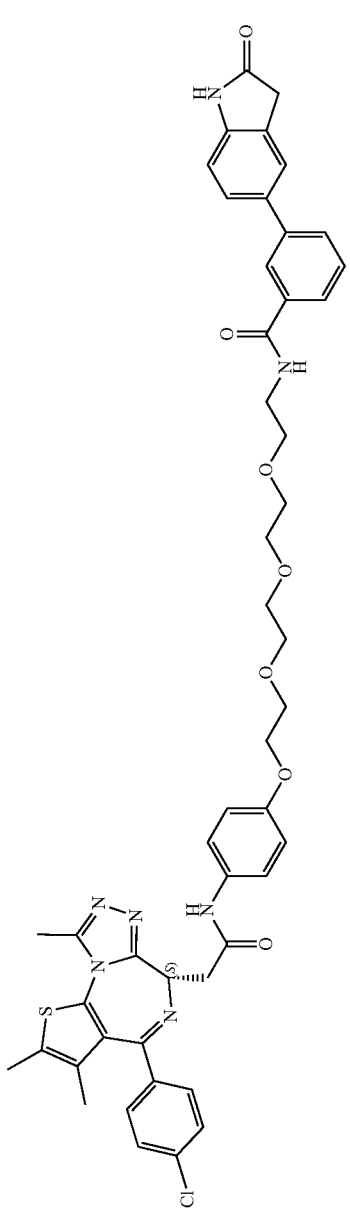 | E |
| 104 | 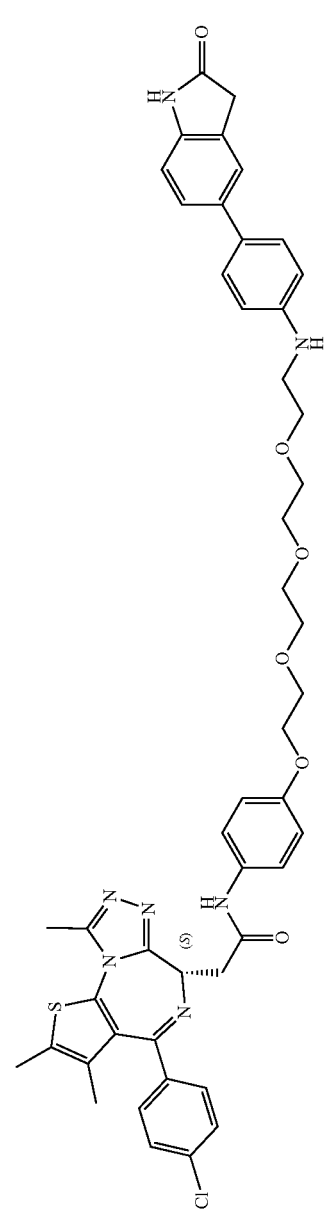 | D |
| 105 | 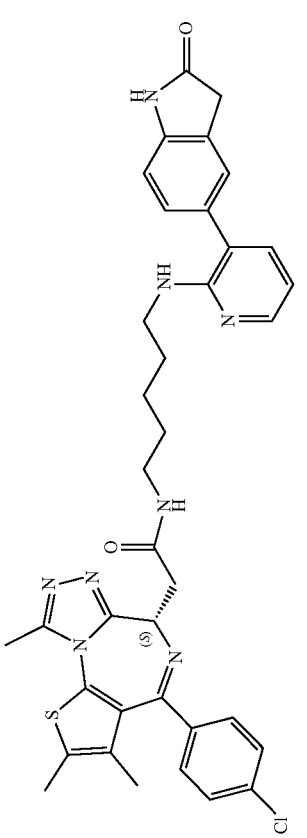 | D |

| Compound ID | Structure | GI$_{50}$ µM (RAMOS) |
|---|---|---|
| 106 | 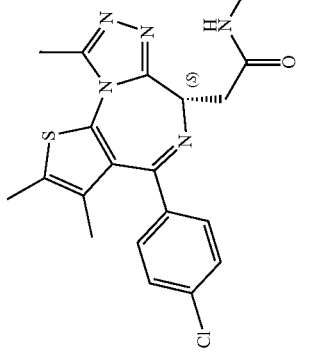 | D |
| 107 | 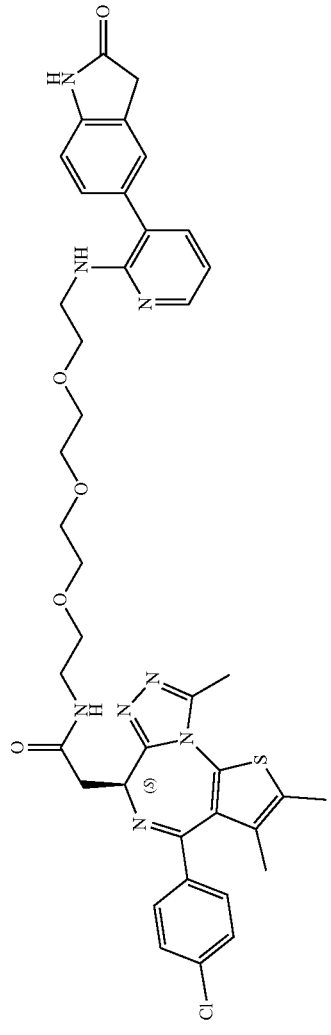 | D |
| 108 | 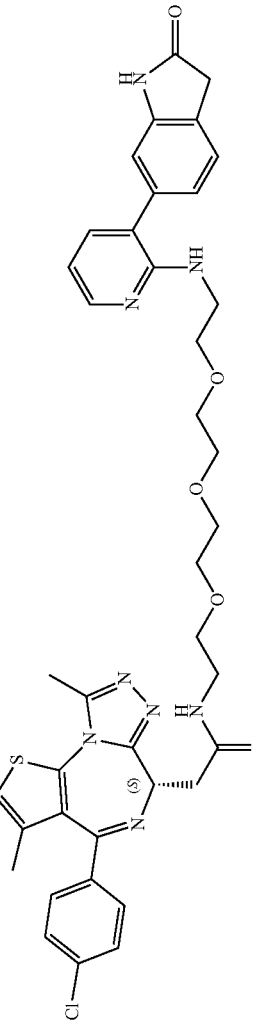 | E |

| Compound ID | Structure | GI$_{50}$ µM (RAMOS) |
|---|---|---|
| 109 | 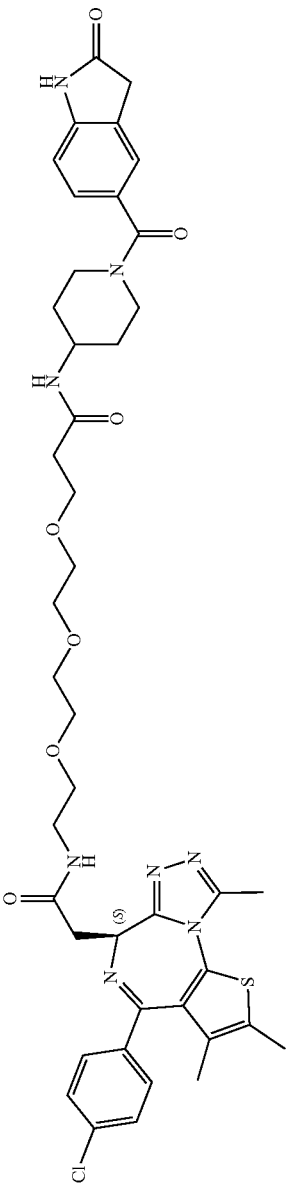 | D |
| 110 | 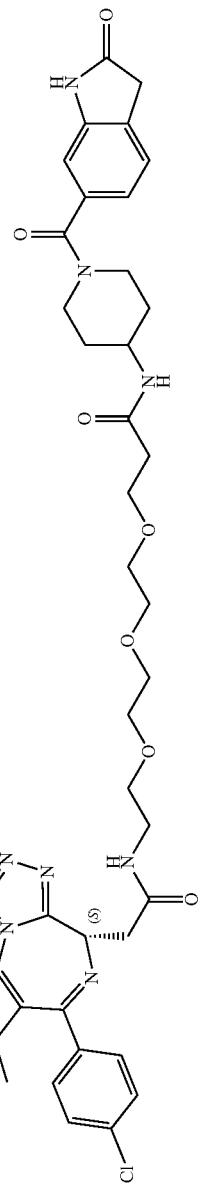 | F |
| 111 | 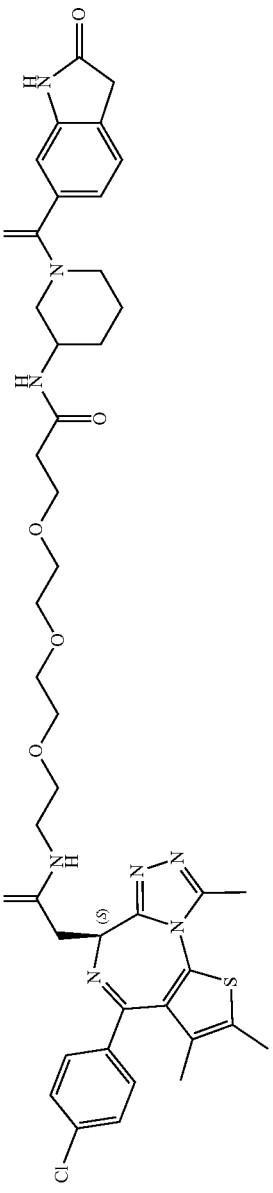 | F |

-continued

| Compound ID | Structure | GI$_{50}$ μM (RAMOS) |
|---|---|---|
| 112 | 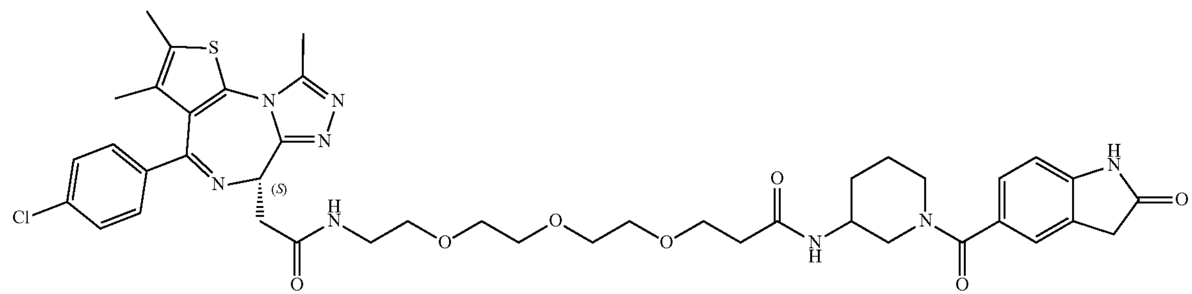 | E |
| 113 | 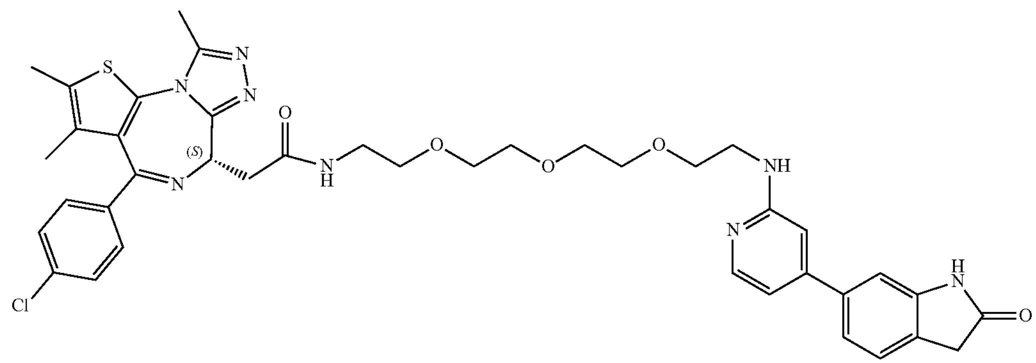 | E |
| 114 | 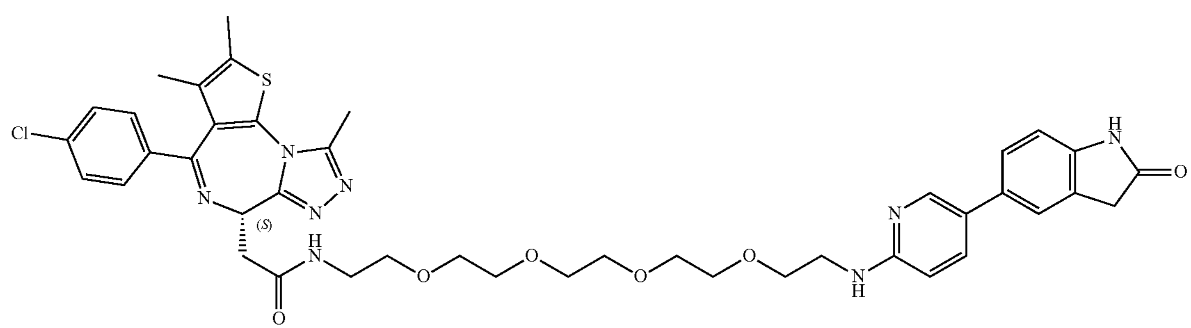 | E |

-continued

| Compound ID | Structure | GI₅₀ μM (RAMOS) |
|---|---|---|
| 115 | 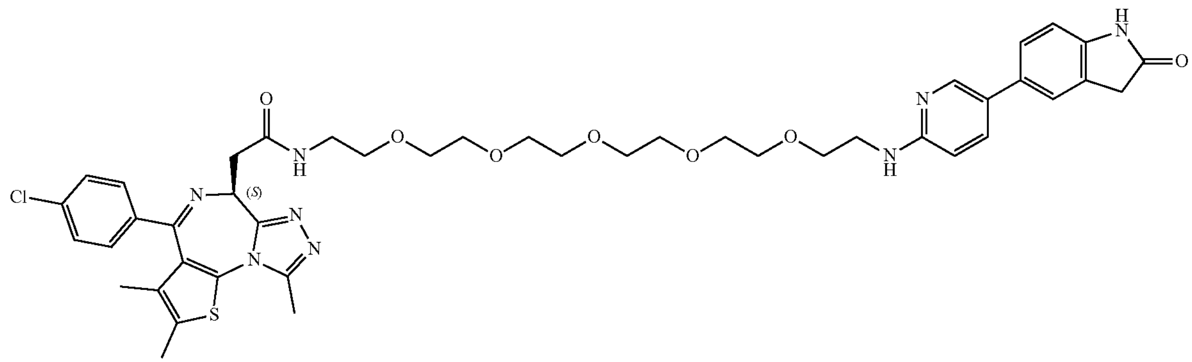 | E |
| 116 | 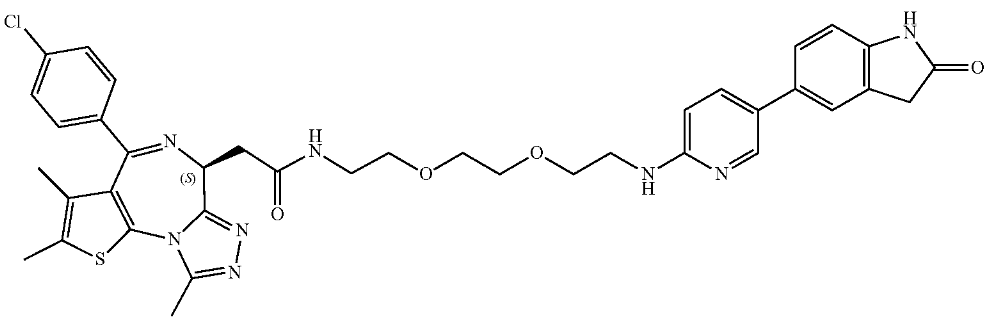 | D |
| 117 | 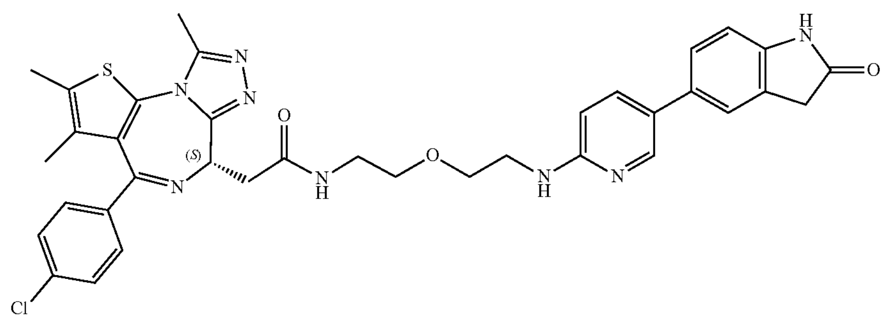 | D |

-continued
| Compound ID | Structure | GI$_{50}$ μM (RAMOS) |
|---|---|---|
| 118 | 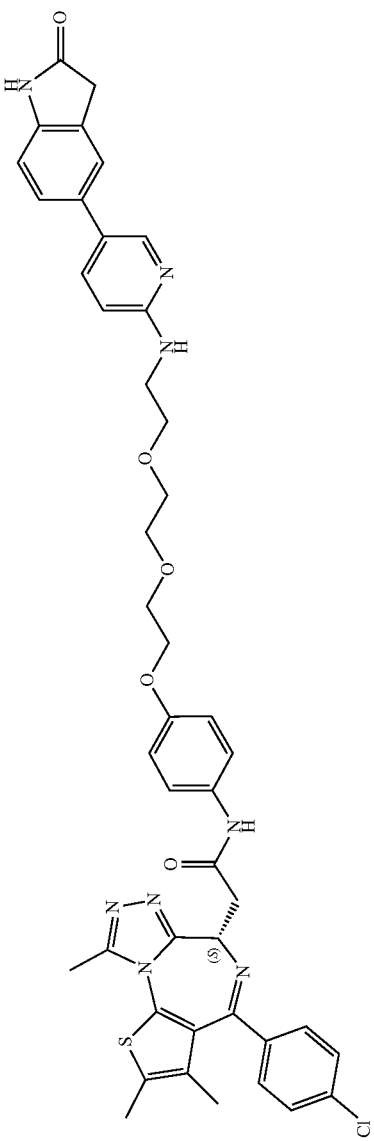 | E |
| 119 | 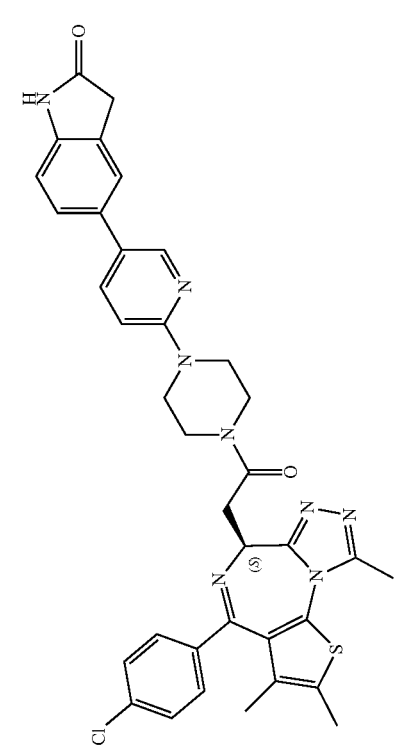 | E |

| Compound ID | Structure | GI$_{50}$ μM (RAMOS) |
|---|---|---|
| 120 | 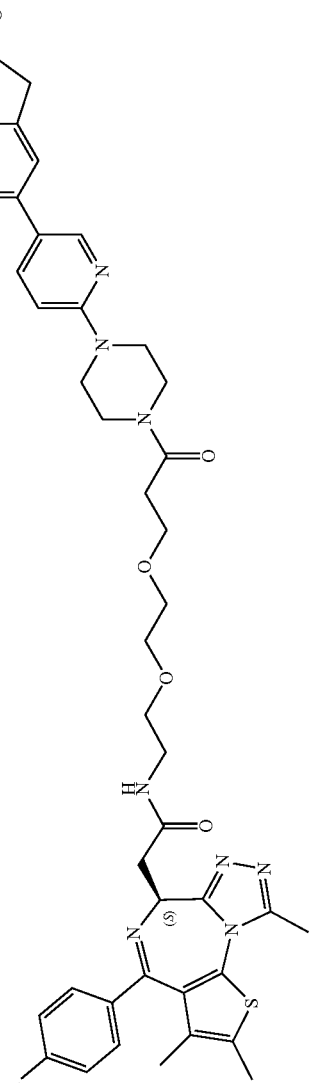 | D |
| 121 | 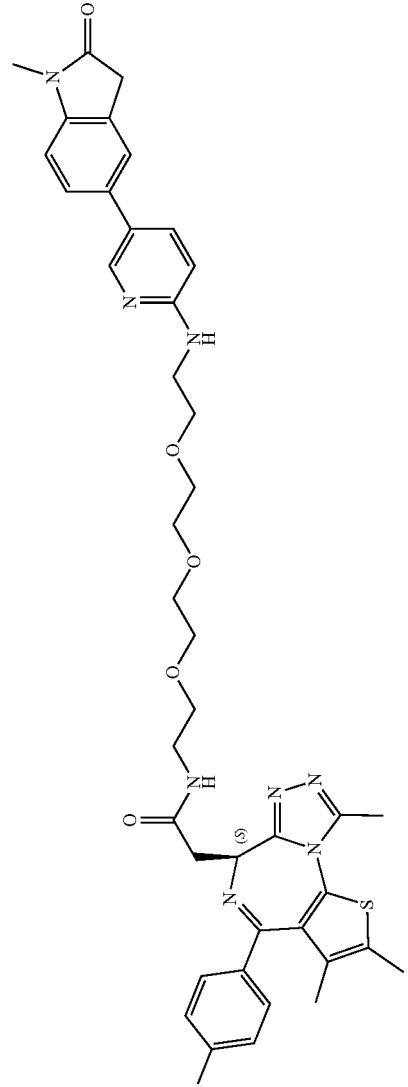 | E |

| Compound ID | Structure | GI$_{50}$ µM (RAMOS) |
|---|---|---|
| 122 | 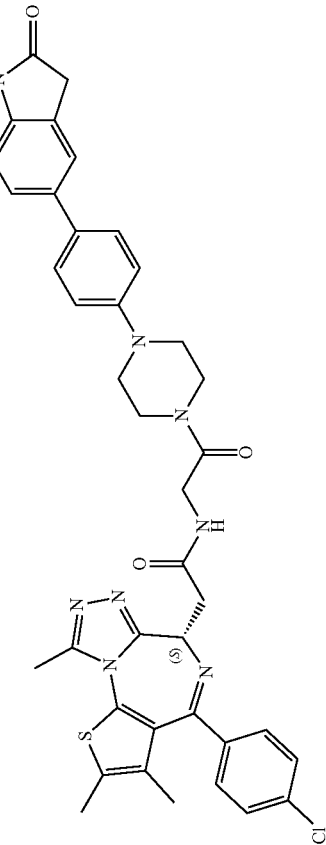 | D |
| 123 | 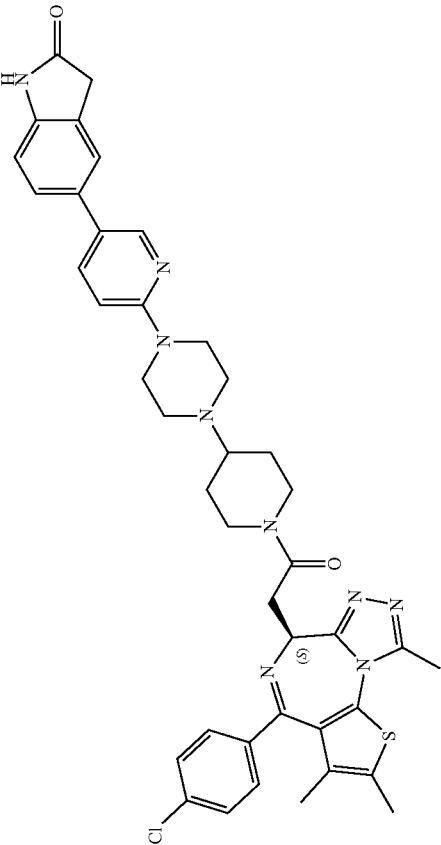 | D |

-continued
| Compound ID | Structure | GI$_{50}$ μM (RAMOS) |
|---|---|---|
| 124 | 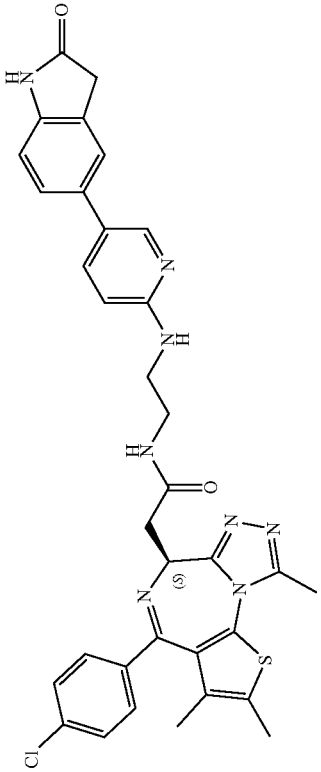 | D |
| 125 | 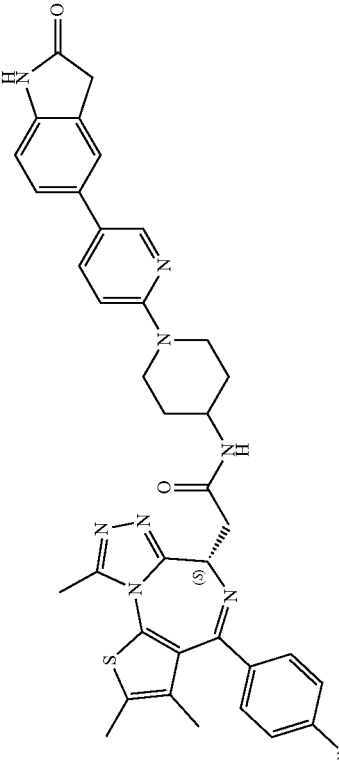 | D |
| 126 | 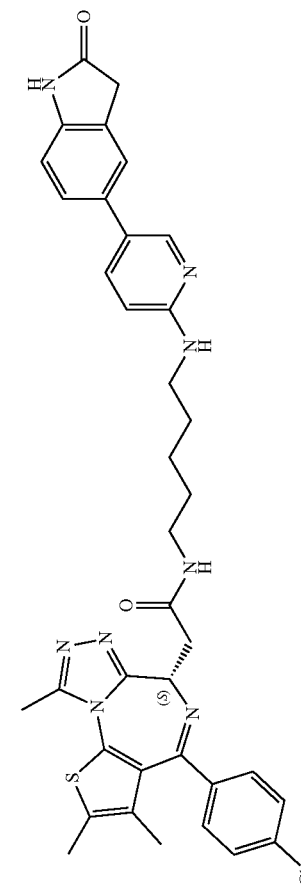 | D |

-continued
| Compound ID | Structure | GI$_{50}$ μM (RAMOS) |
|---|---|---|
| 127 | 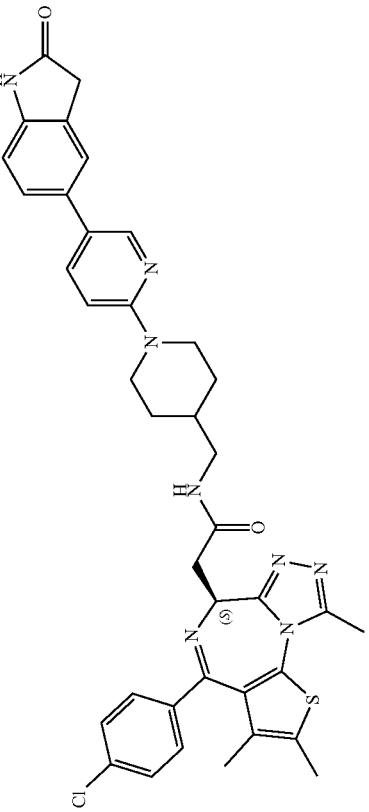 | E |
| 128 | 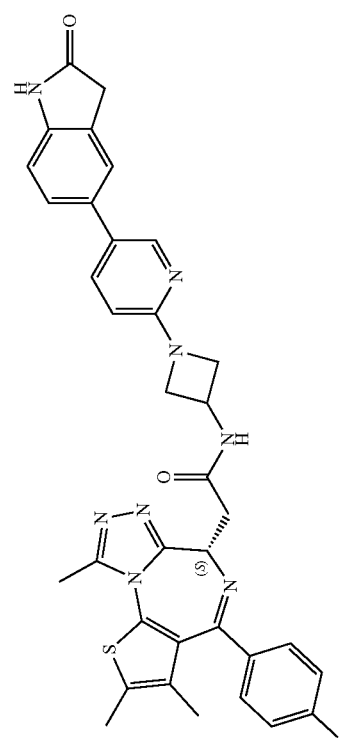 | E |

-continued

| Compound ID | Structure | GI₅₀ μM (RAMOS) |
|---|---|---|
| 129 | 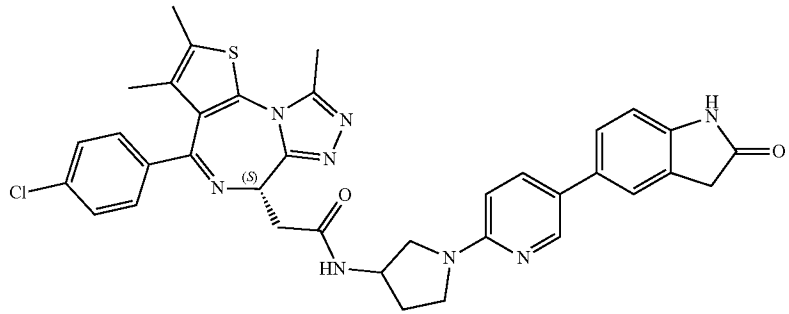 | D |
| 130 | 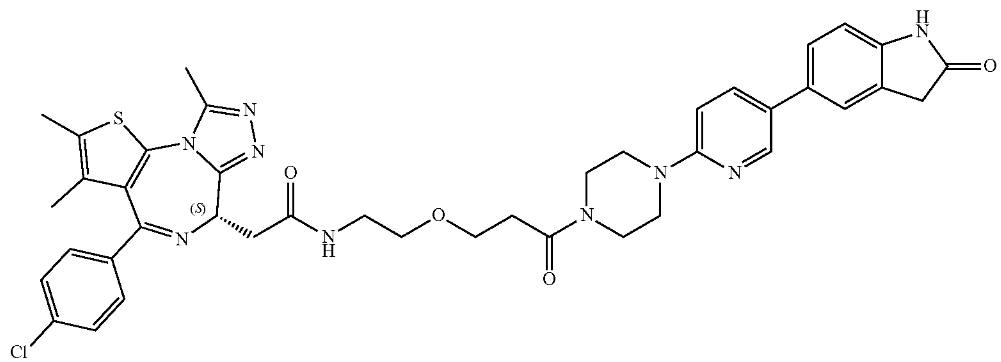 | D |
| 131 | 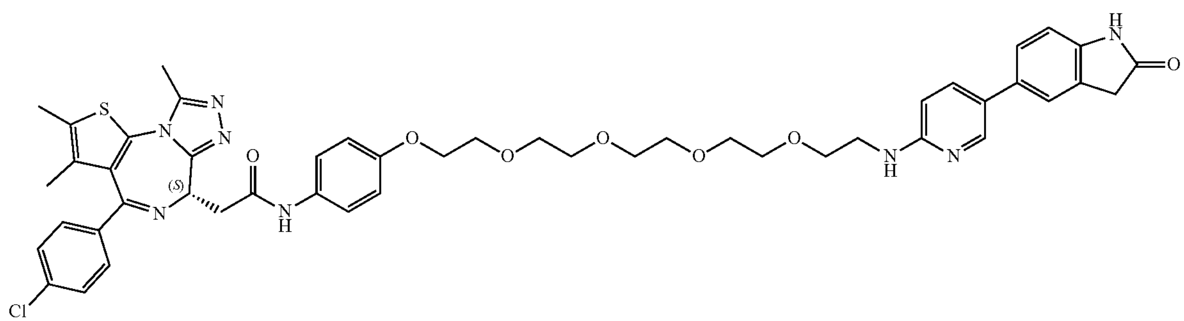 | D |

| Compound ID | Structure | GI$_{50}$ μM (RAMOS) |
|---|---|---|
| 132 | 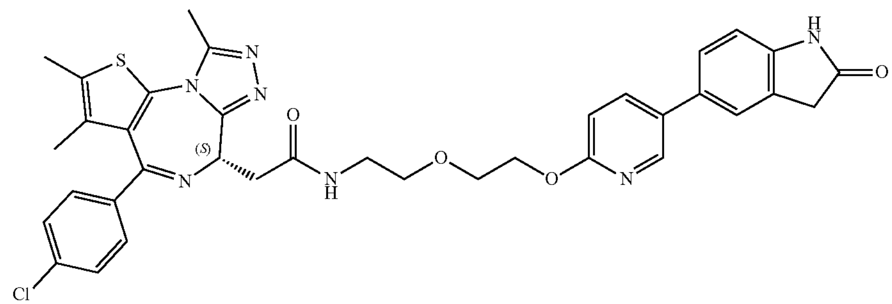 | D |
| 133 | 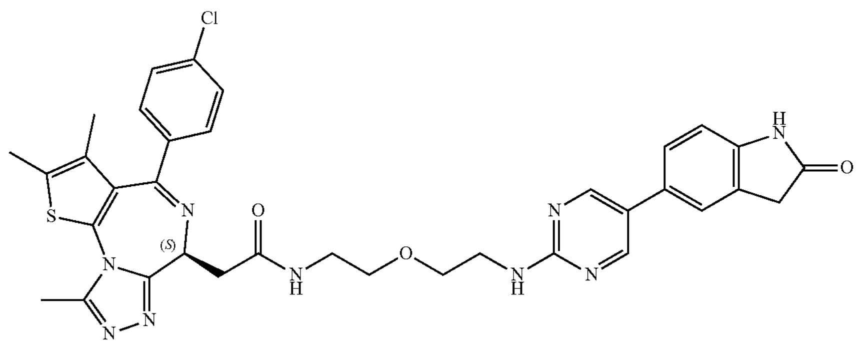 | D |
| 134 | 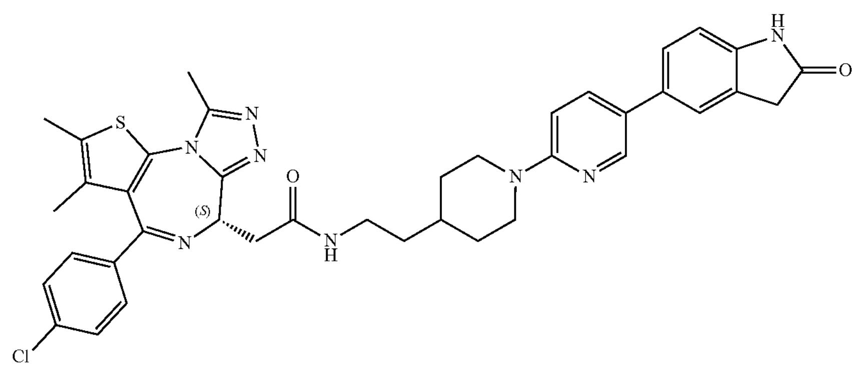 | D |

| Compound ID | Structure | GI$_{50}$ μM (RAMOS) |
|---|---|---|
| 135 | 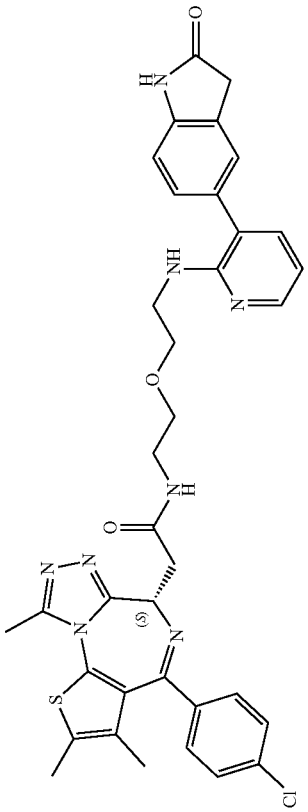 | D |
| 136 | 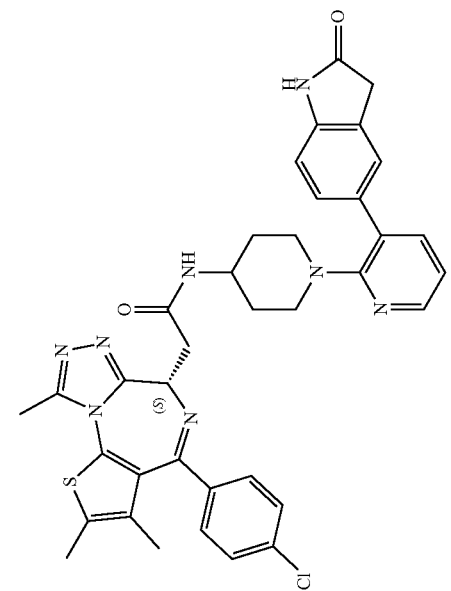 | D |

| Compound ID | Structure | GI$_{50}$ μM (RAMOS) |
|---|---|---|
| 137 | 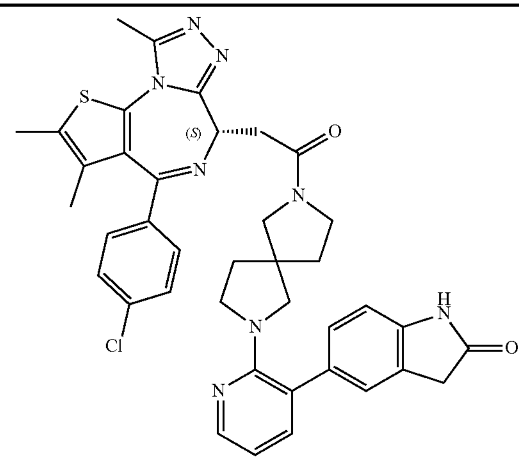 | E |
| 138 | 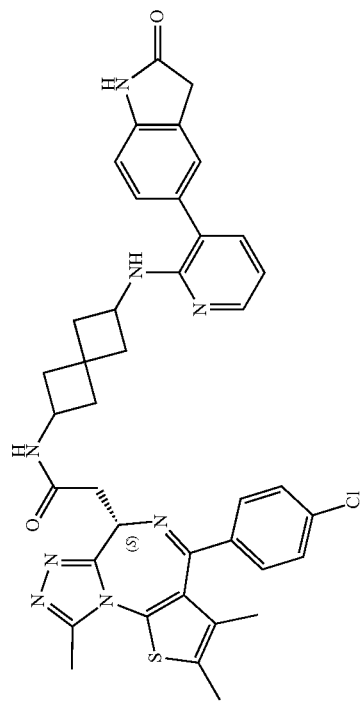 | D |

-continued
| Compound ID | Structure | GI$_{50}$ µM (RAMOS) |
|---|---|---|
| 139 | 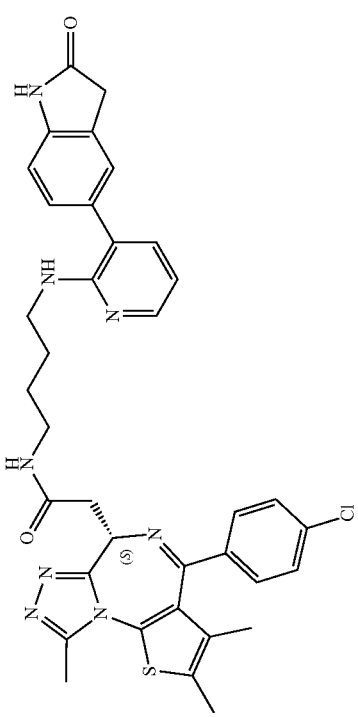 | E |
| 140 | 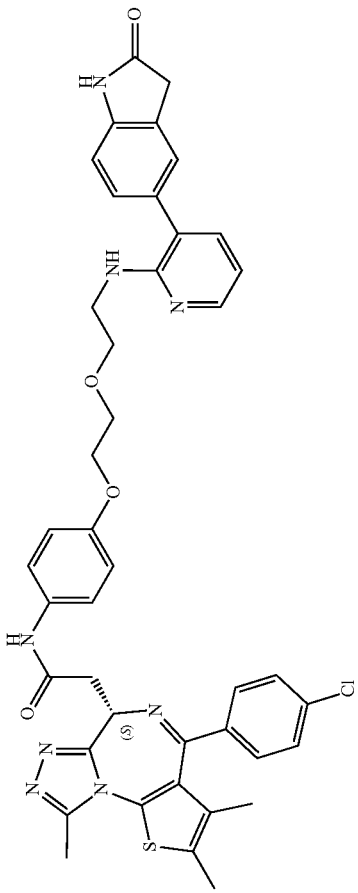 | E |

Example 6

6.1 NMR Ternary Complex Experiments

Figure 2:
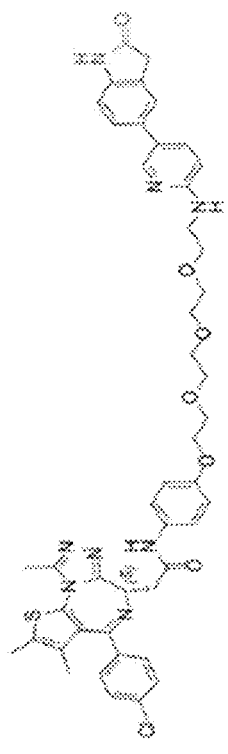
Figure 2:
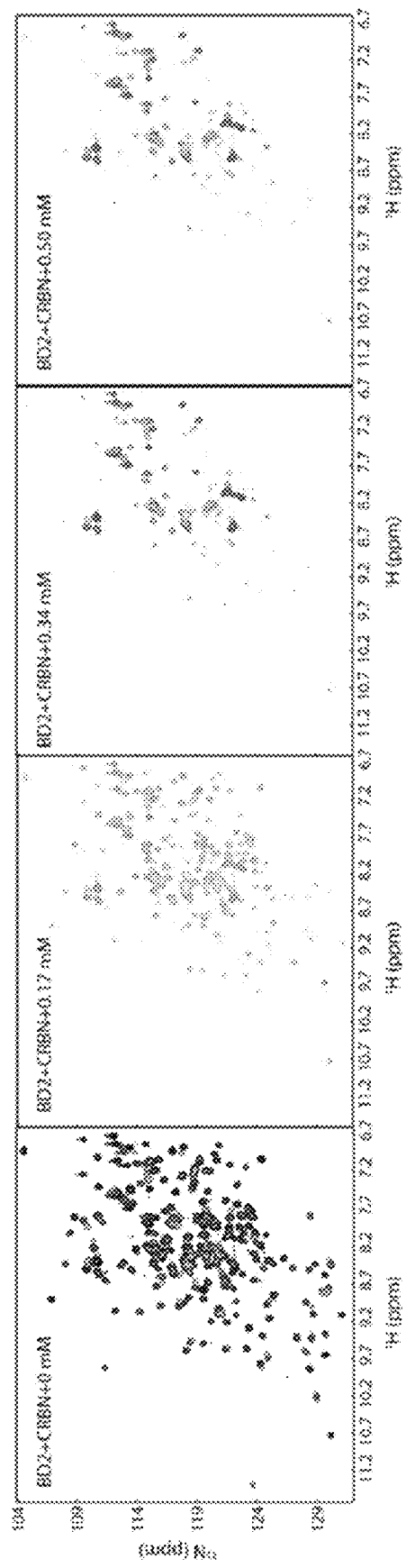

All the NMR experiments were carried out on a Bruker magnet with proton frequency of 600 MHz or 700 MHz equipped with a cryo-probe. The experiments were performed at 25° C. the $^1$H-$^{15}$N HSQC spectrum was collected using a standard pulse from the pulse library (Topspin version 2.1). To test whether the developed compounds bind to CRBN and BRD4, respectively, the $^1$H-$^{15}$N HSQC of $^{15}$N—CRBN, $^{15}$N-BD2, a mixture of equal molar (0.5 mM) of $^{15}$N—CRBN and $^{15}$N-BD2 in the absence and presence of a PROTAC (0.5 mM) were collected and compared. In the titration experiment, a mixture of equal molar (0.5 mM) of $^{15}$N—CRBN and $^{15}$N-BD2 was used. To avoid the hook effect, $^1$H-$^{15}$N HSQC spectra of mixture in the absence and presence 0.17, 0.34 and 0.5 mM of compounds were collected and compared. As protein complexes have a higher molecular weight than the free proteins, line broadening of the cross peaks in the $^1$H-$^{15}$N HSQC spectrum suggest the formation of ternary complex. The data were collected using Topspin (ver 2.1) provided with equipment. The data were processed with topspin (ver 2.1), NMRPipe (Delaglio et al. 1995) and visualized using NMRView (Johnson 2004). The truncated CRBN: residues 319-427 was used in the NMR experiments. See FIG. 2 for an example of the ternary complex study.

The ternary complex formation is graded as follows:
G: Ternary complex formed at low concentration of compound (stoichiometry of BD2:CRBN:Compound=1:1:0.3)
H: Ternary complex formed at intermediate concentration of compound (stoichiometry of BD2:CRBN:Compound=1:1:0.6)
I: Ternary complex formed at high concentration of compound (stoichiometry of BD2:CRBN:Compound=1:1:1)
J: Weak or no ternary complex formed at high concentration of compound (stoichiometry of BD2:CRBN:Compound=1:1:1)

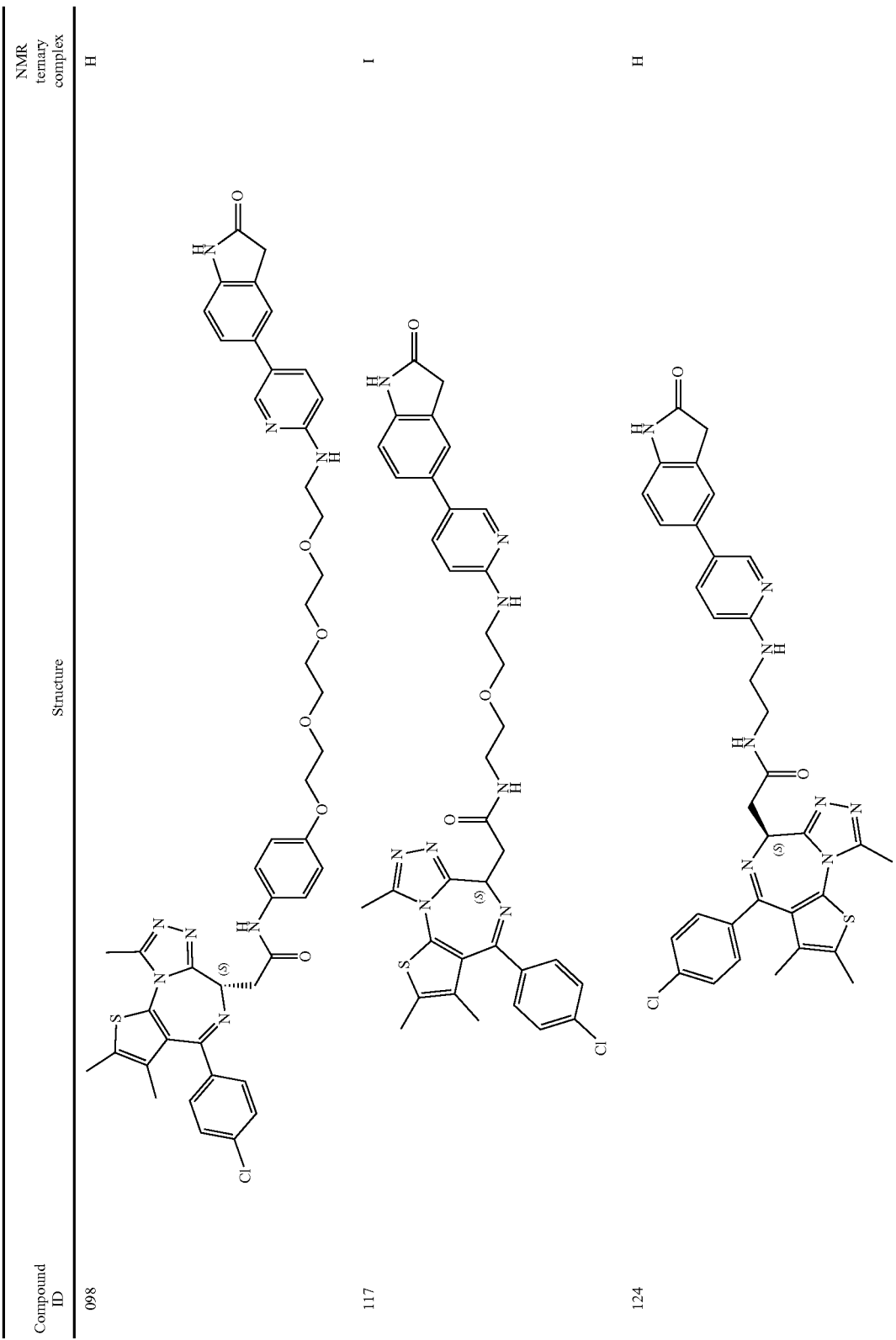

-continued
| Compound ID | Structure | NMR ternary complex |
|---|---|---|
| 135 | 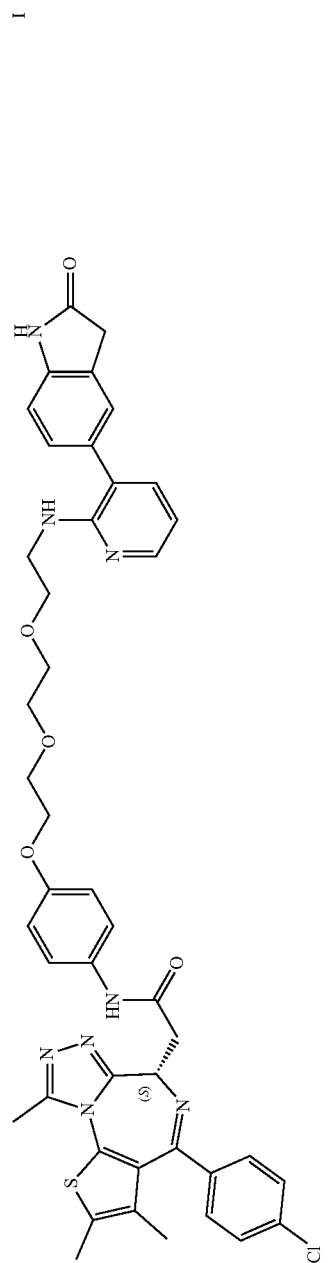 | I |
| 141 | 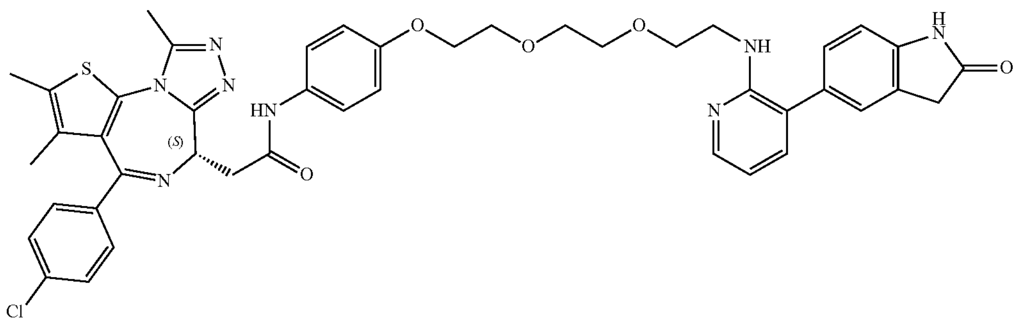 | I |

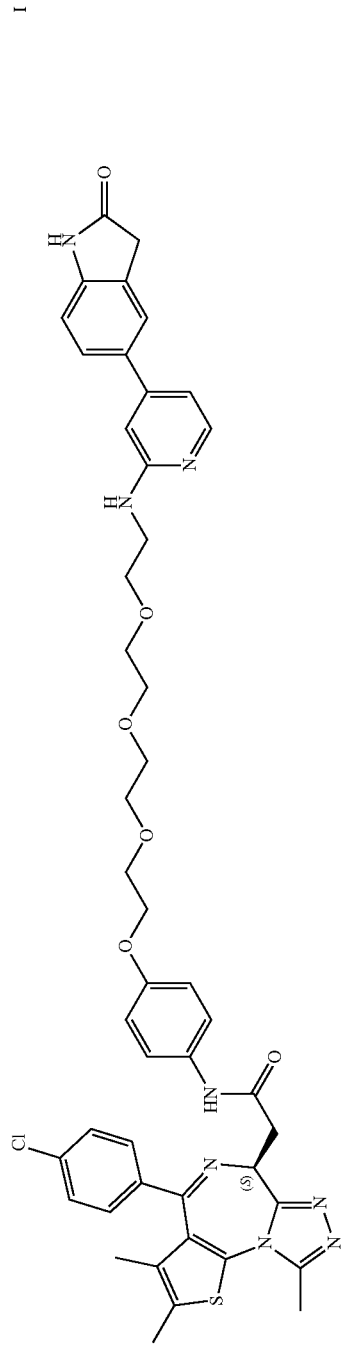

-continued
| Compound ID | Structure | NMR ternary complex |
|---|---|---|
| 144 | 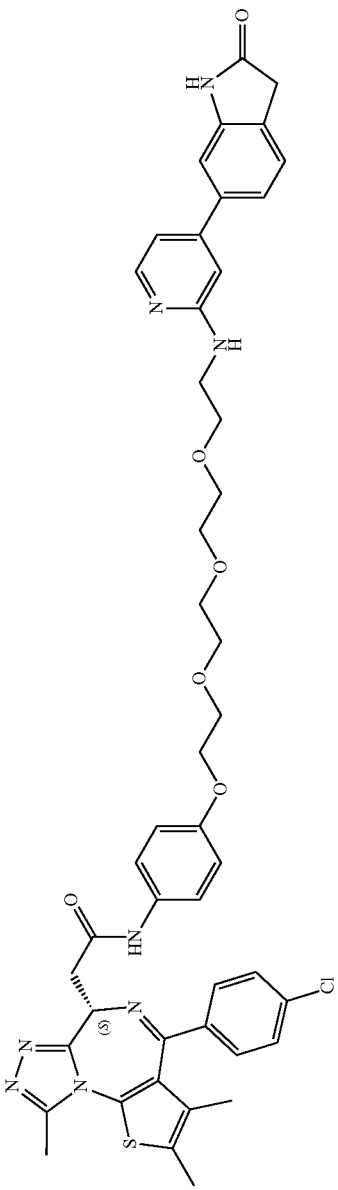 | I |
| 145 | 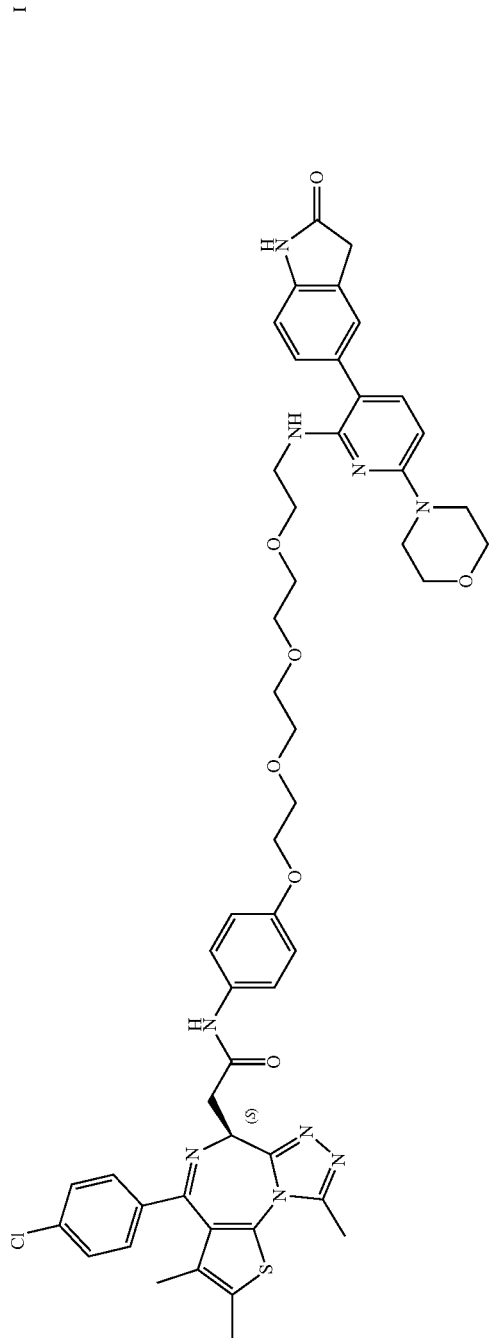 | I |

-continued

| Compound ID | Structure | NMR ternary complex |
|---|---|---|
| 146 | 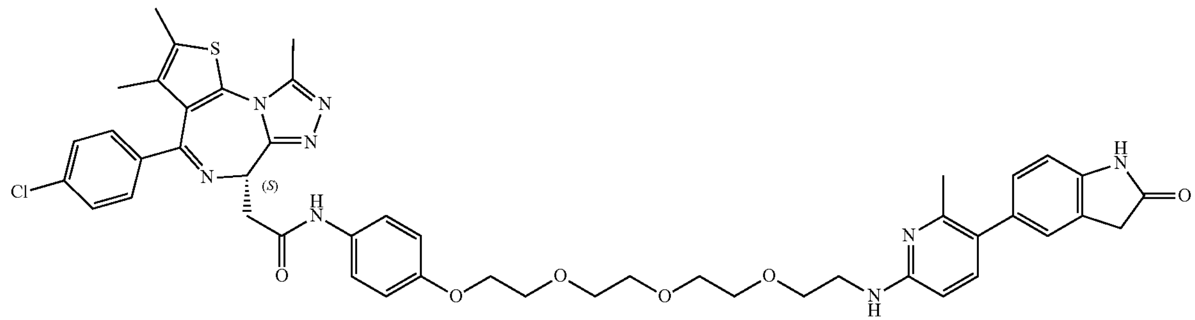 | H |
| 147 | 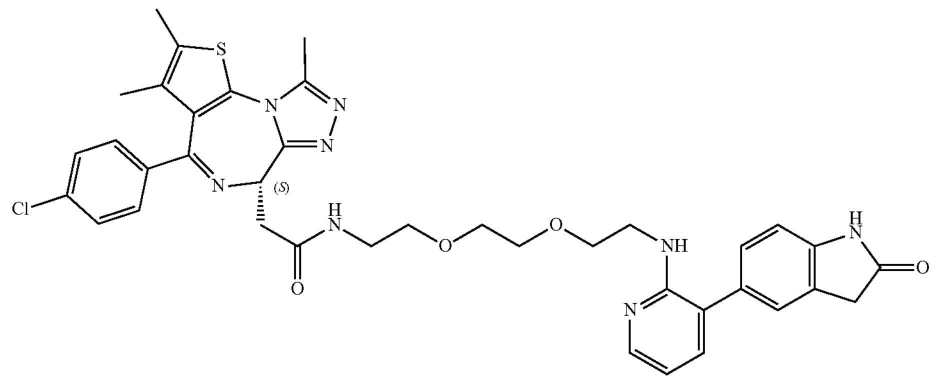 | I |
| 148 | 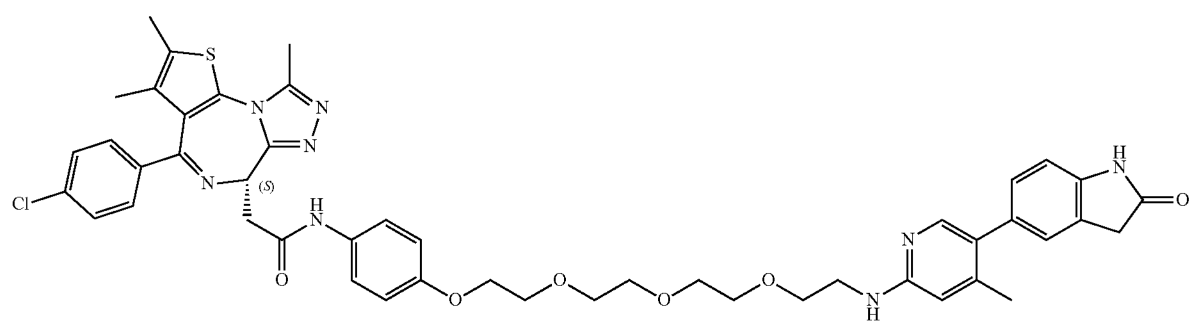 | G |

| Compound ID | Structure | NMR ternary complex |
|---|---|---|
| 149 | 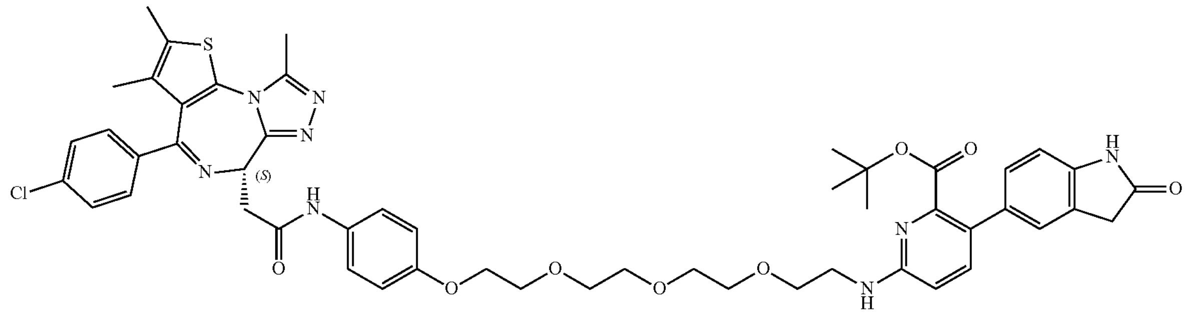 | I |
| 150 | 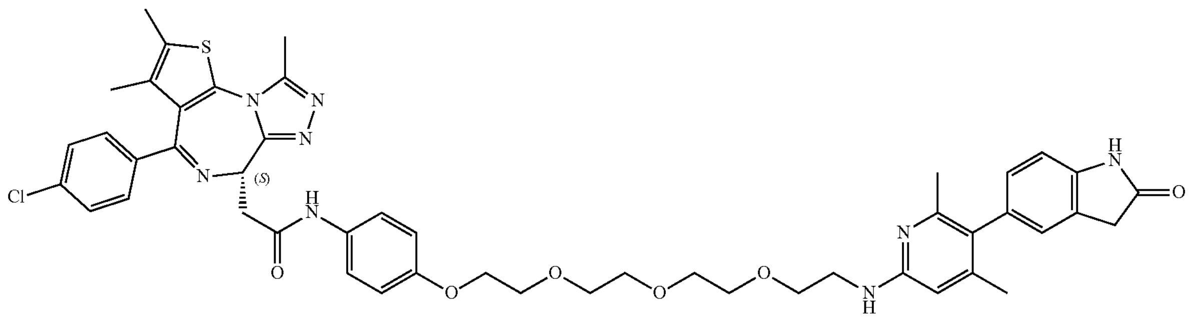 | H |
| 151 | 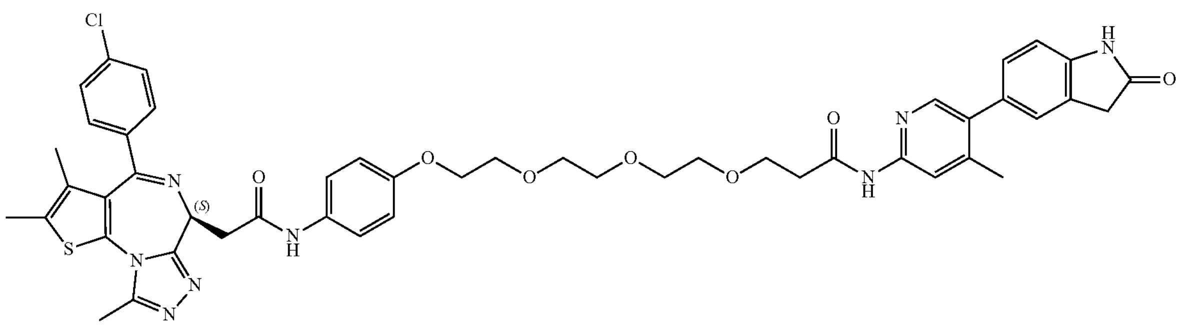 | G |

-continued
| Compound ID | Structure | NMR ternary complex |
|---|---|---|
| 152 | 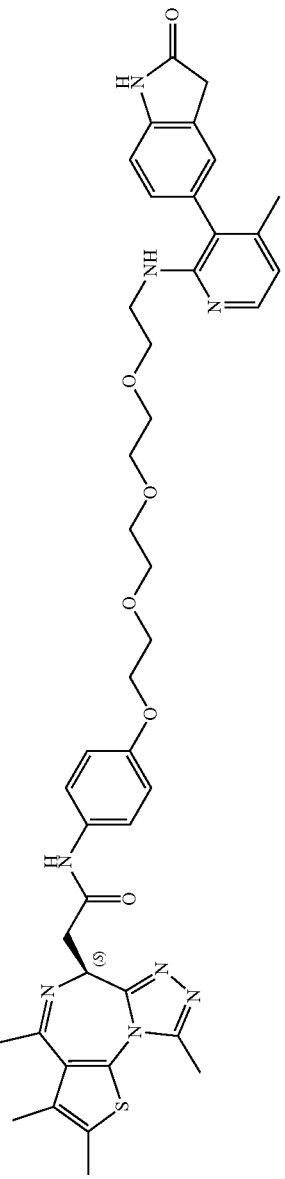 | I |
| 153 | 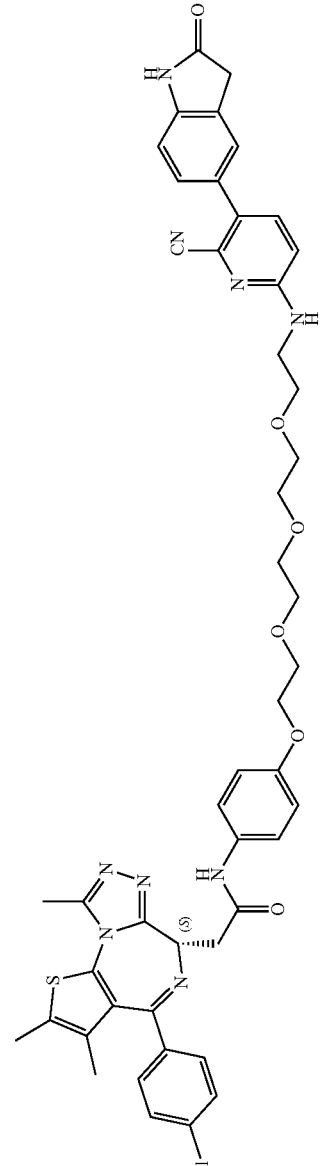 | H |

-continued

| Compound ID | Structure | NMR ternary complex |
|---|---|---|
| 154 | 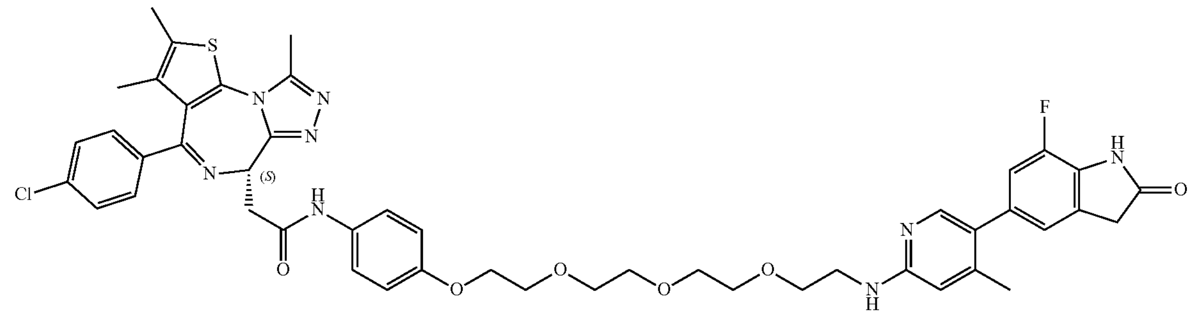 | G |
| 155 | 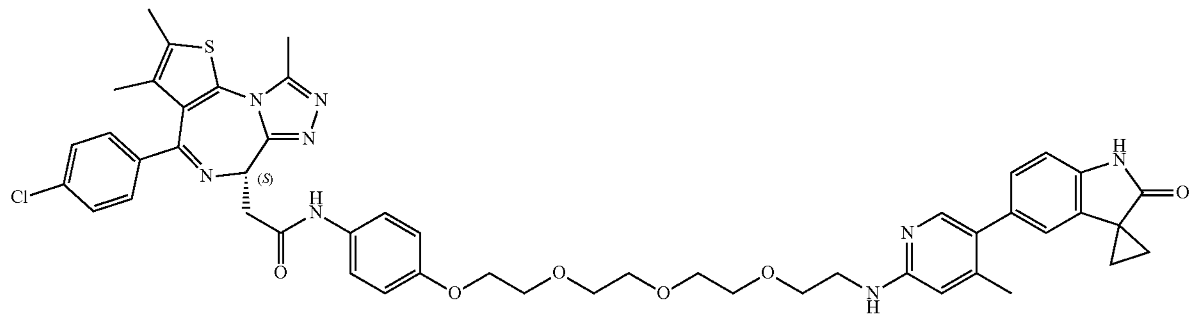 | I |
| 156 | 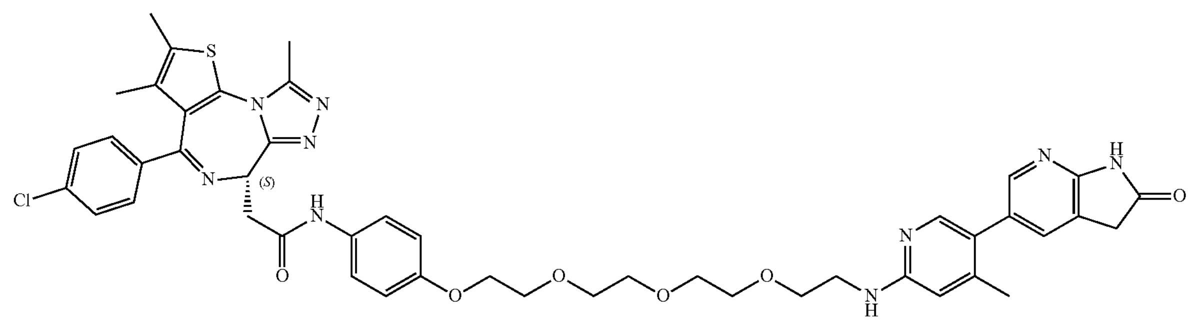 | G |

-continued
| Compound ID | Structure | NMR ternary complex |
|---|---|---|
| 157 | 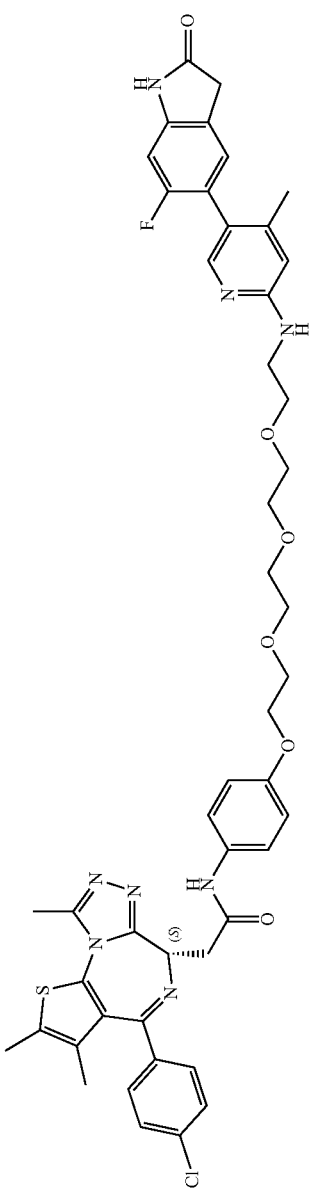 | G |
| 158 | 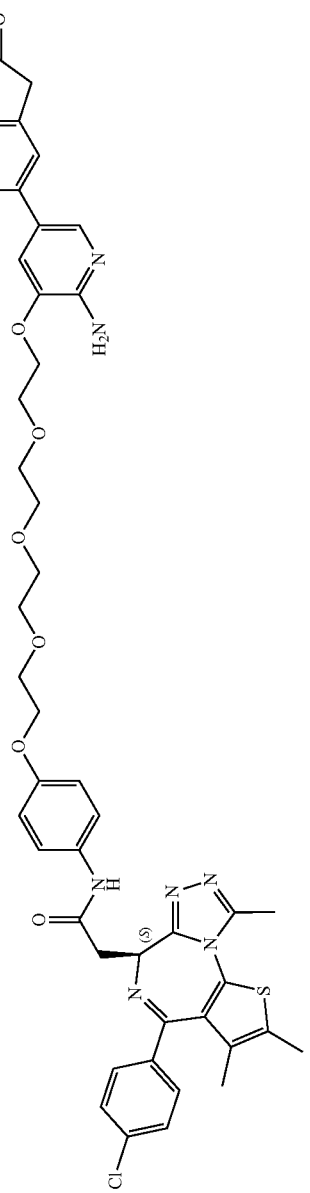 | I |

| Compound ID | Structure | NMR ternary complex |
|---|---|---|
| 159 | 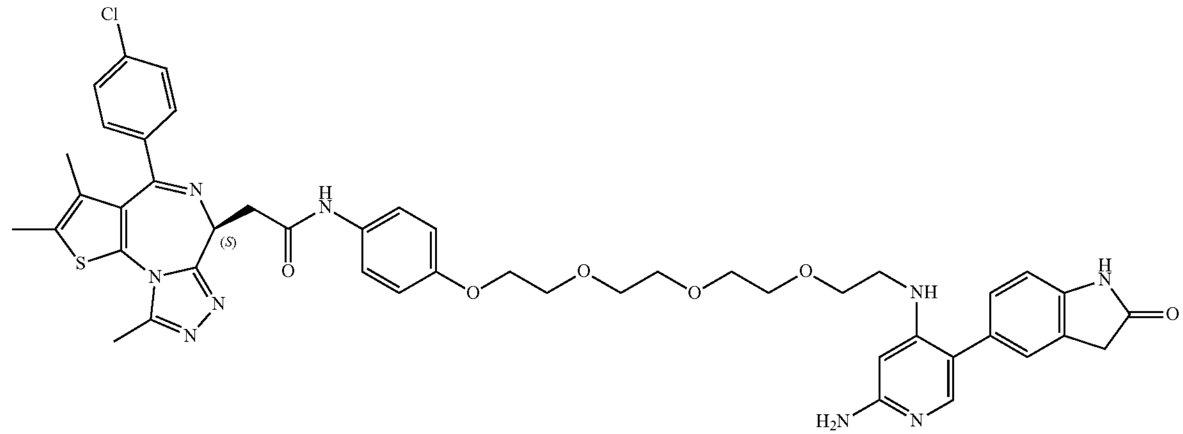 | I |
| 160 | 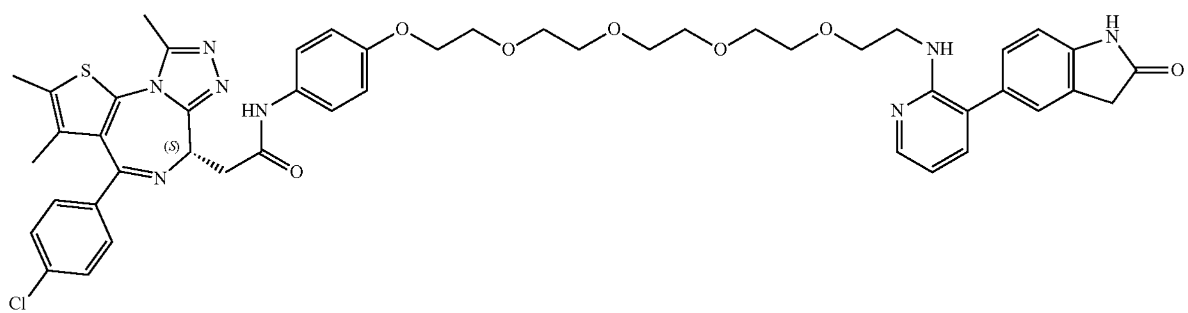 | J |

-continued

| Compound ID | Structure | NMR ternary complex |
|---|---|---|
| 161 | 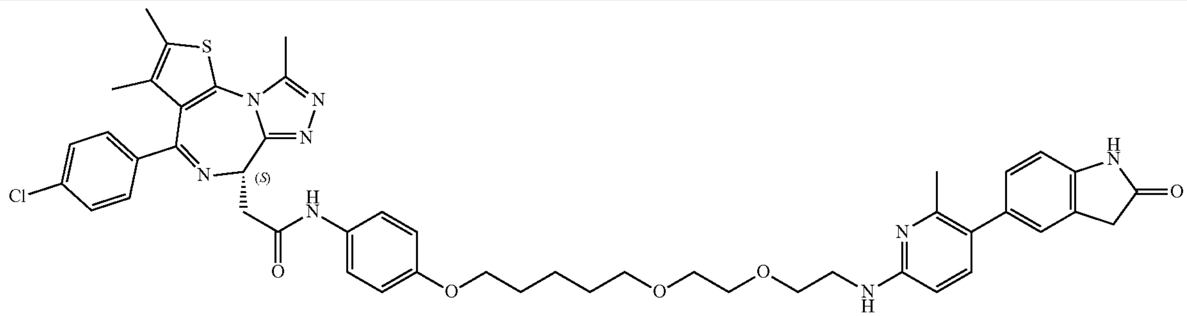 | I |
| 162 | 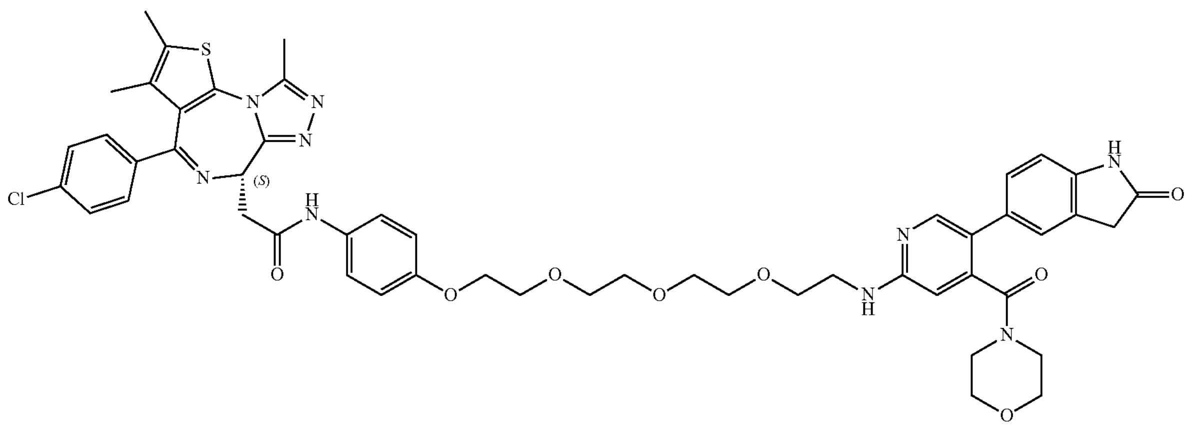 | J |

-continued
| Compound ID | Structure | NMR ternary complex |
|---|---|---|
| 163 | 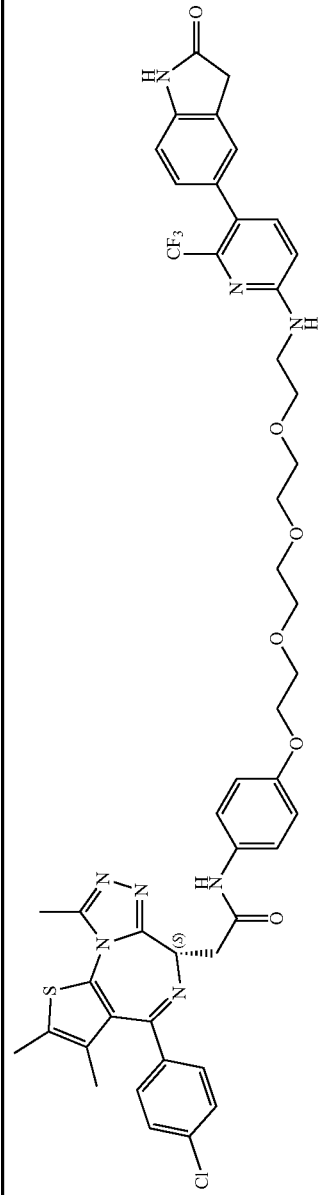 | J |
| 164 | 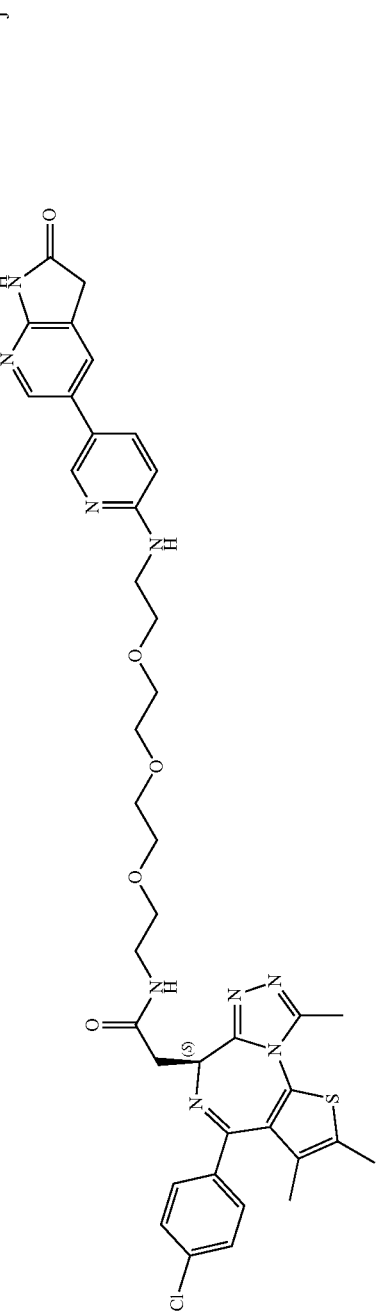 | J |
| 165 | 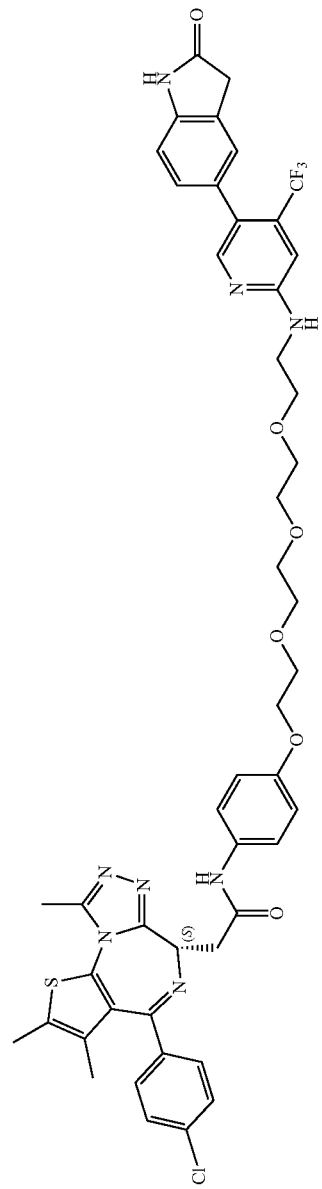 | J |

-continued
| Compound ID | Structure | NMR ternary complex |
|---|---|---|
| 166 | 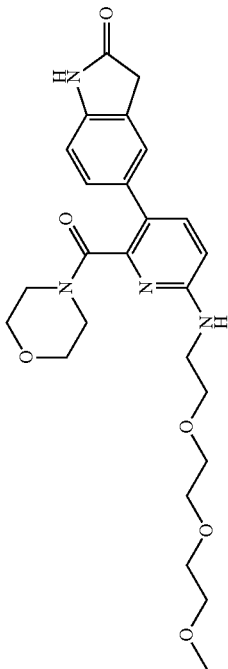 | J |
| 167 | 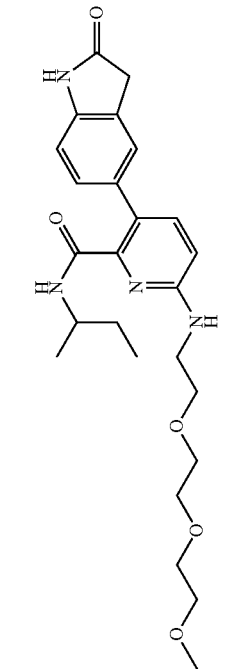 | J |
| 168 | 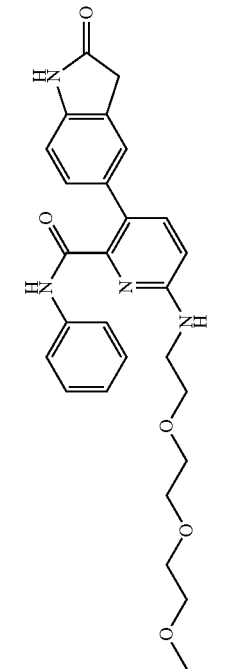 | J |

-continued

| Compound ID | Structure | NMR ternary complex |
|---|---|---|
| 169 | (structure: (S)-configured methyl-triazolo-thienodiazepine with 4-chlorophenyl, CH2C(O)NH-phenyl-O-(CH2CH2O)4-CH2CH2-NH-pyridine-2,3-dihydro-1H-benzimidazol-2-one) | J |
| 170 | (structure: same as 169 but with benzoxazol-2(3H)-one in place of benzimidazol-2-one) | J |

Example 7

7.1 Western Blot Analysis Procedure

Ramos (ATCC, CRL-1596) cells cultured in Roswell Park Memorial Institute (RPMI) 1640 Medium supplemented with 10% Fetal bovine serum and 1% Penicillin-streptomycin at 37° C. in humidified atmosphere with 5% $CO_2$. In 6-well plate, 1.2 million cells were treated with indicated PROTAC compounds at 0.1% final concentration (v/v) of DMSO for desired duration of time. Pelleted cells were lysed in RIPA buffer (1% Nonidet P-40, 0.5% sodium deoxycholate, 0.1% SDS in 1× Tris-buffered saline) supplemented with protease inhibitor cocktail, 0.5 U/μL Benzonase (Novagen) and 1 mM $MgCl_2$. Lysates were incubated on ice for 10 minutes followed by 15 minutes' centrifugation at 15000×g at 4° C. Supernatant was collected and subjected to Bradford protein quantification assay. Heat-denatured lysates (50 μg total protein) were loaded on NuPAGE 3-8% Tris-Acetate SDS protein gels. Proteins were transferred to PVDF membrane using iBlot 2 Dry Blotting Device (Thermo Fisher Scientific) at 20V for 13 minutes. Membranes were processed using iBind Flex Western Device (Thermo Fisher Scientific) by following the manufacturer's guideline. Membranes were probed with anti-BRD4 (Cell Signaling, Cat. #13440S), anti-c-Myc (Cell Signaling, Cat. #5605S), anti-β-actin (Proteintech, Cat. #66009-1-lg) antibodies, and developed with anti-Rabbit IgG, HRP-linked F(ab')$_2$ fragment (from donkey) (GE Life Sciences, Cat. #NA-9340) or anti-mouse IgG, AP-linked Antibody (Cell Signaling Technologies, Cat. #7056S) secondary antibodies. Membranes were incubated with Amersham ECL Select Western Blotting Detection Reagent (GE life sciences, Cat. #RPN2235) and Immun-Star™ AP Chemiluminescence Kits (Biorad, Cat. #1705018), visualized under FluorChem system (Protein Simple).

The compounds were tested against BRD4 and are found to be effective in promoting degradation of BRD4.

Table 1 shows % BRD4 degradation induced by select compounds in RAMOS cells using Western Blot analysis. The protocol was run at 4 different inhibitor concentrations: 5 μM, 1 μM, 0.3 μM, 0.1 μM, using neat DMSO as the negative control. The numbers correspond to the compounds selected as examples shown in Table 1. The % BRD4 degradation in western blot analysis is graded as follows:

K: Protein degradation >70%
L: 40%≤protein degradation<70%
M: protein degradation<40%

TABLE 1

| BRD4 Degradation Results | | | | |
|---|---|---|---|---|
| Compound # | 5 μM | 1 μM | 0.3 μM | 0.1 μM |
| 148 | K | L | L | M |
| 156 | K | L | M | M |

What is claimed is:

1. A compound of the formula:

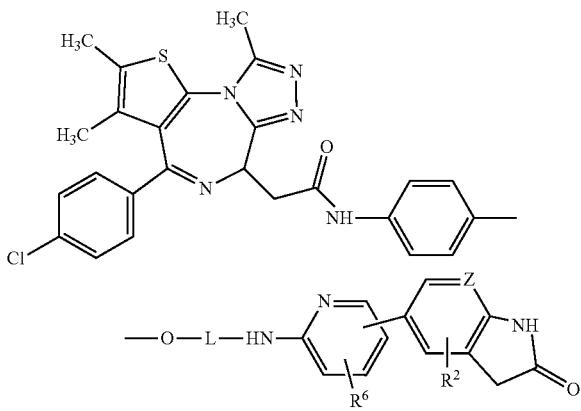

wherein
  $R^2$ is a selected from H, halogen, and optionally substituted $C_1$-$C_6$ alkyl
  $R^6$ is selected from H and $C_1$-$C_6$ alkyl;
  Z is N or CH; and
  L is a linker selected from optionally substituted $C_2$-$C_{15}$ alkyl, and optionally substituted poly(ethoxy).

2. The compound according to claim 1, wherein $R^2$ is fluoro.

3. The compound according to claim 1, wherein $R^6$ is methyl.

4. The compound according to claim 1, wherein $R^2$ is fluoro; and $R^6$ is methyl.

5. The compound according to claim 4, wherein Z is N.

6. A compound of a formula selected from Table 1:

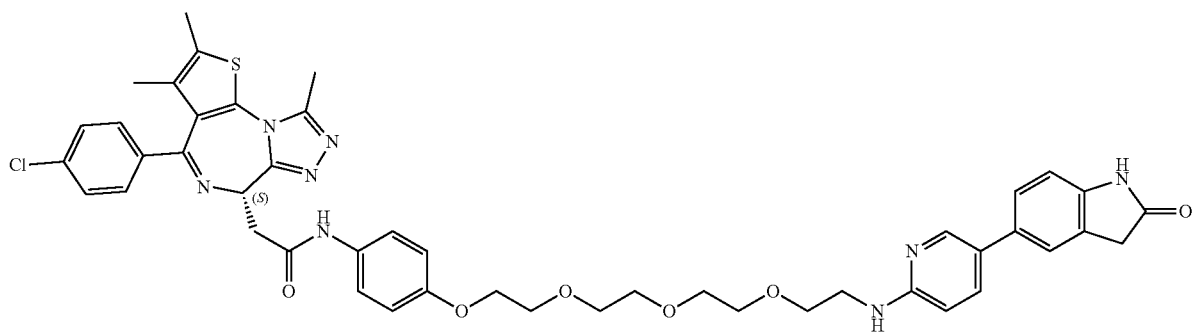

315
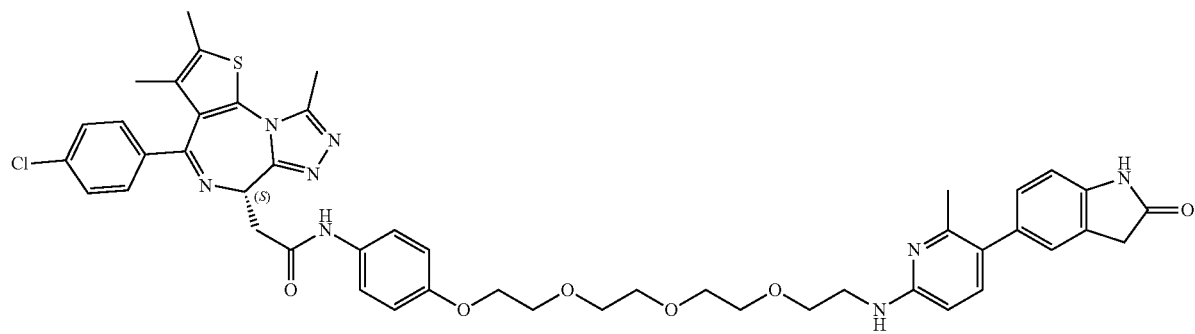
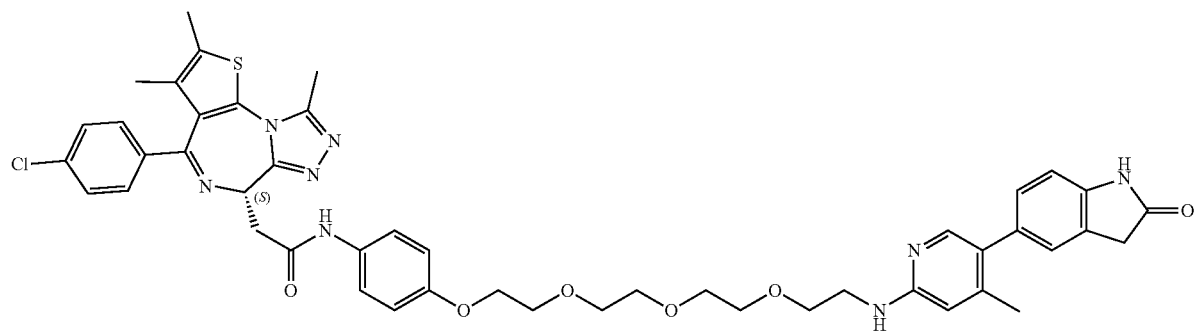
316
-continued
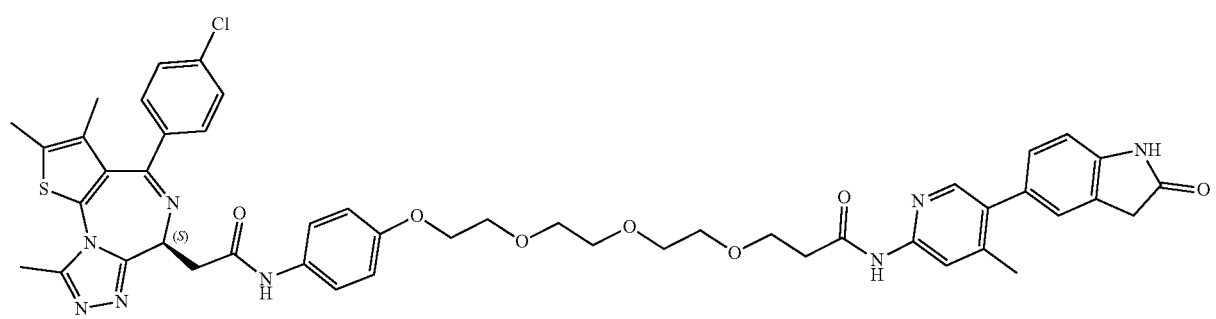
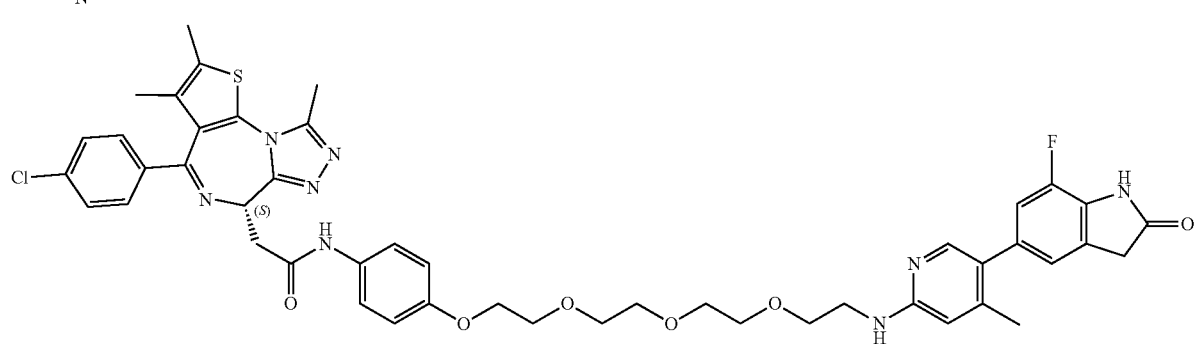
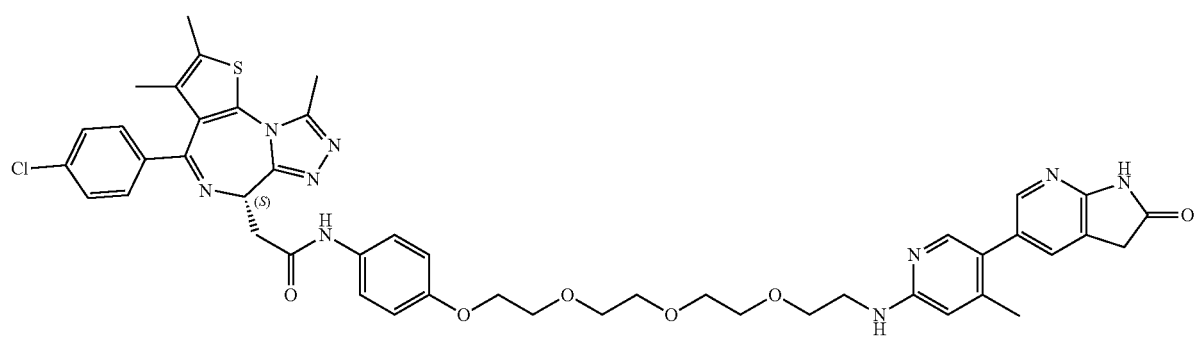

317 318
-continued
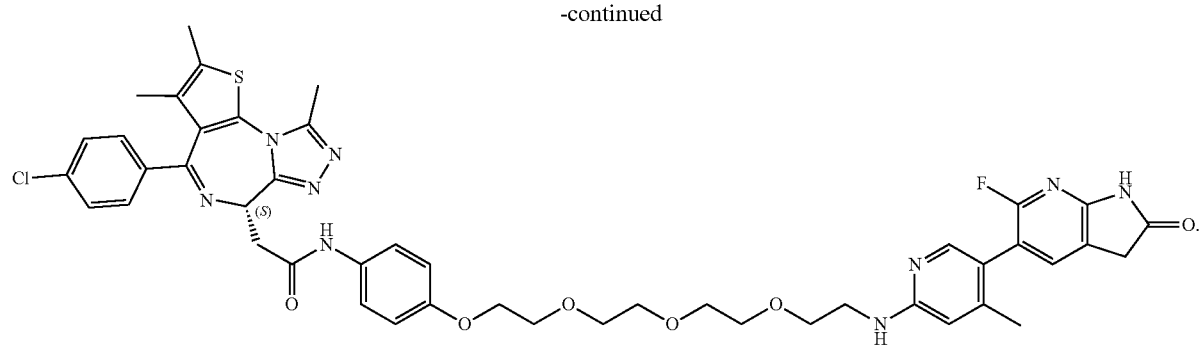
* * * * *